(12) United States Patent
La Motte-Mohs et al.

(10) Patent No.: US 11,072,653 B2
(45) Date of Patent: Jul. 27, 2021

(54) LAG-3-BINDING MOLECULES AND METHODS OF USE THEREOF

(71) Applicant: MacroGenics, Inc., Rockville, MD (US)

(72) Inventors: Ross La Motte-Mohs, Boyds, MD (US); Kalpana Shah, Boyds, MD (US); Douglas H. Smith, San Mateo, CA (US); Leslie S. Johnson, Darnestown, MD (US); Paul A. Moore, North Potomac, MD (US); Ezio Bonvini, Potomac, MD (US); Scott Koenig, Rockville, MD (US)

(73) Assignee: MacroGenics, Inc., Rockville, MD (US)

( * ) Notice: Subject to any disclaimer, the term of this patent is extended or adjusted under 35 U.S.C. 154(b) by 51 days.

(21) Appl. No.: 15/580,029

(22) PCT Filed: Jun. 7, 2016

(86) PCT No.: PCT/US2016/036172
§ 371 (c)(1),
(2) Date: Dec. 6, 2017

(87) PCT Pub. No.: WO2016/200782
PCT Pub. Date: Dec. 15, 2016

(65) Prior Publication Data
US 2019/0085075 A1   Mar. 21, 2019

Related U.S. Application Data

(60) Provisional application No. 62/255,094, filed on Nov. 13, 2015, provisional application No. 62/172,277, filed on Jun. 8, 2015.

(51) Int. Cl.
*C07K 16/28* (2006.01)
*A61K 47/68* (2017.01)
*A61P 31/04* (2006.01)
*A61K 39/00* (2006.01)

(52) U.S. Cl.
CPC .......... *C07K 16/2803* (2013.01); *A61P 31/04* (2018.01); *C07K 16/2818* (2013.01); *A61K 2039/505* (2013.01); *C07K 2317/24* (2013.01); *C07K 2317/31* (2013.01); *C07K 2317/33* (2013.01); *C07K 2317/35* (2013.01); *C07K 2317/52* (2013.01); *C07K 2317/522* (2013.01); *C07K 2317/524* (2013.01); *C07K 2317/526* (2013.01); *C07K 2317/565* (2013.01); *C07K 2317/626* (2013.01); *C07K 2317/76* (2013.01); *C07K 2317/92* (2013.01); *C07K 2317/94* (2013.01); *C07K 2319/21* (2013.01)

(58) Field of Classification Search
CPC ............ C07K 16/2803; C07K 16/2896; C07K 2317/33; C07K 2317/51; C07K 2317/515; C07K 2317/565; C07K 2317/56; C07K 2317/76; A61K 2039/505; A61K 47/6877; A61K 49/0001; A61K 49/0013; A61K 49/0017; A61K 49/0043
See application file for complete search history.

(56) References Cited

U.S. PATENT DOCUMENTS

| | | |
|---|---|---|
| 4,524,390 A | 6/1985 | Lemke et al. |
| 4,526,938 A | 7/1985 | Churchill |
| 4,816,567 A | 3/1989 | Cabilly et al. |
| 4,880,078 A | 11/1989 | Inque et al. |
| 4,928,535 A | 5/1990 | Perryman et al. |
| 4,946,819 A | 8/1990 | Sasaki et al. |
| 4,980,286 A | 12/1990 | Morgan et al. |
| 5,026,822 A | 6/1991 | Vora |
| 5,128,326 A | 7/1992 | Balazs |
| 5,290,540 A | 3/1994 | Prince et al. |
| 5,565,332 A | 10/1996 | Baier et al. |
| 5,580,717 A | 12/1996 | Dower |
| 5,624,821 A | 4/1997 | Winter et al. |

(Continued)

FOREIGN PATENT DOCUMENTS

| | | |
|---|---|---|
| EP | 0 359 096 | 11/1997 |
| EP | 1 293 514 | 11/2006 |

(Continued)

OTHER PUBLICATIONS

Lloyd et al. Protein Engineering, Design & Selection 22:159-168 (Year: 2009).*
Edwards et al., J Mol Biol. 334(1): 103-118 (Year: 2003).*
Rudikoff et al., Proc. Natl. Acad. Sci. USA, 79:1979-1983 (Year: 1982).*
Lund et al., The Journal of Immunology 157:4963-4969 (Year: 1996).*
Agarwal, A. et al. (2008) "*The Role of Positive Costimulatory Molecules in Transplantation and Tolerance*," Curr. Opin. Organ Transplant. 13:366-337.

(Continued)

*Primary Examiner* — Phuong Huynh
(74) *Attorney, Agent, or Firm* — Jeffrey I. Auerbach; AuerbachSchrot LLC

(57) ABSTRACT

The present invention is directed to the anti-LAG-3 antibodies, LAG-3 mAb 1, LAG-3 mAb 2, LAG-3 mAb 4, LAG-3 mAb 5, and LAG-3 mAb 6, and to humanized and chimeric versions of such antibodies. The invention additionally pertains to LAG-3-binding molecules that comprise LAG-3 binding fragments of such anti-LAG-3 antibodies, immunoconugates, and to bispecific molecules, including diabodies, BiTEs, bispecific antibodies, etc., that comprise (i) such LAG-3-binding fragments, and (ii) a domain capable of binding an epitope of a molecule involved in regulating an immune check point present on the surface of an immune cells. The present invention also pertains to methods of detecting LAG-3, as well as methods of using molecules that bind LAG-3 for stimulating immune responses.

17 Claims, 26 Drawing Sheets

Specification includes a Sequence Listing.

(56) References Cited

U.S. PATENT DOCUMENTS

| | | |
|---|---|---|
| 5,679,377 A | 10/1997 | Bernstein et al. |
| 5,733,743 A | 3/1998 | Johsnon et al. |
| 5,773,578 A | 6/1998 | Hercend et al. |
| 5,807,715 A | 9/1998 | Morrison et al. |
| 5,811,097 A | 9/1998 | Allison et al. |
| 5,855,913 A | 1/1999 | Hanes et al. |
| 5,866,692 A | 2/1999 | Shitara et al. |
| 5,874,064 A | 2/1999 | Edwards et al. |
| 5,885,573 A | 3/1999 | Bluestone et al. |
| 5,888,533 A | 3/1999 | Dunn |
| 5,912,015 A | 6/1999 | Bernstein et al. |
| 5,916,597 A | 6/1999 | Lee et al. |
| 5,934,272 A | 8/1999 | Lloyd et al. |
| 5,945,155 A | 8/1999 | Grill et al. |
| 5,955,300 A | 9/1999 | Faure et al. |
| 5,985,309 A | 11/1999 | Edwards et al. |
| 5,985,320 A | 11/1999 | Edwards et al. |
| 5,989,463 A | 11/1999 | Tracy et al. |
| 5,997,867 A | 12/1999 | Waldmann et al. |
| 6,019,968 A | 2/2000 | Platz |
| 6,054,297 A | 4/2000 | Carter et al. |
| 6,180,377 B1 | 1/2001 | Morgan et al. |
| 6,194,551 B1 | 2/2001 | Presta et al. |
| 6,197,524 B1 | 3/2001 | Romagnani |
| 6,218,149 B1 | 4/2001 | Morrison et al. |
| 6,265,150 B1 | 7/2001 | Terstappen |
| 6,277,375 B1 | 8/2001 | Ward |
| 6,331,415 B1 | 12/2001 | Cabilly et al. |
| 6,472,511 B1 | 10/2002 | Leung et al. |
| 6,482,925 B1 | 11/2002 | El Tayar et al. |
| 7,083,784 B2 | 8/2006 | Dall'Acqua et al. |
| 7,129,330 B1 | 10/2006 | Little et al. |
| 7,563,869 B2 | 7/2009 | Honjo et al. |
| 7,595,048 B2 | 9/2009 | Honjo et al. |
| 7,858,746 B2 | 12/2010 | Honjo et al. |
| 7,998,479 B2 | 8/2011 | Honjo et al. |
| 8,008,449 B2 | 8/2011 | Korman et al. |
| 8,088,376 B2 | 1/2012 | Chamberlain et al. |
| 8,354,509 B2 | 1/2013 | Carven et al. |
| 8,460,886 B2 | 6/2013 | Shibayama et al. |
| 8,552,154 B2 | 10/2013 | Freeman et al. |
| 8,728,474 B2 | 5/2014 | Honjo et al. |
| 8,735,553 B1 | 5/2014 | Li et al. |
| 8,779,105 B2 | 7/2014 | Korman et al. |
| 8,900,587 B2 | 12/2014 | Carven et al. |
| 8,952,136 B2 | 2/2015 | Carven et al. |
| 9,005,629 B2 | 4/2015 | Pardoll et al. |
| 9,067,999 B1 | 6/2015 | Honjo et al. |
| 9,073,994 B2 | 7/2015 | Honjo et al. |
| 9,084,776 B2 | 7/2015 | Korman et al. |
| 9,163,087 B2 | 10/2015 | Kuchroo et al. |
| 9,217,034 B2 | 12/2015 | Li et al. |
| 9,220,776 B2 | 12/2015 | Sharma et al. |
| 9,296,816 B2 | 3/2016 | Johnson et al. |
| 9,358,289 B2 | 6/2016 | Korman et al. |
| 9,387,247 B2 | 7/2016 | Korman et al. |
| 9,492,539 B2 | 11/2016 | Korman et al. |
| 9,492,540 B2 | 11/2016 | Korman et al. |
| 2002/0028486 A1 | 3/2002 | Morrison et al. |
| 2002/0147311 A1 | 10/2002 | Gillies et al. |
| 2003/0115614 A1 | 6/2003 | Kanda et al. |
| 2004/0058400 A1 | 3/2004 | Holliger et al. |
| 2004/0185045 A1 | 9/2004 | Koenig et al. |
| 2004/0220388 A1 | 11/2004 | Mertens et al. |
| 2005/0037000 A1 | 2/2005 | Stavenhagen et al. |
| 2005/0064514 A1 | 3/2005 | Stavenhagen et al. |
| 2005/0079170 A1 | 4/2005 | Little et al. |
| 2005/0215767 A1 | 9/2005 | Koenig et al. |
| 2007/0004909 A1 | 1/2007 | Johnson et al. |
| 2007/0031436 A1 | 2/2007 | Little et al. |
| 2007/0036783 A1 | 2/2007 | Humeau et al. |
| 2007/0036799 A1 | 2/2007 | Stavenhagen et al. |
| 2007/0048301 A1 | 3/2007 | Bodary-Winter |
| 2007/0077246 A1 | 4/2007 | Koenig et al. |
| 2007/0087006 A1 | 4/2007 | Frantz et al. |
| 2007/0148164 A1 | 6/2007 | Farrington et al. |
| 2007/0244303 A1 | 10/2007 | Johnson et al. |
| 2009/0060910 A1 | 3/2009 | Johnson et al. |
| 2010/0099853 A1 | 4/2010 | Little et al. |
| 2010/0174053 A1 | 7/2010 | Johnson et al. |
| 2010/0233183 A1 | 9/2010 | Triebel et al. |
| 2011/0070238 A1 | 3/2011 | Triebel et al. |
| 2011/0150892 A1 | 6/2011 | Thudium et al. |
| 2013/0017199 A1 | 1/2013 | Langermann |
| 2013/0109843 A1 | 5/2013 | Carven et al. |
| 2013/0189263 A1 | 7/2013 | Little et al. |
| 2013/0295121 A1 | 11/2013 | Johnson et al. |
| 2014/0093511 A1 | 4/2014 | Lonberg et al. |
| 2014/0099318 A1 | 4/2014 | Huang et al. |
| 2014/0234296 A1 | 8/2014 | Sharma et al. |
| 2014/0255407 A1 | 9/2014 | Koenig |
| 2014/0348743 A1 | 11/2014 | Korman et al. |
| 2015/0079109 A1 | 3/2015 | Li et al. |
| 2015/0175697 A1 | 6/2015 | Bonvini et al. |
| 2015/0307620 A1 | 10/2015 | Vella et al. |
| 2017/0210806 A1 | 7/2017 | Liu |

FOREIGN PATENT DOCUMENTS

| | | | |
|---|---|---|---|
| EP | 1 078 004 | 10/2007 | |
| EP | 2 371 866 | 6/2013 | |
| EP | 2 361 936 | 4/2016 | |
| EP | 2 714 079 | 9/2016 | |
| EP | 2 601 216 | 1/2018 | |
| WO | WO 1991/003493 | 3/1991 | |
| WO | WO 1991/005548 | 5/1991 | |
| WO | WO 1991/010682 | 7/1991 | |
| WO | WO 1991/019244 | 12/1991 | |
| WO | WO 1992/022583 | 12/1992 | |
| WO | WO 1995/020605 | 8/1995 | |
| WO | WO 1995/030750 | 11/1995 | |
| WO | WO 1996/020698 | 7/1996 | |
| WO | WO 1997/032572 | 9/1997 | |
| WO | WO 1997/044013 | 11/1997 | |
| WO | WO 1998/002463 | 1/1998 | |
| WO | WO 1998/023289 | 6/1998 | |
| WO | WO 1998/023741 | 6/1998 | |
| WO | WO 1998/031346 | 7/1998 | |
| WO | WO 1998/058059 | 12/1998 | |
| WO | WO 1999/015154 | 4/1999 | |
| WO | WO 1999/020253 | 4/1999 | |
| WO | WO 1999/057150 | 11/1999 | |
| WO | WO 1999/058572 | 11/1999 | |
| WO | WO 1999/066903 | 12/1999 | |
| WO | WO 2000/042072 | 7/2000 | |
| WO | WO 2002/002781 | 1/2002 | |
| WO | WO 2003/011911 | 2/2003 | |
| WO | WO 2003/012069 | 2/2003 | |
| WO | WO 2003/025018 | 3/2003 | |
| WO | WO 2003/035835 | 5/2003 | |
| WO | WO 2003/042402 | 5/2003 | |
| WO | WO-03074679 A2 * | 9/2003 | ............ C07K 16/00 |
| WO | WO 2003/099196 | 12/2003 | |
| WO | WO 2004/004771 | 1/2004 | |
| WO | WO 2004/056875 | 7/2004 | |
| WO | WO 2004/063351 | 7/2004 | |
| WO | WO 2004/072286 | 8/2004 | |
| WO | WO 2004/078928 | 9/2004 | |
| WO | WO 2005/019258 | 3/2005 | |
| WO | WO 2005/070966 | 8/2005 | |
| WO | WO 2005/077415 | 8/2005 | |
| WO | WO 2006/021955 | 3/2006 | |
| WO | WO 2006/088494 | 8/2006 | |
| WO | WO 2006/107617 | 10/2006 | |
| WO | WO 2006/107786 | 10/2006 | |
| WO | WO 2006/113665 | 10/2006 | |
| WO | WO 2006/121168 | 11/2006 | |
| WO | WO 2006/133396 | 12/2006 | |
| WO | WO 2008/156712 | 12/2006 | |
| WO | WO 2007/021841 | 2/2007 | |
| WO | WO 2007/024249 | 3/2007 | |
| WO | WO 2007/024715 | 3/2007 | |
| WO | WO 2007/046893 | 4/2007 | |
| WO | WO 2007/075270 | 7/2007 | |

(56) References Cited

FOREIGN PATENT DOCUMENTS

| | | |
|---|---|---|
| WO | WO 2007/106707 | 9/2007 |
| WO | WO 2007/110205 | 10/2007 |
| WO | WO 2007/146968 | 12/2007 |
| WO | WO 2008/003103 | 1/2008 |
| WO | WO 2008/003116 | 1/2008 |
| WO | WO 2008/024188 | 2/2008 |
| WO | WO 2008/027236 | 3/2008 |
| WO | WO 2008/132601 | 11/2008 |
| WO | WO 2008/140603 | 11/2008 |
| WO | WO 2008/145142 | 12/2008 |
| WO | WO 2008/157379 | 12/2008 |
| WO | WO 2009/018386 | 2/2009 |
| WO | WO 2009/058492 | 5/2009 |
| WO | WO 2009/101611 | 8/2009 |
| WO | WO 2009/132876 | 11/2009 |
| WO | WO 2010/019570 | 2/2010 |
| WO | WO 2010/028795 | 3/2010 |
| WO | WO 2010/028796 | 3/2010 |
| WO | WO 2010/028797 | 3/2010 |
| WO | WO 2010/033279 | 3/2010 |
| WO | WO 2010/036959 | 4/2010 |
| WO | WO 2010/080538 | 7/2010 |
| WO | WO 2010/089411 | 8/2010 |
| WO | WO 2010/108127 | 9/2010 |
| WO | WO 2010/136172 | 12/2010 |
| WO | WO 2011/066342 | 6/2011 |
| WO | WO 2011/086091 | 7/2011 |
| WO | WO 2011/110604 | 9/2011 |
| WO | WO 2011/133886 | 10/2011 |
| WO | WO 2011/143545 | 11/2011 |
| WO | WO 2011/159877 | 12/2011 |
| WO | WO 2012/009544 | 1/2012 |
| WO | WO 2012/018687 | 2/2012 |
| WO | WO 2012/058768 | 5/2012 |
| WO | WO 2012/135408 | 10/2012 |
| WO | WO 2012/145493 | 10/2012 |
| WO | WO 2012/145549 | 10/2012 |
| WO | WO 2012/156430 | 11/2012 |
| WO | WO 2012/162068 | 11/2012 |
| WO | WO 2012/162583 | 11/2012 |
| WO | WO 2013/003652 | 1/2013 |
| WO | WO 2013/003761 | 1/2013 |
| WO | WO 2013/006544 | 1/2013 |
| WO | WO 2013/006867 | 1/2013 |
| WO | WO 2013/013700 | 1/2013 |
| WO | WO 2013/014668 | 1/2013 |
| WO | WO 2013/070565 | 5/2013 |
| WO | WO 2013/119903 | 8/2013 |
| WO | WO 2013/163427 | 10/2013 |
| WO | WO 2013/173223 | 11/2013 |
| WO | WO 2013/174873 | 11/2013 |
| WO | WO 2014/008218 | 1/2014 |
| WO | WO 2014/022540 | 2/2014 |
| WO | WO 2014/022758 | 2/2014 |
| WO | WO 2014/043708 | 3/2014 |
| WO | WO 2014/055648 | 4/2014 |
| WO | WO 2014/059251 | 4/2014 |
| WO | WO 2014/066532 | 5/2014 |
| WO | WO 2014/066834 | 5/2014 |
| WO | WO 2014/140180 | 9/2014 |
| WO | WO 2014/140180 | 11/2014 |
| WO | WO 2014/179664 | 11/2014 |
| WO | WO 2014/194302 | 12/2014 |
| WO | WO 2014/209804 | 12/2014 |
| WO | WO 2015/026684 | 2/2015 |
| WO | WO 2015/026894 | 2/2015 |
| WO | WO 2015/036394 | 3/2015 |
| WO | WO 2015/042246 | 3/2015 |
| WO | WO 2015/048312 | 4/2015 |
| WO | WO 2015/103072 | 7/2015 |
| WO | WO 2015/112534 | 7/2015 |
| WO | WO 2015/112800 | 7/2015 |
| WO | WO 2015/116539 | 8/2015 |
| WO | WO 2015/138920 | 9/2015 |
| WO | WO 2015/176033 | 11/2015 |
| WO | WO 2015/184203 | 12/2015 |
| WO | WO 2015/184207 | 12/2015 |
| WO | WO 2015/195163 | 12/2015 |
| WO | WO 2015/200828 | 12/2015 |
| WO | WO 2016/014688 | 1/2016 |
| WO | WO 2016/015685 | 2/2016 |
| WO | WO 2016/020856 | 2/2016 |
| WO | WO 2016/022630 | 2/2016 |
| WO | WO 2016/028672 | 2/2016 |
| WO | WO 2016/068801 | 5/2016 |
| WO | WO 2016/077397 | 5/2016 |
| WO | WO 2016/092419 | 6/2016 |
| WO | WO 2016/106159 | 6/2016 |
| WO | WO 2016/127179 | 8/2016 |
| WO | WO 2016/168716 | 10/2016 |
| WO | WO 2017/079112 | 5/2017 |

OTHER PUBLICATIONS

Al Hussaini, M. et al. (2015) "*Targeting CD123 in AML Using a T-Cell Directed Dual-Affinity Re-Targeting (DART®) Platform,*" Blood 127(1):122-131.

Alegre, M.L. et al. (1994) "*A Non Activating "Humanized" Anti-CD3 Monoclonal Antibody Retains Immunosuppressive Properties In Vivo,*" Transplantation 57:1537-1543.

Alt, M. et al. (1999) "*Novel Tetravalent and Bispecific IgG-like Antibody Molecules Combining Sngle-Chain Diabodies with the Immunoglobulin γ1 Fc or CH3 Region,*" FEBS Lett. 454(1-2):90-94.

Apostolovic, B. et al. (2008) "*pH-Sensitivity of the E3/K3 Heterodimeric Coiled Coil,*" Biomacromolecules 9:3173-3180.

Armour, K.L. et al. (1999) "*Recombinant human IgG Molecules Lacking Fcgamma Receptor I Binding and Monocyte Triggering Activities,*" Eur. J. Immunol. 29:2613-24.

Arndt, K.M. et al. (2001) "*Helix-stabilized Fv (hsFv) Antibody Fragments: Substituting the Constant Domains of a Fab Fragment for a Heterodimeric Coiled-coil Domain,*" J. Molec. Biol. 312:221-228.

Arndt, K.M. et al. (2002) "*Comparison of In Vivo Selection and Rational Design of Heterodimeric Coiled Coils,*" Structure 10:1235-1248.

Aruffo, A. et al. (1987) "*Molecular Cloning of a CD28 cDNA by a High-Efficiency COS Cell Expression System,*" Proc. Natl. Acad. Sci. (U.S.A.) 84:8573-8577.

Asano et al. (2004) "*A Diabody for Cancer Immunotherapy and its Functional Enhancement by Fusion of Human Fc Domain,*" Abstract 3P-683, J. Biochem. 76(8):992.

Atwell et al. (1997) "*Stable Heterodimers From Remodeling The Domain Interface of a Homodimer Using a Phage Display Library,*" J. Mol. Biol. 270: 26-35.

Baeuerle, P.A. et al. (2009) "*Bispecific T-Cell Engaging Antibodies for Cancer Therapy,*" Cancer Res. 69(12):4941-4944.

Barber, D. L. et al. (2006) "*Restoring Function in Exhausted CD8 T Cells During Chronic Viral Infection,*" Nature 439,682-687.

Bennett F, et al., (2003) "*Program Death-1 Engagement Upon TCR Activation Has Distinct Effects on Costimulation and and Cytokine-Driven Proliferation: Attenuation of ICOS, IL-4, and IL-21, But Not CD28, IL-7, IL-15 Responses*" J Immunol 170:711-718.

Bird et al. (1988) "*Single-Chain Antigen-Binding Proteins,*" Science 242:423-426.

Boucher, C. et al. (2010) "*Protein Detection by Western Blot Via Coiled—Coil Interactions,*" Analytical Biochemistry 399:138-140.

Brahmer JR, et al., (2010) "*Phase I Study of Single-Agent Anti-Programmed Death-1 (MDC-1106) in Refractory Solid Tumors: Safety, Clinical Activity, Pharmacodynamics, and Immunologic Correlates*" J Clin Oncol 28:3167-75.

Brown et al. (1987) "*Tumor-Specific Genetically Engineered Murine/Human Chimeric Monoclonal Antibody,*" Cancer Res. 47:3577-3583.

Brüggemann et al. (1987) "*Comparison of the Effector Functions of Human Immunoglobins Using a Matched Set of Chimeric Antibodies*" J. Exp. Med 166:1351-1361.

Buchwald et al. (1980) "*Long-Term, Continuous Intravenous Heparin Administration by an Implantable Infusion Pump in Ambulatory Patients With Recurrent Venous Thrombosis,*" Surgery 88:507-516.

(56) References Cited

OTHER PUBLICATIONS

Cachia, P.J. et al. (2004) "*Synthetic Peptide Vaccine Development: Measurement of Polyclonal Antibody Affinity and Cross-Reactivity Using a New Peptide Capture and Release System for Surface Plasmon Resonance Spectroscopy*," J. Mol. Recognit. 17:540-557.
Caron, P.C. et al. (1992) "*ngineered Humanized Dimeric Forms of IgG Are More Effective Antibodies*," J. Exp. Med. 176:1191-1195.
Carter, P. et al. (1992) "*Humanization of an Anti-p185her2 Antibody for Human Cancer Therapy*," Proc. Natl. Acad. Sci. (U.S.A.) 89:4285-4289.
Chan, C.E. et al. (2009) "*The Use of Antibodies in the Treatment of Infectious Diseases*," Singapore Med. J. 50(7):663-666.
Chappel et al. (1991) "*Identification of the Fcγ receptor class I binding site in human IgG through the use of recombinant IgGl/IgG2 hybrid and point-mutated antibodies*" Proc. Natl. Acad. Sci. (U.S.A.) 88:9036-9040.
Chappel et al. (1993) "*Identification of a Secondary FcγRI Binding Site within a Genetically Engineered Human IgG Antibody*" J. Biol. Chem. 33:25124-25131.
Chichili, G.R. et al. (2015) "*A CD3×CD123 Bispecific DART for Redirecting Host T Cells to Myelogenous Leukemia: Preclinical Activity and Safety in Nonhuman Primates*," Sci. Transl. Med. 7(289):289ra82.
Chothia, C. & Lesk, A. M. ((1987) "*Canonical structures for the hypervariable regions of immunoglobulins,*". J. Mol. Biol. 196:901-917.
Co, M. S. et al. (1991) "*Humanized Antibodies for Antiviral Therapy*," Proc. Natl. Acad. Sci. (U.S.A.) 88:2869-2873.
Co, M.S. et al. (1992) "*Chimeric and Humanized Antibodies With Specificity for the CD33 Antigen*," J. Immunol. 148:1149-1154.
Collins, M. et al. (2005) "*The B7 Family of Immune-Regulatory Ligands*," Genome Biol. 6:223.1-223.7.
Daugherty et al. (1991) "*Polymerase Chain Reaction Facilitates The Cloning, CDR-Grafting, and Rapid Expression of a Murine Monoclonal Antibody Directed Against the CD18 Component of Leukocyte Integrins*," Nucl. Acids Res. 19:2471-2476.
De Crescenzo, G.D. et al. (2003) "*Real-Time Monitoring of the Interactions of Two-Stranded de novo Designed Coiled-Coils: Effect of Chain Length on the Kinetic and Thermodynamic Constants of Binding,*" Biochemistry 42:1754-1763.
Del Rio, M-L. et al. (2005) "*Antibody-Mediated Signaling Through PD-1 Costimulates T Cells and Enhances CD28-Dependent Proliferation*," Eur. J. Immunol 35:3545-3560.
Disis, M. L. et al. (2002) "*Generation of T-cell Immunity to the HER-2/neu Protein After Active Immunization with HER-2/neu Peptide-Based Vaccines*" J. Clin. Oncol. 20:2624-2632.
Dong, C. et al. (2003) "*Immune Regulation by Novel Costimulatory Molecules*," Immunolog. Res. 28(1):39-48.
Dorfman DM, et al., (2006) "*Programmed Death-1 (PD-1) is a Marker of Germinal Center-assoicated T Cells and Angioimmunoblastic T-Cell Lymphoma*" Am J Surg Pathol 30:802-10.
Duncan, A.R. et al. (1988) "*Localization of the Binding Site for The Human High-Affinity Fc Receptor on IgG*," Nature 332:563-564.
During et al. (1989) "*Controlled Release of Dopamine From a Polymeric Brain Implant: In Vivo Characterization*," Ann. Neurol. 25:351-356.
Eppihimer MJ, et al., (2009) "*Expression and Regulation of the PD-LI Immunoinhibitory Molecule on Microvascular Endothelial Cells*" Microcirculation 9: 133-145.
Fernandez-Rodriquez, J. et al. (2012) "*Induced Heterodimerization and Purification of Two Target Proteins by a Synthetic Coiled-Coil Tag,*" Protein Science 21:511-519.
Fitzgerald et al. (1997) "*Improved Tumour Targeting by Disulphide Stabilized Diabodies Expressed in Pichia pastoris*," Protein Eng. 10:1221.
Flajnik, M.F. et al. (2012) "*Evolution of the B7 Family: Co-Evolution of B7H6 and Nkp30, Identification of a New B7 Family Member, B7H7, and of B7's Historical Relationship With the MHC*," Immunogenetics 64(8):571-90.

Flesch and Neppert (1999) "*Functions of the Fc Receptors for Immunoglobulin G*" J. Clin. Lab. Anal. 14:141-156.
Flies, D.B. et al. (2007) "*The New B7s: Playing a Pivotal Role in Tumor Immunity*," J. Immunother. 30(3):251-260.
Ganesan, A. (2006) "*Solid-Phase Synthesis in the Twenty-First Century*," Mini Rev. Med. Chem. 6(1):3-10).
Ghosh, T.S. et al. (2009) "*End-To-End and End-To-Middle Interhelical Interactions: New Classes of Interacting Helix Pairs in Protein Structures*," Acta Crystallographica D65:1032-1041.
Gill, S. et al. (2014) "*Efficacy Against Human Acute Myeloid Leukemia and Myeloablation of Normal Hematopoiesis in a Mouse Model Using Chimeric Antigen Receptor-Modified T Cells,*" Blood 123(15): 2343-2354.
Gorman, S. D. et al. (1991) "*Reshaping a Therapeutic CD4 Antibody*," Proc. Natl. Acad. Sci. (U.S.A.) 88:4181-4185.
Greenwald, R.J. et al. (2005) "*The B7 Family Revisited*," Ann. Rev. Immunol. 23:515-548.
Grigoryan, G. et al. (2008) "*Structural Specificity in Coiled-Coil Interactions*," Curr. Opin. Struc. Biol. 18:477-483.
Gross, J., et al. (1992) "*Identification and Distribution of the Costimulatory Receptor CD28 in the Mouse,*" J. Immunol. 149:380-388.
Grosso, J.F. et al. (2007) "*LAG-3 Regulates CD8+ T-Cell Accumulation and Effector Function During Self and Tumor Tolerance*," J. Clin. Invest. 117:3383-3392.
Grosso, J.F. et al. (2009) "*Functionally Distinct LAG-3 and PD-1 Subsets on Activated and Chronically Stimulated CD8 T-Cells*," J. Immunol. 182(11):6659-6669.
Hamid O, et al., (2013) "*Safety and tumor responses with lambrolizumab (anti-PD-1) in melanoma*" N Engl J Med 369:134-44.
Hannier, S. et al. (1998) "*CD3/TCR Complex Associated Lymphocyte Activation Gene-3 Molecules Inhibit CD3/TCR Signaling*," J. Immunol. 161:4058-4065.
Hardy B, et al., (1994) "*A Monoclonal Antibody against a Human B Lymphoblastoid Cell Line Induces Tumor Regression in Mice*" Cancer Res 54:5793-5796.
Hardy B, et al., (1997) "*A lymphocyte-activating monoclonal antibody induces regression of human tumors in severe combined immunodeficient mice*" PNAS 94:5756-5760.
Holliger et al. (1993) "'*Diabodies*': *Small Bivalent and Bispecific Antibody Fragments*," Proc. Natl. Acad. Sci. (U.S.A.) 90:6444-6448.
Holliger et al. (1996) "*Specific Killing of Lymphoma Cells by Cytotoxic T-Cells Mediated by a Bispecific Diabody*," Protein Eng. 9:299-305.
Houghten, R.A. (1985) "*General Method for the Rapid Solid-Phase Synthesis of Large Numbers of Peptides: Specificity of Antigen-Antibody Interaction at the Level of Individual Amino Acids*," Proc. Natl. Acad. Sci. (U.S.A.) 82(15):5131-5135.
Howard et al. (1989) "*Intracerebral Drug Delivery in Rats With Lesion Induced Memory Deficits*" J. Neurosurg. 7(1):105-112.
Huang, C.T. et al. (2004) "*Role of LAG-3 in Regulatory T-Cells,*" Immunity 21:503-513.
Huard, B. et al. (1994) "*Cellular Expression and Tissue Distribution of the Human LAG-3-Encoded Protein, an MHC Class II Ligand*," Immunogenetics 39:213-217.
Huard, B. et al. (1994) "*Lymphocyte Activation Gene 3/Major Histocompatibility Complex Class II Interaction Modulates the Antigenic Response of CD4+ T Lymphocytes*," Eur. J. Immunol. 24:3216-3221.
Huard, B. et al. (1995) "*CD4/Major Histocompatibility Complex Class II Interaction Analyzed With CD4- and Lymphocyte Activation Gene-3 (LAG-3)-Ig Fusion Proteins*," Eur. J. Immunol. 25:2718-2721.
Hutchins et al. (1995) "*Improved Biodistribution, Tumor Targeting, and Reduced Immunogenicity in Mice With a Gamma 4 Variant of Campath-1H*," Proc. Natl. Acad. Sci. (U.S.A.) 92:11980-84.
Hutloff et al. (1999) "*ICOS is an Inducible T-Cell Co-Stimulator Structurally and Functionally Related to CD28*," Nature 397: 263-266.
Idusogie, E.E. et al. (2000) "*Mapping of the Clq Binding Site on Rituxan, a Chimeric Antibody With a Human IgG Fc*," J. Immunol. 164:4178-4184.

(56) References Cited

OTHER PUBLICATIONS

Idusogie, E.E. et al. (2001) "*Engineered Antibodies With Increased Activity to Recruit Complement*," J. Immunol. 166:2571-2575.

Ito et al. (2000) "*Effective Priming of Cytotoxic T Lymphocyte Precursors by Subcutaneous Administration of Peptide Antigens in Liposomes Accompanied by Anti-CD40 and Anti-CTLA-4 Antibodies*" Immunobiology 201:527-540.

Iwai, Y. et al. (2002) "*Involvement of PD-L1 on Tumor Cells in the Escape From Host Immune System and Tumor Immunotherapy by PD-L1 blockade*," Proc. Natl Acad. Sci. USA 99, 12293-12297.

Jefferis et al., (1995) "*Recognition sites on human IgG for Fcγ receptors: the role of glycosylation*" Immunology Letters, 44: 111-117.

Jefferis, B.J. et al. (2002) "*Interaction Sites on Human IgG-Fc for FcgammaR: Current Models*," Immunol. Lett. 82:57-65.

Jefferis, R. et al. (1996) "*Modulation of Fc(Gamma)R and Human Complement Activation by IgG3-Core Oligosaccharide Interactions*," Immunol. Lett. 54:101-104.

Jennings, V.M. (1995) "*Review of Selected Adjuvants Used in Antibody Production*," ILAR J. 37(3):119-125.

Johansson, M.U. et al. (2002) "*Structure, Specificity, and Mode of Interaction for Bacterial Albumin-Binding Modules*," J. Biol. Chem. 277(10):8114-8120.

Johnson, S. et al. (2010) "*Effector Cell Recruitment With Novel Fv-Based Dual-Affinity Re-Targeting Protein Leads to Potent Tumor Cytolysis and in vivo B-Cell Depletion*," J. Mol. Biol. 399(3):436-449.

Joliot et al. (1991) "*Antennapedia Homeobox Peptide Regulates Neural Morphogenesis*," Proc. Natl. Acad. Sci. (U.S.A.) 88:1864-1868.

Jones et al. (1986) "*Replacing the Complementarity-Determining Regions in a Human Antibody With Those From a Mouse*," Nature 321:522-525.

Kettleborough, C. A. et al. (1991) "*Humanization of a Mouse Monoclonal Antibody by CDR-Grafting: The Importance of Framework Residues on Loop Conformation*," Protein Engineering 4:773-3783.

Kohler, G. et al. (1975) "*Continuous Cultures of Fused Cells Secreting Antibody of Predefined Specificity*," Nature 256:495-497.

Korman, A.J. et al. (2007) "*Checkpoint Blockade in Cancer Immunotherapy*," Adv. Immunol. 90:297-339.

La Motte-Mohs, R. ""*MGD013, a Bispecific PD-1×LAG-3 Dual-Affinity Re-Targeting (DART®) Protein with T-cell Immunomodulatory Activity for Cancer Treatment*"" American Association for Cancer Research Annual Meeting (AACR) Apr. 16-20, 2016, New Orleans, LA.

Langer (1990) "*New Methods of Drug Delivery*," Science 249:1527-1533.

Leach, D. R., et al., (1996) "*Enhancement of Antitumor Immunity by CTLA-4 Blockade*," Science 271, 1734-1736.

Lefranc, G. et al., (1979) "*Gm, Am and Km Immunoglobulin Allotypes of Two Populations in Tunishia*" Hum. Genet.: 50, 199-211.

Lepenies, B. et al. (2008) "*The Role of Negative Costimulators During Parasitic Infections*," Endocrine, Metabolic & Immune Disorders—Drug Targets 8:279-288.

Levy et al. (1985) "*Inhibition of Calcification of Bioprosthetic Heart Valves by Local Controlled-Release Diphosphonate*," Science 228:190-192.

Lindley, P.S. et al. (2009) "*The Clinical Utility of Inhibiting CD28-Mediated Costimulation*," Immunol. Rev. 229:307-321.

Linsley, P. et al. (1996) "*Intracellular Trafficking of CTLA4 and Focal Localization Towards Sites of TCR Engagement*," Immunity 4:535-543.

Litowski, J.R. et al. (2002) "*Designing Heterodimeric Two-Stranded α-Helical Coiled-Coils: The Effects of Hydrophobicity and α-Helical Propensity on Protein Folding, Stability, and Specificity*," J. Biol. Chem. 277:37272-37279.

Lobuglio et al. (1989) "*Mouse/Human Chimeric Monoclonal Antibody in Man: Kinetics and Immune Response*," Proc. Natl. Acad. Sci. (U.S.A.) 86:4220-4224.

Loke, P. et al. (2004) "*Emerging Mechanisms of Immune Regulation: The Extended B7 Family and Regulatory T-Cells*" Arthritis Res. Ther. 6:208-214.

Lonberg, N. et al. (1995) "*Human Antibodies From Transgenic Mice*," Int. Rev. Immunol 13:65-93.

Lu et al., (2008) "*The Effect of a Point Mutation on the Stability of Igg4 as Monitored by Analytical Ultracentrifugation*," J. Pharmaceutical Sciences 97:960-969.

Lu, D. et al. (2005) "*A Fully Human Recombinant IgG-Like Bispecific Antibody to Both the Epidermal Growth Factor Receptor and the Insulin-Like Growth Factor Receptor for Enhanced Antitumor Activity*," J. Biol. Chem. 280(20):19665-19672.

Lund et al. (1991) "*Human Fc Gamma RI and Fc Gamma RII Interact With Distinct But Overlapping Sites on Human IgG,*" J. Immunol. 147:2657-2662.

Lund et al. (1992) "*Multiple Binding Sites on the CH2 Domain of IgG for Mouse Fc Gamma RII,*" Mol. Immunol. 29:53-59.

Lund, J. et al. (1995) "*Oligosaccharide-Protein Interactions in IgG Can Modulate Recognition by Fc Gamma Receptors*," FASEB J. 9:115-19.

Lund, J. et al. (1996) "*Multiple Interactions of IgG With Its Core Oligosaccharide Can Modulate Recognition by Complement and Human Fc Gamma Receptor I and Influence The Synthesis of Its Oligosaccharide Chains*," J. Immunol. 157:4963-4969.

MacroGenics Research Day Oct. 13, 2015.

Maeda, H. et al. (1991) "*Construction of Reshaped Human Antibodies With HIV-Neutralizing Activity*," Human Antibodies Hybridoma 2:124-134.

Mardiros, A. et al. (2013) "*T Cells Expressing CD123-Specific Chimeric Antigen Receptors Exhibit Specific Cytolytic Effector Functions and Antitumor Effects Against Human Acute Myeloid Leukemia*," Blood 122:3138-3148.

Marvin et al. (2005) "*Recombinant Approaches to IgG-Like Bispecific Antibodies*," Acta Pharmacol. Sin. 26:649-658.

Matsuzaki, J. et al. (2010) "*Tumor-Infiltrating NY-ESO-1-Specific CD8+ T-Cells Are Negatively Regulated by LAG-3 and PD-1 in Human Ovarian Cancer*," Proc. Natl. Acad. Sci. (U.S.A.) 107(17):7875-7880.

Melero et al. (1997) "*Monoclonal Antibodies Against the 4-1BB T-Cell Activation Molecule Eradicate Established Tumors*," Nature Medicine 3: 682-685.

Mellman, I., et al. (2011) "*Cancer immunotherapy comes of age*," Nature 480, 480-489.

Merrifield, B. (1986) "*Solid Phase Synthesis*," Science 232(4748):341-347.

Mokyr. M.B. et al. (1998) "*Realization of the Therapeutic Potential of CTLA-4 Blockade in Low-Dose Chemotherapy-Treated Tumor-Bearing Mice*," Cancer Research 58: 5301-5304.

Moore, P. "DART Molecules for Immunomodulatory Therapeutic Strategies" 8th GTC Immunotherapeutics and Immunomonitoring Conference, Jan. 25, 2016, San Diego, CA.

Moore, P.A. et al. (2011) "*Application of Dual Affinity Retargeting Molecules to Achieve Optimal Redirected T-Cell Killing of B-Cell Lymphoma*," Blood 117(17):4542-4551.

Moran, A.E. et al. (2013) "*The TNFRs OX40, 4-1BB, and CD40 as Targets for Cancer Immunotherapy*," Curr Opin Immunol. Apr. 2013; 25(2): 10.1016.

Ning et al. (1996) "*Intratumoral Radioimmunotherapy of a Human Colon Cancer Xenograft Using a Sustained Release Gel*," Radiotherapy & Oncology 39:179 189.

Oganesyan, V. et al. (2009) "*Structural characterization of a human Fc fragment engineered for extended serum half-life*," Molecular Immunology 46:1175-1755.

Olafsen et al. (2004) "*Covalent Disulfide-Linked Anti-CEA Diabody Allows Site-Specific Conjugation and Radiolabeling for Tumor Targeting Applications*," Prot. Engr. Des. Sel. 17:21-27.

Palena, C., et al., (2006) "*Cancer vaccines: preclinical studies and novel strategies*," Adv. Cancer Res. 95, 115-145.

Peeters et al. (2001) "*Production of Antibodies and Antibody Fragments in Plants*," Vaccine 19:2756.

(56) References Cited

OTHER PUBLICATIONS

Peters, P et al., (2012) "*Engineering an Improved IgG4 Molecule with Reduced Disulfide Bond Heterogeneity and Increased Fab Domain Thermal Stability*," J. Biol. Chem., 287:24525-24533.

Pizzitola, I. et al. (2014) "*Chimeric Antigen Receptors Against CD33/CD123 Antigens Efficiently Target Primary Acute Myeloid Leukemia Cells in vivo*," Leukemia 28(8):1596-1605.

Pollock et al. (1999) "*Transgenic Milk as a Method for the Production of Recombinant Antibodies*," J. Immunol Methods 231:147-157.

Presta, L.G. et al. (2002) "*Engineering Therapeutic Antibodies for Improved Function*," Biochem. Soc. Trans. 30:487-90.

Reddy, M.P. et al. (2000) "*Elimination of Fc Receptor-Dependent Effector Functions of a Modified IgG4 Monoclonal Antibody to Human CD4*," J. Immunol. 164:1925-1933.

Ridgway et al. (1996) "*'Knobs-Into-Holes' Engineering of Antibody CH3 Domains for Heavy Chain Heterodimerization*," Protein Engr. 9:617-621.

Riechmann, L. et al. (1988) "*Reshaping Human Antibodies for Therapy*," Nature 332:323-327.

Sato, K. et al. (1993) "*Reshaping a Human Antibody to Inhibit the Interleukin 6-Dependent Tumor Cell Growth*," Cancer Res 53:851-856.

Saudek et al. (1989) "*A Preliminary Trial of the Programmable Implantable Medication System for Insulin Delivery*," N. Engl. J. Med. 321:574-579.

Sefton, (1987) "*Implantable Pumps*," CRC Crit. Rev. Biomed. Eng. 14:201-240 (Abstract Only).

Sharpe, A.H. et al. (2002) "*The B7-CD28 Superfamily*," Nature Rev. Immunol. 2:116-126.

Shaw et al. (1987) "*Characterization Of A Mouse/Human Chimeric Monoclonal Antibody (17-1A) to a Colon Cancer Tumor-Associated Antigen*," J. Immunol. 138:4534-4538.

Shields, R.L. et al. (2001) "*High Resolution Mapping of the Binding Site on Human IgG1 for Fc Gamma RI, Fc Gamma RII, Fc Gamma RIII, and FcRn and Design of IgG1 Variants With Improved Binding to the Fc gamma R*," J. Biol. Chem. 276:6591-6604.

Shopes, B. (1992) "*A Genetically Engineered Human IgG Mutant With Enhanced Cytolytic Activity*," J. Immunol. 148(9):2918-2922.

Sloan, D.D. et al. (2015) "*Targeting HIV Reservoir in Infected CD4 T Cells by Dual-Affinity Re-targeting Molecules (DARTs) that Bind HIV Envelope and Recruit Cytotoxic T Cells*," PLoS Pathog. 11(11):e1005233.

Song et al. (1995) "*Antibody Mediated Lung Targeting of Long Circulating Emulsions*," PDA Journal of Pharmaceutical Science & Technology 50:372 397.

Staerz et al. (1985) "*Hybrid Antibodies Can Target Sites for Attack by T Cells*," Nature 314:628-631.

Stavenhagen, J.B. et al. (2007) "*Fc Optimization of Therapeutic Antibodies Enhances Their Ability to Kill Tumor Cells In Vitro and Controls Tumor Expansion In Vivo Via Low Affinity Activating Fcgamma Receptors*," Cancer Res. 57(18):8882-8890).

Steinkruger, J.D. et al. (2012) "*The d'-d-d' Vertical Triad is Less Discriminating Than the a'-a-a' Vertical Triad in the Antiparallel Coiled-coil Dimer Motif*," J. Amer. Chem. Soc. 134(5):2626-2633.

Stephan, J. et al. (1999) "*Selective Cloning of Cell Surface Proteins Involved in Organ Development: Epithelial Glycoprotein Is Involved in Normal Epithelial Differentiation*," Endocrinol. 140:5841-5854.

Stevenson, G.T. et al. (1989) "*A Chimeric Antibody With Dual Fc Regions (bisFabFc) Prepared by Manipulations at the IgG Hinge*," Anti-Cancer Drug Design 3:219-230 (Abstract Only).

Straussman, R. et al. (2007) "*Kinking the Coiled Coil—Negatively Charged Residues at the Coiled-coil Interface*," J. Molec. Biol. 366:1232-1242.

Takemura, S. et al. (2000) "*Construction of a Diabody (Small Recombinant Bispecific Antibody) Using a Refolding System*," Protein Eng. 13(8):583-588.

Tempest, P.R. et al. (1991) "*Reshaping a Human Monoclonal Antibody to Inhibit Human Respiratory Syncytial Virus Infection in vivo*," Bio/Technology 9:266-271.

Tettamanti, S et al. (2013) "*Targeting Of Acute Myeloid Leukaemia by Cytokine-Induced Killer Cells Redirected With a Novel CD123-Specific Chimeric Antigen Receptor*," Br. J. Haematol. 161:389-401.

Topalian SL, et al. (2012) "*Safety, activity, and immune correlates of anti-PD-1 antibody in cancer*" N Engl J Med 366:2443-54.

Triebel, F. et al. (1990) "*LAG-3, A Novel Lymphocyte Activation Gene Closely Related to CD4*," J. Exp. Med. 171(5):1393-1405.

Tripet, B. et al. (2002) "*Kinetic Analysis of the Interactions between Troponin C and the C-terminal Troponin I Regulatory Region and Validation of a New Peptide Delivery/Capture System used for Surface Plasmon Resonance*," J. Molec. Biol. 323:345-362.

Turnis M, et al., (2012) "*Combinatorial immunotherapy PD-1 may not be LAG-ing behind any more*" OncoImmunology 1:7, 1172-1174.

Verhoeyen, M. et al. (1988) "*Reshaping Human Antibodies: Grafting An Antilysozyme Activity*," Science 239:1534-1536.

Veri, M.C. et al. (2010) "*Therapeutic Control of B Cell Activation Via Recruitment of Fcgamma Receptor IIb (CD32B) Inhibitory Function With a Novel Bispecific Antibody Scaffold*," Arthritis Rheum. 62(7):1933-1943.

Vermeij, R. et al. (2012) "*Potentiation of a p53-SLP Vaccine by Cyclophosphamide in Ovarian Cancer: A Single-Arm Phase II Study*," Int. J. Cancer 131:E670-E680.

Viglietta, V. et al. (2007) "*Modulating Co-Stimulation*," Neurotherapeutics 4:666-675.

Wang, L. et al. (2011) "*VISTA, A Novel Mouse Ig Superfamily Ligand That Negatively Regulates T-Cell Responses*," J. Exp. Med. 10.1084/jem.20100619:1-16.

Wang, S. et al. (2004) "*Co-Signaling Molecules of the B7-CD28 Family in Positive and Negative Regulation of T Lymphocyte Responses*," Microbes Infect. 6:759-766.

Weinberg et al. (2000) "*Engagement of the OX-40 Receptor In Vivo Enhances Antitumor Immunity*," Immunol 164:2160-2169.

Winter et al. (1991) "*Man-made Antibodies*," Nature 349:293-299.

Winter, G. et al. (1994) "*Making Antibodies by Phage Display Technology*," Annu. Rev. Immunol. 12.433-455.

Wolff, E.A. et al. (1993) "*Monoclonal Antibody Homodimers: Enhanced Antitumor Activity in Nude Alice*," Cancer Research 53:2560-256.

Woolfson, D.N. (2005) "*The Design of Coiled-Coil Structures and Assemblies*," Adv. Prot. Chem. 70:79-112.

Woo S-R, et al., (2012) "*Immune inhibitory molecules LAG-3 and PD-1 synergistically regulate T cell function to promote tumoral immune escape*," Cancer Res. 72:917-927.

Workman C.J., et al. (2004) "*Lymphocyte Activation Gene-3 (CD223) Regulates the Size of the Expanding T-Cell Population Following Antigen Activation in vivo*," J. Immunol. 172:5450-5455.

Workman, C.J. (2005) "*Negative Regulation of T-Cell Homeostasis by Lymphocyte Activation Gene-3 (CD223)*," J. Immunol. 174:688-695.

Workman, C.J. et al. (2002) "*Cutting Edge: Molecular Analysis of the Negative Regulatory Function of Lymphocyte Activation Gene-3*," J. Immunol. 169:5392-5395.

Workman, C.J. et al. (2002) "*Phenotypic Analysis of the Murine CD4-Related Glycoprotein, CD223 (LAG-3)*," Eur. J. Immunol. 32:2255-2263.

Workman, C.J. et al. (2003) "*The CD4-Related Molecule, LAG-3 (CD223), Regulates the Expansion Of Activated T-Cells*," Eur. J. Immunol. 33:970-979.

Workman, C.J. et al. (2009) "*LAG-3 Regulates Plasmacytoid Dendritic Cell Homeostasis*," J. Immunol. 182(4):1885-1891.

Wu et al. (1987) "*Receptor-Mediated In Vitro Gene Transformation by a Soluble DNA Carrier System*," J. Biol. Chem. 262:4429-4432.

Wu, A. et al. (2001) "*Multimerization of a Chimeric Anti-CD20 Single Chain Fv-Fv Fusion Protein Is Mediated Through Variable Domain Exchange*," Protein Engineering 14(2):1025-1033.

Xie et al. (2005) "*A New Format of Bispecific Antibody: Highly Efficient Heterodimerization, Expression and Tumor Cell Lysis*," J. Immunol. Methods 296:95-101.

Xu, D. et al. (2000) "*In Vitro Characterization of Five Humanized OKT3 Effector Function Variant Antibodies*," Cell. Immunol. 200:16-26.

(56) References Cited

OTHER PUBLICATIONS

Zeng, Y. et al. (2008) "*A Ligand-Pseudoreceptor System Based on de novo Designed Peptides for the Generation of Adenoviral Vectors With Altered Tropism*," J. Gene Med. 10:355-367.

Zhang, X. M. et al. (2008) "*The Anti-Tumor Immune Response Induced by a Combination of MAGE-3/MAGE-n-Derived Peptides*," Oncol. Rep. 20, 245-252.

Alme, A.K.B. et al. (2016) "*Blocking Immune Checkpoints in Prostate, Kidney and Urothelial Cancer: An Overview*," Urol. Oncol. 34(4):171-181.

Communication Pursuant to Rule 164(1) EPC European Patent application 16808113.1 (2018) 16 pages.

Jing, W. et al. (2015) "*Combined Immune Checkpoint Protein Blockade and Low Dose Whole Body Irradiation as Immunotherapy for Myeloma*," J. Immunother. Cancer 3(1):pp. 2:1-15.

Long, L. et al. (2018) "*The Promising Immune Checkpoint LAG-3: From Tumor Microenvironment to Cancer Immunotherapy*," Genes & Cancer 9(5-6):176-189.

Marin-Acevedo, J.A. et al. (2018) "*Next Generation of Immune Checkpoint Therapy in Cancer: New Developments and Challenges*," J. Hematol. Oncol. 11:39 (pp. 1-20).

Nilvebrant, J. et al. (2013) "*The Albumin-Binding Domain as a Scaffold for Protein Engineering*," Computational and Structural Biotechnology Journal 6(7):e201303009:1-8.

Poirier, N. et al. (2011) "*Antibody-Mediated Depletion of Lymphocyte-Activation Gene-3 (LAG-3+)-Activated T Lymphocytes Prevents Delayed-Type Hypersensitivity in Non-Human Primates*," Clin. Exper. Immunol 164:265-274.

Robbie, G.J. et al. (2013) "*A Novel Investigation Fc-Modified Humanized Monoclonal Antibody, Motavizumab-YTE, Has an Extended Half-Life in Healthy Adults*," Antimicrobial Agents and Chemotherapy 57(12):6147-6153.

Search Report for SG Application No. 11201710097R, Intellectual Property Office of Singapore (2019) (4 pages).

Written Opinion for Singapore Application No. 11201710097R, Intellectual Property Office of Singapore (2019) (7 pages).

International Search Report PCT/US2016/036172 (WO 2016/200782) (2016) (3 pages).

Written Opinion of the International Searching Authority PCT/US2016/036172 (WO 2016/200782) (2016) (6 pages).

Kabat, E.A. et al. (1971) "*Attempts to Locate Residues in Complementarity-Determining Regions of Antibody Combining Sites That Make Contact With Antigen*," Proc. Natl. Acad. Sci. (U.S.A.) 73(2):617-619.

Martin, C.R. (2010) "*Protein Sequence and Structure Analysis of Antibody Variable Domains*," In: Antibody Engineering vol. 2 (Kontermann, R. and Dübel, S. (eds.), Springer-Verlag Berlin Heidelberg, Chapter 3 (pp. 33-51).

Wu, T.T. et al. (1975) "*Similarities Among Hypervariable Segments of Immunoglobulin Chains*," Proc. Natl. Acad. Sci. (U.S.A.) 72(12):5107-5110.

Wu, T.T. and Kabat, E.A., (1970) "*An Analysis of the Sequences of the Variable Regions of Bence Jones Proteins and Myeloma Light Chains and Their Implicants for Antibody Complementarity*" J Exp Med. 132(2): 211-250.

\* cited by examiner

US 11,072,653 B2

LAG-3-BINDING MOLECULES AND METHODS OF USE THEREOF

CROSS-REFERENCE TO RELATED APPLICATIONS

This application is a § 371 National Stage Application of PCT/US2016/036172 (filed on Jun. 7, 2016), which application claims priority to U.S. Provisional Patent Appln. Ser. Nos. 62/255,094 (filed on Nov. 13, 2015) and 62/172,277 (filed on Jun. 8, 2015), each of which applications is herein incorporated by reference in its entirety.

REFERENCE TO SEQUENCE LISTING

This application includes one or more Sequence Listings pursuant to 37 C.F.R. 1.821 et seq., which are disclosed in computer-readable media (file name: 1301 0121PCT-SUB-STITUTE-Sequence Listing ST25.txt, created on Feb. 27, 2020, and having a size of 106,544 bytes), which file is herein incorporated by reference in its entirety.

FIELD OF THE INVENTION

The present invention is directed to LAG-3 binding molecules that comprise the LAG-3-binding domain of selected anti-LAG-3 antibodies: LAG-3 mAb 1, LAG-3 mAb 2, LAG-3 mAb 3, LAG-3 mAb 4, LAG-3 mAb 5, or LAG-3 mAb 6 that are capable of binding to both cynomolgus monkey LAG-3 and to human LAG-3. The invention particularly concerns LAG-3 binding molecules that are humanized or chimeric versions of such antibodies, or that comprise LAG-3 binding-fragments of such anti-LAG-3 antibodies (especially immunocongujates, diabodies, BiTEs, bispecific antibodies, etc.). The invention particularly concerns such LAG-3-binding molecules that are additionally capable of binding an epitope of a molecule involved in regulating an immune check point that is present on the surface of an immune cell. The present invention also pertains to methods of using such LAG-3 binding molecules to detect LAG-3 or to stimulate an immune response. The present invention also pertains to methods of combination therapy in which a LAG-3-binding molecule that comprises one or more LAG-3-binding domain(s) of such selected anti-LAG-3 antibodies is administered in combination with one or more additional molecules that are effective in stimulating an immune response to thereby further enhance, stimulate or upregulate such immune response in a subject.

BACKGROUND OF THE INVENTION

I. Cell Mediated Immune Responses

The immune system of humans and other mammals is responsible for providing protection against infection and disease. Such protection is provided both by a humoral immune response and by a cell-mediated immune response. The humoral response results in the production of antibodies and other biomolecules that are capable of recognizing and neutralizing foreign targets (antigens). In contrast, the cell-mediated immune response involves the activation of macrophages, Natural Killer cells (NK), and antigen-specific cytotoxic T-lymphocytes by T-cells, and the release of various cytokines in response to the recognition of an antigen (Dong, C. et al. (2003) "*Immune Regulation by Novel Costimulatory Molecules*," Immunolog. Res. 28(1): 39-48).

The ability of T-cells to optimally mediate an immune response against an antigen requires two distinct signaling interactions (Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol. 90:297-339). First, antigen that has been arrayed on the surface of Antigen-Presenting Cells (APC) must be presented to an antigen-specific naïve $CD4^+$ T-cell. Such presentation delivers a signal via the T-Cell Receptor (TCR) that directs the T-cell to initiate an immune response that will be specific to the presented antigen. Second, a series of costimulatory and inhibitory signals, mediated through interactions between the APC and distinct T-cell surface molecules, triggers first the activation and proliferation of the T-cells and ultimately their inhibition. Thus, the first signal confers specificity to the immune response whereas the second signal serves to determine the nature, magnitude and duration of the response.

The immune system is tightly controlled by costimulatory and co-inhibitory ligands and receptors. These molecules provide the second signal for T-cell activation and provide a balanced network of positive and negative signals to maximize immune responses against infection while limiting immunity to self (Wang, L. et al. (2011) "*VISTA, A Novel Mouse Ig Superfamily Ligand That Negatively Regulates T-Cell Responses*," J. Exp. Med. 10.1084/jem.20100619:1-16; Lepenies, B. et al. (2008) "*The Role Of Negative Costimulators During Parasitic Infections*," Endocrine, Metabolic & Immune Disorders—Drug Targets 8:279-288). The inhibitory pathways crucial for maintaining self-tolerance and modulating the duration and amplitude of immune responses are collectively referred to as immune checkpoints. Of particular importance is binding between the B7.1 (CD80) and B7.2 (CD86) ligands of the Antigen-Presenting Cell and the CD28 and CTLA-4 receptors of the $CD4^+$ T-lymphocyte (Sharpe, A. H. et al. (2002) "*The B7-CD28 Superfamily*," Nature Rev. Immunol. 2:116-126; Dong, C. et al. (2003) "*Immune Regulation by Novel Costimulatory Molecules*," Immunolog. Res. 28(1):39-48; Lindley, P. S. et al. (2009) "*The Clinical Utility Of Inhibiting CD28-Mediated Costimulation*," Immunol. Rev. 229:307-321). Binding of B7.1 or of B7.2 to CD28 stimulates T-cell activation; binding of B7.1 or B7.2 to CTLA-4 inhibits such activation (Dong, C. et al. (2003) "*Immune Regulation by Novel Costimulatory Molecules*," Immunolog. Res. 28(1):39-48; Lindley, P. S. et al. (2009) "*The Clinical Utility Of Inhibiting CD28-Mediated Costimulation*," Immunol. Rev. 229:307-321; Greenwald, R. J. et al. (2005) "*The B7 Family Revisited*," Ann. Rev. Immunol. 23:515-548). CD28 is constitutively expressed on the surface of T-cells (Gross, J., et al. (1992) "*Identification And Distribution Of The Costimulatory Receptor CD28 In The Mouse*," J. Immunol. 149:380-388), whereas CTLA-4 expression is rapidly upregulated following T-cell activation (Linsley, P. et al. (1996) "*Intracellular Trafficking Of CTLA4 And Focal Localization Towards Sites Of TCR Engagement*," Immunity 4:535-543). Since CTLA-4 is the higher affinity receptor (Sharpe, A. H. et al. (2002) "*The B7-CD28 Superfamily*," Nature Rev. Immunol. 2:116-126), binding first initiates T-cell proliferation (via CD28) and then inhibits it (via nascent expression of CTLA-4), thereby dampening the effect when proliferation is no longer needed.

Further investigations into the ligands of the CD28 receptor have led to the identification and characterization of a set of related B7 molecules (the "B7 Superfamily") (Sharpe, A. H. et al. (2002) "*The B7-CD28 Superfamily*," Nature Rev. Immunol. 2:116-126; Greenwald, R. J. et al. (2005) "*The B7*

Family Revisited," Ann. Rev. Immunol. 23:515-548; Collins, M. et al. (2005) "*The B7 Family Of Immune-Regulatory Ligands*," Genome Biol. 6:223.1-223.7; Loke, P. et al. (2004) "*Emerging Mechanisms Of Immune Regulation: The Extended B7 Family And Regulatory T-Cells*." Arthritis Res. Ther. 6:208-214; Korman, A. J. et al. (2007) "*Checkpoint Blockade in Cancer Immunotherapy*," Adv. Immunol. 90:297-339; Flies, D. B. et al. (2007) "*The New B7s: Playing a Pivotal Role in Tumor Immunity*," J. Immunother. 30(3): 251-260; Agarwal, A. et al. (2008) "*The Role Of Positive Costimulatory Molecules In Transplantation And Tolerance*," Curr. Opin. Organ Transplant. 13:366-372; Wang, S. et al. (2004) "*Co-Signaling Molecules Of The B7-CD28 Family In Positive And Negative Regulation Of T Lymphocyte Responses*," Microbes Infect. 6:759-766). There are currently several known members of the family: B7.1 (CD80), B7.2 (CD86), the inducible co-stimulator ligand (ICOS-L), the programmed death-1 ligand (PD-L1; B7-H1), the programmed death-2 ligand (PD-L2; B7-DC), B7-H3, B7-H4 and B7-H6 (Collins, M. et al. (2005) "*The B7 Family Of Immune-Regulatory Ligands*," Genome Biol. 6:223.1-223.7; Flajnik, M. F. et al. (2012) "*Evolution Of The B7 Family: Co-Evolution Of B7H6 And Nkp30, Identification Of A New B7 Family Member, B7H7, And Of B7's Historical Relationship With The MHC*," Immunogenetics 64(8):571-90).

II. Lymphocyte Activation Gene-3 ("LAG-3")

The Lymphocyte Activation Gene 3 encodes a cell surface receptor protein that is referred to as "LAG-3," or CD223 (Triebel, F. et al. (1990) "*LAG-3, A Novel Lymphocyte Activation Gene Closely Related To CD4*," J. Exp. Med. 171(5):1393-1405). LAG-3 is expressed by activated CD4+ and CD8+ T-cells and by NK cells, and is constitutively expressed by plasmacytoid dendritic cells. LAG-3 is not expressed by B cells, monocytes or any other cell types tested (Workman, C. J. et al. (2009) "*LAG-3 Regulates Plasmacytoid Dendritic Cell Homeostasis,*" J. Immunol. 182(4): 1885-1891).

LAG-3 has been found to be closely related to the T-cell co-receptor CD4 (Triebel, F. et al. (1990) "*LAG-3, A Novel Lymphocyte Activation Gene Closely Related To CD4*," J. Exp. Med. 171(5):1393-1405; Grosso, J. F. et al. (2009) "*Functionally Distinct LAG-3 and PD-1 Subsets on Activated and Chronically Stimulated CD8 T-Cells*," J. Immunol. 182(11):6659-6669; Huang, C. T. et al. (2004) "*Role Of LAG-3 In Regulatory T-Cells*," Immunity 21:503-513; Workman, C. J. (2009) "*LAG-3 Regulates Plasmacytoid Dendritic Cell Homeostasis*," J. Immunol. 182(4):1885-1891). Like CD4, LAG-3 also binds to MHC class II molecules but does so with significantly higher affinity (Workman, C. J. et al. (2002) "*Phenotypic Analysis Of The Murine CD4-Related Glycoprotein, CD223 (LAG-3)*," Eur. J. Immunol. 32:2255-2263; Huard, B. et al. (1995) "*CD4/Major Histocompatibility Complex Class II Interaction Analyzed With CD4– And Lymphocyte Activation Gene-3 (LAG-3)-Ig Fusion Proteins*," Eur. J. Immunol. 25:2718-2721; Huard, B. et al. (1994) "*Cellular Expression And Tissue Distribution Of The Human LAG-3-Encoded Protein, An MHC Class II Ligand*," Immunogenetics 39:213-217).

Studies have shown that LAG-3 plays an important role in negatively regulating T-cell proliferation, function and homeostasis (Workman, C. J. et al. (2009) "*LAG-3 Regulates Plasmacytoid Dendritic Cell Homeostasis*," J. Immunol. 182(4):1885-1891; Workman, C. J. et al. (2002) "*Cutting Edge: Molecular Analysis Of The Negative Regulatory Function Of Lymphocyte Activation Gene-3*," J. Immunol. 169:5392-5395; Workman, C. J. et al. (2003) "*The CD4-Related Molecule, LAG-3 (CD223), Regulates The Expansion Of Activated T-Cells*," Eur. J. Immunol. 33:970-979; Workman, C. J. (2005) "*Negative Regulation Of T-Cell Homeostasis By Lymphocyte Activation Gene-3 (CD223)*," J. Immunol. 174:688-695; Hannier, S. et al. (1998) "*CD3/TCR Complex-Associated Lymphocyte Activation Gene-3 Molecules Inhibit CD3/TCR Signaling*," J. Immunol. 161: 4058-4065; Huard, B. et al. (1994) "*Lymphocyte-Activation Gene 3/Major Histocompatibility Complex Class II Interaction Modulates The Antigenic Response Of CD4+ T Lymphocytes*," Eur. J. Immunol. 24:3216-3221).

Studies have suggested that inhibiting LAG-3 function through antibody blockade can reverse LAG-3-mediated immune system inhibition and partially restore effector function (Grosso, J. F. et al. (2009) "*Functionally Distinct LAG-3 and PD-1 Subsets on Activated and Chronically Stimulated CD8 T-Cells*," J. Immunol. 182(11):6659-6669; Grosso, J. F. et al. (2007) "*LAG-3 Regulates CD8+ T-Cell Accumulation And Effector Function During Self And Tumor Tolerance*," J. Clin. Invest. 117:3383-3392). LAG-3 has been found to negatively regulate T-cell expansion via inhibition of TCR-induced calcium fluxes, and controls the size of the memory T-cell pool (Matsuzaki, J. et al. (2010) "*Tumor-Infiltrating NY-ESO-1-Specific CD8– T-Cells Are Negatively Regulated By LAG-3 and PD-1 In Human Ovarian Cancer*," Proc. Natl. Acad. Sci. (U.S.A.) 107(17):7875-7880; Workman C. J., et al. (2004) "*Lymphocyte Activation Gene-3 (CD223) Regulates The Size Of The Expanding T-Cell Population Following Antigen Activation in vivo*," J. Immunol. 172:5450-5455).

However, despite all such prior advances, a need remains for improved compositions capable of more vigorously directing the body's immune system to attack cancer cells or pathogen-infected cells, especially at lower therapeutic concentrations. For although the adaptive immune system can be a potent defense mechanism against cancer and disease, it is often hampered by immune suppressive mechanisms in the tumor microenvironment, such as the expression of LAG-3. Furthermore, co-inhibitory molecules expressed by tumor cells, immune cells, and stromal cells in the tumor milieu can dominantly attenuate T-cell responses against cancer cells. Thus, a need remains for potent LAG-3-binding molecules. In particular, a need exists for LAG-3-binding molecules that a desirable binding kinetic profile, bind different LAG-3 epitopes and/or exhibit single agent activity that could provide improved therapeutic value to patients suffering from cancer or other diseases and conditions. The present invention is directed to these and other goals.

SUMMARY OF THE INVENTION

The present invention is directed to LAG-3 binding molecules that comprise the LAG-3-binding domain of selected anti-LAG-3 antibodies: LAG-3 mAb 1, LAG-3 mAb 2, LAG-3 mAb 3, LAG-3 mAb 4, LAG-3 mAb 5, or LAG-3 mAb 6 that are capable of binding to both cynomolgus monkey LAG-3 and to human LAG-3. The invention particularly concerns LAG-3 binding molecules that are humanized or chimeric versions of such antibodies, or that comprise LAG-3 binding-fragments of such anti-LAG-3 antibodies (especially immunocongugates, diabodies, BiTEs, bispecific antibodies, etc.). The invention particularly concerns such LAG-3-binding molecules that are additionally capable of binding an epitope of a molecule involved in regulating an immune check point that is present on the surface of an immune cell. The present invention also pertains to methods of using such LAG-3-binding molecules to detect LAG-3 or to stimulate an immune response. The present invention also pertains to methods of combination therapy in which a LAG-3-binding molecule that comprises one or more LAG-3-binding domain(s) of such selected anti-LAG-3 antibodies is administered in combination with one or more additional molecules that are effective in stimulating an immune response to thereby further enhance, stimulate or upregulate such immune response in a subject.

In detail, the invention provides a LAG-3-binding molecule that is capable of binding both to human LAG-3 and to cynomolgus monkey LAG-3, wherein said comprises the three Heavy Chain CDR Domains, $CDR_H1$, $CDR_H2$ and $CDR_H3$, and the three Light Chain CDR Domains, $CDR_L1$, $CDR_L2$, and $CDR_L3$, wherein:

(A) (1) the $CDR_H1$ Domain, $CDR_H2$ Domain, and $CDR_H3$ Domain are the Heavy Chain CDRs of LAG-3 mAb 1, and respectively have the amino acid sequences: SEQ ID NO:8, SEQ ID NO:9, and SEQ ID NO:10; and
  (2) the $CDR_L1$ Domain, $CDR_L2$ Domain, and $CDR_L3$ Domain are the Light Chain CDRs of LAG-3 mAb 1, and respectively have the amino acid sequences: SEQ ID NO:13, SEQ ID NO:14, and SEQ ID NO:15; or
(B) (1) the $CDR_H1$ Domain, $CDR_H2$ Domain, and $CDR_H3$ Domain are the Heavy Chain CDRs of hLAG-3 mAb 1, and respectively have the amino acid sequences: SEQ ID NO:8, SEQ ID NO:9, and SEQ ID NO:10; and
  (2) the $CDR_L1$ Domain, $CDR_L2$ Domain, and $CDR_L3$ Domain are the Light Chain CDRs of hLAG-3 mAb 1, and respectively have the amino acid sequences: SEQ ID NO:28, SEQ ID NO:14, and SEQ ID NO:15; or
(C) (1) the $CDR_H1$ Domain, $CDR_H2$ Domain, and $CDR_H3$ Domain are the Heavy Chain CDRs of LAG-3 mAb 2, and respectively have the amino acid sequences: SEQ ID NO:31, SEQ ID NO:32, and SEQ ID NO:33; and
  (2) the $CDR_L1$ Domain, $CDR_L2$ Domain, and $CDR_L3$ Domain are the Light Chain CDRs of LAG-3 mAb 2, and, respectively have the amino acid sequences: SEQ ID NO:36, SEQ ID NO:37, and SEQ ID NO:38; or
(D) (1) the $CDR_H1$ Domain, $CDR_H2$ Domain, and $CDR_H3$ Domain are the Heavy Chain CDRs of LAG-3 mAb 3, and respectively have the amino acid sequences: SEQ ID NO:41, SEQ ID NO:42, and SEQ ID NO:43; and
  (2) the $CDR_L1$ Domain, $CDR_L2$ Domain, and $CDR_L3$ Domain are the Light Chain CDRs of LAG-3 mAb 3, and, respectively have the amino acid sequences: SEQ ID NO:46, SEQ ID NO:47, and SEQ ID NO:48; or
(E) (1) the $CDR_H1$ Domain, $CDR_H2$ Domain, and $CDR_H3$ Domain are the Heavy Chain CDRs of LAG-3 mAb 4, and respectively have the amino acid sequences: SEQ ID NO:51, SEQ ID NO:52, and SEQ ID NO:53; and
  (2) the $CDR_L1$ Domain, $CDR_L2$ Domain, and $CDR_L3$ Domain are the Light Chain CDRs of LAG-3 mAb 4, and, respectively have the amino acid sequences: SEQ ID NO:56, SEQ ID NO:57, and SEQ ID NO:58; or
(F) (1) the $CDR_H1$ Domain, $CDR_H2$ Domain, and $CDR_H3$ Domain are the Heavy Chain CDRs of LAG-3 mAb 5, and respectively have the amino acid sequences: SEQ ID NO:61, SEQ ID NO:62, and SEQ ID NO:63; and
  (2) the $CDR_L1$ Domain, $CDR_L2$ Domain, and $CDR_L3$ Domain are the Light Chain CDRs of LAG-3 mAb 5, and, respectively have the amino acid sequences: SEQ ID NO:66, SEQ ID NO:67, and SEQ ID NO:68; or
(G) (1) the $CDR_H1$ Domain, $CDR_H2$ Domain, and $CDR_H3$ Domain are the Heavy Chain CDRs of LAG-3 mAb 6 VH1, and respectively have the amino acid sequences: SEQ ID NO:71, SEQ ID NO:72, and SEQ ID NO:73; and
  (2) the $CDR_L1$ Domain, $CDR_L2$ Domain, and $CDR_L3$ Domain are the Light Chain CDRs of LAG-3 mAb 6, and, respectively have the amino acid sequences: SEQ ID NO:76, SEQ ID NO:77, and SEQ ID NO:78; or
(H) (1) the $CDR_H1$ Domain, $CDR_H2$ Domain, and $CDR_H3$ Domain are the Heavy Chain CDRs of LAG-3 hAb 6, and respectively have the amino acid sequences: SEQ ID NO:71, SEQ ID NO:72, and SEQ ID NO:73; and
  (2) the $CDR_L1$ Domain, $CDR_L2$ Domain, and $CDR_L3$ Domain are the Light Chain CDRs of hLAG-3 hAb 6, and respectively have the amino acid sequences: SEQ ID NO:87, SEQ ID NO:77, and SEQ ID NO:78.

The invention further concerns the embodiments of such LAG-3-binding molecules wherein the Heavy Chain Variable Domain has the amino acid sequence of SEQ ID NO:6, SEQ ID NO:29, SEQ ID NO:39, SEQ ID NO:49, or SEQ ID NO:59.

The invention further concerns the embodiments of such LAG-3-binding molecules wherein the Light Chain Variable Domain has the amino acid sequence of SEQ ID NO:11, SEQ ID NO:34, SEQ ID NO:44, SEQ ID NO:54, or SEQ ID NO:64.

The invention further concerns the embodiments of such LAG-3-binding molecules wherein the Heavy Chain Variable Domain has the amino acid sequence of SEQ ID NO:16, SEQ ID NO:18, SEQ ID NO:79, or SEQ ID NO:81.

The invention further concerns the embodiments of such LAG-3-binding molecules wherein the Light Chain Variable Domain has the amino acid sequence of SEQ ID NO:20, SEQ ID NO:22, SEQ ID NO:24, SEQ ID NO:26, SEQ ID NO:83, or SEQ ID NO:85.

The invention further concerns the embodiments of all such LAG-3-binding molecules wherein the molecule is an antibody, and especially wherein the molecule is a chimeric antibody or a humanized antibody.

The invention further concerns the embodiment wherein the LAG-3-binding molecule is a bispecific binding molecule, capable of simultaneously binding to human LAG-3 and to a second epitope, and particularly concerns the embodiment wherein the second epitope is an epitope of a molecule involved in regulating an immune check point present on the surface of an immune cell (especially wherein the second epitope is an epitope of B7-H3, B7-H4, BTLA, CD40, CD40L, CD47, CD70, CD80, CD86, CD94, CD137, CD137L, CD226, CTLA-4, Galectin-9, GITR, GITRL, HHLA2, ICOS, ICOSL, KIR, LAG-3, LIGHT, MHC class I or II, NKG2a, NKG2d, OX40, OX40L, PD1H, PD-1, PD-L1, PD-L2, PVR, SIRPa, TCR, TIGIT, TIM-3 or VISTA, and most particularly wherein the second epitope is an epitope of CD137, OX40, PD-1, TIGIT or TIM-3).

The invention further concerns the embodiment of such LAG-3-binding molecules wherein the molecule is a diabody, and especially, wherein the diabody is a covalently bonded complex that comprises two, or three, or four, or five, or more than five polypeptide chains. The invention further concerns the embodiment of such anti-LAG-3-binding molecules wherein the molecule is a trivalent binding molecule, the trivalent binding molecule being a covalently bonded complex that comprises three, four, five or more polypeptide chains. The invention additionally concerns the embodiment of such LAG-3-binding molecules in which the molecule comprises an Fc Region. The invention additionally concerns the embodiment of such LAG-3-binding molecules in which the molecule comprises an Albumin-Binding Domain, and especially a deimmunized Albumin-Binding Domain.

The invention further concerns the embodiments of all such LAG-3-binding molecules wherein the molecule comprises an Fc (Fraction Crystalizable) Region, and wherein the Fc Region is a variant Fc Region that comprises one or more amino acid modifications that reduces the affinity of the variant Fc Region for an FcγR and/or enhances serum half-life, and more particularly, wherein the modifications comprise at least one amino acid substitution selected from the group consisting of:
(1) L234A;
(2) L235A;
(3) L234A and L235A;
(4) M252Y; M252Y and S254T;
(5) M252Y and T256E;
(6) M252Y, S254T and T256E; or
(7) K288D and H435K;
wherein the numbering is that of the EU index according to Kabat.

The invention further concerns the embodiments in which any of the above-described LAG-3-binding molecules is used to stimulate a T-cell mediate immune response. The invention additionally concerns the embodiments in which any of the above-described LAG-3-binding molecules is used in the treatment of a disease or condition associated with a suppressed immune system, especially cancer or an infection.

The invention particularly concerns such use in the treatment or diagnosis or prognosis of cancer, wherein the cancer is characterized by the presence of a cancer cell selected from the group consisting of a cell of: an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

The invention particularly concerns such use in the treatment or diagnosis or prognosis of cancer, wherein the cancer is colorectal cancer, hepatocellular carcinoma, glioma, kidney cancer, breast cancer, multiple myeloma, bladder cancer, neuroblastoma; sarcoma, non-Hodgkin's lymphoma, non-small cell lung cancer, ovarian cancer, pancreatic cancer, rectal cancer, acute myeloid leukemia (AML), chronic myelogenous leukemia (CML), acute B lymphoblastic leukemia (B-ALL), chronic lymphocytic leukemia (CLL), hairy cell leukemia (HCL), blastic plasmacytoid dendritic cell neoplasm (BPDCN), non-Hodgkin's lymphomas (NHL), including mantel cell leukemia (MCL), and small lymphocytic lymphoma (SLL), Hodgkin's lymphoma, systemic mastocytosis, or Burkitt's lymphoma.

The invention further concerns the embodiments in which any of the above-described LAG-3-binding molecules is detectably labeled and is used in the detection of LAG-3.

BRIEF DESCRIPTION OF THE DRAWINGS

FIG. 3A shows an Fc diabody which contains a peptide Heterodimer-Promoting Domain comprising a cysteine residue. FIG. 3B shows an Fc Region-containing diabody, which contains E-coil and K-coil Heterodimer-Promoting Domains comprising a cysteine residue and a linker (with an optional cysteine residue). FIG. 3C, shows an Fc Region-containing diabody, which contains antibody CH1 and CL domains.

FIGS. 6A and 6B, respectively, illustrate schematically the domains of trivalent binding molecules comprising two diabody-type binding domains and a Fab-type binding domain having different domain orientations in which the diabody-type binding domains are N-terminal or C-terminal to an Fc Region. The molecules in FIGS. 6A and 6B comprise four chains. FIGS. 6C and 6D, respectively, illustrate schematically the domains of trivalent binding molecules comprising two diabody-type binding domains N-terminal to an Fc Region, and a Fab-type binding domain in which the light chain and heavy chain are linked via polypeptide linker spacer, or an scFv-type binding domain. The trivalent binding molecules in FIGS. 6E and 6F, respectively illustrate schematically the domains of trivalent binding molecules comprising two diabody-type binding domains C-terminal to an Fc Region, and a linked Fab-type binding domain, or an scFv-type binding domain in which the diabody-type binding domains are. The trivalent binding molecules in FIGS. 6C-6F comprise three chains. VL and VH Domains that recognize the same epitope are shown using the same shading or fill pattern.

FIG. 9A shows the inhibition curves of LAG-3 mAb 1, LAG-3 mAb 2, LAG-3 mAb 3, LAG-3 mAb 4, and LAG-3 mAb 5. FIG. 9B shows the inhibition curves of LAG-3 mAb A, humanized hLAG-3 1 (1.4), and hLAG-3 6 (1.1) (RLU; Relative Luminesence Units).

FIG. 10A shows the inhibition curves of LAG-3 mAb 1, LAG-3 mAb 2, LAG-3 mAb 3, LAG-3 mAb 4, LAG-3 mAb 5, and the reference antibody LAG-3 mAb A. FIG. 10B shows the inhibition curves of LAG-3 mAb 1, LAG-3 mAb 6 and LAG-3 mAb A. FIG. 10C shows the inhibition curves of LAG-3 mAb 1 and humanized hLAG-3 1 (1.4), hLAG-3 1 (1.2), hLAG-3 1 (2.2), hLAG-3 1 (1.1). Each figure represents a separate experiment; MFI, mean fluorescence intensity.

DETAILED DESCRIPTION OF THE INVENTION

Figure 1:
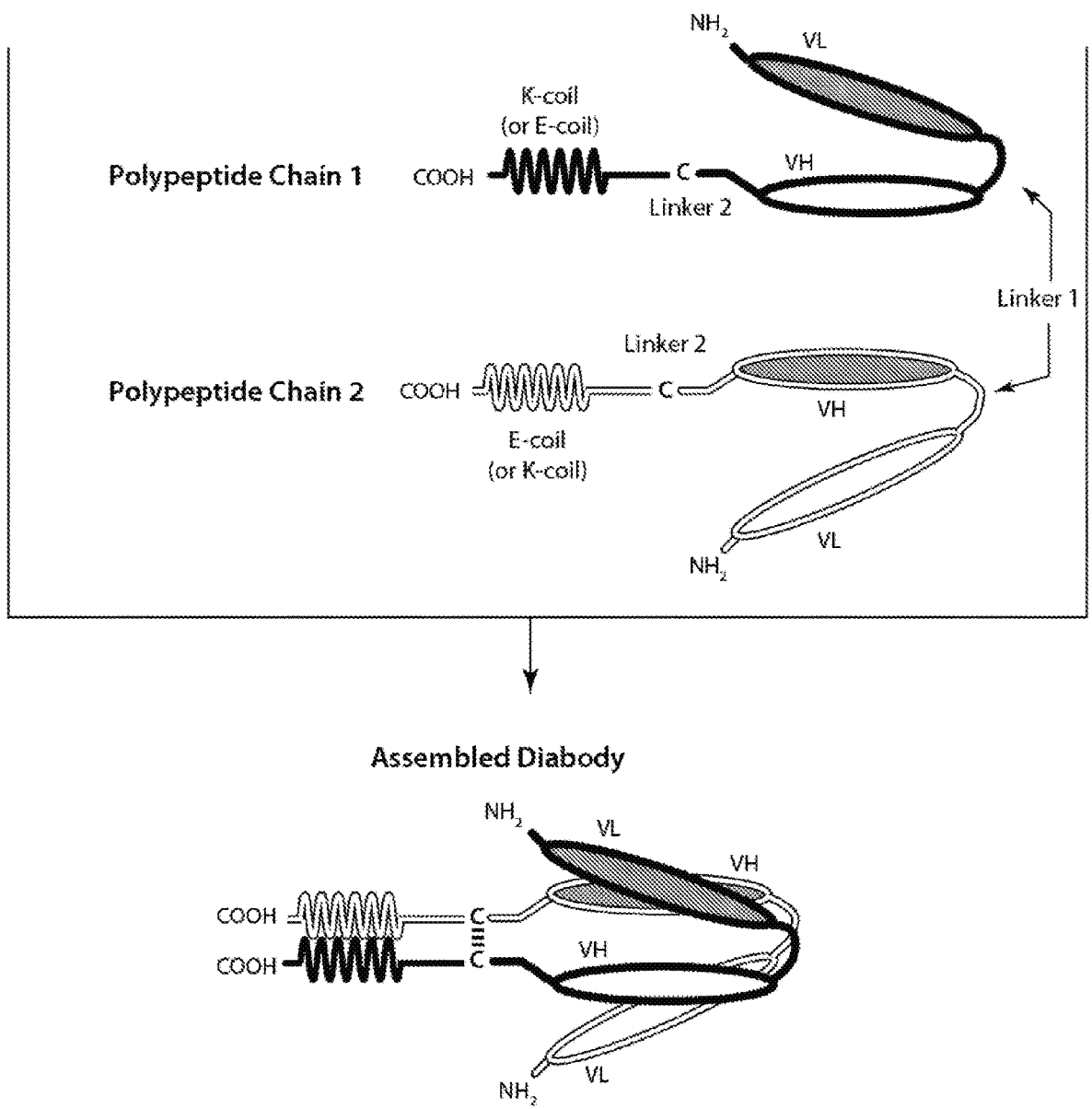
FIG. 1 provides a schematic of a representative covalently bonded diabody having two epitope-binding sites composed of two polypeptide chains, each having an E-coil or K-coil Heterodimer-Promoting Domain. A cysteine residue may be present in a linker and/or in the Heterodimer-Promoting Domain as shown in FIG. 3B. VL and VH Domains that recognize the same epitope are shown using the same shading or fill pattern.

The present invention is directed to LAG-3 binding molecules that comprise the LAG-3-binding domain of selected anti-LAG-3 antibodies: LAG-3 mAb 1, LAG-3 mAb 2, LAG-3 mAb 3, LAG-3 mAb 4, LAG-3 mAb 5, or LAG-3 mAb 6 that are capable of binding to both cynomolgus monkey LAG-3 and to human LAG-3. The invention particularly concerns LAG-3 binding molecules that are humanized or chimeric versions of such antibodies, or that comprise LAG-3 binding-fragments of such anti-LAG-3 antibodies (especially immunocongugates, diabodies, BiTEs, bispecific antibodies, etc.). The invention particularly concerns such LAG-3-binding molecules that are additionally capable of binding an epitope of a molecule involved in regulating an immune check point that is present on the surface of an immune cell. The present invention also pertains to methods of using such LAG-3 binding molecules to detect LAG-3 or to stimulate an immune response. The present invention also pertains to methods of combination therapy in which a LAG-3-binding molecule that comprises one or more LAG-3-binding domain(s) of such selected anti-LAG-3 antibodies is administered in combination with one or more additional molecules that are effective in stimulating an immune response to thereby further enhance, stimulate or upregulate such immune response in a subject.

I. Antibodies and Their Binding Domains

The antibodies of the present invention are immunoglobulin molecules capable of immunospecific binding to a target, such as a carbohydrate, polynucleotide, lipid, polypeptide, etc., through at least one epitope recognition site, located in the Variable Domain of the immunoglobulin molecule.

As used herein, the term "antibody" refers to an immunoglobulin molecule capable of immunospecific binding to a polypeptide or protein or a non-protein molecule due to the presence on such molecule of a particular domain or moiety or conformation (an "epitope"). An epitope-containing molecule may have immunogenic activity, such that it elicits an antibody production response in an animal; such molecules are termed "antigens"). Epitope-containing molecules need not necessarily be immunogenic.

The binding domains of the present invention bind to epitopes in an "immunospecific" manner. As used herein, an antibody, diabody or other epitope-binding molecule is said to "immunospecifically" bind (or to exhibit "specific" binding to) a region of another molecule (i.e., an epitope) if it reacts or associates more frequently, more rapidly, with greater duration and/or with greater affinity with that epitope relative to alternative epitopes. For example, an antibody that specifically binds to a LAG-3 epitope is an antibody that binds such LAG-3 epitope with greater affinity, avidity, more readily, and/or with greater duration than it binds to other LAG-3 epitopes or to a non-LAG-3 epitope. It is also understood by reading this definition that, for example, an antibody (or moiety or epitope) that immunospecifically binds to a first target may or may not specifically or preferentially bind to a second target. As such, "immunospecific binding" does not necessarily require (although it can include) exclusive binding. Generally, but not necessarily, reference to binding means "specific" binding. Two molecules are said to be capable of binding to one another in a "physiospecific" manner, if such binding exhibits the specificity with which receptors bind to their respective ligands. The ability of an antibody to immunospecifically bind to an epitope may be determined by, for example, an immunoassay.

Natural antibodies (such as IgG antibodies) are composed of two Light Chains complexed with two Heavy Chains. Each light chain contains a Variable Domain (VL) and a Constant Domain (CL). Each heavy chain contains a Variable Domain (VH), three Constant Domains (CH1, CH2 and CH3), and a "Hinge" Domain ("H") located between the CH1 and CH2 Domains. The basic structural unit of naturally occurring immunoglobulins (e.g., IgG) is thus a tetramer having two light chains and two heavy chains, usually expressed as a glycoprotein of about 150,000 Da. The amino-terminal ("N-terminal") portion of each chain includes a Variable Domain of about 100 to 110 or more amino acids primarily responsible for antigen recognition. The carboxy-terminal ("C-terminal") portion of each chain defines a constant region, with light chains having a single Constant Domain and heavy chains usually having three Constant Domains and a Hinge Domain. Thus, the structure of the light chains of an IgG molecule is n-VL-CL-c and the structure of the IgG heavy chains is n-VH-CH1-H-CH2-CH3-c (where n and c represent, respectively, the N-terminus and the C-terminus of the polypeptide). The ability of an antibody to bind an epitope of an antigen depends upon the presence and amino acid sequence of the antibody's VL and VH Domains. Interaction of an antibody light chain and an antibody heavy chain and, in particular, interaction of its VL and VH Domains forms one of the two epitope-binding sites of a natural antibody. Natural antibodies are capable of binding to only one epitope species (i.e., they are monospecific), although they can bind multiple copies of that species (i.e., exhibiting bivalency or multivalency). The Variable Domains of an IgG molecule consist of the complementarity determining regions (CDR), which contain the residues in contact with epitope, and non-CDR segments, referred to as framework segments (FR), which in general maintain the structure and determine the positioning of the CDR loops so as to permit such contacting (although certain framework residues may also contact antigen). Thus, the $V_L$ and VH Domains have the structure n-FR1-CDR1-FR2-CDR2-FR3-CDR3-FR4-c. Polypeptides that are (or may serve as) the first, second and third CDR of an antibody Light Chain are herein respectively designated $CDR_L1$ Domain, $CDR_L2$ Domain, and $CDR_L3$ Domain. Similarly, polypeptides that are (or may serve as) the first, second and third CDR of an antibody heavy chain are herein respectively designated $CDR_H1$ Domain, $CDR_H2$ Domain, and $CDR_H3$ Domain. Thus, the terms $CDR_L1$ Domain, $CDR_L2$ Domain, $CDR_L3$ Domain, $CDR_H1$ Domain, $CDR_H2$ Domain, and $CDR_H3$ Domain are directed to polypeptides that when incorporated into a protein cause that protein to be able to bind to a specific epitope regardless of whether such protein is an antibody having light and heavy chains or a diabody or a single-chain binding molecule (e.g., an scFv, a BiTe, etc.), or is another type of protein. Accordingly, as used herein, the term "Epitope-Binding Domain" refers to that portion of an epitope-binding molecule that is responsible for the ability of such molecule to immunospecifically bind an epitope. An epitope-binding fragment may contain 1, 2, 3, 4, 5 or all 6 of the CDR Domains of such antibody and, although capable of immunospecifically binding to such epitope, may exhibit an immunospecificity, affinity or selectivity toward such epitope that differs from that of such antibody. Preferably, however, an epitope-binding fragment will contain all 6 of the CDR Domains of such antibody. An epitope-binding fragment of an antibody may be a single polypeptide chain (e.g., an scFv), or may comprise two or more polypeptide chains, each having an amino terminus and a carboxy terminus (e.g., a diabody, a Fab fragment, an F(ab')2 fragment, etc.).

As used herein, the term "antibody" encompasses monoclonal antibodies, multispecific antibodies, human antibodies, humanized antibodies, synthetic antibodies, chimeric antibodies, polyclonal antibodies, camelized antibodies, single-chain Fvs (scFv), single-chain antibodies, immunologically active antibody fragments (e.g., antibody fragments capable of binding to an epitope, e.g., Fab fragments, Fab' fragments, F(ab')$_2$ fragments, Fv fragments, fragments containing a $V_L$ and/or $V_H$ domain, or that contain 1, 2, or 3 of the complementary determining regions (CDRs) of such VL domain (i.e., $CDR_L1$, $CDR_L2$, and/or $CDR_L3$) or VH domain (i.e., $CDR_H1$, $CDR_H2$, and/or $CDR_H3$)) that specifically bind an antigen, etc., bi-functional or multi-functional antibodies, disulfide-linked bispecific Fvs (sdFv), intrabodies, and diabodies, and epitope binding fragments of any of the above. In particular, the term "antibody" is intended to encompass immunoglobulin molecules and immunologically active fragments of immunoglobulin molecules, i.e., molecules that contain an epitope-binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass (see, e.g., United States Patent Publication Nos.: 20040185045; 20050037000; 20050064514; 20050215767; 20070004909; 20070036799; 20070077246; and 20070244303). The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases*," Singapore Med. J. 50(7):663-666). Over 200 antibody-based drugs have been approved for use or are under development.

The anti-LAG-3 antibodies of the present invention include humanized, chimeric or caninized variants of antibodies LAG-3 mAb 1, LAG-3 mAb 2, LAG-3 mAb 3, LAG-3 mAb 4, LAG-3 mAb 5, or LAG-3 mAb 6.

The term "chimeric antibody" refers to an antibody in which a portion of a heavy and/or light chain is identical to or homologous with an antibody from one species (e.g., mouse) or antibody class or subclass, while the remaining portion is identical to or homologous with an antibody of another species (e.g., human) or antibody class or subclass, so long as they exhibit the desired biological activity. Chimeric antibodies of interest herein include "primatized" antibodies comprising variable domain antigen binding sequences derived from a non-human primate (e.g., Old World Monkey, Ape, etc.) and human constant region sequences.

The term "monoclonal antibody" as used herein refers to an antibody of a population of substantially homogeneous antibodies, i.e., the individual antibodies comprising the population are identical except for possible antibodies possessing naturally occurring mutations that may be present in minor amounts, and the term "polyclonal antibody" as used herein refers to an antibody obtained from a population of heterogeneous antibodies. The term "monoclonal" indicates the character of the antibody as being a substantially homogeneous population of antibodies, and is not to be construed as requiring production of the antibody by any particular method (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity*," Nature 256:495-497 or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi (see, e.g., Jennings, V. M. (1995) "*Review of Selected Adjuvants Used in Antibody Production*," ILAR J. 37(3):119-125). In general, cells should be kept intact and preferably viable when used as immunogens. Intact cells may allow antigens to be better detected than ruptured cells by the immunized animal. Use of denaturing or harsh adjuvants, e.g., Freud's adjuvant, may rupture cells and therefore is discouraged. The immunogen may be administered multiple times at periodic intervals such as, bi-weekly, or weekly, or may be administered in such a way as to maintain viability in the animal (e.g., in a tissue recombinant). Alternatively, existing monoclonal antibodies and any other equivalent antibodies that are immunospecific for a desired pathogenic epitope can be sequenced and produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate the monospecific or multispecific (e.g., bispecific, trispecific and tetraspecific) molecules of the invention as well as an affinity optimized, a chimeric antibody, a humanized antibody, and/or a caninized antibody, to improve the affinity, or other characteristics of the antibody.

The term "scFv" refers to single-chain Variable Domain fragments. scFv molecules are made by linking Light and/or Heavy Chain Variable Domain using a short linking peptide. Bird et al. (1988) ("*Single-Chain Antigen-Binding Proteins*," Science 242:423-426) describes example of linking peptides which bridge approximately 3.5 nm between the carboxy terminus of one Variable Domain and the amino terminus of the other Variable Domain. Linkers of other sequences have been designed and used (Bird et al. (1988) "*Single-Chain Antigen-Binding Proteins*," Science 242:423-426). Linkers can in turn be modified for additional functions, such as attachment of drugs or attachment to solid supports. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

The invention particularly encompasses humanized variants of the anti-LAG-3 antibodies of the invention and multi specific binding molecules comprising the same. The term "humanized" antibody refers to a chimeric molecule, generally prepared using recombinant techniques, having an epitope-binding site of an immunoglobulin from a non-human species and a remaining immunoglobulin structure of the molecule that is based upon the structure and/or sequence of a human immunoglobulin. The epitope-binding site may comprise either complete variable domains fused onto constant domains or only the CDRs grafted onto appropriate framework regions in the variable domains. Epitope-binding sites may be wild-type or modified by one or more amino acid substitutions. This eliminates the constant region as an immunogen in human individuals, but the possibility of an immune response to the foreign variable region remains (LoBuglio, A. F. et al. (1989) "*Mouse/ Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable regions as well so as to reshape them as closely as possible to human form. It is known that the variable regions of both heavy and light chains contain three CDRs which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable regions can be "reshaped" or "humanized" by grafting CDRs derived from a non-human antibody on the FRs present in the human antibody to be modified. Application of this approach to various antibodies has been reported by Sato, K. et al. (1993) "*Reshaping A Human Antibody To Inhibit The Interleukin 6-Dependent Tumor Cell Growth*," Cancer Res 53:851-856. Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/ Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five or six) that are altered in their amino acid sequence (s) relative to the original antibody, which are also termed one or more CDRs "derived from" one or more CDRs from the original antibody (i.e., derived from such CDRs, derived from knowledge of the amino acid sequences of such CDRs, etc.). A polynucleotide sequence that encodes the variable domain of an antibody may be used to generate such derivatives and to improve the affinity, or other characteristics of such antibodies. The general principle in humanizing an antibody involves retaining the basic sequence of the epitope-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody or caninized antibody, i.e., deciding which antibody framework region to use during the humanizing or canonizing process (3) the actual humanizing or caninizing methodologies/techniques and (4) the transfection and expression of the humanized antibody. See, for example, U.S. Pat. Nos. 4,816,567; 5,807,715; 5,866,692; and 6,331,415.

The epitope-binding site of the molecules of the present invention may comprise a complete Variable Domain fused to a Constant Domain or only the complementarity determining regions (CDRs) of such Variable Domain grafted to appropriate framework regions. Epitope-binding sites may be wild-type or modified by one or more amino acid substitutions. This eliminates the constant region as an immunogen in human individuals, but the possibility of an immune response to the foreign variable domain remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable domains as well so as to reshape them as closely as possible to human form. It is known that the variable domains of both heavy and light chains contain three complementarity determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable domains can be "reshaped" or "humanized" by grafting CDRs derived from non-human antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which differ in sequence relative to the original antibody.

A number of "humanized" antibody molecules comprising an epitope-binding site derived from a non-human immunoglobulin have been described, including chimeric antibodies having rodent or modified rodent Variable Domain and their associated complementarity determining regions (CDRs) fused to human Constant Domains (see, for example, Winter et al. (1991) "*Man-made Antibodies*," Nature 349:293-299; Lobuglio et al. (1989) "*Mouse/Human Chimeric Monoclonal Antibody In Man: Kinetics And Immune Response*," Proc. Natl. Acad. Sci. (U.S.A.) 86:4220-4224 (1989), Shaw et al. (1987) "*Characterization Of A Mouse/Human Chimeric Monoclonal Antibody* (17-1A) *To A Colon Cancer Tumor-Associated Antigen*," J. Immunol. 138: 4534-4538, and Brown et al. (1987) "*Tumor-Specific Genetically Engineered Murine/Human Chimeric Monoclonal Antibody*," Cancer Res. 47:3577-3583). Other references describe rodent CDRs grafted into a human supporting framework region (FR) prior to fusion with an appropriate human antibody Constant Domain (see, for example, Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; and Jones et al. (1986) "*Replacing The Complementarity-Determining Regions In A Human Antibody With Those From A Mouse*," Nature 321: 522-525). Another reference describes rodent CDRs supported by recombinantly veneered rodent framework regions. See, for example, European Patent Publication No. 519,596. These "humanized" molecules are designed to minimize unwanted immunological response towards rodent anti-human antibody molecules, which limits the duration and effectiveness of therapeutic applications of those moieties in human recipients. Other methods of humanizing antibodies that may also be utilized are disclosed by Daugherty et al. (1991) "*Polymerase Chain Reaction Facilitates The Cloning, CDR-Grafting, And Rapid Expression Of A Murine Monoclonal Antibody Directed Against The CD*18 *Component Of Leukocyte Integrins*," Nucl. Acids Res. 19:2471-2476 and in U.S. Pat. Nos. 6,180,377; 6,054,297; 5,997,867; and 5,866,692.

II. Fcγ Receptors (FcγRs)

The CH2 and CH3 Domains of the two heavy chains interact to form the Fc Region, which is a domain that is recognized by cellular Fc Receptors including but not limited to Fc gamma Receptors (FcγRs). As used herein, the term "Fc Region" is used to define a C-terminal region of an IgG heavy chain. The amino acid sequence of the CH2-CH3 Domain of an exemplary human IgG1 is (SEQ ID NO:1):

```
      231       240             250            260           270            280
      APELLGGPSV FLFPPKPKDT     LMISRTPEVT     CVVVDVSHED    PEVKFNWYVD 290             300            310           320            330
      GVEVHNAKTK PREEQYNSTY     RVVSVLTVLH     QDWLNGKEYK    CKVSNKALPA 340             350            360           370            380
      PIEKTISKAK GQPREPQVYT     LPPSREEMTK     NQVSLTCLVK    GFYPSDIAVE 390             400            410           420            430
      WESNGQPENN YKTTPPVLDS     DGSFFLYSKL     TVDKSRWQQG    NVFSCSVMHE 440             447
      ALHNHYTQKS LSLSPGX
``` as numbered by the EU index according to Kabat, wherein, X is a lysine (K) or is absent.

The amino acid sequence of the CH2-CH3 Domain of an exemplary human IgG2 is (SEQ ID NO:2):

```
      231       240             250            260           270            280
      APPVA-GPSV FLFPPKPKDT     LMISRTPEVT     CVVVDVSHED    PEVQFNWYVD 290             300            310           320            330
      GVEVHNAKTK PREEQFNSTF     RVVSVLTVVH     QDWLNGKEYK    CKVSNKGLPA 340             350            360           370            380
      PIEKTISKTK GQPREPQVYT     LPPSREEMTK     NQVSLTCLVK    GFYPSDISVE 390             400            410           420            430
      WESNGQPENN YKTTPPMLDS     DGSFFLYSKL     TVDKSRWQQG    NVFSCSVMHE 440             447
      ALHNHYTQKS LSLSPGX
``` as numbered by the EU index according to Kabat, wherein, X is a lysine (K) or is absent.

The amino acid sequence of the CH2-CH3 Domain of an exemplary human IgG3 is (SEQ ID NO:3):

```
      231       240             250            260           270            280
      APELLGGPSV FLFPPKPKDT     LMISRTPEVT     CVVVDVSHED    PEVQFKWYVD 290             300            310           320            330
      GVEVHNAKTK PREEQYNSTF     RVVSVLTVLH     QDWLNGKEYK    CKVSNKALPA 340             350            360           370            380
```

```
                                         -continued
PIEKTISKTK    GQPREPQVYT    LPPSREEMTK    NQVSLTCLVK    GFYPSDIAVE 390           400           410           420           430
WESSGQPENN    YNTTPPMLDS    DGSFFLYSKL    TVDKSRWQQG    NIFSCSVMHE 440           447
ALHNRFTQKS    LSLSPGX
``` as numbered by the EU index according to Kabat, wherein, X is a lysine (K) or is absent.

The amino acid sequence of the CH2-CH3 Domain of an exemplary human IgG4 is (SEQ ID NO:4):

```
231           240           250           260           270           280
APEFLGGPSV    FLFPPKPKDT    LMISRTPEVT    CVVVDVSQED    PEVQFNWYVD 290           300           310           320           330
GVEVHNAKTK    PREEQFNSTY    RVVSVLTVLH    QDWLNGKEYK    CKVSNKGLPS 340           350           360           370           380
SIEKTISKAK    GQPREPQVYT    LPPSQEEMTK    NQVSLTCLVK    GFYPSDIAVE 390           400           410           420           430
WESNGQPENN    YKTTPPVLDS    DGSFFLYSRL    TVDKSRWQEG    NVFSCSVMHE 440           447
ALHNHYTQKS    LSLSLGX
``` as numbered by the EU index according to Kabat, wherein, X is a lysine (K) or is absent.

Throughout the present specification, the numbering of the residues in the constant region of an IgG heavy chain is that of the EU index according to Kabat et al., SEQUENCES OF PROTEINS OF IMMUNOLOGICAL INTEREST, 5$^{th}$ Ed. Public Health Service, NH1, MD (1991) ("Kabat"), expressly incorporated herein by references. The "EU index according to Kabat" refers to the numbering of the human IgG1 EU antibody. Amino acids from the Variable Domains of the mature heavy and light chains of immunoglobulins are designated by the position of an amino acid in the chain, and the CDRs are identified as defined by Kabat (it will be understood that CDR$_H$1 as defined by Chothia, C. & Lesk, A. M. ((1987) "Canonical structures for the hypervariable regions of immunoglobulins,". J. Mol. Biol. 196:901-917) begins five residues earlier). Kabat described numerous amino acid sequences for antibodies, identified an amino acid consensus sequence for each subgroup, and assigned a residue number to each amino acid. Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain.

Polymorphisms have been observed at a number of different positions within antibody constant regions (e.g., Fc positions, including but not limited to positions 270, 272, 312, 315, 356, and 358 as numbered by the EU index according to Kabat), and thus slight differences between the presented sequence and sequences in the prior art can exist. Polymorphic forms of human immunoglobulins have been well-characterized. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b3, b0, b3, b4, s, t, g1, c5, u, v, g5) (Lefranc, et al., "The Human IgG Subclasses: Molecular Analysis Of Structure, Function And Regulation." Pergamon, Oxford, pp. 43-78 (1990); Lefranc, G. et al., 1979, Hum. Genet.: 50, 199-211). It is specifically contemplated that the antibodies of the present invention may be incorporate any allotype, isoallotype, or haplotype of any immunoglobulin gene, and are not limited to the allotype, isoallotype or haplotype of the sequences provided herein. Furthermore, in some expression systems the C-terminal amino acid residue (bolded above) of the CH3 Domain may be post-translationally removed. Accordingly, the C-terminal residue of the CH3 Domain is an optional amino acid residue in the LAG-3-binding molecules of the invention. Specifically encompassed by the instant invention are LAG-3-binding molecules lacking the C-terminal residue of the CH3 Domain. Also specifically encompassed by the instant invention are such constructs comprising the C-terminal lysine residue of the CH3 Domain.

Activating and inhibitory signals are transduced through the ligation of an Fc Region to a cellular Fc Receptor (FcγR). The ability of such ligation to result in diametrically opposing functions results from structural differences among the different receptor isoforms. Two distinct domains within the cytoplasmic signaling domains of the receptor called immunoreceptor tyrosine-based activation motifs (ITAMs) and immunoreceptor tyrosine-based inhibitory motifs (ITIMS) account for the different responses. The recruitment of different cytoplasmic enzymes to these structures dictates the outcome of the FcγR-mediated cellular responses. ITAM-containing FcγR complexes include FcγRI, FcγRIIA, FcγRIIIA, whereas ITIM-containing complexes only include FcγRIIB Human neutrophils express the FcγRIIA gene. FcγRIIA clustering via immune complexes or specific antibody cross-linking serves to aggregate ITAMs along with receptor-associated kinases which facilitate ITAM phosphorylation. ITAM phosphorylation serves as a docking site for Syk kinase, activation of which results in activation of downstream substrates (e.g., PI3K). Cellular activation leads to release of proinflammatory mediators. The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When co-ligated along with an activating FcγR, the ITIM in FcγRIIB becomes phosphorylated and attracts the SH2 domain of the inositol polyphosphate 5'-phosphatase (SHIP), which hydrolyzes phosphoinositol messengers released as a consequence of ITAM-containing FcγR-mediated tyrosine kinase activation, consequently preventing the influx of intracellular $Ca^{++}$. Thus cross-linking of FcγRIIB dampens the activating response to FcγR ligation and inhibits cellular responsiveness. B-cell activation, B-cell proliferation and antibody secretion is thus aborted.

III. Bispecific Antibodies, Multispecific Diabodies and DART® Diabodies

The functionality of antibodies can be enhanced by generating multispecific antibody-based molecules that can simultaneously bind two separate and distinct antigens (or different epitopes of the same antigen) and/or by generating antibody-based molecule having higher valency (i.e., more than two binding sites) for the same epitope and/or antigen.

In order to provide molecules having greater capability than natural antibodies, a wide variety of recombinant bispecific antibody formats have been developed (see, e.g., PCT Publication Nos. WO 2008/003116, WO 2009/132876, WO 2008/003103, WO 2007/146968, WO 2009/018386, WO 2012/009544, WO 2013/070565), most of which use linker peptides either to fuse a further epitope-binding fragment (e.g., an scFv, VL, VH, etc.) to, or within the antibody core (IgA, IgD, IgE, IgG or IgM), or to fuse multiple epitope-binding fragments (e.g., two Fab fragments or scFvs). Alternative formats use linker peptides to fuse an epitope-binding fragment (e.g., an scFv, VL, VH, etc.) to a dimerization domain such as the CH2-CH3 Domain or alternative polypeptides (WO 2005/070966, WO 2006/107786A WO 2006/107617A, WO 2007/046893). Typically, such approaches involve compromises and trade-offs. For example, PCT Publications Nos. WO 2013/174873, WO 2011/133886 and WO 2010/136172 disclose that the use of linkers may cause problems in therapeutic settings, and teaches a trispecific antibody in which the CL and CH1 Domains are switched from their respective natural positions and the VL and VH Domains have been diversified (WO 2008/027236; WO 2010/108127) to allow them to bind to more than one antigen. Thus, the molecules disclosed in these documents trade binding specificity for the ability to bind additional antigen species. PCT Publications Nos. WO 2013/163427 and WO 2013/119903 disclose modifying the CH2 Domain to contain a fusion protein adduct comprising a binding domain. The document notes that the CH2 Domain likely plays only a minimal role in mediating effector function. PCT Publications Nos. WO 2010/028797, WO2010028796 and WO 2010/028795 disclose recombinant antibodies whose Fc Regions have been replaced with additional VL and VH Domains, so as to form trivalent binding molecules. PCT Publications Nos. WO 2003/025018 and WO2003012069 disclose recombinant diabodies whose individual chains contain scFv Domains. PCT Publications No. WO 2013/006544 discloses multivalent Fab molecules that are synthesized as a single polypeptide chain and then subjected to proteolysis to yield heterodimeric structures. Thus, the molecules disclosed in these documents trade all or some of the capability of mediating effector function for the ability to bind additional antigen species. PCT Publications Nos. WO 2014/022540, WO 2013/003652, WO 2012/162583, WO 2012/156430, WO 2011/086091, WO 2008/024188, WO 2007/024715, WO 2007/075270, WO 1998/002463, WO 1992/022583 and WO 1991/003493 disclose adding additional binding domains or functional groups to an antibody or an antibody portion (e.g., adding a diabody to the antibody's light chain, or adding additional VL and VH Domains to the antibody's light and heavy chains, or adding a heterologous fusion protein or chaining multiple Fab Domains to one another). Thus, the molecules disclosed in these documents trade native antibody structure for the ability to bind additional antigen species.

The art has additionally noted the capability to produce diabodies that differ from such natural antibodies in being capable of binding two or more different epitope species (i.e., exhibiting bispecificity or multispecificity in addition to bivalency or multivalency) (see, e.g., Holliger et al. (1993) "*'Diabodies': Small Bivalent And Bispecific Antibody Fragments*," Proc. Natl. Acad. Sci. (U.S.A.) 90:6444-6448; US 2004/0058400 (Hollinger et al.); US 2004/0220388/WO 02/02781 (Mertens et al.); Alt et al. (1999) FEBS Lett. 454(1-2):90-94; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672; WO 02/02781 (Mertens et al.); Olafsen, T. et al. (2004) "*Covalent Disulfide-Linked Anti-CEA Diabody Allows Site-Specific Conjugation And Radiolabeling For Tumor Targeting Applications*," Protein Eng. Des. Sel. 17(1):21-27; Wu, A. et al. (2001) "*Multimerization Of A Chimeric Anti-CD20 Single Chain Fv-Fv Fusion Protein Is Mediated Through Variable Domain Exchange*," Protein Engineering 14(2): 1025-1033; Asano et al. (2004) "*A Diabody For Cancer Immunotherapy And Its Functional Enhancement By Fusion Of Human Fc Domain*," Abstract 3P-683, J. Biochem. 76(8):992; Takemura, S. et al. (2000) "*Construction Of A Diabody (Small Recombinant Bispecific Antibody) Using A Refolding System*," Protein Eng. 13(8):583-588; Baeuerle, P. A. et al. (2009) "*Bispecific T-Cell Engaging Antibodies For Cancer Therapy*," Cancer Res. 69(12):4941-4944).

The design of a diabody is based on the antibody derivative known as a single-chain Variable Domain fragment (scFv). Such molecules are made by linking Light and/or Heavy chain Variable Domains by using a short linking peptide. Linkers can in turn be modified for additional functions, such as attachment of drugs or attachment to solid supports. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The provision of non-monospecific diabodies provides a significant advantage over antibodies, including but not limited to, the capacity to co-ligate and co-localize cells that express different epitopes. Bispecific diabodies thus have wide-ranging applications including therapy and immunodiagnosis. Bispecificity allows for great flexibility in the design and engineering of the diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below ~50 kDa), diabody molecules known in the art have also shown particular use in the field of tumor imaging (Fitzgerald et al. (1997) "*Improved Tumour Targeting By Disulphide Stabilized Diabodies Expressed In Pichia pastoris*," Protein Eng. 10:1221).

The bispecificity of diabodies has led to their use for co-ligating differing cells, for example, the cross-linking of cytotoxic T-cells to tumor cells (Staerz et al. (1985) "*Hybrid Antibodies Can Target Sites For Attack By T Cells*," Nature 314:628-631, and Holliger et al. (1996) "*Specific Killing Of Lymphoma Cells By Cytotoxic T-Cells Mediated By A Bispecific Diabody*," Protein Eng. 9:299-305; Marvin et al. (2005) "*Recombinant Approaches To IgG-Like Bispecific Antibodies*," Acta Pharmacol. Sin. 26:649-658). Alternatively, or additionally, bispecific diabodies can be used to co-ligate receptors on the surface of different cells or on a single cell. Co-ligation of different cells and/or receptors is useful to modulation effector functions and/or immune cell signaling. Multispecific molecules (e.g., bispecific diabodies) comprising epitope-binding sites may be directed to a surface determinant of any immune cell such as B7-H3 (CD276), B7-H4 (VTCN1), BTLA (CD272), CD3, CD8, CD16, CD27, CD32, CD40, CD40L, CD47, CD64, CD70 (CD27L), CD80 (B7-1), CD86 (B7-2), CD94 (KLRD1), CD137 (4-1BB), CD137L (4-1BBL), CD226, CTLA-4 (CD152), Galectin-9, GITR, GITRL, HHLA2, ICOS (CD278), ICOSL (CD275), Killer Activation Receptor (KIR), LAG-3 (CD223), LIGHT (TNFSF14, CD258), MHC class I or II, NKG2a, NKG2d, OX40 (CD134), OX40L (CD134L), PD1H, PD-1 (CD279), PD-L1 (B7-H1, CD274), PD-L2 (B7-CD, CD273), PVR (NECL5, CD155), SIRPa, TCR, TIGIT, TIM-3 (HAVCR2), and/or VISTA (PD-1H), which are expressed on T lymphocytes, Natural Killer (NK) cells, Antigen-presenting cells or other mononuclear cell. In particular, epitope-binding sites directed to a cell surface receptor that is involved in regulating an immune checkpoint (or the ligand thereof) are useful in the generation of bispecific or multispecific binding molecules which antagonize or block the inhibitory signaling of immune checkpoint molecules and thereby stimulate, upregulate or enhance, immune responses in a subject. Molecules involved in regulating immune checkpoints include, but are not limited to B7-H3, B7-H4, BTLA, CD40, CD40L, CD47, CD70, CD80, CD86, CD94, CD137, CD137L, CD226, CTLA-4, Galectin-9, GITR, GITRL, HHLA2, ICOS, ICOSL, KIR, LAG-3, LIGHT, MHC class I or II, NKG2a, NKG2d, OX40, OX40L, PD1H, PD-1, PD-L1, PD-L2, PVR, SIRPa, TCR, TIGIT, TIM-3 and/or VISTA.

However, the above advantages come at a salient cost. The formation of such non-monospecific diabodies requires the successful assembly of two or more distinct and different polypeptides (i.e., such formation requires that the diabodies be formed through the heterodimerization of different polypeptide chain species). This fact is in contrast to monospecific diabodies, which are formed through the homodimerization of identical polypeptide chains. Because at least two dissimilar polypeptides (i.e., two polypeptide species) must be provided in order to form a non-monospecific diabody, and because homodimerization of such polypeptides leads to inactive molecules (Takemura, S. et al. (2000) "*Construction Of A Diabody (Small Recombinant Bispecific Antibody) Using A Refolding System*," Protein Eng. 13(8): 583-588), the production of such polypeptides must be accomplished in such a way as to prevent covalent bonding between polypeptides of the same species (i.e., so as to prevent homodimerization) (Takemura, S. et al. (2000) "*Construction Of A Diabody (Small Recombinant Bispecific Antibody) Using A Refolding System*," Protein Eng. 13(8): 583-588). The art has therefore taught the non-covalent association of such polypeptides (see, e.g., Olafsen et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27; Asano et al. (2004) "*A Diabody For Cancer Immunotherapy And Its Functional Enhancement By Fusion Of Human Fc Domain*," Abstract 3P-683, J. Biochem. 76(8): 992; Takemura, S. et al. (2000) "*Construction Of A Diabody (Small Recombinant Bispecific Antibody) Using A Refolding System*," Protein Eng. 13(8):583-588; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

However, the art has recognized that bispecific diabodies composed of non-covalently associated polypeptides are unstable and readily dissociate into non-functional monomers (see, e.g., Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

In the face of this challenge, the art has succeeded in developing stable, covalently bonded heterodimeric non-monospecific diabodies, termed DART® (Dual Affinity Re-Targeting Reagents) diabodies; see, e.g., United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538; WO 2008/157379; WO 2006/113665 and Sloan, D. D. et al. (2015) "*Targeting HIV Reservoir in Infected CD4 T Cells by Dual-Affinity Re-targeting Molecules (DARTs) that Bind HIV Envelope and Recruit Cytotoxic T Cells*," PLoS Pathog. 11(11):e1005233. doi: 10.1371/journal.ppat.1005233; Al Hussaini, M. et al. (2015) "*Targeting CD123 In AML Using A T-Cell Directed Dual-Affinity Re-Targeting (DART®) Platform*," Blood 127(1): 122-131; Chichili, G. R. et al. (2015) "*A CD3xCD123 Bispecific DART For Redirecting Host T Cells To Myelogenous Leukemia: Preclinical Activity And Safety In Nonhuman Primates*," Sci. Transl. Med. 7(289):289ra82; Moore, P. A. et al. (2011) "*Application Of Dual Affinity Retargeting Molecules To Achieve Optimal Redirected T-Cell Killing Of B-Cell Lymphoma*," Blood 117(17):4542-4551; Veri, M. C. et al. (2010) "*Therapeutic Control Of B Cell Activation Via Recruitment Of Fcgamma Receptor IIb (CD32B) Inhibitory Function With A Novel Bispecific Antibody Scaffold*," Arthritis Rheum. 62(7):1933-1943; Johnson, S. et al. (2010) "*Effector Cell Recruitment With Novel Fv-Based Dual-Affinity Re-Targeting Protein Leads To Potent Tumor Cytolysis And in vivo B-Cell Depletion*," J. Mol. Biol. 399(3):436-449; Marvin, J. S. et al. (2005) "*Recombinant Approaches To IgG-Like Bispecific Antibodies*," Acta Pharmacol. Sin. 26:649-658; Olafsen, T. et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27; Holliger, P. et al. (1993) "'*Diabodies': Small Bivalent And Bispecific Antibody Fragments*," Proc. Natl. Acad. Sci. (U.S.A.) 90:6444-6448. Such diabodies comprise two or more covalently complexed polypeptides and involve engineering one or more cysteine residues into each of the employed polypeptide species that permit disulfide bonds to form and thereby covalently bond two polypeptide chains. For example, the addition of a cysteine residue to the C-terminus of such constructs has been shown to allow disulfide bonding between the polypeptide chains, stabilizing the resulting heterodimer without interfering with the binding characteristics of the bivalent molecule.

Each of the two polypeptides of the simplest bispecific DART® diabody comprises three domains. The first polypeptide comprises (in the N-terminal to C-terminal direction): (i) a First Domain that comprises a binding region of a Light Chain Variable Domain of a first immunoglobulin (VL1), (ii) a Second Domain that comprises a binding region of a Heavy Chain Variable Domain of a second immunoglobulin (VH2), and (iii) a Third Domain that contains a cysteine residue (or a cysteine-containing domain) and a Heterodimer-Promoting Domain that serves to promote heterodimerization with the second polypeptide of the diabody and to covalently bond the diabody's first and second polypeptides to one another. The second polypeptide contains (in the N-terminal to C-terminal direction): (i) a First Domain that comprises a binding region of a Light Chain Variable Domain of the second immunoglobulin (VL2), (ii) a Second Domain that comprises a binding region of a Heavy Chain Variable Domain of the first immunoglobulin (VH1), and (iii) a Third Domain that contains a cysteine residue (or a cysteine-containing domain) and a complementary Heterodimer-Promoting Domain that complexes with the Heterodimer-Promoting Domain of the first polypeptide chain in order to promote heterodimerization with the first polypeptide chain. The cysteine residue (or a cysteine-containing domain) of the third domain of the second polypeptide chain serves to promote the covalent bonding of the second polypeptide chain to the first polypeptide chain of the diabody. Such molecules are stable, potent and have the ability to simultaneously bind two or more antigens. In one embodiment, the Third Domains of the first and second polypeptides each contain a cysteine residue, which serves to bind the polypeptides together via a disulfide bond. FIG. 1 provides a schematic of such a diabody, which utilizes E-coil/K-coil Heterodimer-Promoting domains and a cysteine containing linker for covalent bonding. As provided in FIG. 2 and FIGS. 3A-3C, one or both of the polypeptides may additionally possesses the sequence of a CH2-CH3 Domain, such that complexing between the two diabody polypeptides forms an Fc Region that is capable of binding to the Fc receptor of cells (such as B lymphocytes, dendritic cells, natural killer cells, macrophages, neutrophils, eosinophils, basophils and mast cells). As provided in more detail below, the CH2 and/or CH3 Domains of such polypeptide chains need not be identical in sequence, and advantageously are modified to foster complexing between the two polypeptide chains.

Figure 3A:
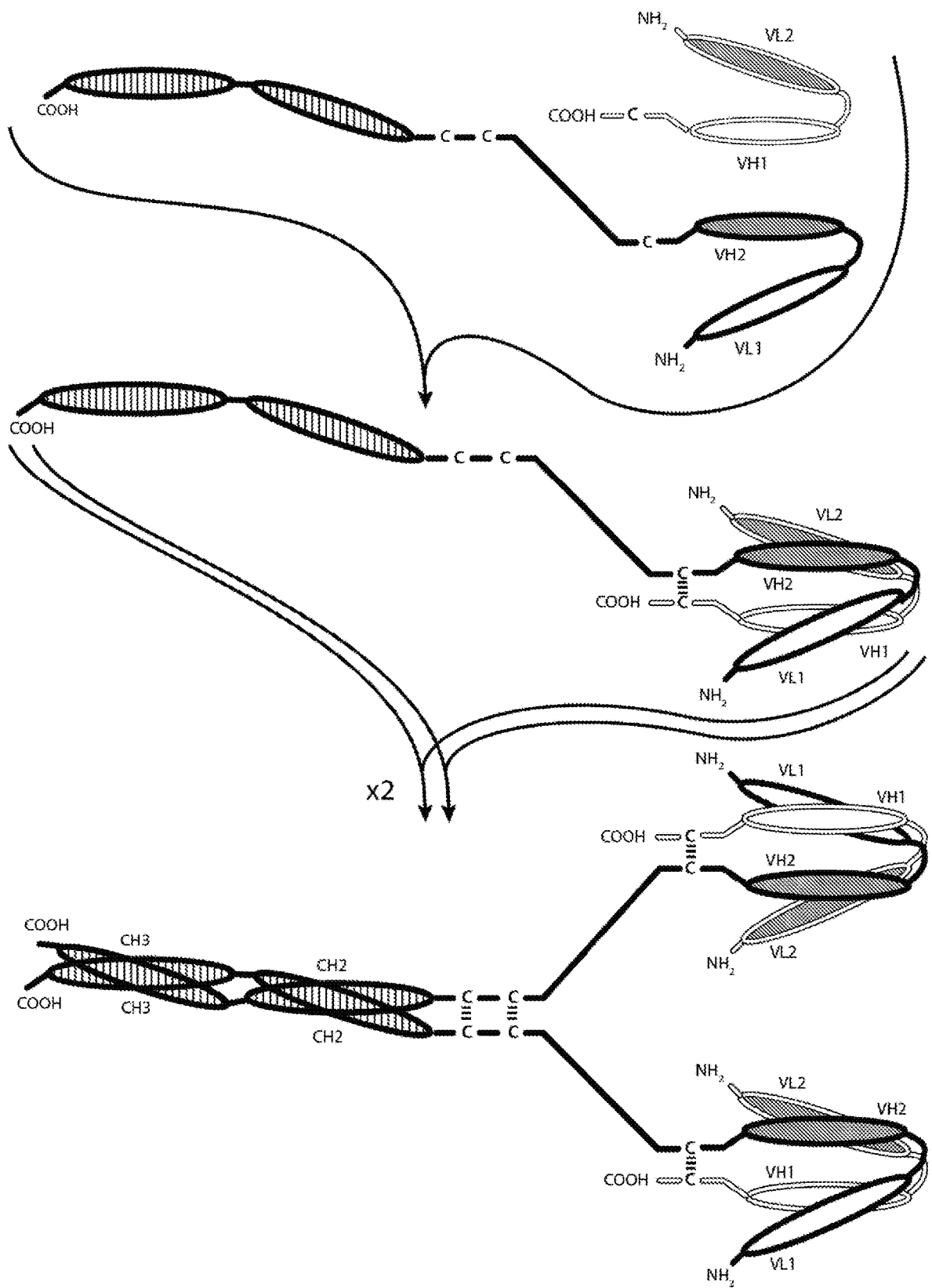
FIGS. 3A-3C provide schematics showing representative tetravalent diabodies having four epitope-binding sites composed of two pairs of polypeptide chains (i.e., four polypeptide chains in all). One polypeptide of each pair possesses a CH2 and CH3 Domain, such that the associated chains form all or part of an Fc Region. VL and VH Domains that recognize the same epitope are shown using the same shading or fill pattern. The two pairs of polypeptide chains may be same. In such embodiments wherein the VL and VH Domains recognize different epitopes (as shown in FIGS. 3A-3C) the resulting molecule possesses four epitope-binding sites and is bispecific and bivalent with respect to each bound epitope. In such embodiments wherein the VL and VH Domains recognize the same epitope (e.g., the same VL Domain CDRs and the same VH Domain CDRs are used on both chains), the resulting molecule possesses four epitope-binding sites and is monospecific and tetravalent with respect to a single epitope. Alternatively, the two pairs of polypeptides may be different. In such embodiments wherein the VL and VH Domains of each pair of polypeptides recognize different epitopes (as shown in FIG. 3C), the resulting molecule possesses four epitope-binding sites and is tetraspecific and monovalent with respect to each bound epitope.
Figure 3B:
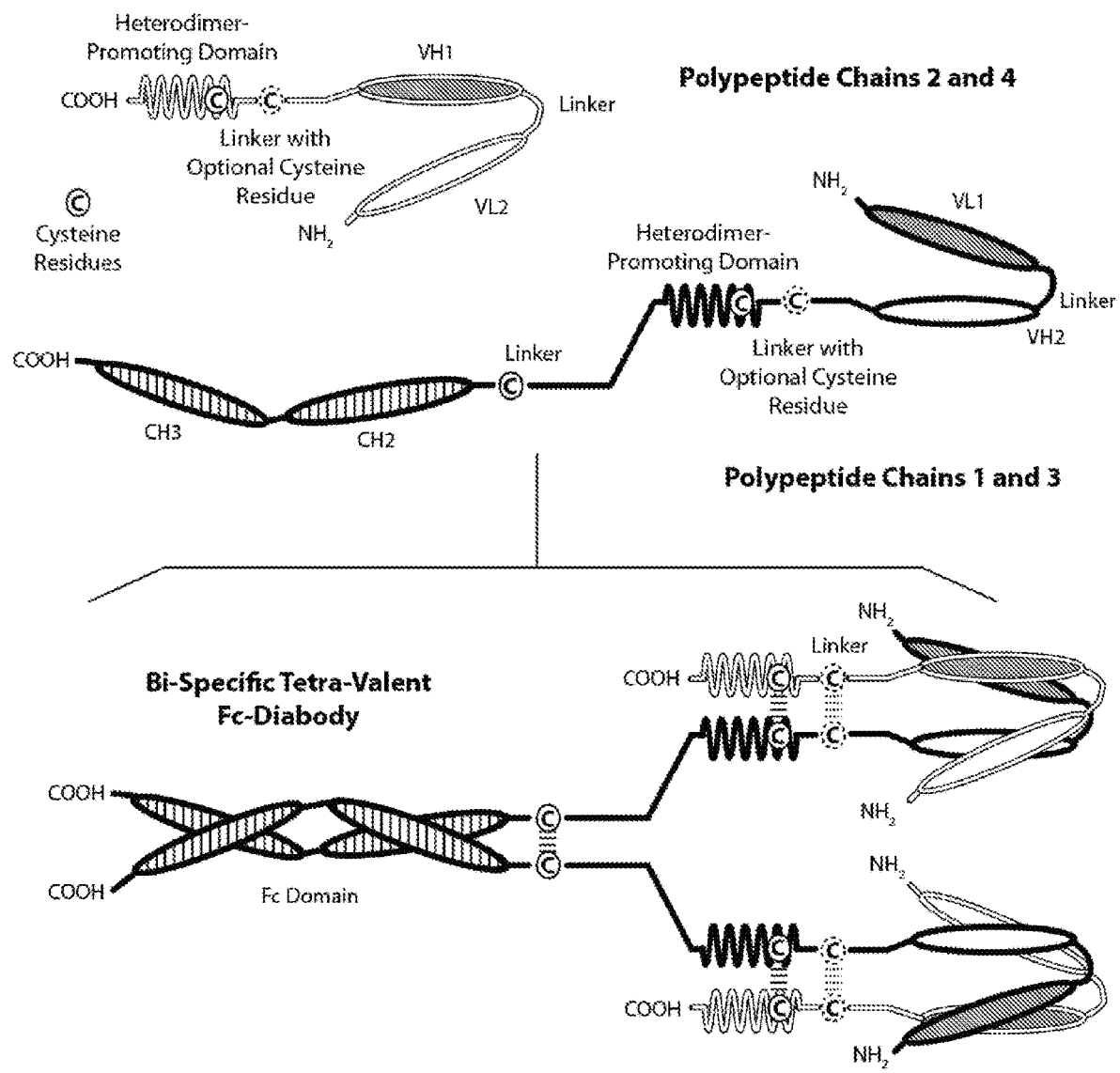
Figure 3C:
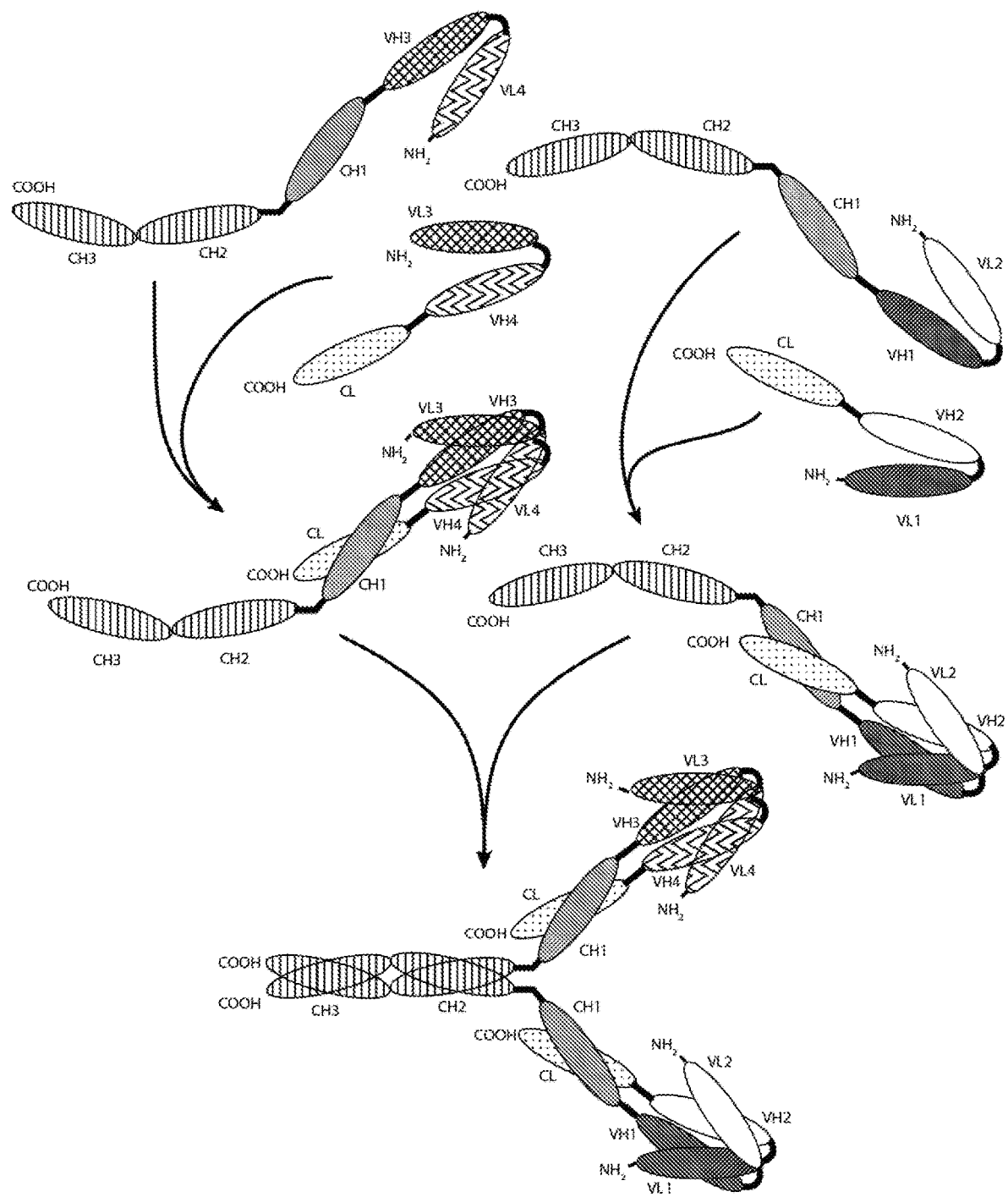

Many variations of such molecules have been described (see, e.g., United States Patent Publications No. 2015/0175697; 2014/0255407; 2014/0099318; 2013/0295121; 2010/0174053 and 2009/0060910; European Patent Publication No. EP 2714079; EP 2601216; EP 2376109; EP 2158221 and PCT Publications No. WO 2012/162068; WO 2012/018687; WO 2010/080538). These Fc Region-containing DART® diabodies may comprise two pairs of polypeptide chains. The first polypeptide chain comprises (in the N-terminal to C-terminal direction): (i) a First Domain that comprises a binding region of a Light Chain Variable Domain of a first immunoglobulin (VL1), (ii) a Second Domain that comprises a binding region of a Heavy Chain Variable Domain of a second immunoglobulin (VH2), (iii) a Third Domain that contains a cysteine residue (or a cysteine-containing domain) and a serves to promote heterodimerization with the second polypeptide of the diabody and to covalently bond the diabody's first and second polypeptides to one another, and (iv) a CH2-CH3 Domain. The second polypeptide contains (in the N-terminal to C-terminal direction): (i) a First Domain that comprises a binding region of a Light Chain Variable Domain of the second immunoglobulin (VL2), (ii) a Second Domain that comprises a binding region of a Heavy Chain Variable Domain of the first immunoglobulin (VH1), and (iii)) a Third Domain that contains a cysteine residue (or a cysteine-containing domain) and a Heterodimer-Promoting Domain that promotes heterodimerization with the first polypeptide chain. Here, two first polypeptides complex with each other to form an Fc Region. FIGS. 3A-3C provide schematics of three variations of such diabodies utilizing different Heterodimer-Promoting Domains.

Figure 4A:
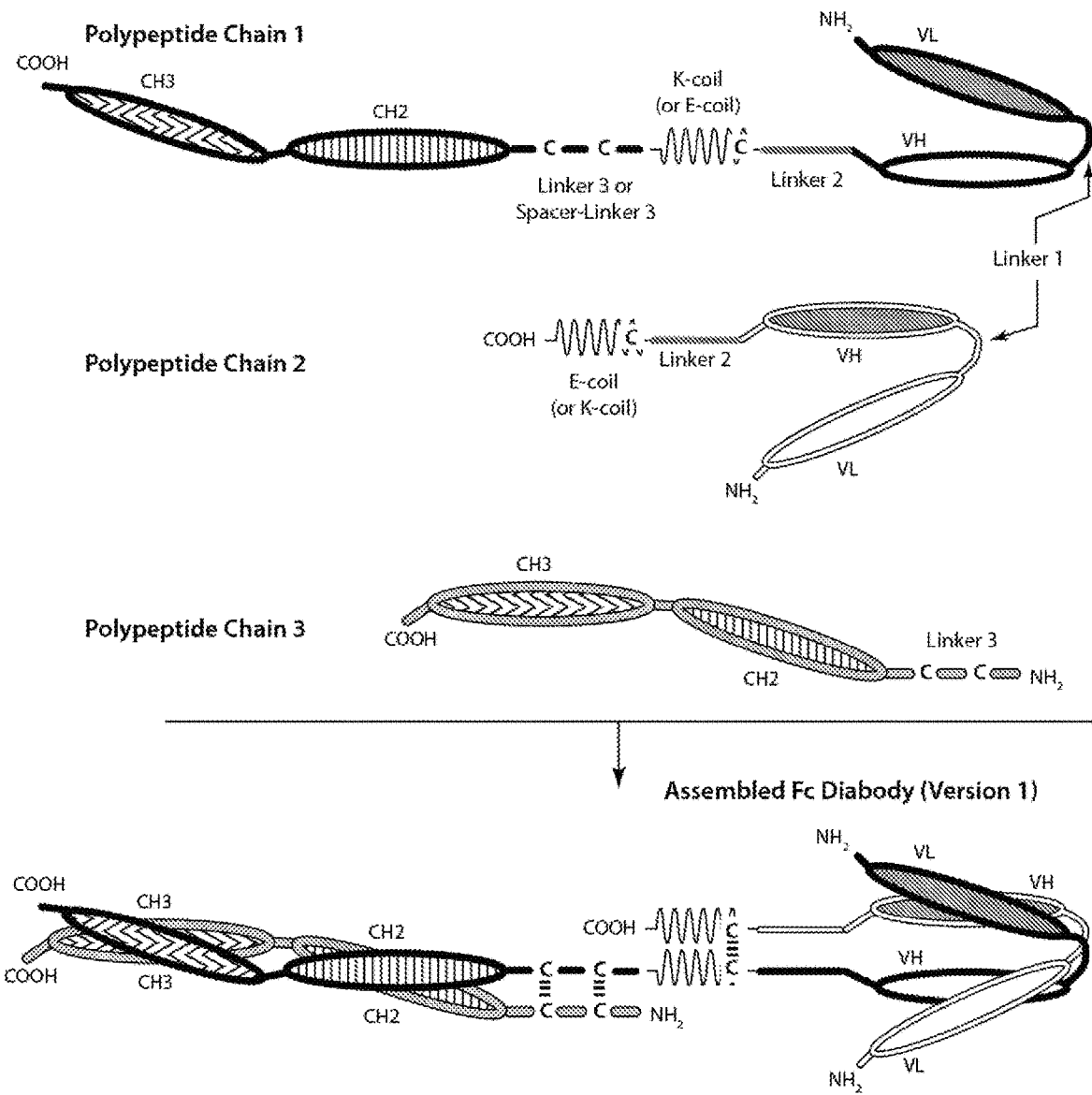
FIGS. 4A and 4B provide schematics of a representative covalently bonded diabody molecule having two epitope-binding sites composed of three polypeptide chains. Two of the polypeptide chains possess a CH2 and CH3 Domain, such that the associated chains form all or part of an Fc Region. The polypeptide chains comprising the VL and VH Domain further comprise a Heterodimer-Promoting Domain. VL and VH Domains that recognize the same epitope are shown using the same shading or fill pattern.
Figure 4B:
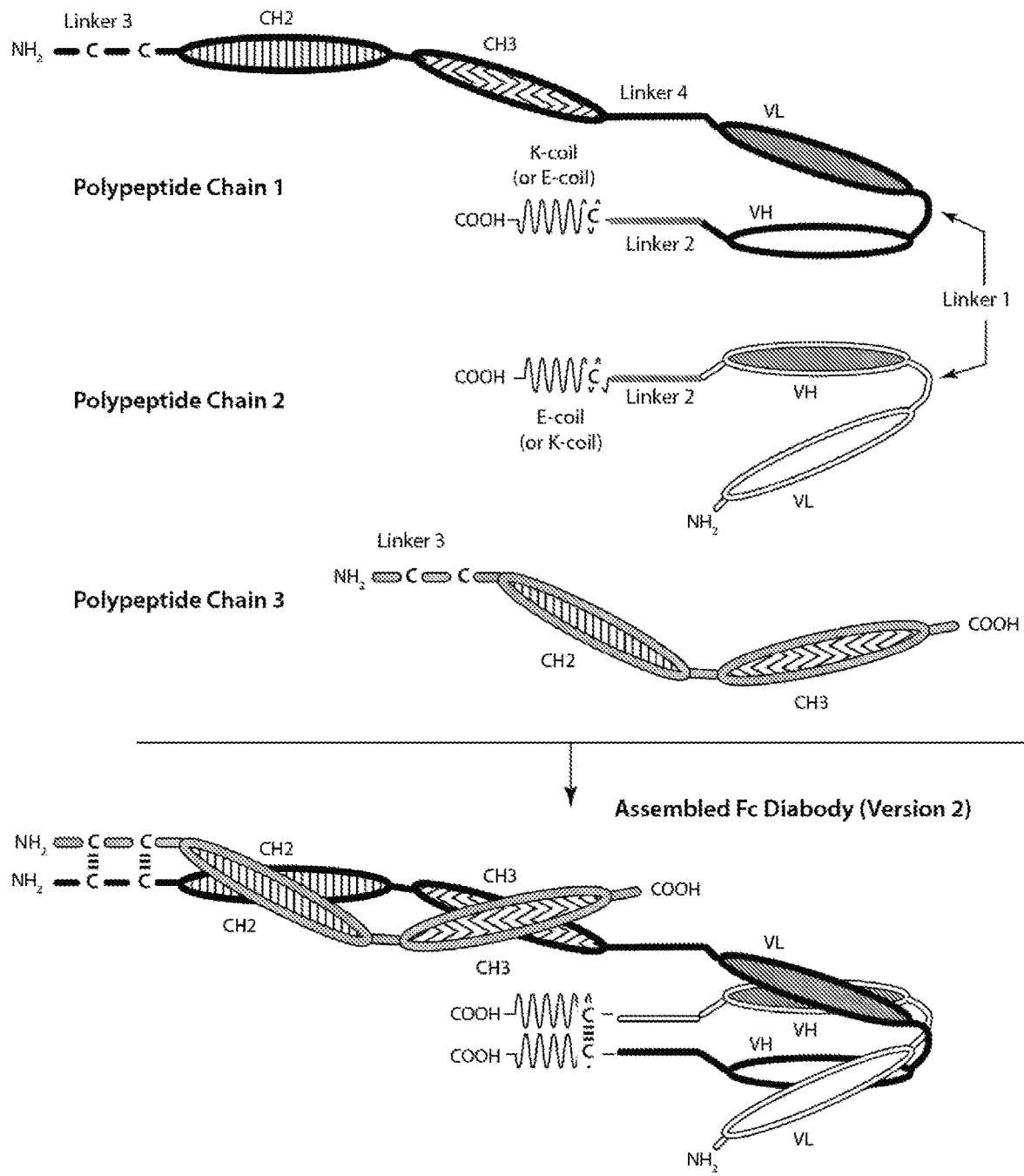

Other Fc-Region-containing DART® diabodies may comprise three polypeptide chains. The first polypeptide of such DART® diabodies contains three domains: (i) a VL1-containing Domain, (ii) a VH2-containing Domain and (iii) a Domain containing a CH2-CH3 sequence. The second polypeptide of such DART® diabodies contains: (i) a VL2-containing Domain, (ii) a VH1-containing Domain and (iii) a Domain that promotes heterodimerization and covalent bonding with the diabody's first polypeptide chain. The third polypeptide of such DART® diabodies comprises a CH2-CH3 sequence. Thus, the first and second polypeptide chains of such DART® diabodies associate together to form a VL1/VH1 binding site that is capable of binding to the epitope, as well as a VL2/VH2 binding site that is capable of binding to the second epitope. Such more complex DART® molecules also possess cysteine-containing domains which function to form a covalently bonded complex. Thus, the first and second polypeptides are bonded to one another through a disulfide bond involving cysteine residues in their respective Third Domains. Notably, the first and third polypeptide chains complex with one another to form an Fc Region that is stabilized via a disulfide bond. FIGS. 4A-4B provide schematics of such diabodies comprising three polypeptide chains.

Still other Fc-Region-containing DART® diabodies may comprise five polypeptide chains which may comprise the binding regions from the Light and Heavy Chain Variable Domains of up to three different immunoglobulins (referred to as VL1/VH1, VL2/VH2 and VL3/VH3). For example, the first polypeptide chain of such diabodies may contain: (i) a VH1-containing domain, (ii) a CH1-containing domain, and (iii) a Domain containing a CH2-CH3 sequence. The second and fifth polypeptide chains of such diabodies may contain: (i) a VL1-containing domain, and (ii) a CL-containing domain. The third polypeptide chain of such diabodies may contain: (i) a VH1-containing domain, (ii) a CH1-containing domain, (iii) a Domain containing a CH2-CH3 sequence, (iv) a VL2-containing Domain, (v) a VH3-containing Domain and (vi) a Heterodimer-Promoting Domain, where the Heterodimer-Promoting Domains promote the dimerization of the third chain with the fourth chain. The fourth polypeptide of such diabodies may contain: (i) a VL3-containing Domain, (ii) a VH2-containing Domain and (iii) a Domain that promotes heterodimerization and covalent bonding with the diabody's third polypeptide chain. Here, the first and third polypeptides complex with each other to form an Fc Region. Such more complex DART® molecules also possess cysteine-containing domains which function to form a covalently bonded complex, such that each polypeptide chain is bonded to at least one addition polypeptide chain through a disulfide bond involving cysteine residues.

Figure 5:
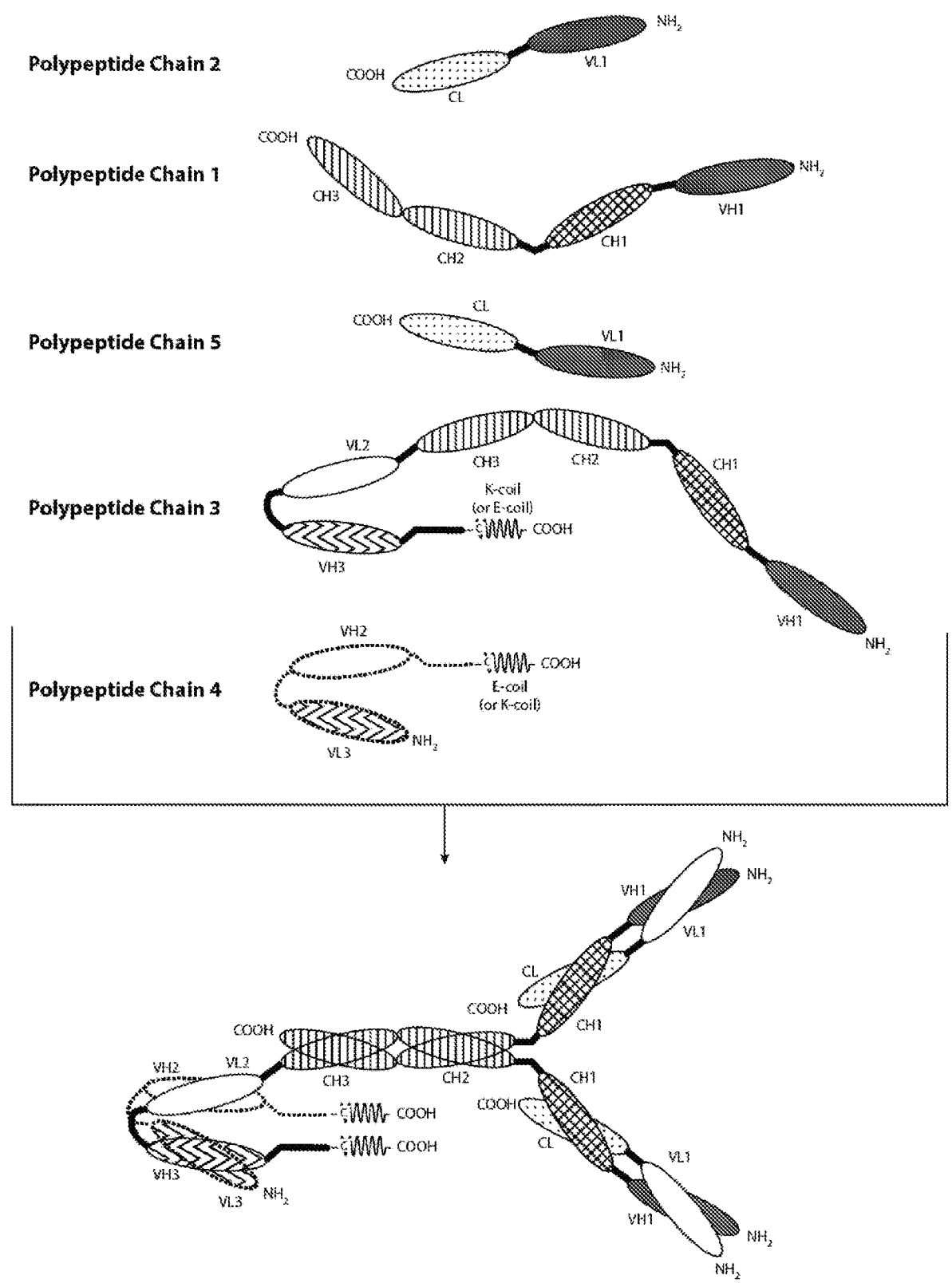
FIG. 5 provides the schematics of a representative covalently bonded diabody molecule having four epitope-binding sites composed of five polypeptide chains. Two of the polypeptide chains possess a CH2 and CH3 Domain, such that the associated chains form an Fc Region that comprises all or part of an Fc Region. The polypeptide chains comprising the linked VL and VH Domains further comprise a Heterodimer-Promoting Domain. VL and VH Domains that recognize the same epitope are shown using the same shading or fill pattern.

Preferably, such domains are ordered in the N-terminal to C-terminal direction. FIG. 5 provides schematics of such diabodies comprising five polypeptide chains Alternative constructs are known in the art for applications where a tetravalent molecule is desirable but an Fc is not required including, but not limited to, tetravalent tandem antibodies, also referred to as "TandAbs" (see, e.g. United States Patent Publications Nos. 2005-0079170, 2007-0031436, 2010-0099853, 2011-020667 2013-0189263; European Patent Publication Nos. EP 1078004, EP 2371866, EP 2361936 and EP 1293514; PCT Publications Nos. WO 1999/057150, WO 2003/025018, and WO 2013/013700) which are formed by the homo-dimerization of two identical chains each possessing a VH1, VL2, VH2, and VL2 Domain.

Recently, trivalent structures incorporating two diabody-type binding domains and one non-diabody-type domain and an Fc Region have been described (see, e.g., PCT Application No: PCT/US15/33076, titled "Tri-Specific Binding Molecules and Methods of Use Thereof," filed May 29, 2015; and PCT/US15/33081, titled "Tri-Specific Binding Molecules That Specifically Bind to Multiple Cancer Antigens and Methods of Use Thereof," filed May 29, 2015). Such trivalent molecules may be utilized to generate monospecific, bispecific or trispecific molecules. FIGS. 6A-6F provide schematics of such trivalent molecules comprising 3 or 4 polypeptide chains.

IV. The LAG-3-Binding Molecules of the Present Invention

The preferred LAG-3-binding molecules of the present invention include antibodies, diabodies, BiTEs, etc. and are capable of binding to a continuous or discontinuous (e.g., conformational) portion (epitope) of human LAG-3. The LAG-3-binding molecules of the present invention will preferably also exhibit the ability to bind to LAG-3 molecules of one or more non-human species, in particular, primate species (and especially a primate species, such as cynomolgus monkey). A representative human LAG-3 polypeptide (NCBI Sequence NP_002277.4; including a 22 amino acid residue signal sequence (shown underlined) and the 503 amino acid residue mature protein) has the amino acid sequence (SEQ ID NO:5):

MWEAQFLGLL FLQPLWVAPV KPLQPGAEVP VVWAQEGAPA

QLPCSPTIPL QDLSLLRRAG VTWQHQPDSG PPAAAPGHPL

APGPHPAAPS SWGPRPRRYT VLSVGPGGLR SGRLPLQPRV

QLDERGRQRG DFSLWLRPAR RADAGEYRAA VHLRDRALSC

RLRLRLGQAS MTASPPGSLR ASDWVILNCS FSRPDRPASV

HWFRNRGQGR VPVRESPHHH LAESFLFLPQ VSPMDSGPWG

CILTYRDGFN VSIMYNLTVL GLEPPTPLTV YAGAGSRVGL

PCRLPAGVGT RSFLTAKWTP PGGGPDLLVT GDNGDFTLRL

EDVSQAQAGT YTCHIHLQEQ QLNATVTLAI ITVTPKSFGS

PGSLGKLLCE VTPVSGQERF VWSSLDTPSQ RSFSGPWLEA

QEAQLLSQPW QCQLYQGERL LGAAVYFTEL SSPGAQRSGR

APGALPAGHL LLFLILGVLS LLLLVTGAFG FHLWRRQWRP

RRFSALEQGI HPPQAQSKIE ELEQEPEPEP EPEPEPEPEP EPEQL

In certain embodiments the LAG-3-binding molecules of the invention are characterized by any (one or more) of the following criteria:

(1) specifically binds human LAG-3 as endogenously expressed on the surface of a stimulated human T-cell;
(2) specifically binds human LAG-3 with an equilibrium binding constant ($K_D$) of 40 nM or less;
(3) specifically binds human LAG-3 with an equilibrium binding constant ($K_D$) of 0.5 nM or less;
(4) specifically binds non-human primate LAG-3 (e.g., LAG-3 of cynomolgus monkey);
(5) specifically binds non-human primate LAG-3 with an equilibrium binding constant ($K_D$) of 50 nM or less;
(6) specifically binds non-human primate LAG-3 with an equilibrium binding constant ($K_D$) of 5 nM or less;
(7) inhibits (i.e., blocks or interferes with) the binding of LAG-3 to MHC class II;
(8) stimulates an immune response;
(9) stimulates antigen specific T-cell response as a single agent;
(10) synergizes with an anti-PD-1 antibody to stimulate an antigen specific T-cell response;
(11) binds the same epitope of LAG-3 as the anti-LAG-3 antibody LAG-3 mAb 1 or LAG-3 mAb 6 and/or
(12) does not compete with the anti-LAG-3 antibody 257F (BMS 986016, Medarex/BMS) for LAG-3 binding (e.g., as measured by Biacore Analysis).

As used here the term "antigen specific T-cell response" refers to responses by a T-cell that result from stimulation of the T-cell with the antigen for which the T-cell is specific. Non-limiting examples of responses by a T-cell upon antigen specific stimulation include proliferation and cytokine production (e.g., TNF-α, IFN-γ production). The ability of a molecule to stimulate an antigen specific T-cell response may be determined, for example, using the Staphylococcus aureus Enterotoxin type B antigen ("SEB")-stimulated PBMC assay described herein.

The preferred LAG-3-binding molecules of the present invention possess the VH and/or VL Domains of murine anti-LAG-3 monoclonal antibodies "LAG-3 mAb 1," "LAG-3 mAb 2," "LAG-3 mAb 3," "LAG-3 mAb 4," "LAG-3 mAb 5," and/or "LAG-3 mAb 6" and more preferably possess 1, 2 or all 3 of the $CDR_{HS}$ of the VH Domain and/or 1, 2 or all 3 of the $CDR_{LS}$ of the VL Domain of such anti-LAG-3 monoclonal antibodies. Such preferred LAG-3-binding molecules include bispecific (or multispecific) antibodies, chimeric or humanized antibodies, BiTes, diabodies, etc, and such binding molecules having variant Fc Regions.

The invention particularly relates to LAG-3-binding molecules comprising a LAG-3 binding domain that possess:

(A) (1) the three $CDR_{HS}$ of the VH Domain of the anti-LAG-3 antibody LAG-3 mAb 1, or hLAG-3 mAb 1 VL4;
(2) the three $CDR_{LS}$ of the VL Domain of the anti-LAG-3 antibody LAG-3 mAb 1;
(3) the three $CDR_{HS}$ of the VH Domain of the anti-LAG-3 antibody LAG-3 mAb 1 and the three $CDR_{LS}$ of the VL Domain of the anti-LAG-3 antibody LAG-3 mAb 1;
(4) the VH Domain of the anti-LAG-3 antibody LAG-3 mAb 1;
(5) the VL Domain of the anti-LAG-3 antibody LAG-3 mAb 1;
(6) the VH and VL Domains of the anti-LAG-3 antibody LAG-3 mAb 1;
(B) (1) the three $CDR_{HS}$ of the VH Domain of the anti-LAG-3 antibody LAG-3 mAb 2;
(2) the three $CDR_{LS}$ of the VL Domain of the anti-LAG-3 antibody LAG-3 mAb 2;

(3) the three CDR$_{HS}$ of the VH Domain of the anti-LAG-3 antibody LAG-3 mAb 2 and the three CDR$_{LS}$ of the VL Domain of the anti-LAG-3 antibody LAG-3 mAb 2;
(4) the VH Domain of the anti-LAG-3 antibody LAG-3 mAb 2;
(5) the VL Domain of the anti-LAG-3 antibody LAG-3 mAb 2;
(6) the VH and VL Domains of the anti-LAG-3 antibody LAG-3 mAb 2;
(C) (1) the three CDR$_{HS}$ of the VH Domain of the anti-LAG-3 antibody LAG-3 mAb 3;
(2) the three CDR$_{LS}$ of the VL Domain of the anti-LAG-3 antibody LAG-3 mAb 3;
(3) the three CDR$_{HS}$ of the VH Domain of the anti-LAG-3 antibody LAG-3 mAb 3 and the three CDR$_{LS}$ of the VL Domain of the anti-LAG-3 antibody LAG-3 mAb 3;
(4) the VH Domain of the anti-LAG-3 antibody LAG-3 mAb 3;
(5) the VL Domain of the anti-LAG-3 antibody LAG-3 mAb 3;
(6) the VH and VL Domains of the anti-LAG-3 antibody LAG-3 mAb 3;
(D) (1) the three CDR$_{HS}$ of the VH Domain of the anti-LAG-3 antibody LAG-3 mAb 4;
(2) the three CDR$_{LS}$ of the VL Domain of the anti-LAG-3 antibody LAG-3 mAb 4;
(3) the three CDR$_{HS}$ of the VH Domain of the anti-LAG-3 antibody LAG-3 mAb 4 and the three CDR$_{LS}$ of the VL Domain of the anti-LAG-3 antibody LAG-3 mAb 4;
(4) the VH Domain of the anti-LAG-3 antibody LAG-3 mAb 4;
(5) the VL Domain of the anti-LAG-3 antibody LAG-3 mAb 4;
(6) the VH and VL Domains of the anti-LAG-3 antibody LAG-3 mAb 4;
(E) (1) the three CDR$_{HS}$ of the VH Domain of the anti-LAG-3 antibody LAG-3 mAb 5;
(2) the three CDR$_{LS}$ of the VL Domain of the anti-LAG-3 antibody LAG-3 mAb 5;
(3) the three CDR$_{HS}$ of the VH Domain of the anti-LAG-3 antibody LAG-3 mAb 5 and the three CDR$_{LS}$ of the VL Domain of the anti-LAG-3 antibody LAG-3 mAb 5;
(4) the VH Domain of the anti-LAG-3 antibody LAG-3 mAb 5;
(5) the VL Domain of the anti-LAG-3 antibody LAG-3 mAb 5;
(6) the VH and VL Domains of the anti-LAG-3 antibody LAG-3 mAb 5;
(F) (1) the three CDR$_{HS}$ of the VH Domain of the anti-LAG-3 antibody LAG-3 mAb 6;
(2) the three CDR$_{LS}$ of the VL Domain of the anti-LAG-3 antibody LAG-3 mAb 6;
(3) the three CDR$_{HS}$ of the VH Domain of the anti-LAG-3 antibody LAG-3 mAb 6 and the three CDR$_{LS}$ of the VL Domain of the anti-LAG-3 antibody LAG-3 mAb 6;
(4) the VH Domain of the anti-LAG-3 antibody LAG-3 mAb 6;
(5) the VL Domain of the anti-LAG-3 antibody LAG-3 mAb 6;
(6) the VH and VL Domains of the anti-LAG-3 antibody LAG-3 mAb 6,
(G) (1) the three CDR$_{LS}$ of the VL Domain of the anti-LAG-3 antibody hLAG-3 mAb 1 VL4;
(2) the three CDR$_{HS}$ of the VH Domain of the anti-LAG-3 antibody LAG-3 mAb 1 and the three CDRs of the VL Domain of the anti-LAG-3 antibody hLAG-3 mAb 1 VL4; or that binds, or competes for binding with, the epitope that LAG-3 mAb 1, LAG-3 mAb 2, LAG-3 mAb 3, LAG-3 mAb 4, LAG-3 mAb 5 or LAG-3 mAb 6 immunospecifically binds.

A. The Anti-LAG-3 Antibody LAG-3 mAb 1

1. Murine Anti-Human Antibody LAG-3 mAb 1

The amino acid sequence of the VH Domain of LAG-3 mAb 1 (SEQ ID NO:6) is shown below (CDR$_H$ residues are shown underlined).

```
QIQLVQSGPE LKKPGETVKI SCKASGYTFR NYGMNWVKQA

PGKVLKWMGW INTYTGESTY ADDFEGRFAF SLGTSASTAY

LQINILKNED TATYFCARES LYDYYSMDYW GQGTSVTVSS

CDR_H1 of LAG-3 mAb 1 (SEQ ID NO: 8):

NYGMN

CDR_H2 of LAG-3 mAb 1 (SEQ ID NO: 9):

WINTYTGESTYADDFEG

CDR_H3 of LAG-3 mAb 1 (SEQ ID NO: 10):

ESLYDYYSMDY
```

An exemplary polynucleotide that encodes the VH Domain of LAG-3 mAb 1 is SEQ ID NO:7 (nucleotides encoding the CDR$_H$ residues are shown underlined):

```
cagatccagt tggtgcagtc tggacctgag ctgaagaagc ctggagagac agtcaagatc tcctgcaagg cttctgggta taccttcaga aactatggaa tgaactgggt gaagcaggct ccaggaaagg ttttaaagtg gatgggctgg ataaacacct acactggaga gtcaacatat gctgatgact cgagggacg gtttgccttc tctttgggaa cctctgccag cactgcctat ttgcagatca acatcctcaa aaatgaggac acggctacat atttctgtgc aagagaatcc ctctatgatt actattctat ggactactgg ggtcaaggaa cctcagtcac cgtctcctca
```

The amino acid sequence of the VL Domain of LAG-3 mAb 1 (SEQ ID NO:11) is shown below (CDR$_L$ residues are shown underlined):

```
DVVVTQTPLT LSVTIGQPAS ISCKSSQSLL HSDGKTYLNW

LLQRPGQSPE RLIYLVSELD SGVPDRFTGS GSGTDFTLKI

SRVEAEDLGV YYCWQGTHFP YTFGGGTKLE IK

CDR_L1 of LAG-3 mAb 1 (SEQ ID NO: 13):

KSSQSLLHSDGKTYLN

CDR_L2 of LAG-3 mAb 1 (SEQ ID NO: 14):

LVSELDS

CDR_L3 of LAG-3 mAb 1 (SEQ ID NO: 15):

WQGTHFPYT
```

An exemplary polynucleotide that encodes the VL Domain of LAG-3 mAb 1 is SEQ ID NO:12 (nucleotides encoding the CDR$_L$ residues are shown underlined):

```
gatgttgtgg tgacccagac tccactcact ttgtcggtta ccattggaca accagcctcc atctcttgca agtcaagtca gagcctctta catagtgatg gaaagacata tttgaattgg ttgttacaga ggccaggcca gtctccagag cgcctaatct atctggtgtc tgaactggac tctggagtcc ctgacaggtt cactggcagt ggatcaggga cagatttcac actgaaaatc agcagagtgg aggctgagga tttgggagtt tattattgct ggcaaggtac acatttccg tacacgttcg gagggggac caagctggaa ataaaa
```

2. Humanization of the Anti-LAG-3 Antibody LAG-3 mAb 1 to Form "hLAG-3 mAb 1"

The above-described murine anti-LAG-3 antibody LAG-3mAb 1 was humanized in order to demonstrate the capability of humanizing an anti-LAG-3 antibody so as to decrease its antigenicity upon administration to a human recipient. The humanization yielded two humanized VH Domains, designated herein as "hLAG-3 mAb 1 VH-1," and "hLAG-3 mAb 1 VH-2," and four humanized VL Domains designated herein as "hLAG-3 mAb 1 VL-1," "hLAG-3 mAb 1 VL-2," "hLAG-3 mAb 1 VL-3," and "hLAG-3 mAb 1 VL-4." Any of the humanized VL Domains may be paired with the humanized VH Domains. Accordingly, any antibody comprising one of the humanized VL Domains paired with the humanized VH Domain is referred to generically as "hLAG-3 mAb 1," and particular combinations of humanized VH/VL Domains are referred to by reference to the specific VH/VL Domains, for example a humanized antibody comprising hLAG-3 mAb 1 VH-1 and hLAG-3 mAb 1 VL-2 is specifically referred to as "hLAG-3 mAb 1(1.2)."

The amino acid sequence of the VH Domain of hLAG-3 mAb 1 VH-1 (SEQ ID NO:16) is shown below (CDR$_H$ residues are shown underlined):

```
QVQLVQSGAE VKKPGASVKV SCKASGYTFT NYGMNWVRQA

PGQGLEWMGW INTYTGESTY ADDFEGRFVF SMDTSASTAY

LQISSLKAED TAVYYCARES LYDYYSMDYW GQGTTVTVSS
```

An exemplary polynucleotide that encodes hLAG-3 mAb 1 VH-1 is SEQ ID NO:17 (nucleotides encoding the CDR$_H$ residues are shown underlined):

```
caggtgcaac tggttcaatc cggcgccgag gtgaaaaagc ctggcgcctc cgtgaaagtg tcctgtaagg catctgggta tacgttcaca aattatggta tgaactgggt gcgacaggca ccagggcagg gactggaatg gatggggtgg atcaatactt atacaggcga gagtacttat gctgacgatt tcgagggcag atttgtcttc tccatggaca ccagcgctag taccgcttat ctccagatta gttctctcaa ggcggaggac acagctgttt attattgtgc ccgcgagagt ttgtatgact actatagcat ggattactgg ggacaaggta caaccgtgac agtgagttcc
```

The amino acid sequence of the VH Domain of hLAG-3 mAb 1 VH-2 Q ID NO:18) is shown below (CDR$_H$ residues are shown underlined):

```
QVQLVQSGAE VKKPGASVKV SCKASGYTFT NYGMNWVRQA

PGQGLEWMGW INTYTGESTY ADDFEGRFVF SMDTSASTAY

LQISSLKAED TAVYFCARES LYDYYSMDYW GQGTTVTVSS
```

An exemplary polynucleotide that encodes hLAG-3 mAb 1 VH-2 is SEQ ID NO:19 (nucleotides encoding the CDR$_H$ residues are shown underlined):

```
caggtgcaac tggttcaatc cggcgccgag gtgaaaaagc ctggcgcctc cgtgaaagtg tcctgtaagg catctgggta tacgttcaca aattatggta tgaactgggt gcgacaggca ccagggcagg gactggaatg gatggggtgg atcaatactt atacaggcga gagtacttat gctgacgatt tcgagggcag atttgtcttc tccatggaca ccagcgctag taccgcttat ctccagatta gttctctcaa ggcggaggac acagctgttt atttctgtgc ccgcgagagt ttgtatgact actatagcat ggattactgg ggacaaggta caaccgtgac agtgagttcc
```

The amino acid sequence of the VL Domain of hLAG-3 mAb 1 VL-1 (SEQ ID NO:20) is shown below (CDR$_L$ residues are shown underlined):

```
DIVMTQTPLS LSVTPGQPAS ISCKSSQSLL HSDGKTYLNW

LLQKPGQSPE RLIYLVSELD SGVPDRFSGS GSGTDFTLKI

SRVEAEDVGV YYCWQGTHFP YTFGGGTKVE IK
```

An exemplary polynucleotide that encodes hLAG-3 mAb 1 VL-1 is SEQ ID NO:21 (nucleotides encoding the CDR$_L$ residues are shown underlined):

```
gatatcgtta tgactcagac accactgtca ctgagtgtga ccccaggtca gcccgctagt atttcctgta aatcatccca gtccctcctg catagcgatg gaaagaccta tttgaactgg cttctgcaga aaccaggcca aagtccagag agattgatct acctcgtttc agaactcgac agtggagtgc ccgatcgctt ctcagggtcc ggctctggga ctgattttac tctcaagatc tcaagagtgg aggccgagga cgtcggggtt tactactgtt ggcagggtac ccacttccct tatacatttg gcggaggcac aaaagtggag attaaa
```

The amino acid sequence of the VL Domain of hLAG-3 mAb 1 VL-2 (SEQ ID NO:22) is shown below (CDR$_L$ residues are shown underlined):

```
DIVMTQTPLS LSVTPGQPAS ISCKSSQSLL HSDGKTYLNW

LLQRPGQSPE RLIYLVSELD SGVPDRFSGS GSGTDFTLKI

SRVEAEDVGV YYCWQGTHFP YTFGGGTKVE IK
```

An exemplary polynucleotide that encodes hLAG-3 mAb 1 VL-2 is SEQ ID NO:23 (nucleotides encoding the CDR$_L$ residues are shown underlined):

```
gatatcgtta tgactcagac accactgtca ctgagtgtga ccccaggtca gcccgctagt atttcctgta aatcatccca gtccctcctg catagcgatg gaaagaccta tttgaactgg cttctgcaga gaccaggcca aagtccagag agattgatct acctcgtttc agaactcgac agtggagtgc ccgatcgctt ctcagggtcc ggctctggga ctgattttac tctcaagatc tcaagagtgg aggccgagga cgtcggggtt tactactgtt ggcagggtac ccacttccct tatacatttg gcggaggcac aaaagtggag attaaa
```

The amino acid sequence of the VL Domain of hLAG-3 mAb 1 VL-3 (SEQ ID NO:24) is shown below (CDR$_L$ residues are shown underlined):

```
DIVMTQTPLS LSVTPGQPAS ISCKSSQSLL HSDGKTYLNW

LLQKPGQPPE RLIYLVSELD SGVPDRFSGS GSGTDFTLKI

SRVEAEDVGV YYCWQGTHFP YTFGGGTKVE IK
```

An exemplary polynucleotide that encodes hLAG-3 mAb 1 VL-3 is SEQ ID NO:25 (nucleotides encoding the CDR$_L$ residues are shown underlined):

```
gatatcgtta tgactcagac accactgtca ctgagtgtga ccccaggtca gcccgctagt atttcctgta aatcatccca gtccctcctg catagcgatg gaaagaccta tttgaactgg cttctgcaga aaccaggcca accgccagag agattgatct acctcgtttc agaactcgac agtggagtgc ccgatcgctt ctcagggtcc ggctctggga ctgattttac tctcaagatc tcaagagtgg aggccgagga cgtcggggtt tactactgtt ggcagggtac ccacttccct tatacatttg gcggaggcac aaaagtggag attaaa
```

The amino acid sequence of the VL Domain of hLAG-3 mAb 1 VL-4 (SEQ ID NO:26) is shown below (CDR$_L$ residues are shown underlined):

```
DIVMTQTPLS LSVTPGQPAS ISCKSSQSLL HSDAKTYLNW

LLQKPGQPPE RLIYLVSELD SGVPDRFSGS GSGTDFTLKI

SRVEAEDVGV YYCWQGTHFP YTFGGGTKVE IK
```

An exemplary polynucleotide that encodes hLAG-3 mAb 1 VL-4 is SEQ ID NO:27 (nucleotides encoding the CDR$_L$ residues are shown underlined):

```
gatatcgtta tgactcagac accactgtca ctgagtgtga ccccaggtca gcccgctagt atttcctgta aatcatccca gtccctcctg catagcgatg caaagaccta tttgaactgg cttctgcaga aaccaggcca accgccagag agattgatct acctcgtttc agaactcgac agtggagtgc ccgatcgctt ctcagggtcc ggctctggga ctgattttac tctcaagatc tcaagagtgg aggccgagga cgtcggggtt tactactgtt ggcagggtac ccacttccct tatacatttg gcggaggcac aaaagtggag attaaa
```

The CDR$_L$1 of the VL Domain of hLAG-3 mAb 1 VL-4 comprises an glycine to alanine amino acid substitution and has the amino acid sequence: KSSQSLLHSDAKTYLN (SEQ ID NO:28), the substituted alanine is shown underlined). It is contemplated that a similar substitution may be incorporated into any of the LAG-3 mAb 1 CDR$_L$1 Domains described above.

B. The Anti-LAG-3 Antibody LAG-3 mAb 2

The amino acid sequence of the VH Domain of LAG-3 mAb 2 (SEQ ID NO:29) is shown below (CDR$_H$ residues are shown underlined):

```
EVQLQQSGPE LVKPGASVKI SCKTSGYTFT DYNIHWLRQS

HGESLEWIGY IYPYSGDIGY NQKFKNRATL TVDNSSSTAY

MDLRSLTSED SAVFYCARWH RNYFGPWFAY WGQGTPVTVS A
```

CDR$_H$1 of LAG-3 mAb 2 (SEQ ID NO: 31):

DYNIH

VH CDR$_H$2 of LAG-3 mAb 2 (SEQ ID NO: 32):

YIYPYSGDIGYNQKFKN

VH CDR$_H$3 of LAG-3 mAb 2 (SEQ ID NO: 33):

WHRNYFGPWFAY

An exemplary polynucleotide that encodes the VH Domain of LAG-3 mAb 2 is SEQ ID NO:30 (nucleotides encoding the CDR$_H$ residues are shown underlined):

```
gaggtccagc ttcagcagtc aggacctgag ctggtgaaac ctggggcctc agtgaagatt tcctgcaaga cttctggata cacatttact gactacaaca tacactggtt gaggcagagc catggagaga gccttgagtg gattggatat atttatcctt acagtggtga tattggatac aaccagaagt tcaagaacag ggccacattg actgtagaca attcctccag cacagcctac atggatctcc gcagcctgac atctgaagac tctgcagtct tttactgtgc aagatggcac aggaactact ttggcccctg gtttgcttac tggggccaag ggactccggt cactgtctct gca
```

The amino acid sequence of the VL Domain of LAG-3 mAb 2 (SEQ ID NO:34) is shown below (CDR$_L$ residues are shown underlined):

```
DIVLTQSPAS LAVSLGQRAT ISCKASQSVD YDGESYMNWY

QQKPGQPPKL LIYVVSNLES GIPARFSGSG SGTDFTLNIH

PVEEEDAATY YCQQSSEDPL TFGAGTKLEL K
```

CDR$_L$1 of LAG-3 mAb 2 (SEQ ID NO: 36):

KASQSVDYDGESYMN

CDR$_L$2 of LAG-3 mAb 2 (SEQ ID NO: 37):

VVSNLES

CDR$_L$3 of LAG-3 mAb 2 (SEQ ID NO: 38):

QQSSEDPLT

An exemplary polynucleotide that encodes the VL Domain of LAG-3 mAb 2 is SEQ ID NO:35 (nucleotides encoding the CDR$_L$ residues are shown underlined):

```
gacattgtgc tgacccaatc tccagcttct ttggctgtgt ctctagggca gagggccacc atctcctgca aggccagcca aagtgttgat tatgatggtg aaagttatat gaactggtac caacagaaac caggacagcc acccaaactc ctcatttatg ttgtatccaa tctagaatct gggatcccag ccaggtttag tggcagtggg tctgggacag acttcaccct caacatccat cctgtggagg aggaggatgc tgcaacctat tactgtcagc aaagtagtga ggatccgctc acgttcggtg ctgggaccaa gctggagctg aaa
```

C. The Anti-LAG-3 Antibody LAG-3 mAb 3

The amino acid sequence of the VH Domain of LAG-3 mAb 3 (SEQ ID NO:39) is shown below (CDR$_H$ residues are shown underlined):

EVRLQQSGPE LVKPGASVKI SCKASGYTFT DYNIHWVRQS

HGQSLEWIGY IYPYNGDTGY NQKFKTKATL TVDNSSNTAY

MELRSLASED SAVYYCTRWS RNYFGPWFAY WGQGTLVTVS A

CDR$_H$1 of LAG-3 mAb 3 (SEQ ID NO: 41):

DYNIH

CDR$_H$2 of LAG-3 mAb 3 (SEQ ID NO: 42):

YIYPYNGDTGYNQKFKT

CDR$_H$3 of LAG-3 mAb 3 (SEQ ID NO: 43):

WSRNYFGPWFAY

An exemplary polynucleotide that encodes the VH Domain of LAG-3 mAb 3 is SEQ ID NO:40 (nucleotides encoding the CDR$_H$ residues are shown underlined):

```
gaggtccggc ttcagcagtc aggacctgag ctggtgaaac ctggggcctc agtgaagata tcctgcaagg cttctggata cacattcact gactacaaca ttcactgggt gaggcagagc catggacaga gccttgagtg gattggatat atttatcctt ataatggtga tactggctac aaccagaagt tcaagaccaa ggccacattg actgtagaca attcctccaa cacagcctac atggaactcc gcagcctggc atctgaagac tctgcagtct
```
attactgtac aagatggagc aggaactact ttggcccctg gtttgcttac tggggccaag ggactctggt cactgtctct gca

The amino acid sequence of the VL Domain of LAG-3 mAb 3 (SEQ ID NO:44) is shown below (CDR$_L$ residues are shown underlined):

DIVLTQSPTS LAVSLGQRAT ISCKASQSVD YDGDSYMNWY

QQKPGQPPKL LIYAASNLES GIPARFSGSG SGTDFTLNIH

PVEEEDAATY YCQQSSEDPL TFGAGTKLEL K

CDR$_L$1 of LAG-3 mAb 3 (SEQ ID NO: 46):

KASQSVDYDGDSYMN

CDR$_L$2 of LAG-3 mAb 3 (SEQ ID NO: 47):

AASNLES

CDR$_L$3 of LAG-3 mAb 3 (SEQ ID NO: 48):

QQSSEDPLT

An exemplary polynucleotide that encodes the VL Domain of LAG-3 mAb 3 is SEQ ID NO:45 (nucleotides encoding the CDR$_H$ residues are shown underlined):

```
gacattgtgc tgacccaatc tccaacttct ttggctgtgt ctctagggca gagggccacc atctcctgca aggccagcca aagtgttgat tatgatggtg atagttatat gaactggtat caacagaaac caggacagcc acccaaactc ctcatctatg ctgcatccaa tctagaatct gggatcccag ccaggtttag tggcagtggg tctgggacag acttcaccct caacatccat cctgtggagg aggaggatgc tgcaacctat tactgtcagc aaagtagtga ggatccgctc acgttcggtg ctgggaccaa gctggagctg aaa
```

D. The Anti-LAG-3 Antibody LAG-3 mAb 4

The amino acid sequence of the VH Domain of LAG-3 mAb 4 (SEQ ID NO:49) is shown below (CDR$_H$ residues are shown underlined):

EVQLHQSGPE LVKPGASVKI SCKTSGYTFT DYNIHWVKQS

HGKSLEWIGY IYPYNGDAGY NQNFKTKATL TVDNSSSTAY

MELRSLTSED SAVYYCARWN MNYFGPWFAY WGQGTLVTVS A

CDR$_H$1 of LAG-3 mAb 4 (SEQ ID NO: 51):

DYNIH

CDR$_H$2 of LAG-3 mAb 4 (SEQ ID NO: 52):

YIYPYNGDAGYNQNFKT

CDR$_H$3 of LAG-3 mAb 4 (SEQ ID NO: 53):

WNMNYFGPWFAY

An exemplary polynucleotide that encodes the VH Domain of LAG-4 mAb 4 is SEQ ID NO:50 (nucleotides encoding the CDR$_H$ residues are shown underlined):

```
gaggtccagc ttcaccagtc aggacctgag ctggtgaaac ctggggcctc agtgaagata tcctgcaaga cttctggata cactttcact gactacaaca tacactgggt gaagcagagc catggaaaga gccttgagtg gattggatat atttatcctt acaatggtga tgctggctac aaccagaact tcaagaccaa ggccacattg actgtagaca attcctccag cacagcctac atggagctcc gcagcctgac atctgaggac tctgcagtct attactgtgc aagatggaac atgaactact ttggcccctg gtttgcttac tggggccaag ggactctggt cactgtctct gcg
```

The amino acid sequence of the VL Domain of LAG-3 mAb 4 (SEQ ID NO:54) is shown below (CDR$_L$ residues are shown underlined):

```
DIVLTQSPAS LAVSLGQRAT ISCKASQSVD YDGVTYINWY

QQKPGQPPKL LIFAASNLES GIPARFSGSG SGTDFTLNIH

PVEEEDAATY YCQQSNEDPL TFGAGTKLEL K

CDR$_L$1 of LAG-3 mAb 4 (SEQ ID NO: 56):
KASQSVDYDGVTYIN

CDR$_L$2 of LAG-3 mAb 4 (SEQ ID NO: 7570):
AASNLES

CDR$_L$3 of LAG-3 mAb 4 (SEQ ID NO: 58):
QQSNEDPLT
```

An exemplary polynucleotide that encodes the VL Domain of LAG-3 mAb 4 is SEQ ID NO:55 (nucleotides encoding the CDR$_L$ residues are shown underlined):

```
gacattgtgc tgacccaatc tccagcttct ttggctgtgt ctctagggca gagggccacc atctcctgca aggccagcca aagtgttgat tatgatggtg ttacttatat caactggtac caacagaaac caggacagcc acccaaactc ctcatctttg ctgcatccaa tctagaatct gggatcccag ccaggtttag tggcagtggg tctgggacag acttcaccct caacatccat cctgtggagg aggaggatgc tgcaacctat tactgtcagc aaagtaatga ggatccgctc acgttcggtg ctgggaccaa gctggagctg aaa
```

E. The Anti-LAG-3 Antibody LAG-3 mAb 5

The amino acid sequence of the VH Domain of LAG-3 mAb 5 (SEQ ID NO:59) is shown below (CDR$_H$ residues are shown underlined):

```
EVQLQQSGPE LVKPGASVKI SCKASGYTFT DYNIHWVKQS

PGKSLEWIGY IYPYSGDFGY NQKFKSKATL TVDNSSTAY

MDLRSLTSED SAVFYCARWH RNYFGPWFAY WGQGTLVTVS

A

CDR$_H$1 of LAG-3 mAb 5 (SEQ ID NO: 61):
DYNIH

CDR$_H$2 of LAG-3 mAb 5 (SEQ ID NO: 62):
YIYPYSGDFGYNQKFKS

CDR$_H$3 of LAG-3 mAb 5 (SEQ ID NO: 63):
WHRNYFGPWFAY
```

An exemplary polynucleotide that encodes the VH Domain of LAG-3 mAb 5 is SEQ ID NO:60 (nucleotides encoding the CDR$_H$ residues are shown underlined):

```
gaggtccagc ttcagcagtc aggacctgag ctggtgaaac ctggggcctc agtgaagatt tcctgcaaag cttctggata cacatttact gactacaaca tacactgggt gaagcagagc cctggaaaga gccttgaatg gattggatat atttatcctt acagtggtga ttttggatac aaccagaagt tcaagagcaa ggccacattg actgtagaca attcctccag cacagcctac atggatctcc gcagcctgac atctgaggac tctgcagtct tttactgtgc aagatggcac aggaactact ttggcccctg gtttgcttac tggggccaag ggactctggt cactgtctct gca
```

The amino acid sequence of the VL Domain of LAG-3 mAb 5 (SEQ ID NO:64) is shown below (CDR$_L$ residues are shown underlined):

```
DIVLTQSPAS LAVSLGQRAT ISCKASQSVD YDGESYMNWY

QQKPGQPPKL LIYVVSNLES GIPARFSGSG SGTDFTLNIH

PVEEEDAATY YCQQSSEDPL TFGAGTKLEL K

CDR$_L$1 of LAG-3 mAb 5 (SEQ ID NO: 66):
KASQSVDYDGESYMN

CDR$_L$2 of LAG-3 mAb 5 (SEQ ID NO: 67):
VVSNLES

CDR$_L$3 of LAG-3 mAb 5 (SEQ ID NO: 68):
QQSSEDPLT
```

An exemplary polynucleotide that encodes the VL Domain of LAG-3 mAb 5 is SEQ ID NO:65 (nucleotides encoding the CDR$_L$ residues are shown underlined):

```
gacattgtgc tgacccaatc tccagcttct ttggctgtgt ctctagggca gagggccacc atctcctgca aggccagcca aagtgttgat tatgatggtg aaagttatat gaactggtac caacagaaac caggacagcc acccaaactc ctcatttatg ttgtttccaa tctagaatct gggatcccag ccaggtttag tggcagtggg tctgggacag acttcaccct caacatccat cctgtggagg aggaggatgc tgcaacctat tactgtcagc
```

```
aaagtagtga ggatccgctc acgttcggtg ctgggaccaa gctggagctg aaa
```

F. The Anti-LAG-3 Antibody LAG-3 mAb 6

1. Murine Anti-Human Antibody LAG-3 mAb 6

The amino acid sequence of the VH Domain of LAG-3 mAb 6 (SEQ ID NO:69) is shown below (CDR$_H$ residues are shown underlined):

```
EVLLQQSGPE LVKPGASVKI PCKASGYTFT DYNMDWVKQS

HGESLEWIGD INPDNGVTIY NQKFEGKATL TVDKSSSTAY

MELRSLTSED TAVYYCAREA DYFYFDYWGQ GTTLTVSS

CDR_H1 of LAG-3 mAb 6 (SEQ ID NO: 71):
DYNMD

CDR_H2 of LAG-3 mAb 6 (SEQ ID NO: 72):
DINPDNGVTIYNQKFEG

CDR_H3 of LAG-3 mAb 6 (SEQ ID NO: 72):
EADYFYFDY
```

An exemplary polynucleotide that encodes the VH Domain of LAG-3 mAb 6 is SEQ ID NO:70 (nucleotides encoding the CDR$_H$ residues are shown underlined):

```
gaggtcctgc tgcaacagtc tggacctgag ctggtgaagc ctggggcttc agtgaagata ccctgcaagg cttctggata cacattcact gactacaaca tggactgggt gaagcagagc catggagaga gccttgagtg gattggagat attaatcctg acaatggtgt tactatctac aaccagaagt tgagggcaa ggccacactg actgtagaca agtcctccag tacagcctac atggagctcc gcagcctgac atctgaggac actgcagtct attactgtgc aagagaggcg gattacttct actttgacta ctggggccaa ggcaccactc tcacagtctc ctca
```

The amino acid sequence of the VL Domain of LAG-3 mAb 6 (SEQ ID NO:74) is shown below (CDR$_L$ residues are shown underlined):

```
DIVMTQSHRF MSTSVGDRVS ITCKASQDVS SVVAWYQQKP

GQSPKLLIFS ASYRYTGVPD RFTGSGSGTD FTFTISSVQA

ADLAVYYCQQ HYSTPWTFGG GTKLEIK

CDR_L1 of LAG-3 mAb 6 (SEQ ID NO: 76):
KASQDVSSVVA

CDR_L2 of LAG-3 mAb 6 (SEQ ID NO: 77):
SASYRYT

CDR_L3 of LAG-3 mAb 6 (SEQ ID NO: 78):
QQHYSTPWT
```

An exemplary polynucleotide that encodes the VL Domain of LAG-3 mAb 6 is SEQ ID NO:75 (nucleotides encoding the CDRs are shown underlined):

```
gacattgtga tgacccagtc tcacagattc atgtccacat cagttggaga cagggtcagc atcacctgca aggccagtca ggatgtgagt tctgttgtag cctggtatca acagaaacca ggacaatctc ctaaattact gatttttcg gcatcctacc ggtacactgg agtccctgat cgcttcactg gcagtggatc tgggacggat ttcactttca ccatcagcag tgtgcaggct gcagacctgg cagtttatta ctgtcagcaa cattatagta ctccgtggac gttcggtgga ggcaccaagc tggaaatcaa a
```

2. Humanization of the Anti-LAG-3 Antibody LAG-3 mAb 6 to Form "hLAG-3 mAb 6"

The above-described murine anti-LAG-3 antibody LAG-3mAb 6 was humanized in order to demonstrate the capability of humanizing an anti-LAG-3 antibody so as to decrease its antigenicity upon administration to a human recipient. The humanization yielded two humanized VH Domains, designated herein as "hLAG-3 mAb 6 VH-1," and "hLAG-3 mAb 6 VH-2," and two humanized VL Domains designated herein as "hLAG-3 mAb 6 VL-1," and "hLAG-3 mAb 6 VL-2." Any of the humanized VL Domains may be paired with either of the humanized VH Domains. Accordingly, any antibody comprising one of the humanized VL Domains paired with the humanized VH Domain is referred to generically as "hLAG-3 mAb 6," and particular combinations of humanized VH/VL Domains are referred to by reference to the specific VH/VL Domains, for example a humanized antibody comprising hLAG-3 mAb 6 VH-1 and hLAG-3 mAb 6 VL-2 is specifically referred to as "hLAG-3 mAb 6(1.2)."

The amino acid sequence of the VH Domain of hLAG-3 mAb 6 VH-1 (SEQ ID NO:79) is shown below (CDR$_H$ residues are shown underlined):

```
QVQLVQSGAE VKKPGASVKV SCKASGYTFT DYNMDWVRQA

PGQGLEWMGD INPDNGVTIY NQKFEGRVTM TTDTSTSTAY

MELRSLRSDD TAVYYCAREA DYFYFDYWGQ GTTLTVSS
```

An exemplary polynucleotide that encodes hLAG-3 mAb 6 VH-1 is SEQ ID NO:80 (nucleotides encoding the CDR$_H$ residues are shown underlined):

```
caggtccagc tggtgcagtc tggcgccgaa gtgaagaaac ctggcgcaag cgtgaaggtg tcctgcaagg ccagcggcta caccttcacc gactacaaca tggactgggt ccgacaggcc ccaggacagg gcctggaatg gatgggcgac atcaacccg acaacggcgt gaccatctac aaccagaaat tcgagggcag agtgaccatg accaccgaca ccagcaccag caccgcctac atggaactgc ggtccctgcg gagcgacgac accgccgtgt actactgcgc cagagaggcc gactacttct acttcgacta ctggggccag ggcaccaccc tgaccgtgtc ctcc
```

An amino acid sequence of the VH Domain of hLAG-3 mAb 6 VH-2 (SEQ ID NO:81) is shown below (CDR$_H$ residues are shown underlined):

```
EVQLVESGGG LVKPGGSLRL SCAASGFTFS DYNMDWVRQA

PGKGLEWVSD INPDNGVTIY NQKFEGRFTI SRDNAKNSLY

LQMNSLRAED TAVYYCAREA DYFYFDYWGQ GTTLTVSS
```

An exemplary polynucleotide that encodes hLAG-3 mAb 6 VH-2 is SEQ ID NO:82 (nucleotides encoding the CDR$_H$ residues are shown underlined):

```
gaggtccagc tggtggaatc tggcggcgga ctggtcaagc ctggcggcag cctgagactg agctgcgctg ccagcggctt caccttcagc gactacaaca tggactgggt ccgacaggcc cctggcaagg gcctggaatg ggtgtccgac atcaacccg acaacggcgt gaccatctac aaccagaagt tcgagggccg gttccacatc agccgggaca acgccaagaa cagcctgtac ctgcagatga acagcctgcg ggccgaggac accgccgtgt actactgcgc cagagaggcc gactacttct acttcgacta ctggggccag ggcaccaccc tgaccgtgtc ctcc
```

The amino acid sequence of the VL Domain of hLAG-3 mAb 6 VL-1 (SEQ ID NO:83) is shown below (CDR$_L$ residues are shown underlined):

```
DIQMTQSPSS LSASVGDRVT ITCRASQDVS SVVAWYQQKP

GKAPKLLIYS ASYRYTGVPS RFSGSGSGTD FTLTISSLQP

EDFATYYCQQ HYSTPWTFGG GTKLEIK
```

An exemplary polynucleotide that encodes hLAG-3 mAb 6 VL-1 is SEQ ID NO:84 (nucleotides encoding the CDR$_L$ residues are shown underlined):

```
gacatccaga tgacccagag ccccagcagc ctgagcgcca gcgtgggcga cagagtgacc atcacctgtc gggccagcca ggatgtgtcc agcgtggtgg cctggtatca gcagaagccc ggcaaggccc ccaagctgct gatctacagc gccagctacc ggtacacagg cgtgcccagc agattcagcg gcagcggctc cggcaccgac ttcaccctga ccatcagcag cctgcagccc gaggacttcg ccacctacta ctgccagcag cactacagca cccctggac cttcggcgga ggcaccaagc tggaaatcaa g
```

The amino acid sequence of the VL Domain of hLAG-3 mAb 6 VL-2 (SEQ ID NO:85) is shown below (CDR$_L$ residues are shown underlined):

```
DIVMTQSPSS LSASVGDRVT ITCRASQDVS SVVAWYQQKP

GKAPKLLIYS ASYRYTGVPD RFSGSGSGTD FTFTISSLQP

EDIAVYYCQQ HYSTPWTFGG GTKLEIK
```

An exemplary polynucleotide that encodes hLAG-3 mAb 6 VL-2 is SEQ ID NO:86 (nucleotides encoding the CDR$_L$ residues are shown underlined):

```
gacatcgtga tgacccagag ccccagcagc ctgagcgcca gcgtgggcga cagagtgacc atcacctgtc gggccagcca ggatgtgtcc agcgtggtgg cctggtatca gcagaagccc ggcaaggccc ccaagctgct gatctacagc gccagctacc ggtacacagg cgtgcccgat agattcagcg gcagcggctc cggcaccgac ttcaccttca ccatcagcag cctgcagccc gaggacatcg ccgtttacta ctgccagcag cactacagca cccctggac cttcggcgga ggcaccaagc tggaaatcaa g
```

The CDR$_L$1 of the VL Domain of hLAG-3 mAb 2 VL-1 and VL-2 comprises an lysine to arginine amino acid substitution and has the amino acid sequence: RASQDVSSVVA (SEQ ID NO:87), the substituted arginine is shown underlined). It is contemplated that a similar substitution may be incorporated into any of the LAG-3 mAb 6 CDR$_L$1 Domains described above.

Minor changes to the amino acid sequence of the VH and/or VL Domains provided herein are contemplated. For example, the C-terminal amino acid residue of any of the VH and/or VL Domains described herein may be substituted to facilitate sub-cloning.

V. Anti-LAG-3 Antibodies LAG-3 mAb 1, LAG-3 mAb 2, LAG-3 mAb 3, LAG-3 mAb 4, LAG-3 mAb 5, and/or LAG-3 mAb 6 and Their Derivatives Having an Engineered Fc Region In traditional immune function, the interaction of antibody-antigen complexes with cells of the immune system results in a wide array of responses, ranging from effector functions such as antibody dependent cytotoxicity, mast cell degranulation, and phagocytosis to immunomodulatory signals such as regulating lymphocyte proliferation and antibody secretion. All of these interactions are initiated through the binding of the Fc Region of antibodies or immune complexes to specialized cell surface receptors on hematopoietic cells. The diversity of cellular responses triggered by antibodies and immune complexes results from the structural heterogeneity of the three Fc receptors: FcγRI (CD64), FcγRII (CD32), and FcγRIII (CD16). FcγRI (CD64), FcγRIIA (CD32A) and FcγRIII (CD16) are activating (i.e., immune system enhancing) receptors; FcγRIIB (CD32B) is an inhibiting (i.e., immune system dampening) receptor. In addition, interaction with the neonatual Fc Receptor (FcRn) mediates the recycling of IgG molecules from the endosome to the cell surface and release into the blood. The amino acid sequence of exemplary IgG1 (SEQ ID NO:1), IgG2 (SEQ ID NO:2), IgG3 (SEQ ID NO: 3), and IgG4 (SEQ ID NO:4) are presented above.

Modification of the Fc Region normally leads to an altered phenotype, for example altered serum half-life, altered stability, altered susceptibility to cellular enzymes or altered effector function. It may be desirable to modify an antibody or other binding molecule of the present invention with respect to effector function, for example, so as to enhance the effectiveness of such molecule in treating cancer. Reduction or elimination of effector function is desirable in certain cases, for example in the case of antibodies whose mechanism of action involves blocking or antagonism, but not killing of the cells bearing a target antigen. Increased effector function is generally desirable when directed to undesirable cells, such as tumor and foreign cells, where the FcγRs are expressed at low levels, for example, tumor-specific B cells with low levels of FcγRIIB (e.g., non-Hodgkin's lymphoma, CLL, and Burkitt's lymphoma). In said embodiments, molecules of the invention with conferred or altered effector function activity are useful for the treatment and/or prevention of a disease, disorder or infection where an enhanced efficacy of effector function activity is desired.

In certain embodiments, the LAG-3-binding molecules of the present invention comprise an Fc Region that possesses one or more modifications (e.g., substitutions, deletions, or insertions) to the sequence of amino acids of a wild-type Fc Region (e.g., SEQ ID NO:1), which reduce the affinity and avidity of the Fc Region and, thus, the molecule of the invention, for one or more FcγR receptors. In other embodiments, the molecules of the invention comprise an Fc Region that possesses one or more modifications to the amino acids of the wild-type Fc Region, which increase the affinity and avidity of the Fc Region and, thus, the molecule of the invention, for one or more FcγR receptors. In other embodiments, the molecules comprise a variant Fc Region wherein said variant confers or mediates increased antibody dependent cell mediated cytotoxicity (ADCC) activity and/or an increased binding to FcγRIIA, relative to a molecule comprising no Fc Region or comprising a wild-type Fc Region. In alternate embodiments, the molecules comprise a variant Fc Region wherein said variant confers or mediates decreased ADCC activity (or other effector function) and/or an increased binding to FcγRIIB, relative to a molecule comprising no Fc Region or comprising a wild-type Fc Region. In some embodiments, the invention encompasses LAG-3-binding molecules comprising a variant Fc Region, which variant Fc Region does not show a detectable binding to any FcγR, relative to a comparable molecule comprising the wild-type Fc Region. In other embodiments, the invention encompasses LAG-3-binding molecules comprising a variant Fc Region, which variant Fc Region only binds a single FcγR, preferably one of FcγRIIA, FcγRIIB, or FcγRIIIA Any such increased affinity and/or avidity is preferably assessed by measuring in vitro the extent of detectable binding to the FcγR or FcγR-related activity in cells that express low levels of the FcγR when binding activity of the parent molecule (without the modified Fc Region) cannot be detected in the cells, or in cells which express non-FcγR receptor target antigens at a density of 30,000 to 20,000 molecules/cell, at a density of 20,000 to 10,000 molecules/cell, at a density of 10,000 to 5,000 molecules/cell, at a density of 5,000 to 1,000 molecules/cell, at a density of 1,000 to 200 molecules/cell or at a density of 200 molecules/cell or less (but at least 10, 50, 100 or 150 molecules/cell).

The LAG-3-binding molecules of the present invention may comprise a variant Fc Region having altered affinities for an activating and/or inhibitory Fcγreceptor. In one embodiment, the LAG-3-binding molecule comprises a variant Fc Region that has increased affinity for FcγRIIB and decreased affinity for FcγRIIIA and/or FcγRIIA, relative to a comparable molecule with a wild-type Fc Region. In another embodiment, the LAG-3-binding molecule of the present invention comprise a variant Fc Region, which has decreased affinity for FcγRIIB and increased affinity for FcγRIIIA and/or FcγRIIA, relative to a comparable molecule with a wild-type Fc Region. In yet another embodiment, the LAG-3-binding molecules of the present invention comprise a variant Fc Region that has decreased affinity for FcγRIIB and decreased affinity for FcγRIIIA and/or FcγRIIA, relative to a comparable molecule with a wild-type Fc Region. In still another embodiment, the LAG-3-binding molecules of the present invention comprise a variant Fc Region, which has unchanged affinity for FcγRIIB and decreased (or increased) affinity for FcγRIIIA and/or FcγRIIA, relative to a comparable molecule with a wild-type Fc Region.

In certain embodiments, the LAG-3-binding molecules of the present invention comprise a variant Fc Region having an altered affinity for FcγRIIIA and/or FcγRIIA such that the immunoglobulin has an enhanced effector function. Non-limiting examples of effector cell functions include antibody dependent cell mediated cytotoxicity, antibody dependent phagocytosis, phagocytosis, opsonization, opsonophagocytosis, cell binding, rosetting, C1q binding, and complement dependent cell mediated cytotoxicity.

In a preferred embodiment, the alteration in affinity or effector function is at least 2-fold, preferably at least 4-fold, at least 5-fold, at least 6-fold, at least 7-fold, at least 8-fold, at least 9-fold, at least 10-fold, at least 50-fold, or at least 100-fold, relative to a comparable molecule comprising a wild-type Fc Region. In other embodiments of the invention, the variant Fc Region immunospecifically binds one or more FcRs with at least 65%, preferably at least 70%, at least 75%, at least 80%, at least 85%, at least 90%, at least 95%, at least 100%, at least 125%, at least 150%, at least 175%, at least 200%, at least 225%, or at least 250% greater affinity relative to a molecule comprising a wild-type Fc Region. Such measurements can be in vivo or in vitro assays, and in a preferred embodiment are in vitro assays such as ELISA or surface plasmon resonance assays.

In different embodiments, the LAG-3-binding molecules of the present invention comprise a variant Fc Region wherein said variant agonizes at least one activity of an FcγR receptor, or antagonizes at least one activity of an FcγR receptor. In a preferred embodiment, the molecules comprise a variant that antagonizes one or more activities of FcγRIIB, for example, B-cell receptor-mediated signaling, activation of B-cells, B-cell proliferation, antibody production, intracellular calcium influx of B cells, cell cycle progression, FcγRIIB-mediated inhibition of FcεRI signaling, phosphorylation of FcγRIIB, SHIP recruitment, SHIP phosphorylation and association with Shc, or activity of one or more downstream molecules (e.g., MAP kinase, JNK, p38, or Akt) in the FcγRIIB signal transduction pathway. In another embodiment, the LAG-3-binding molecules of the present invention comprise a variant that agonizes one or more activities of FcεRI, for example, mast cell activation, calcium mobilization, degranulation, cytokine production, or serotonin release.

In certain embodiments, the molecules comprise an Fc Region comprising regions from two or more IgG isotypes (e.g., IgG1, IgG2, IgG3 and IgG4). As used herein, an Fc Region is said to be of a particular IgG isotype if its amino acid sequence is most homologous to that isotype relative to other IgG isotypes. The various IgG isotypes exhibit differing physical and functional properties including serum half-life, complement fixation, FcγR binding affinities and effector function activities (e.g., ADCC, CDC, etc.) due to differences in the amino acid sequences of their hinge and/or Fc Regions, for example as described in Flesch and Neppert (1999) J. Clin. Lab. Anal. 14:141-156; Chappel et al. (1993) J. Biol. Chem. 33:25124-25131; Chappel et al. (1991) Proc. Natl. Acad. Sci. (U.S.A.) 88:9036-9040; or Bruggemann et al. (1987) J. Exp. Med 166:1351-1361. This type of variant Fc Region may be used alone, or in combination with an amino acid modification, to affect Fc-mediated effector function and/or binding activity. In combination, the amino acid modification and IgG hinge/Fc Region may display similar functionality (e.g., increased affinity for FcγRIIA) and may act additively or, more preferably, synergistically to modify the effector functionality in the molecule of the invention, relative to a molecule of the invention comprising a wild-type Fc Region. In other embodiments, the amino acid modification and IgG Fc Region may display opposite functionality (e.g., increased and decreased affinity for FcγRIIA, respectively) and may act to selectively temper or reduce a specific functionality in the molecule of the invention, relative to a molecule of the invention not comprising an Fc Region or comprising a wild-type Fc Region of the same isotype.

In a preferred specific embodiment, the LAG-3-binding molecules of the present invention comprise a variant Fc Region, wherein said variant Fc Region comprises at least one amino acid modification relative to a wild-type Fc Region, such that said molecule has an altered affinity for an FcR, provided that said variant Fc Region does not have a substitution at positions that make a direct contact with FcγR based on crystallographic and structural analysis of Fc-FcR interactions such as those disclosed by Sondermann et al. (2000) Nature 406:267-73. Examples of positions within the Fc Region that make a direct contact with FcγR are amino acid residues 234-239 (hinge region), amino acid residues 265-269 (B/C loop), amino acid residues 297-299 (C'/E loop), and amino acid residues 327-332 (F/G loop). In some embodiments, the molecules of the invention comprise variant Fc Regions comprise modification of at least one residue that does not make a direct contact with an FcγR based on structural and crystallographic analysis, e.g., is not within the Fc-FcγR binding site.

Variant Fc Regions are well known in the art, and any known variant Fc Region may be used in the present invention to confer or modify the effector function exhibited by a molecule of the invention comprising an Fc Region (or portion thereof) as functionally assayed, e.g., in an NK dependent or macrophage dependent assay. For example, Fc Region variants identified as altering effector function are disclosed in PCT Publications No. WO 04/063351; WO 06/088494; WO 07/024249; WO 06/113665; WO 07/021841; WO 07/106707; and WO 2008/140603, and any suitable variant disclosed therein may be used in the present molecules.

In certain embodiments, the LAG-3-binding molecules of the present invention comprise a variant Fc Region, having one or more amino acid modifications in one or more regions, which modification(s) alter (relative to a wild-type Fc Region) the Ratio of Affinities of the variant Fc Region to an activating FcγR (such as FcγRIIA or FcγRIIIA) relative to an inhibiting FcγR (such as FcγRIIB):

$$\text{Ratio of Affinities} = \frac{\text{Wild-Type to Variant Change in Affinity to } Fc\gamma R_{Activating}}{\text{Wild-Type to Variant Change in Affinity to } Fc\gamma R_{Inhibiting}}$$

Particularly preferred are LAG-3-binding molecules of the present invention that possess a variant Fc Region (relative to the wild-type Fc Region) in which the variant Fc Region has a Ratio of Affinities greater than 1. Such molecules have particular use in providing a therapeutic or prophylactic treatment of a disease, disorder, or infection, or the amelioration of a symptom thereof, where an enhanced efficacy of effector cell function (e.g., ADCC) mediated by FcγR is desired, e.g., cancer or infectious disease. In contrast, a variant Fc Region having a Ratio of Affinities less than 1 mediates decreased efficacy of effector cell function. Table 1 lists exemplary single, double, triple, quadruple and quintuple mutations by whether their Ratio of Affinities is greater than or less than 1.

TABLE 1

Exemplary Single and Multiple Mutations Listed by Ratio of Affinities

| Single | Double | Triple | Quadruple | Quintuple |
|---|---|---|---|---|
| Ratio of Affinities > 1 | | | | |
| F243L | F243L & R292P | F243L, P247L & N421K | L234F, F243L, R292P & Y300L | L235V, F243L, R292P, Y300L & P396L |
| D270E | F243L & Y300L | F243L, R292P & Y300L | L235I, F243L, R292P & Y300L | L235P, F243L, R292P, Y300L & P396L |
| R292G | F243L & P396L | F243L, R292P & V305I | L235Q, F243L, R292P & Y300L | F243L, R292P, V305I, Y300L & P396L |
| R292P | D270E & P396L | F243L, R292P & P396L | F243L, P247L, D270E & N421K | |
| | R292P & Y300L | F243L, Y300L & P396L | F243L, R255L, D270E & P396L | |
| | R292P & V305I | P247L, D270E & N421K | F243L, D270E, G316D & R416G | |
| | R292P & P396L | R255L, D270E & P396L | F243L, D270E, K392T & P396L | |
| | Y300L & P396L | D270E, G316D & R416G | F243L, D270E, P396L & Q419H | |
| | P396L & Q419H | D270E, K392T & P396L | F243L, R292P, Y300L, & P396L | |
| | | D270E, P396L & Q419H | F243L, R292P, V305I & P396L | |
| | | V284M, R292L & K370N | P247L, D270E, Y300L & N421K | |
| | | R292P, Y300L & P396L | R255L, D270E, R292G & P396L | |
| | | | R255L, D270E, Y300L & P396L | |

TABLE 1-continued

Exemplary Single and Multiple Mutations Listed by Ratio of Affinities

| Single | Double | Triple | Quadruple | Quintuple |
|---|---|---|---|---|
| | | | D270E, G316D, P396L & R416G | |

Ratio of Affinities < 1

| Single | Double | Triple |
|---|---|---|
| Y300L | F243L & P396L | F243L, R292P & V305I |
| P396L | P247L & N421K | |
| | R255L & P396L | |
| | R292P & V305I | |
| | K392T & P396L | |
| | P396L & Q419H | |

In a specific embodiment, in variant Fc Regions, any amino acid modifications (e.g., substitutions) at any of positions 235, 240, 241, 243, 244, 247, 262, 263, 269, 298, 328, or 330 and preferably one or more of the following residues: A240, I240, L241, L243, H244, N298, I328 or V330. In a different specific embodiment, in variant Fc Regions, any amino acid modifications (e.g., substitutions) at any of positions 268, 269, 270, 272, 276, 278, 283, 285, 286, 289, 292, 293, 301, 303, 305, 307, 309, 331, 333, 334, 335, 337, 338, 340, 360, 373, 376, 416, 419, 430, 434, 435, 437, 438 or 439 and preferably one or more of the following residues: H280, Q280, Y280, G290, S290, T290, Y290, N294, K295, P296, D298, N298, P298, V298, I300 or L300.

In a preferred embodiment, in variant Fc Regions that bind an FcγR with an altered affinity, any amino acid modifications (e.g., substitutions) at any of positions 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438 or 439. Preferably, the variant Fc Region has any of the following residues: A256, N268, Q272, D286, Q286, S286, A290, S290, A298, M301, A312, E320, M320, Q320, R320, E322, A326, D326, E326, N326, S326, K330, T339, A333, A334, E334, H334, L334, M334, Q334, V334, K335, Q335, A359, A360 or A430.

In a different embodiment, in variant Fc Regions that bind an FcγR (via its Fc Region) with a reduced affinity, any amino acid modifications (e.g., substitutions) at any of positions 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438 or 439.

In a different embodiment, in variant Fc Regions that bind an FcγR (via its Fc Region) with an enhanced affinity, any amino acid modifications (e.g., substitutions) at any of positions 280, 283, 285, 286, 290, 294, 295, 298, 300, 301, 305, 307, 309, 312, 315, 331, 333, 334, 337, 340, 360, 378, 398 or 430. In a different embodiment, in variant Fc Regions that binds FcγRIIA with an enhanced affinity, any of the following residues: A255, A256, A258, A267, A268, N268, A272, Q272, A276, A280, A283, A285, A286, D286, S286, A290, S290, M301, E320, M320, Q320, R320, E322, A326, D326, E326, S326, K330, A331, Q335, A337 or A430.

Preferred variants include one or more modifications at any of positions: 228, 230, 231, 232, 233, 234, 235, 239, 240, 241, 243, 244, 245, 247, 262, 263, 264, 265, 266, 271, 273, 275, 281, 284, 291, 296, 297, 298, 299, 302, 304, 305, 313, 323, 325, 326, 328, 330 or 332.

Particularly preferred variants include one or more modifications selected from groups A-AI:

| | |
|---|---|
| A | 228E, 228K, 228Y or 228G; |
| B | 230A, 230E, 230Y or 230G; |
| C | 231E, 231K, 231Y, 231P or 231G; |
| D | 232E, 232K, 232Y, 232G; |
| E | 233D; |
| F | 234I or 234F; |
| G | 235D, 235Q, 235P, 235I or 235V; |
| H | 239D, 239E, 239N or 239Q; |
| I | 240A, 240I, 240M or 240T; |
| J | 243R, 243, 243Y, 243L, 243Q, 243W, 243H or 243I; |
| K | 244H; |
| L | 245A; |
| M | 247G, 247V or 247L; |
| N | 262A, 262E, 262I, 262T, 262E or 262F; |
| O | 263A, 263I, 263M or 263T; |
| P | 264F, 264E, 264R, 264I, 264A, 264T or 264W; |
| Q | 265F, 265Y, 265H, 265I, 265L, 265T, 265V, 265N or 265Q; |
| R | 266A, 266I, 266M or 266T; |
| S | 271D, 271E, 271N, 271Q, 271K, 271R, 271S, 271T, 271H, 271A, 271V, 271L, 271I, 271F, 271M, 271Y, 271W or 271G; |
| T | 273I; |
| U | 275L or 275W; |
| V | 281D, 281K, 281Y or 281P; |
| W | 284E, 284N, 284T, 284L, 284Y or284M; |
| X | 291D, 291E, 291Q, 291T, 291H, 291I or 291G; |
| Y | 299A, 299D, 299E, 299F, 299G, 299H, 299I, 299K, 299L, 299M, 299N, 299P, 299Q, 299R, 299S, 299V, 299W or 299Y; |
| Z | 302I; |
| AA | 304D, 304N, 304T, 304H or 304L |
| AB | 305I; |
| AC | 313F; |
| AD | 323I; |
| AE | 325A, 325D, 325E, 325G, 325H, 325I, 325L, 325K, 325R, 325S, 325F, 325M, 325T, 325V, 325Y, 325W or 325P; |
| AF | 328D, 328Q, 328K, 328R, 328S, 328T, 328V, 328I, 328Y, 328W, 328P, 328G, 328A, 328E, 328F, 328H, 328M or 328N; |
| AG | 330L, 330Y, 330I or 330V; |
| AH | 332A, 332D, 332E, 332H, 332N, 332Q, 332T, 332K, 332R, 332S, 332V, 332L, 332F, 332M, 332W, 332P, 332G or 332Y; and |
| AI | 336E, 336K or 336Y |

Still more particularly preferred variants include one or more modifications selected from Groups 1-105:

| Group | Variant |
|---|---|
| 1 | A330L/I332E |
| 2 | D265F/N297E/I332E |
| 3 | D265Y/N297D/I332E |
| 4 | D265Y/N297D/T299L/I332E |
| 5 | F241E/F243Q/V262T/V264F |
| 6 | F241E/F243Q/V262T/V264E/I332E |
| 7 | F241E/F243R/V262E/V264R |
| 8 | F241E/F243R/V262E/V264R/I332E |
| 9 | F241E/F243Y/V262T/V264R |
| 10 | F241E/F243Y/V262T/V264R/I332E |
| 11 | F241L/F243L/V262I/V264I |
| 12 | F241L/V262I |
| 13 | F241R/F243Q/V262T/V264R |
| 14 | F241R/F243Q/V262T/V264R/I332E |
| 15 | F241W/F243W/V262A/V264A |
| 16 | F241Y/F243Y/V262T/V264T |
| 17 | F241Y/F243Y/V262T/V264T/N297D/I332E |
| 18 | F243L/V262I/V264W |
| 19 | P243L/V264I |
| 20 | L328D/I332E |
| 21 | L328E/I332E |
| 22 | L328H/I332E |
| 23 | L328I/I332E |
| 24 | L328M/I332E |
| 25 | L328N/I332E |
| 26 | L328Q/I332E |
| 27 | L328T/I332E |
| 28 | L328V/I332E |
| 29 | N297D/A330Y/I332E |
| 30 | N297D/I332E |
| 31 | N297D/I332E/S239D/A330L |
| 32 | N297D/S298A/A330Y/I332E |
| 33 | N297D/T299L/I332E |
| 34 | N297D/T299F/I332E/N297D/T299H/I332E |
| 35 | N297D/T299I/I332E |
| 36 | N297D/T299L/I332E |
| 37 | N297D/T299V/I332E |
| 38 | N297E/I332E |
| 39 | N297S/I332E |
| 40 | P230A/E233D/I332E |
| 41 | P244H/P245A/P247V |
| 42 | S239D/A330L/I332E |
| 43 | S239D/A330Y/I332E |
| 44 | S239D/A330Y/I332E/K326E |
| 45 | S239D/A330Y/I332E/K326T |
| 46 | S239D/A330Y/I332E/L234I |
| 47 | S239D/A330Y/I332E/L235D |
| 48 | S239D/A330Y/I332E/V240I |
| 49 | S239D/A330Y/I332E/V264T |
| 50 | S239D/A330Y/I332E/V266I |
| 51 | S239D/D265F/N297D/I332E |
| 52 | S239D/D265H/N297D/I332E |
| 53 | S239D/D265I/N297D/I332E |
| 54 | S239D/D265L/N297D/I332E |
| 55 | S239D/D265T/N297D/I332E |
| 56 | S239D/D265V/N297D/I332E |
| 57 | S239D/D265Y/N297D/I332E |
| 58 | S239D/I332D |
| 59 | S239D/I332E |
| 60 | S239D/I332E/A330I |
| 61 | S239D/I332N |
| 62 | S239D/I332Q |
| 63 | S239D/N297D/I332E |
| 64 | S239D/N297D/I332E/A330Y |
| 65 | S239D/N297D/I332E/A330Y/F241S/F243H/V262T/V264T |
| 66 | S239D/N297D/I332E/K326E |
| 67 | S239D/N297D/I332E/L235D |
| 68 | S239D/S298A/I332E |
| 69 | S239D/V264I/A330L/I332E |
| 70 | S239D/V264I/I332E |
| 71 | S239D/V264I/S298A/I332E |
| 72 | S239E/D265N |
| 73 | S239E/D265Q |
| 74 | S239E/I332D |
| 75 | S239E/I332E |
| 76 | S239E/I332N |
| 77 | S239E/I332Q |
| 78 | S239E/N297D/I332E |
| 79 | S239E/V264I/A330Y/I332E |
| 80 | S239E/V264I/I332E |
| 81 | S239E/V264I/S298A/A330Y/I332E |
| 82 | S239N/A330L/I332E |
| 83 | S239N/A330Y/I332E |
| 84 | S239N/I332D |
| 85 | S239N/I332E |
| 86 | S239N/I332N |
| 87 | S239N/I332Q |
| 88 | S239N1S298A/I332E |
| 89 | S239Q/I332D |
| 90 | S239Q/I332E |
| 91 | S239Q/I332N |
| 92 | S239Q/I332Q |
| 93 | S239Q/V264I/I332E |
| 94 | S298A/I332E |
| 95 | V264E/N297D/I332E |
| 96 | V264I/A330L/I332E |
| 97 | V264I/A330Y/I332E |
| 98 | V264I/I332E |
| 99 | V264I/S298A/I332E |
| 100 | Y296D/N297D/I332E |
| 101 | Y296E/N297D/I332E |
| 102 | Y296H/N297D/I332E |
| 103 | Y296N/N297D/I332E |
| 104 | Y296Q/N297I/I332E |
| 105 | Y296T/N297D/I332E |

In one embodiment, a LAG-3 binding molecule of the invention will comprise a variant Fc Region having at least one modification in the Fc Region. In certain embodiments, the variant Fc Region comprises at least one substitution selected from the group consisting of L235V, F243L, R292P, Y300L, V305I, and P396L, wherein said numbering is that of the EU index according to Kabat.

In a specific embodiment, the variant Fc Region comprises:
(A) at least one substitution selected from the group consisting of F243L, R292P, Y300L, V305I, and P396L;
(B) at least two substitutions selected from the group consisting of:
  (1) F243L and P396L;
  (2) F243L and R292P; and
  (3) R292P and V305I;
(C) at least three substitutions selected from the group consisting of:
  (1) F243L, R292P and Y300L;
  (2) F243L, R292P and V305I;
  (3) F243L, R292P and P396L; and
  (4) R292P, V305I and P396L;
(D) at least four substitutions selected from the group consisting of:
  (1) F243L, R292P, Y300L and P396L; and
  (2) F243L, R292P, V305I and P396L; or
(E) at least the five substitutions selected from the group consisting of:
  (1) F243L, R292P, Y300L, V305I and P396L; and
  (2) L235V, F243L, R292P, Y300L and P396L.

In another specific embodiment, the variant Fc Region comprises substitutions of:
(A) F243L, R292P, and Y300L;
(B) L235V, F243L, R292P, Y300L, and P396L; or
(C) F243L, R292P, Y300L, V305I, and P396L.

In one embodiment, a LAG-3-binding molecule of the invention comprises a variant Fc Region that exhibits decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type IgG1 Fc Region (SEQ ID NO:1)). In one embodiment, a LAG-3-binding molecule of the invention will comprise a variant Fc Region that exhibits reduced (or substantially no) binding to an FcγR (e.g., FcγRIIIA) and reduced (or substantially no) ADCC effector function. In certain embodiments, the variant Fc Region comprises at least one substitution selected from the group consisting of L234A, L235A, D265A, N297Q, and N297G. In a specific embodiment, the variant Fc Region comprises the substitution of L234A; L235A; L234A and L235A; D265A; N297Q, or N297G.

In a different embodiment, a LAG-3-binding molecule of the invention comprises an Fc Region which inherently exhibits decreased (or substantially no) binding to FcγRIIIA (CD16a) and/or reduced effector function (relative to the binding exhibited by the wild-type IgG1 Fc Region (SEQ ID NO:1)). In a specific embodiment, a LAG-3-binding molecule of the present invention comprises an IgG2 Fc Region (SEQ ID NO:2) or an IgG4 Fc Region (SEQ ID:NO:4). When an IgG4 Fc Region in utilized, the instant invention also encompasses the introduction of a stabilizing mutation, such the IgG4 hinge region S228P substitution (see, e.g., SEQ ID NO:117: ESKYGPPCPPCP, (Lu et al., (2008) "*The Effect Of A Point Mutation On The Stability Of Igg4 As Monitored By Analytical Ultracentrifugation,*" J. Pharmaceutical Sciences 97:960-969) to reduce the incidence of strand exchange. Other stabilizing mutations known in the art may be introduced into an IgG4 Fc Region (Peters, P et al., (2012) "*Engineering an Improved IgG4 Molecule with Reduced Disulfide Bond Heterogeneity and Increased Fab Domain Thermal Stability,*" J. Biol. Chem., 287:24525-24533; PCT Patent Publication No: WO 2008/145142).

In other embodiments, the invention encompasses the use of any Fc variant known in the art, such as those disclosed in Jefferis, B.J. et al. (2002) "*Interaction Sites On Human IgG-Fc For FcgammaR: Current Models,*" Immunol. Lett. 82:57-65; Presta, L. G. et al. (2002) "*Engineering Therapeutic Antibodies For Improved Function,*" Biochem. Soc. Trans. 30:487-90; Idusogie, E.E. et al. (2001) "*Engineered Antibodies With Increased Activity To Recruit Complement,*" J. Immunol. 166:2571-75; Shields, R. L. et al. (2001) "*High Resolution Mapping Of The Binding Site On Human IgG1 For Fc Gamma RI, Fc Gamma RII, Fc Gamma RIII, And FcRn And Design Of IgG1 Variants With Improved Binding To The Fc gamma R,*" J. Biol. Chem. 276:6591-6604; Idusogie, E. E. et al. (2000) "*Mapping Of The C1q Binding Site On Rituxan, A Chimeric Antibody With A Human IgG Fc,*" J. Immunol. 164:4178-84; Reddy, M. P. et al. (2000) "*Elimination Of Fc Receptor-Dependent Effector Functions Of A Modified IgG4 Monoclonal Antibody To Human CD4,*" J. Immunol. 164:1925-1933; Xu, D. et al. (2000) "*In Vitro Characterization of Five Humanized OKT3 Effector Function Variant Antibodies,*" Cell. Immunol. 200:16-26; Armour, K. L. et al. (1999) "*Recombinant human IgG Molecules Lacking Fcgamma Receptor I Binding And Monocyte Triggering Activities,*" Eur. J. Immunol. 29:2613-24; Jefferis, R. et al. (1996) "*Modulation Of Fc(Gamma)R And Human Complement Activation By IgG3-Core Oligosaccharide Interactions,*" Immunol. Lett. 54:101-04; Lund, J. et al. (1996) "*Multiple Interactions Of IgG With Its Core Oligosaccharide Can Modulate Recognition By Complement And Human Fc Gamma Receptor I And Influence The Synthesis Of Its Oligosaccharide Chains,*" J. Immunol. 157:4963-4969; Hutchins et al. (1995) "*Improved Biodistribution, Tumor Targeting, And Reduced Immunogenicity In Mice With A Gamma 4 Variant Of Campath-1H,*" Proc. Natl. Acad. Sci. (U.S.A.) 92:11980-84; Jefferis, R. et al. (1995) "*Recognition Sites On Human IgG For Fc Gamma Receptors: The Role Of Glycosylation,*" Immunol. Lett. 44:111-17; Lund, J. et al. (1995) "*Oligosaccharide-Protein Interactions In IgG Can Modulate Recognition By Fc Gamma Receptors,*" FASEB J. 9:115-19; Alegre, M. L. et al. (1994) "*A Non-Activating "Humanized" Anti-CD3 Monoclonal Antibody Retains Immunosuppressive Properties In Vivo,*" Transplantation 57:1537-1543; Lund et al. (1992) "*Multiple Binding Sites On The CH2 Domain Of IgG For Mouse Fc Gamma R11,*" Mol. Immunol. 29:53-59; Lund et al. (1991) "*Human Fc Gamma RI And Fc Gamma RII Interact With Distinct But Overlapping Sites On Human IgG,*" J. Immunol. 147:2657-2662; Duncan, A. R. et al. (1988) "*Localization Of The Binding Site For The Human High-Affinity Fc Receptor On IgG,*" Nature 332:563-564; U.S. Pat. Nos. 5,624,821; 5,885,573; 6,194,551; 7,276,586; and 7,317,091; and PCT Publications WO 00/42072 and PCT WO 99/58572.

In some embodiments, the molecules of the invention further comprise one or more glycosylation sites, so that one or more carbohydrate moieties are covalently attached to the molecule. Preferably, the molecules of the invention with one or more glycosylation sites and/or one or more modifications in the Fc Region confer or have an enhanced antibody mediated effector function, e.g., enhanced ADCC activity, compared to the unmodified antibody. In some embodiments, the invention further comprises molecules comprising one or more modifications of amino acids that are directly or indirectly known to interact with a carbohydrate moiety of the Fc Region, including but not limited to amino acids at positions 241, 243, 244, 245, 245, 249, 256, 258, 260, 262, 264, 265, 296, 299, or 301. Amino acids that directly or indirectly interact with a carbohydrate moiety of an Fc Region are known in the art, see, e.g., Jefferis et al., 1995 *Immunology Letters,* 44: 111-7, which is incorporated herein by reference in its entirety.

In another embodiment, the invention encompasses molecules that have been modified by introducing one or more glycosylation sites into one or more sites of the molecules, preferably without altering the functionality of the molecules, e.g., binding activity to target antigen or FcγR. Glycosylation sites may be introduced into the variable and/or constant region of the molecules of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. The molecules of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention is the amino acid sequence: Asn-X-Thr/Ser, wherein X may be any amino acid and Thr/Ser indicates a threonine or a serine. Such a site or sites may be introduced into a molecule of the invention using methods well known in the art to which this invention pertains (see for example, IN VITRO MUTAGENESIS, RECOMBINANT DNA: A SHORT COURSE, J. D. Watson, et al. W.H. Freeman and Company, New York, 1983, chapter 8, pp. 106-116, which is incorporated herein by reference in its entirety. An exemplary method for introducing a glycosylation site into a molecule of the invention may comprise: modifying or mutating an amino acid sequence of the molecule so that the desired Asn-X-Thr/Ser sequence is obtained.

In some embodiments, the invention encompasses methods of modifying the carbohydrate content of a molecule of the invention by adding or deleting a glycosylation site. Methods for modifying the carbohydrate content of antibodies (and molecules comprising antibody domains, e.g., Fc Region) are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety. In other embodiments, the invention encompasses methods of modifying the carbohydrate content of a molecule of the invention by deleting one or more endogenous carbohydrate moieties of the molecule. In a specific embodiment, the invention encompasses shifting the glycosylation site of the Fc Region of an antibody, by modifying positions adjacent to 297. In a specific embodiment, the invention encompasses modifying position 296 so that position 296 and not position 297 is glycosylated.

Effector function can also be modified by techniques such as by introducing one or more cysteine residues into the Fc Region, thereby allowing interchain disulfide bond formation in this region to occur, resulting in the generation of a homodimeric antibody that may have improved internalization capability and/or increased complement-mediated cell killing and ADCC (Caron, P. C. et al. (1992) "*Engineered Humanized Dimeric Forms Of IgG Are More Effective Antibodies,*" J. Exp. Med. 176:1191-1195; Shopes, B. (1992) "*A Genetically Engineered Human IgG Mutant With Enhanced Cytolytic Activity,*" J. Immunol. 148(9):2918-2922. Homodimeric antibodies with enhanced antitumor activity may also be prepared using heterobifunctional cross-linkers as described in Wolff, E. A. et al. (1993) "*Monoclonal Antibody Homodimers: Enhanced Antitumor Activity In Nude Mice,*" Cancer Research 53:2560-2565. Alternatively, an antibody can be engineered which has dual Fc Regions and may thereby have enhanced complement lysis and ADCC capabilities (Stevenson, G. T. et al. (1989) "*A Chimeric Antibody With Dual Fc Regions (bisFabFc) Prepared By Manipulations At The IgG Hinge,*" Anti-Cancer Drug Design 3:219-230).

The serum half-life of the molecules of the present invention comprising Fc Regions may be increased by increasing the binding affinity of the Fc Region for FcRn. The term "half-life" as used herein means a pharmacokinetic property of a molecule that is a measure of the mean survival time of the molecules following their administration. Half-life can be expressed as the time required to eliminate fifty percent (50%) of a known quantity of the molecule from a subject's body (e.g., human patient or other mammal) or a specific compartment thereof, for example, as measured in serum, i.e., circulating half-life, or in other tissues. In general, an increase in half-life results in an increase in mean residence time (MRT) in circulation for the molecule administered.

In some embodiments, the LAG-3-binding molecules of the present invention comprise a variant Fc Region that comprises at least one amino acid modification relative to a wild-type Fc Region and that exhibit an increased half-life (relative to a wild-type Fc Region).

In some embodiments, the LAG-3-binding molecules of the present invention comprise a variant Fc Region that comprises a half-life-extending amino acid substitution at one or more positions selected from the group consisting of 238, 250, 252, 254, 256, 257, 256, 265, 272, 286, 288, 303, 305, 307, 308, 309, 311, 312, 317, 340, 356, 360, 362, 376, 378, 380, 382, 413, 424, 428, 433, 434, 435, and 436, as numbered by the EU index according to Kabat. Numerous specific mutations capable of increasing the half-life of an Fc Region-containing molecule are known in the art and include, for example M252Y, S254T, T256E, and combinations thereof. For example, see the mutations described in U.S. Pat. Nos. 6,277,375, 7,083,784; 7,217,797, 8,088,376; U.S. Publication Nos. 2002/0147311; 2007/0148164; and International Publication Nos. WO 98/23289 WO 2009/058492, and WO 2010/033279, which are herein incorporated by reference in their entireties. Fc Region-containing molecules with enhanced half-life also include those with substitutions at two or more of Fc Region residues 250, 252, 254, 256, 257, 288, 307, 308, 309, 311, 378, 428, 433, 434, 435 and 436. In particular, two or more substitutions selected from: T250Q, M252Y, S254T, T256E, K288D, T307Q, V308P, A378V, M428L, N434A, H435K, and Y436I.

In a specific embodiment, the variant Fc Region comprises substitutions of:
 (A) 252Y, 254T and 256E;
 (B) M252Y and S254T;
 (C) M252Y and T256E;
 (D) 250Q and 428L;
 (E) T307Q and N434A;
 (F) A378V and N434A;
 (G) N434A and Y436I;
 (H) V308P and N434A; or
 (I) K288D and H435K.

The instant invention further encompasses variant Fc Regions comprising:
 (A) one or more mutations which alter effector function and/or FcγR; and
 (B) one or more mutations which extend serum half-life.

VI. Bispecific LAG-3-Binding Molecules of the Present Invention

One embodiment of the present invention relates to bispecific binding molecules that are capable of binding to a "first epitope" and a "second epitope," wherein the first epitope is an epitope of human LAG-3 and the second epitope is the same or a different epitope of LAG-3, or is an epitope of another molecule that is present on the surface of an immune cell (such as a T lymphocyte) and is involved in regulating an immune checkpoint. In certain embodiments, the second epitope is preferably not an epitope of LAG-3. In one embodiment, the second epitope is an epitope of B7-H3, B7-H4, BTLA, CD3, CD8, CD16, CD27, CD32, CD40, CD40L, CD47, CD64, CD70, CD80, CD86, CD94, CD137, CD137L, CD226, CTLA-4, Galectin-9, GITR, GITRL, HHLA2, ICOS, ICOSL, KIR, LAG-3, LIGHT, MHC class I or II, NKG2a, NKG2d, OX40, OX40L, PD1H, PD-1, PD-L1, PD-L2, PVR, SIRPa, TCR, TIGIT, TIM-3 or VISTA. In a specific embodiment, the second epitope is CD137, PD-1, OX40, TIGIT, or TIM-3. In certain embodiments, such bispecific molecules comprise more than two epitope-binding sites. Such bispecific molecules may, for example, bind two or more different epitopes of LAG-3 and at least one epitope of a molecule that is not LAG-3.

The instant invention encompasses bispecific antibodies capable of simultaneously binding to LAG-3 and the second epitope (e.g. B7-H3, B7-H4, BTLA, CD40, CD80, CD86, CD137, CTLA-4, ICOS, KIR, MHC class I or II, OX40, PD-1, PD-L1, TCR, TIM-3, etc.). In some embodiments, the bispecific antibody capable of simultaneously binding to PD-1 and the second epitope is produced using any of the methods described in PCT Publication Nos. WO 1998/002463, WO 2005/070966, WO 2006/107786 WO 2007/024715, WO 2007/075270, WO 2006/107617, WO 2007/046893, WO 2007/146968, WO 2008/003103, WO 2008/003116, WO 2008/027236, WO 2008/024188, WO 2009/132876, WO 2009/018386, WO 2010/028797, WO2010028796, WO 2010/028795, WO 2010/108127, WO 2010/136172, WO 2011/086091, WO 2011/133886, WO 2012/009544, WO 2013/003652, WO 2013/070565, WO 2012/162583, WO 2012/156430, WO 2013/174873, and WO 2014/022540, each of which is hereby incorporated herein by reference in its entirety.

1. Bispecific Diabodies Lacking Fc Regions

One embodiment of the present invention relates to bispecific monovalent diabodies that comprise, and most preferably consist of, a first polypeptide chain and a second polypeptide chain, whose sequences permit the polypeptide chains to covalently bind to each other to form a covalently associated diabody that is capable of simultaneously binding to a first epitope ("Epitope 1") and a second epitope (Epitope 2"), such epitopes not being identical to one another. Such bispecific diabodies thus comprise "VL1"/"VH1" domains that are capable of binding to the first epitope ($VL_{Epitope\ 1}$/$VH_{Epitope\ 1}$) and "VL2"/"VH2" domains that are capable of binding to the second epitope ($VL_{Epitope\ 2}$/$VH_{Epitope\ 2}$). The notation "VL1" and "VH1" denote respectively, the Variable Light Chain Domain and Variable Heavy Chain Domain that bind the "first" epitope of such bispecific diabody. Similarly, the notation "VL2" and "VH2" denote respectively, the Variable Light Chain Domain and Variable Heavy Chain Domain that bind the "second" epitope of such bispecific diabody. In one embodiment, Epitope 1 of such diabody molecules is an epitope of LAG-3 and Epitope 2 of such diabody molecules is not an epitope of LAG-3 (for example, it is an epitope of B7-H3, B7-H4, BTLA, CD40, CD80, CD86, CD137, CTLA-4, ICOS, KIR, MHC class I or II, OX40, PD-1, PD-L1, TCR, TIM-3, etc.).

The VL Domain of the first polypeptide chain of such LAG-2 binding diabodies interacts with the VH Domain of the second polypeptide chain to form a first functional epitope-binding site that is specific for a first antigen (i.e., either LAG-3 or an antigen that contains the second epitope). Likewise, the VL Domain of the second polypeptide chain interacts with the VH Domain of the first polypeptide chain in order to form a second functional epitope-binding site that is specific for a second antigen (i.e., either an antigen that contains the second epitope or LAG-3). Thus, the selection of the VL and VH Domains of the first and second polypeptide chains is coordinated, such that the two polypeptide chains of the diabody collectively comprise VL and VH Domains capable of binding to both an epitope of LAG-3 and to the second epitope (i.e., they collectively comprise $VL_{LAG-3}$/$VH_{LAG-3}$ and $VL_{Epitope\ 2}$/$VH_{Epitope\ 2}$ Domains). It is irrelevant whether a particular pair of binding domains (i.e $VL_{Epitope\ 1}$/$VH_{Epitope\ 1}$ or $VL_{Epitope\ 2}$/$VH_{Epitope\ 2}$) an epitope of an antigen having Epitope 1 or an epitope of an antigen having Epitope 2) is designated as the first vs. the second epitope of the diabody; such notation having relevance only with respect to the presence and orientation of domains of the polypeptide chains of the binding molecules of the present invention The first polypeptide chain of an embodiment of such bispecific monovalent diabodies comprises, in the N-terminal to C-terminal direction, an N-terminus, the VL Domain of a monoclonal antibody capable of binding to either the first epitope or the VL Domain of a monoclonal antibody capable of binding to the second epitope (i.e., either $VL_{LAG-3}$ or $VL_{Epitope\ 2}$), a first intervening spacer peptide (Linker 1), a VH Domain of a monoclonal antibody capable of binding to either the second epitope (if such first polypeptide chain contains $VL_{LAG-3}$) or a VH Domain of a monoclonal antibody capable of binding to the first epitope (if such first polypeptide chain contains $VL_{Epitope\ 2}$), a second intervening spacer peptide (Linker 2), optionally comprising a cysteine residue, a Heterodimer-Promoting Domain and a C-terminus (FIG. 1).

The second polypeptide chain of this embodiment of bispecific monovalent diabodies comprises, in the N-terminal to C-terminal direction, an N-terminus, a VL Domain of a monoclonal antibody capable of binding to LAG-3 or a VL Domain of a monoclonal antibody capable of binding to the second epitope (i.e., either $VL_{LAG-3}$ or $VL_{Epitope\ 2}$, and being the VL Domain not selected for inclusion in the first polypeptide chain of the diabody), an intervening linker peptide (Linker 1), a VH Domain of a monoclonal antibody capable of binding to either the second epitope (if such second polypeptide chain contains $VL_{LAG-3}$) or a VH Domain of a monoclonal antibody capable of binding to LAG-3 (if such second polypeptide chain contains $VL_{Epitope\ 2}$), a second intervening spacer peptide (Linker 2) optionally containing a cysteine residue, a Heterodimer-Promoting Domain, and a C-terminus (FIG. 1).

Most preferably, the length of the intervening linker peptide (e.g., Linker 1) that separates such VL and VH Domains) is selected to substantially or completely prevent the VL and VH Domains of the polypeptide chain from binding to one another. Thus the VL and VH Domains of the first polypeptide chain are substantially or completely incapable of binding to one another. Likewise, the VL and VH Domains of the second polypeptide chain are substantially or completely incapable of binding to one another. A preferred intervening spacer peptide (Linker 1) has the sequence (SEQ ID NO:88): GGGSGGGG.

The length and composition of the second intervening linker peptide (Linker 2) is selected based on the choice of heterodimer-promoting domains. Typically, the second intervening linker peptide (Linker 2) will comprise 3-20 amino acid residues. In particular, where the heterodimer-promoting domains do not comprise a cysteine residue a cysteine-containing second intervening linker peptide (Linker 2) is utilized. The cysteine-containing second intervening spacer peptide (Linker 2) will contain 1, 2, 3 or more than 3 cysteine residue(s). A preferred cysteine-containing spacer peptide (Linker 2) has the sequence is SEQ ID NO:89: GGCGGG. Alternatively, Linker 2 does not comprise a cysteine (e.g., GGG, GGGS (SEQ ID NO:90), LGGGSG (SEQ ID NO:91), GGGSGGGSGGG (SEQ ID NO:92), ASTKG (SEQ ID NO:93), LEPKSS (SEQ ID NO:94), APSSS (SEQ ID NO:95), etc.) and a Cysteine-Containing Heterodimer-Promoting Domain, as described below is used. Optionally, both a cysteine-containing Linker 2 and a cysteine-containing Heterodimer-Promoting Domain are used.

The Heterodimer-Promoting Domains may be GVEPKSC (SEQ ID NO:96) or VEPKSC (SEQ ID NO:97) or AEPKSC (SEQ ID NO:98) on one polypeptide chain and GFNRGEC (SEQ ID NO:99) or FNRGEC (SEQ ID NO:100) on the other polypeptide chain (US2007/0004909).

More preferably, however, the Heterodimer-Promoting Domains of such diabodies are formed from one, two, three or four tandemly repeated coil domains of opposing charge that comprise a sequence of at least six, at least seven or at least eight amino acid residues such that the Heterodimer-Promoting Domain possesses a net charge (Apostolovic, B. et al. (2008) "*pH-Sensitivity of the E3/K3 Heterodimeric Coiled Coil*," Biomacromolecules 9:3173-3180; Arndt, K. M. et al. (2001) "*Helix-stabilized Fv (hsFv) Antibody Fragments: Substituting the Constant Domains of a Fab Fragment for a Heterodimeric Coiled-coil Domain*," J. Molec. Biol. 312:221-228; Arndt, K. M. et al. (2002) "*Comparison of In Vivo Selection and Rational Design of Heterodimeric Coiled Coils*," Structure 10:1235-1248; Boucher, C. et al. (2010) "*Protein Detection By Western Blot Via Coiled-Coil Interactions*," Analytical Biochemistry 399:138-140; Cachia, P. J. et al. (2004) "*Synthetic Peptide Vaccine Development: Measurement Of Polyclonal Antibody Affinity And Cross-Reactivity Using A New Peptide Capture And Release System For Surface Plasmon Resonance Spectroscopy*," J. Mol. Recognit. 17:540-557; De Crescenzo, G. D. et al. (2003) "*Real-Time Monitoring of the Interactions of Two-Stranded de novo Designed Coiled-Coils: Effect of Chain Length on the Kinetic and Thermodynamic Constants of Binding*," Biochemistry 42:1754-1763; Fernandez-Rodriquez, J. et al. (2012) "*Induced Heterodimerization And Purification Of Two Target Proteins By A Synthetic Coiled-Coil Tag*," Protein Science 21:511-519; Ghosh, T. S. et al. (2009) "*End-To-End And End-To-Middle Interhelical Interactions: New Classes Of Interacting Helix Pairs In Protein Structures*," Acta Crystallographica D65:1032-1041; Grigoryan, G. et al. (2008) "*Structural Specificity In Coiled-Coil Interactions*," Curr. Opin. Struc. Biol. 18:477-483; Litowski, J. R. et al. (2002) "*Designing Heterodimeric Two-Stranded α-Helical Coiled-Coils: The Effects Of Hydrophobicity And α-Helical Propensity On Protein Folding, Stability, And Specificity*," J. Biol. Chem. 277:37272-37279; Steinkruger, J. D. et al. (2012) "*The d'-d-d' Vertical Triad is Less Discriminating Than the a'-a-a' Vertical Triad in the Antiparallel Coiled-coil Dimer Motif*," J. Amer. Chem. Soc. 134(5):2626-2633; Straussman, R. et al. (2007) "*Kinking the Coiled Coil—Negatively Charged Residues at the Coiled-coil Interface*," J. Molec. Biol. 366:1232-1242; Tripet, B. et al. (2002) "*Kinetic Analysis of the Interactions between Troponin C and the C-terminal Troponin I Regulatory Region and Validation of a New Peptide Delivery/Capture System used for Surface Plasmon Resonance*," J. Molec. Biol. 323:345-362; Woolfson, D. N. (2005) "*The Design Of Coiled-Coil Structures And Assemblies*," Adv. Prot. Chem. 70:79-112; Zeng, Y. et al. (2008) "*A Ligand-Pseudoreceptor System Based On de novo Designed Peptides For The Generation Of Adenoviral Vectors With Altered Tropism*," J. Gene Med. 10:355-367).

Such repeated coil domains may be exact repeats or may have substitutions. For example, the coil domain of the Heterodimer-Promoting Domain of the first polypeptide chain may comprise a sequence of eight amino acid residues selected to confer a negative charge to such Heterodimer-Promoting Domain, and the coil domain of the Heterodimer-Promoting Domain of the second polypeptide chain may comprise a sequence of eight amino acid residues selected to confer a positive charge to such Heterodimer-Promoting Domain. It is immaterial which coil is provided to the first or second polypeptide chains, provided that, when both polypeptide chains are provided with such Heterodimer-Promoting Domains, a coil of opposite charge is used for the other polypeptide chain. The positively charged amino acid may be lysine, arginine, histidine, etc. and/or the negatively charged amino acid may be glutamic acid, aspartic acid, etc.

The positively charged amino acid is preferably lysine and/or the negatively charged amino acid is preferably glutamic acid. It is possible for only a single Heterodimer-Promoting Domain to be employed (since such domain will inhibit homodimerization and thereby promote heterodimerization), however, it is preferred for both the first and second polypeptide chains of the diabodies of the present invention to contain Heterodimer-Promoting Domains.

In a preferred embodiment, one of the Heterodimer-Promoting Domains will comprise four tandem "E-coil" helical domains (SEQ ID NO:101: EVAALEK-EVAALEK-EVAALEK-EVAALEK), whose glutamate residues will form a negative charge at pH 7, while the other of the Heterodimer-Promoting Domains will comprise four tandem "K-coil" helical domains (SEQ ID NO:102: KVAALKE-KVAALKE-KVAALKE-KVAALKE), whose lysine residues will form a positive charge at pH 7. The presence of such charged domains promotes association between the first and second polypeptides, and thus fosters heterodimer formation. Especially preferred is a Heterodimer-Promoting Domain in which one of the four tandem "E-coil" helical domains of SEQ ID NO:101 has been modified to contain a cysteine residue: EVAACEK-EVAALEK-EVAALEK-EVAALEK (SEQ ID NO:103). Likewise, especially preferred is a Heterodimer-Promoting Domain in which one of the four tandem "K-coil" helical domains of SEQ ID NO:102 has been modified to contain a cysteine residue: KVAACKE-KVAALKE-KVAALKE-KVAALKE (SEQ ID NO:104).

As disclosed in WO 2012/018687, in order to improve the in vivo pharmacokinetic properties of diabodies, a diabody may be modified to contain a polypeptide portion of a serum-binding protein at one or more of the termini of the diabody. Most preferably, such polypeptide portion of a serum-binding protein will be installed at the C-terminus of the diabody. Albumin is the most abundant protein in plasma and has a half-life of 19 days in humans. Albumin possesses several small molecule binding sites that permit it to non-covalently bind to other proteins and thereby extend their serum half-lives. The Albumin-Binding Domain 3 (ABD3) of protein G of Streptococcus strain G148 consists of 46 amino acid residues forming a stable three-helix bundle and has broad albumin-binding specificity (Johansson, M. U. et al. (2002) "*Structure, Specificity, And Mode Of Interaction For Bacterial Albumin-Binding Modules*," J. Biol. Chem. 277(10):8114-8120. Thus, a particularly preferred polypeptide portion of a serum-binding protein for improving the in vivo pharmacokinetic properties of a diabody is the Albumin-Binding Domain (ABD) from streptococcal protein G, and more preferably, the Albumin-Binding Domain 3 (ABD3) of protein G of Streptococcus strain G148 (SEQ ID NO:105): LAEAKVLANR ELDKYGVSDY YKNLID-NAKS AEGVKALIDE ILAALP.

As disclosed in WO 2012/162068 (herein incorporated by reference), "deimmunized" variants of SEQ ID NO:105 have the ability to attenuate or eliminate MHC class II binding. Based on combinational mutation results, the following combinations of substitutions are considered to be preferred substitutions for forming such a deimmunized ABD: 66D/70S+71A; 66S/70S+71A; 66S/70S+79A; 64A/65A/71A; 64A/65A/71A+66S; 64A/65A/71A+66D; 64A/65A/71A+66E; 64A/65A/79A+66S; 64A/65A/79A+66D; 64A/65A/79A+66E. Variant ABDs having the modifications L64A, I65A and D79A or the modifications N66S, T70S and D79A. Variant deimmunized ABD having the amino acid sequence:

LAEAKVLANR ELDKYGVSDY YKNLI$\underline{D}_{66}$NAK$\underline{S}_{70}$ $\underline{A}_{71}$EGVKALIDE (SEQ ID NO: 106)

ILAALP, or the amino acid sequence:

LAEAKVLANR ELDKYGVSDY YKN$\underline{A}_{64}\underline{A}_{65}$NNAKT VEGVKALI$\underline{A}_{79}$E (SEQ ID NO: 107)

ILAALP, or the amino acid sequence:

LAEAKVLANR ELDKYGVSDY YKNLI$\underline{S}_{66}$NAK$\underline{S}_{70}$ VEGVKALI$\underline{A}_{79}$E (SEQ ID NO: 108)

ILAALP, are particularly preferred as such deimmunized ABD exhibit substantially wild-type binding while providing attenuated MHC class II binding. Thus, the first polypeptide chain of such a diabody having an ABD contains a third linker (Linker 3) preferably positioned C-terminally to the E-coil (or K-coil) Domain of such polypeptide chain so as to intervene between the E-coil (or K-coil) Domain and the ABD (which is preferably a deimmunized ABD). A preferred sequence for such Linker 3 is SEQ ID NO:90: GGGS.

2. Bispecific Diabodies Containing Fc Regions

Figure 2:
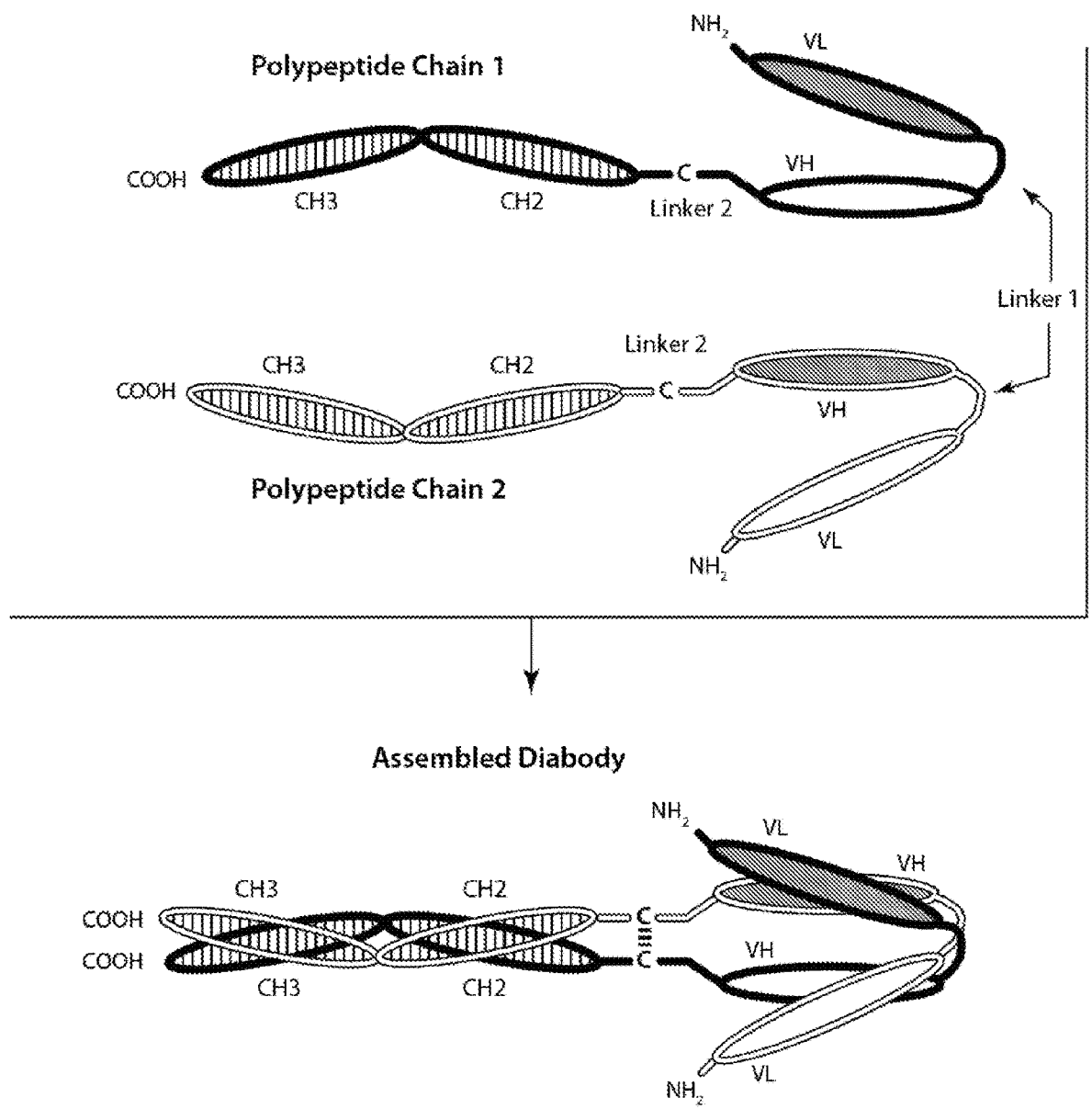
FIG. 2 provides a schematic of a representative covalently bonded diabody molecule having two epitope-binding sites composed of two polypeptide chains, each having a CH2 and CH3 Domain, such that the associated chains form all or part of an Fc Region. VL and VH Domains that recognize the same epitope are shown using the same shading or fill pattern.

One embodiment of the present invention relates to bispecific diabodies comprising an Fc Region capable of simultaneously binding to LAG-3 and a second epitope (e.g. B7-H3, B7-H4, BTLA, CD40, CD80, CD86, CD137, CTLA-4, ICOS, KIR, MEW class I or II, OX40, PD-1, PD-L1, TCR, TIM-3, etc.). The addition of an IgG CH2-CH3 Domain to one or both of the diabody polypeptide chains, such that the complexing of the diabody chains results in the formation of an Fc Region, increases the biological half-life and/or alters the valency of the diabody. Incorporating an IgG CH2-CH3 Domain onto both of the diabody polypeptides will permit a two-chain bispecific Fc-Region-containing diabody to form (FIG. 2).

Alternatively, incorporating an IgG CH2-CH3 Domain onto only one of the diabody polypeptides will permit a more complex four-chain bispecific Fc Region-containing diabody to form (FIGS. 3A-3C). FIG. 3C shows a representative four-chain diabody possessing the Constant Light (CL) Domain and the Constant Heavy CH1 Domain, however fragments of such domains as well as other polypeptides may alternatively be employed (see, e.g., FIGS. 3A and 3B, United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538). Thus, for example, in lieu of the CH1 Domain, one may employ a peptide having the amino acid sequence GVEPKSC (SEQ ID NO:96) VEPKSC (SEQ ID NO:97), or AEPKSC (SEQ ID NO:98), derived from the hinge domain of a human IgG, and in lieu of the CL Domain, one may employ the C-terminal 6 amino acids of the human kappa light chain, GFNRGEC (SEQ ID NO:99) or FNRGEC (SEQ ID NO:100). A representative peptide containing four-chain diabody is shown in FIG. 3A. Alternatively, or in addition, one may employ a peptide comprising tandem coil domains of opposing charge such as the "E-coil" helical domains (SEQ ID NO:101: $\underline{E}$VAAL$\underline{E}$K-$\underline{E}$VAAL$\underline{E}$K-$\underline{E}$VAAL$\underline{E}$K-$\underline{E}$VAAL$\underline{E}$K or SEQ ID NO:103: $\underline{E}$VAA$\underline{C}$EK-$\underline{E}$VAAL$\underline{E}$K-$\underline{E}$VAAL$\underline{E}$K-$\underline{E}$VAAL$\underline{E}$K); and the "K-coil" domains (SEQ ID NO:102: $\underline{K}$VAAL$\underline{K}$E-$\underline{K}$VAAL $\underline{K}$E-$\underline{K}$VAAL$\underline{K}$E-$\underline{K}$VAAL$\underline{K}$E or SEQ ID NO:104: $\underline{K}$VAA$\underline{C}$ $\underline{K}$E-$\underline{K}$VAAL$\underline{K}$E-$\underline{K}$VAAL$\underline{K}$E-$\underline{K}$VAAL$\underline{K}$E). A representative coil domain containing four-chain diabody is shown in FIG. 3B.

The Fc Region-containing diabody molecules of the present invention generally include additional intervening linker peptides (Linkers). Typically, the additional Linkers will comprise 3-20 amino acid residues. Additional or alternative linkers that may be employed in the Fc Region-containing diabody molecules of the present invention include: GGGS (SEQ ID NO:90), LGGGSG (SEQ ID NO:91), GGGSGGGSGGG (SEQ ID NO:92), ASTKG (SEQ ID NO:93), DKTHTCPPCP (SEQ ID NO:109), LEPKSS (SEQ ID NO:94), APSSS (SEQ ID NO:95), and APSSSPME (SEQ ID NO:110), LEPKSADKTHTCPPC (SEQ ID NO:111), GGC, and GGG. SEQ ID NO:94 may be used in lieu of GGG or GGC for ease of cloning. Additionally, the amino acid GGG, or SEQ ID NO:94 may be immediately followed by SEQ ID NO:109 to form the alternate linkers: GGGDKTHTCPPCP (SEQ ID NO:112); and LEPKSSDKTHTCPPCP; (SEQ ID NO:113). Fc Region-containing diabody molecule of the present invention may incorporate an IgG hinge region in addition to or in place of a linker. Exemplary hinge regions include: EPKSCDKTHTCPPCP (SEQ ID NO:114) from IgG1, ERKCCVECPPCP (SEQ ID NO:115) from IgG2, ESKYGPPCPSCP (SEQ ID NO:116) from IgG4, and ESKYGPPCPPCP (SEQ ID NO:117) an IgG4 hinge variant comprising a stabilizing substitute to reduce strand exchange.

As provided in FIG. 3A-3C, diabodies of the invention may comprise four different chains. The first and third polypeptide chains of such a diabody contain three domains: (i) a VL1-containing Domain, (ii) a VH2-containing Domain, (iii) Heterodimer-Promoting Domain and (iv) a Domain containing a CH2-CH3 sequence. The second and fourth polypeptide chains contain: (i) a VL2-containing Domain, (ii) a VH1-containing Domain and (iii) a Heterodimer-Promoting Domain, where the Heterodimer-Promoting Domains promote the dimerization of the first/third polypeptide chains with the second/fourth polypeptide chains. The VL and/or VH Domains of the third and fourth polypeptide chains, and VL and/or VH Domains of the first and second polypeptide chains may be the same or different so as to permit tetravalent binding that is either monospecific, bispecific or tetraspecific. The notation "VL3" and "VH3" denote respectively, the Variable Light Chain Domain and Variable Heavy Chain Domain that bind the "third" epitope of such diabody ("Epitope 3"). Similarly, the notation "VL4" and "VH4" denote respectively, the Variable Light Chain Domain and Variable Heavy Chain Domain that bind the "fourth" epitope of such diabody ("Epitope 4"). The general structure of the polypeptide chains of a representative four-chain Fc Region-containing diabodies of invention is provided in Table 2:

TABLE 2

| Bispecific | 2$^{nd}$ Chain | NH$_2$-VL2-VH1-HPD-COOH |
|---|---|---|
| | 1$^{st}$ Chain | NH$_2$-VL1-VH2-HPD-CH2—CH3—COOH |
| | 1$^{st}$ Chain | NH$_2$-VL1-VH2-HPD-CH2—CH3—COOH |
| | 2$^{nd}$ Chain | NH$_2$-VL2-VH1-HPD-COOH |
| Tetraspecific | 2$^{nd}$ Chain | NH$_2$-VL2-VH1-HPD-COOH |
| | 1$^{st}$ Chain | NH$_2$-VL1-VH2-HPD-CH2—CH3—COOH |
| | 3$^{rd}$ Chain | NH$_2$-VL3-VH4-HPD-CH2—CH3—COOH |
| | 4$^{th}$ Chain | NH$_2$-VL4-VH3-HPD-COOH |

HPD = Heterodimer-Promoting Domain

In a specific embodiment, diabodies of the present invention are bispecific, tetravalent (i.e., possess four epitope-binding sites), Fc-containing diabodies (FIGS. 3A-3C) that are composed of four total polypeptide chains. The bispecific, tetravalent, Fc-containing diabodies of the invention comprise two epitope-binding sites immunospecific for LAG-3 (which may be capable of binding to the same epitope of LAG-3 or to different epitopes of LAG-3), and two epitope-binding sites specific for a second epitope (e.g., B7-H3, B7-H4, BTLA, CD40, CD80, CD86, CD137, CTLA-4, ICOS, KIR, MHC class I or II, OX40, PD-1, PD-L1, TCR, TIM-3, etc.).

In a further embodiment, the bispecific Fc Region-containing diabodies may comprise three polypeptide chains. The first polypeptide of such a diabody contains three domains: (i) a VL1-containing Domain, (ii) a VH2-containing Domain and (iii) a Domain containing a CH2-CH3 sequence. The second polypeptide of such diabodies contains: (i) a VL2-containing Domain, (ii) a VH1-containing Domain and (iii) a Domain that promotes heterodimerization and covalent bonding with the diabody's first polypeptide chain. The third polypeptide of such diabodies comprises a CH2-CH3 sequence. Thus, the first and second polypeptide chains of such diabodies associate together to form a VL1/VH1 binding site that is capable of binding to the first epitope, as well as a VL2/VH2 binding site that is capable of binding to the second epitope. The first and second polypeptides are bonded to one another through a disulfide bond involving cysteine residues in their respective Third Domains. Notably, the first and third polypeptide chains complex with one another to form an Fc Region that is stabilized via a disulfide bond. Such diabodies have enhanced potency. FIGS. 4A and 4B illustrate the structures of such diabodies. Such Fc-Region-containing bispecific diabodies may have either of two orientations (Table 3):

TABLE 3

| First Orientation | 3$^{rd}$ Chain | NH$_2$—CH2—CH3—COOH |
|---|---|---|
| | 1$^{st}$ Chain | NH$_2$-VL1-VH2-HPD-CH2—CH3—COOH |
| | 2$^{nd}$ Chain | NH$_2$-VL2-VH1-HPD-COOH |
| Second Orientation | 3$^{rd}$ Chain | NH$_2$—CH2—CH3—COOH |
| | 1$^{st}$ Chain | NH$_2$—CH2—CH3-VL1-VH2-HPD-COOH |
| | 2$^{nd}$ Chain | NH$_2$-VL2-VH1-HPD-COOH |

HPD = Heterodimer-Promoting Domain

In a specific embodiment, diabodies of the present invention are bispecific, bivalent (i.e., possess two epitope-binding sites), Fc-containing diabodies (FIGS. 4A-4B) that are composed of three total polypeptide chains. The bispecific, bivalent Fc-containing diabodies of the invention comprise one epitope-binding site immunospecific for LAG-3, and one epitope-binding site specific for a second epitope (e.g., B7-H3, B7-H4, BTLA, CD40, CD80, CD86, CD137, CTLA-4, ICOS, KIR, LAG-3 MEW class I or II, OX40, PD-L1, TCR, TIM-3, etc.).

In a further embodiment, the bispecific Fc Region-containing diabodies may comprise a total of five polypeptide chains. In a particular embodiment, two of said five polypeptide chains have the same amino acid sequence. The first polypeptide chain of such diabodies contains: (i) a VH1-containing domain, (ii) a CH1-containing domain, and (iii) a Domain containing a CH2-CH3 sequence. The first polypeptide chain may be the heavy chain of an antibody that contains a VH1 and a heavy chain constant region. The second and fifth polypeptide chains of such diabodies contain: (i) a VL1-containing domain, and (ii) a CL-containing domain. The second and/or fifth polypeptide chains of such diabodies may be light chains of an antibody that contains a VL1 complementary to the VH1 of the first/third polypeptide chain. The first, second and/or fifth polypeptide chains may be isolated from naturally occurring antibodies. Alternatively, they may be constructed recombinantly. The third polypeptide chain of such diabodies contains: (i) a VH1-containing domain, (ii) a CH1-containing domain, (iii) a Domain containing a CH2-CH3 sequence, (iv) a VL2-containing Domain, (v) a VH3-containing Domain and (vi) a Heterodimer-Promoting Domain, where the Heterodimer-Promoting Domains promote the dimerization of the third chain with the fourth chain. The fourth polypeptide of such diabodies contains: (i) a VL3-containing Domain, (ii) a VH2-containing Domain and (iii) a Domain that promotes heterodimerization and covalent bonding with the diabody's third polypeptide chain.

Thus, the first and second, and the third and fifth, polypeptide chains of such diabodies associate together to form two VL1/VH1 binding sites capable of binding a first epitope. The third and fourth polypeptide chains of such diabodies associate together to form a VL2/VH2 binding site that is capable of binding to a second epitope, as well as a VL3/VH3 binding site that is capable of binding to a third epitope. The first and third polypeptides are bonded to one another through a disulfide bond involving cysteine residues in their respective constant regions. Notably, the first and third polypeptide chains complex with one another to form an Fc Region. Such diabodies have enhanced potency. FIG. 5 illustrates the structure of such diabodies. It will be understood that the VL1/VH1, VL2/VH2, and VL3/VH3 Domains may be the same or different so as to permit binding that is monospecific, bispecific or trispecific. However, as provided herein, these domains are preferably selected so as to bind LAG-3 and a second epitope (or a second and a third epitope (e.g., B7-H3, B7-H4, BTLA, CD40, CD80, CD86, CD137, CTLA-4, ICOS, KIR, LAG-3 MHC class I or II, OX40, PD-L1, TCR, TIM-3, etc.). The second and third epitope may be different epitopes of the same antigen molecule, or may be epitopes of different antigen molecules. Such aspects of the invention are discussed in detail below.

Thus, the VL and VH Domains of the polypeptide chains are selected so as to form VL/VH binding sites specific for the desired epitopes. The VL/VH binding sites formed by the association of the polypeptide chains may be the same or different so as to permit tetravalent binding that is monospecific, bispecific, trispecific or tetraspecific. In particular, the VL and VH Domains maybe selected such that a bispecific diabody may comprise two binding sites for a first epitope and two binding sites for a second epitope, or three binding sites for a first epitope and one binding site for a second epitope, or two binding sites for a first epitope, one binding site for a second epitope and one binding site for a third epitope (as depicted in FIG. 5). The general structure of the polypeptide chains of representative five-chain Fc Region-containing diabodies of invention is provided in Table 4:

TABLE 4

| Bispecific (2 × 2) | 2nd Chain | NH2-VL1-CL-COOH |
|---|---|---|
| | 1st Chain | NH2-VH1-CH1—CH2—CH3—COOH |
| | 3rd Chain | NH2-VH1-CH1—CH2—CH3-VL2-VH2-HPD-COOH |
| | 5nd Chain | NH2-VL1-CL-COOH |
| | 4th Chain | NH2-VL2-VH2-HPD-COOH |
| Bispecific (3 × 1) | 2nd Chain | NH2-VL1-CL-COOH |
| | 1st Chain | NH2-VH1-CH1—CH2—CH3—COOH |
| | 3rd Chain | NH2-VH1-CH1—CH2—CH3-VL1-VH2-HPD-COOH |
| | 5nd Chain | NH2-VL1-CL-COOH |
| | 4th Chain | NH2-VL2-VH1-HPD-COOH |
| Trispecific (2 × 1 × 1) | 2nd Chain | NH2-VL1-CL-COOH |
| | 1st Chain | NH2-VH1-CH1—CH2—CH3—COOH |
| | 3rd Chain | NH2-VH1-CH1—CH2—CH3-VL2-VH3-HPD-COOH |
| | 5nd Chain | NH2-VL1-CL-COOH |
| | 4th Chain | NH2-VL3-VH2-HPD-COOH |

HPD = Heterodimer-Promoting Domain

In a specific embodiment, diabodies of the present invention are bispecific, tetravalent (i.e., possess four epitope-binding sites), Fc-containing diabodies that are composed of five total polypeptide chains having two binding sites for a first epitope and two binding sites for a second epitope. In one embodiment, the bispecific, tetravalent, Fc-containing diabodies of the invention comprise two epitope-binding sites immunospecific for LAG-3 (which may be capable of binding to the same epitope of LAG-3 or to different epitopes of LAG-3), and two epitope-binding sites specific for a second epitope (e.g., B7-H3, B7-H4, BTLA, CD40, CD80, CD86, CD137, CTLA-4, ICOS, KIR, LAG-3 MHC class I or II, OX40, PD-L1, TCR, TIM-3, etc.). In another embodiment, the bispecific, tetravalent, Fc-containing diabodies of the invention comprise three epitope-binding sites immunospecific for LAG-3 (which may be capable of binding to the same epitope of LAG-3 or to different epitopes of LAG-3), and one epitope-binding sites specific for a second epitope (e.g., B7-H3, B7-H4, BTLA, CD40, CD80, CD86, CD137, CTLA-4, ICOS, KIR, LAG-3 MHC class I or II, OX40, PD-L1, TCR, TIM-3, etc.). In another embodiment, the bispecific, tetravalent, Fc-containing diabodies of the invention comprise one epitope-binding sites immunospecific for LAG-3, and three epitope-binding sites specific for a second epitope (e.g., B7-H3, B7-H4, BTLA, CD40, CD80, CD86, CD137, CTLA-4, ICOS, KIR, LAG-3 MHC class I or II, OX40, PD-L1, TCR, TIM-3, etc.).

3. Bispecific Trivalent Binding Molecules Containing Fc Regions

A further embodiment of the present invention relates to bispecific, trivalent binding molecules, comprising an Fc Region, and being capable of simultaneously binding to a first epitope, a second epitope and a third epitope, wherein at least one of such epitopes is not identical to another of such epitopes. Such bispecific diabodies thus comprise "VL1"/"VH1" domains that are capable of binding to the first epitope, "VL2"/"VH2" domains that are capable of binding to the second epitope and "VL3"/"VH3" domains that are capable of binding to the third epitope. In one embodiment, one or two of such epitopes is an epitope of LAG-3 and another (or the other) of such epitopes is not an epitope of LAG-3 (for example, an epitope of B7-H3, B7-H4, BTLA, CD40, CD80, CD86, CD137, CTLA-4, ICOS, KIR, LAG-3, MHC class I or II, OX40, PD-1, PD-L1, TCR, TIM-3, etc.). Such bispecific trivalent binding molecules comprise three epitope-binding sites, two of which are diabody-type binding domains, which provide binding Site A and binding Site B, and one of which is a non-diabody-type binding domain, which provides binding Site C (see, e.g., FIGS. 6A-6F, and PCT Application No: PCT/US15/33081; and PCT/US15/33076).

Typically, the trivalent binding molecules of the present invention will comprise four different polypeptide chains (see FIGS. 6A-6B), however, the molecules may comprise fewer or greater numbers of polypeptide chains, for example, by fusing such polypeptide chains to one another (e.g., via a peptide bond) or by "dividing" such polypeptide chains to form additional polypeptide chains, or by associating fewer or additional polypeptide chains via disulfide bonds. FIGS. 6B-6F illustrate this aspect of the present invention by schematically depicting such molecules having three polypeptide chains. As provided in FIGS. 6A-6F, the trivalent binding molecules of the present invention may have alternative orientations in which the diabody-type binding domains are N-terminal (FIGS. 6A, 6C and 6D) or C-terminal (FIGS. 6B, 6E and 6F) to an Fc Region.

Figure 6A:
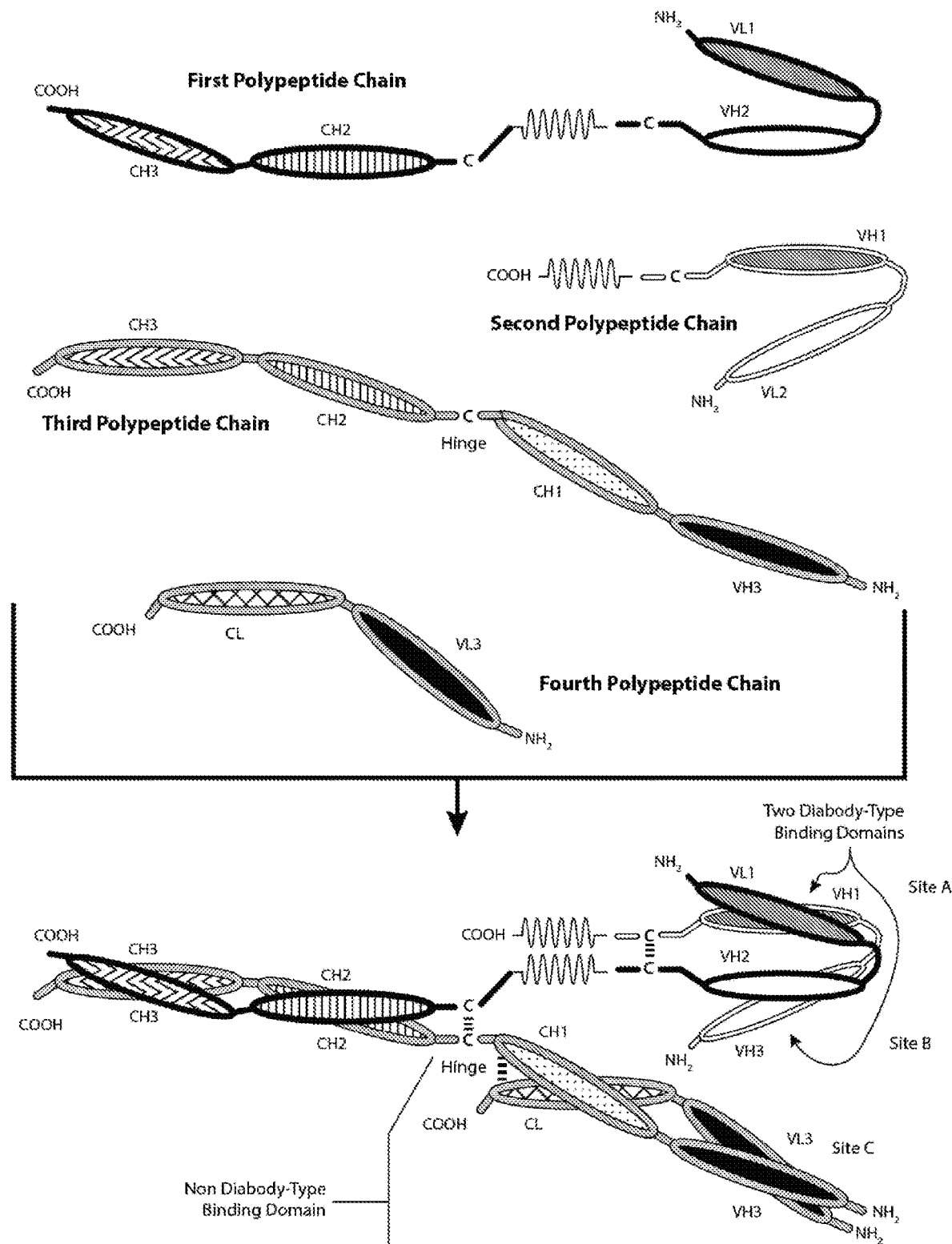
FIGS. 6A-6F provide schematics of representative Fc Region-containing trivalent binding molecules having three epitope-binding sites.
Figure 6B:
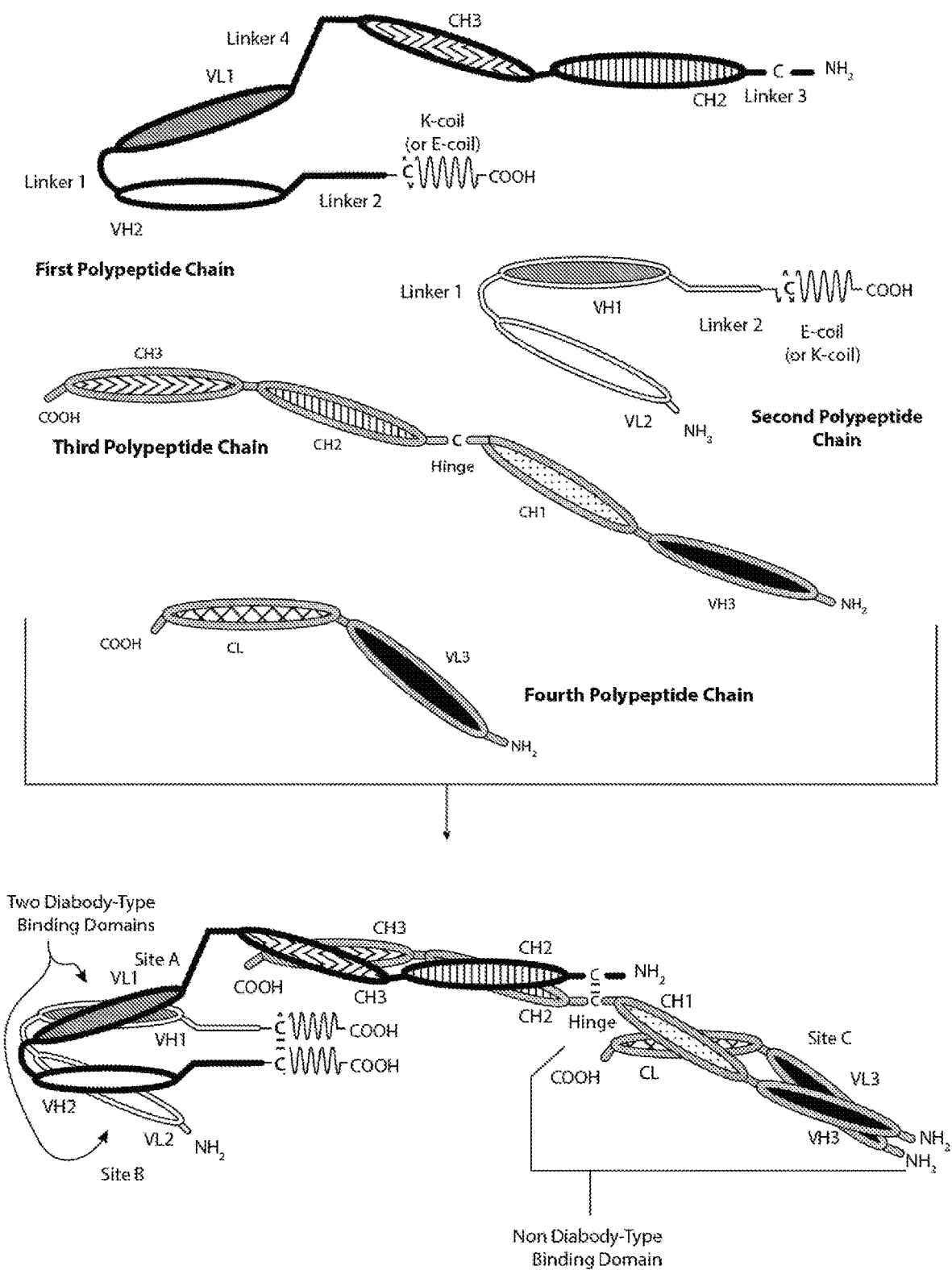
Figure 6C:
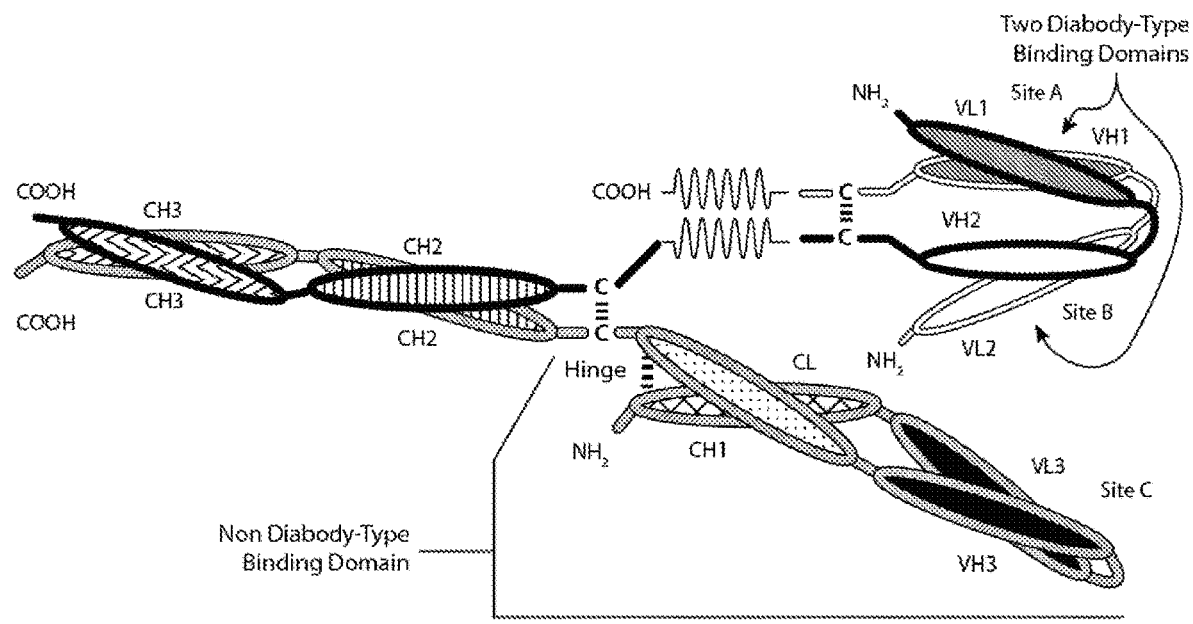
Figure 6D:
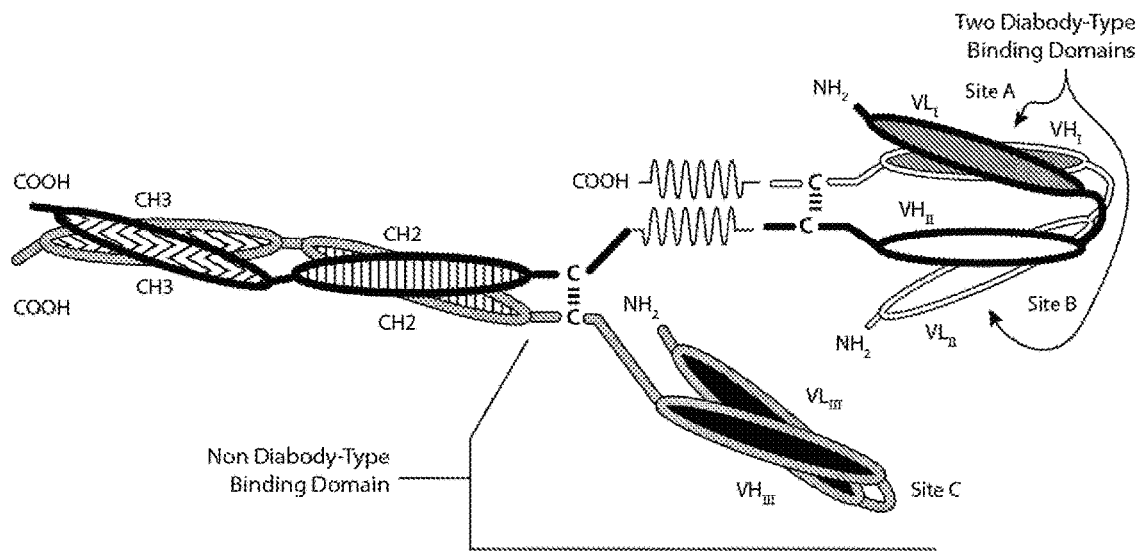
Figure 6E:
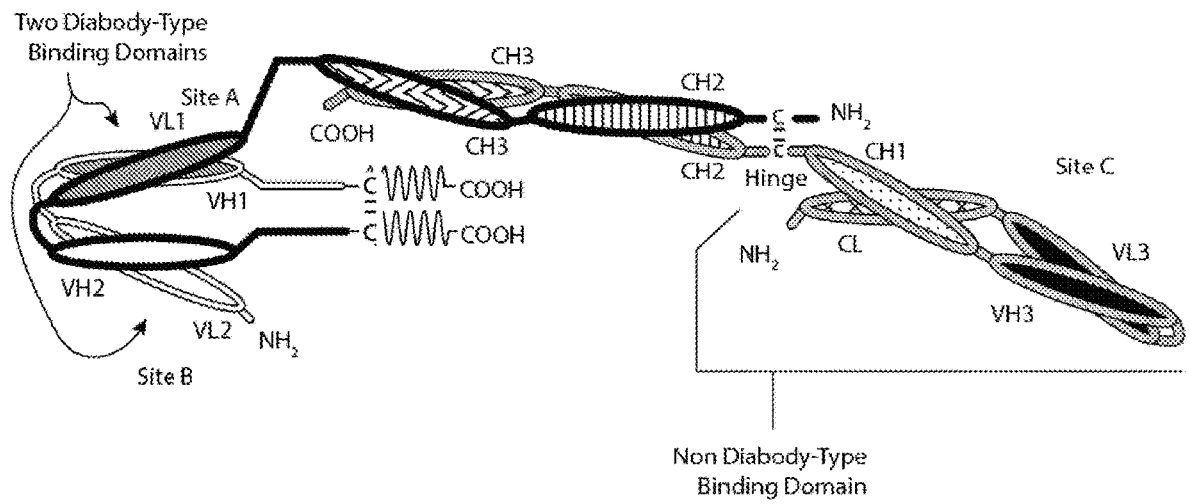
Figure 6F:
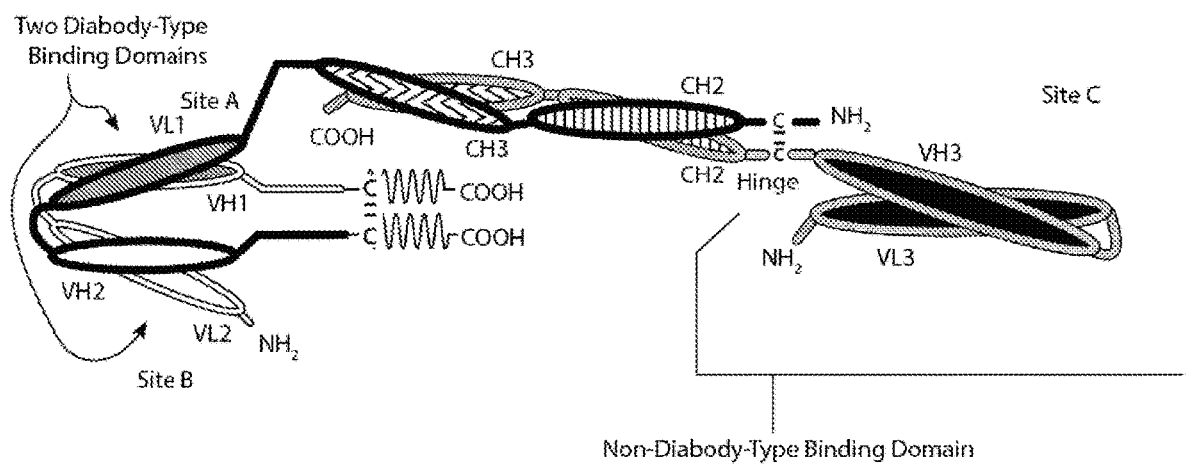

In certain embodiments, the first polypeptide chain of such trivalent binding molecules of the present invention contains: (i) a VL1-containing Domain, (ii) a VH2-containing Domain, (iii) a Heterodimer-Promoting Domain, and (iv) a Domain containing a CH2-CH3 sequence. The VL1 and VL2 Domains are located N-terminal or C-terminal to the CH2-CH3-containing domain as presented in Table 5 (FIGS. 6A and 6B). The second polypeptide chain of such embodiments contains: (i) a VL2-containing Domain, (ii) a VH1-containing Domain, and (iii) a Heterodimer-Promoting Domain. The third polypeptide chain of such embodiments contains: (i) a VH3-containing Domain, (ii) a CH1-containing Domain and (iii) a Domain containing a CH2-CH3 sequence. The third polypeptide chain may be the heavy chain of an antibody that contains a VH3 and a heavy chain constant region. The fourth polypeptide of such embodiments contains: (i) a VL3-containing Domain and (ii) a CL-containing Domain. The fourth polypeptide chains may be light chain of an antibody that contains a VL3 complementary to the VH3 of the third polypeptide chain. The third or fourth polypeptide chains may be isolated from naturally occurring antibodies. Alternatively, they may be constructed recombinantly, synthetically or by other means.

The Variable Light Chain Domain of the first and second polypeptide chains are separated from the Variable Heavy Chain Domains of such polypeptide chains by an intervening spacer linker having a length that is too short to permit their VL1/VH2 (or their VL2/VH1) domains to associate together to form epitope-binding site capable of binding to either the first or second epitope. A preferred intervening spacer peptide (Linker 1) for this purpose has the sequence (SEQ ID NO:14): GGGSGGGG. Other Domains of the trivalent binding molecules may be separated by one or more intervening spacer peptides, optionally comprising a cysteine residue. Exemplary linkers useful for the generation of trivalent binding molecules are provided herein and are also provided in PCT Application Nos: PCT/US15/33081; and PCT/US15/33076. Thus, the first and second polypeptide chains of such trivalent binding molecules associate together to form a VL1/VH1 binding site capable of binding a first epitope, as well as a VL2/VH2 binding site that is capable of binding to a second epitope. The third and fourth polypeptide chains of such trivalent binding molecules associate together to form a VL3/VH3 binding site that is capable of binding to a third epitope.

As described above, the trivalent binding molecules of the present invention may comprise three polypeptides. Trivalent binding molecules comprising three polypeptide chains may be obtained by linking the domains of the fourth polypeptide N-terminal to the VH3-containing Domain of the third polypeptide. Alternatively, a third polypeptide chain of a trivalent binding molecule of the invention containing the following three domains is utilized: (i) a VL3-containing Domain, (ii) a VH3-containing Domain, and (iii) a Domain containing a CH2-CH3 sequence, wherein the VL3 and VH3 are spaced apart from one another by an intervening spacer peptide that is sufficiently long (at least 9 or more amino acid residues) so as to allow the association of these domains to form an epitope-binding site.

It will be understood that the VL1/VH1, VL2/VH2, and VL3/VH3 Domains of such diabody molecules may be the same or different so as to permit binding that is monospecific, bispecific or trispecific. However, as provided herein, these domains are preferably selected so as to bind LAG-3 and a second epitope (or a second and third epitope) (preferably, such epitopes are epitopes of B7-H3, B7-H4, BTLA, CD40, CD80, CD86, CD137, CTLA-4, ICOS, KIR, LAG-3 MHC class I or II, OX40, PD-L1, TCR, TIM-3, etc.).

In particular, the VL and VH Domains maybe selected such that a trivalent binding molecule comprises two binding sites for a first epitope and one binding sites for a second epitope, or one binding site for a first epitope and two binding sites for a second epitope, or one binding site for a first epitope, one binding site for a second epitope and one binding site for a third epitope. The general structure of the polypeptide chains of representative trivalent binding molecules of invention is provided in FIGS. 6A-6F and in Table 5:

CD137, CTLA-4, ICOS, KIR, LAG-3, MHC class I or II, OX40, PD-L1, TCR, TIM-3, etc.). The two epitope-binding sites for LAG-3 may bind the same epitope or different epitopes. Another embodiment of the present invention relates to bispecific trivalent binding molecules that comprise, one epitope-binding site for LAG-3 and two epitope-binding sites that bind a second antigen present on a molecule other than LAG-3 (e.g. B7-H3, B7-H4, BTLA, CD40, CD80, CD86, CD137, CTLA-4, ICOS, KIR, LAG-3, MHC class I or II, OX40, PD-L1, TCR, TIM-3, etc.). The two epitope-binding sites for the second antigen may bind the same epitope or different epitopes of the antigen (e.g., the same or different epitopes of LAG-3). As provided above, such bispecific trivalent binding molecules may comprise three or four polypeptide chains.

VII. Constant Domains and Fc Regions

Provided herein are antibody Constant Domains useful in the generation of LAG-3-binding molecules (e.g., antibodies, diabodies, trivalent binding molecules, etc.) of the invention.

A preferred CL Domain is a human IgG CL Kappa Domain. The amino acid sequence of an exemplary human CL Kappa Domain is (SEQ ID NO:118):

RTVAAPSVFI FPPSDEQLKS GTASVVCLLN NFYPREAKVQ

WKVDNALQSG NSQESVTEQD SKDSTYSLSS TLTLSKADYE

KHKVYACEVT HQGLSSPVTK SFNRGEC

Alternatively, an exemplary CL Domain is a human IgG CL Lambda Domain. The amino acid sequence of an exemplary human CL Kappa Domain is (SEQ ID NO:119):

QPKAAPSVTL FPPSSEELQA NKATLVCLIS DFYPGAVTVA

WKADSSPVKA GVETTPSKQS NNKYAASSYL SLTPEQWKSH

RSYSCQVTHE GSTVEKTVAP TECS

As provided herein, the LAG-3-binding molecules of the invention may comprise an Fc Region. The Fc Region of such molecules of the invention may be of any isotype (e.g., IgG1, IgG2, IgG3, or IgG4). The LAG-3-binding molecules

TABLE 5

| | | |
|---|---|---|
| Four Chain 1st Orientation | 2nd Chain | NH2-VL2-VH1-HPD-COOH |
| | 1st Chain | NH2-VL1-VH2-HPD-CH2—CH3—COOH |
| | 3rd Chain | NH2-VH3-CH1—CH2—CH3—COOH |
| | 4th Chain | NH2-VL3-CL-COOH |
| Four Chain 2nd Orientation | 2nd Chain | NH2-VL2-VH1-HPD-COOH |
| | 1st Chain | NH2—CH2—CH3-VL1-VH2-HPD COOH |
| | 3rd Chain | NH2-VH3-CH1—CH2—CH3—COOH |
| | 4th Chain | NH2-VL3-CL-COOH |
| Three Chain 1st Orientation | 2nd Chain | NH2-VL2-VH1-HPD-COOH |
| | 1st Chain | NH2-VL1-VH2-HPD-CH2—CH3—COOH |
| | 3rd Chain | NH2-VL3-VH3-HPD-CH2—CH3—COOH |
| Three Chain 2nd Orientation | 2nd Chain | NH2-VL2-VH1-HPD-COOH |
| | 1st Chain | NH2—CH2—CH3-VL1-VH2-HPD COOH |
| | 3rd Chain | NH2-VL3-VH3-HPD-CH2—CH3—COOH |

HPD = Heterodimer-Promoting Domain

One embodiment of the present invention relates to bispecific trivalent binding molecules that comprise two epitope-binding sites for LAG-3 and one epitope-binding site for the second epitope present on a molecule other than LAG-3 (e.g. B7-H3, B7-H4, BTLA, CD40, CD80, CD86, of the invention may further comprise a CH1 Domain and/or a hinge region. When present, the CH1 Domain and/or hinge region may be of any isotype (e.g., IgG1, IgG2, IgG3, or IgG4), and is preferably of the same isotype as the desired Fc Region.

An exemplary CH1 Domain is a human IgG1 CH Domain. The amino acid sequence of an exemplary human IgG1 CH1 Domain is (SEQ ID NO:120):

```
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKRV
```

An exemplary CH1 Domain is a human IgG2 CH Domain. The amino acid sequence of an exemplary human IgG2 CH1 Domain is (SEQ ID NO:121):

```
ASTKGPSVFP LAPCSRSTSE STAALGCLVK DYFPEPVTVS
WNSGALTSGV HTFPAVLQSS GLYSLSSVVT VPSSNFGTQT
YTCNVDHKPS NTKVDKTV
```

An exemplary CH1 Domain is a human IgG4 CH1 Domain. The amino acid sequence of an exemplary human IgG4 CH1 Domain is (SEQ ID NO:122):

```
ASTKGPSVFP LAPCSRSTSE STAALGCLVK DYFPEPVTVS
WNSGALTSGV HTFPAVLQSS GLYSLSSVVT VPSSSLGTKT
YTCNVDHKPS NTKVDKRV
```

One exemplary hinge region is a human IgG1 hinge region. The amino acid sequence of an exemplary human IgG1 hinge region is (SEQ ID NO:114): EPKSCDKTH-TCPPCP.

Another exemplary hinge region is a human IgG2 hinge region. The amino acid sequence of an exemplary human IgG2 hinge region is (SEQ ID NO:115): ERKCCVECPPCP.

Another exemplary hinge region is a human IgG4 hinge region. The amino acid sequence of an exemplary human IgG4 hinge region is (SEQ ID NO:116): ESKYGPPCPSCP. As described herein, an IgG4 hinge region may comprise a stabilizing mutation such as the S228P substitution. The amino acid sequence of an exemplary stabilized IgG4 hinge region is (SEQ ID NO:117): ESKYGPPCPPCP.

The Fc Region of the Fc Region-containing molecules (e.g., antibodies, diabodies, and trivalent molecules) of the present invention may be either a complete Fc Region (e.g., a complete IgG Fc Region) or only a fragment of an Fc Region. Optionally, the Fc Region of the Fc Region-containing molecules of the present invention lacks the C-terminal lysine amino acid residue. In particular, the Fc Region of the Fc Region-containing molecules of the present invention may be an engineered variant Fc Region. Although the Fc Region of the bispecific Fc Region-containing molecules of the present invention may possess the ability to bind to one or more Fc receptors (e.g., FcγR(s)), more preferably such variant Fc Region will have altered binding to FcγRIA (CD64), FcγRIIA (CD32A), FcγRIIB (CD32B), FcγRIIIA (CD16a) or FcγRIIIB (CD16b) (relative to the binding exhibited by a wild-type Fc Region) or will have substantially reduced or no ability to bind to inhibitory receptor(s). Thus, the Fc Region of the Fc Region-containing molecules of the present invention may include some or all of the CH2 Domain and/or some or all of the CH3 Domain of a complete Fc Region, or may comprise a variant CH2 and/or a variant CH3 sequence (that may include, for example, one or more insertions and/or one or more deletions with respect to the CH2 or CH3 domains of a complete Fc Region). Such Fc Regions may comprise non-Fc polypeptide portions, or may comprise portions of non-naturally complete Fc Regions, or may comprise non-naturally occurring orientations of CH2 and/or CH3 Domains (such as, for example, two CH2 domains or two CH3 domains, or in the N-terminal to C-terminal direction, a CH3 Domain linked to a CH2 Domain, etc.).

Fc Region modifications identified as altering effector function are known in the art, including modifications that increase binding to activating receptors (e.g., FcγRIIA (CD16A) and reduce binding to inhibitory receptors (e.g., FcγRIM (CD32B) (see, e.g., Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors*," Cancer Res. 57(18):8882-8890). Exemplary variants of human IgG1 Fc Regions with reduced binding to CD32B and/or increased binding to CD16A contain F243L, R292P, Y300L, V305I or P296L substitutions. These amino acid substitutions may be present in a human IgG1 Fc Region in any combination or subcombination. In one embodiment, the human IgG1 Fc Region variant contains a F243L, R292P and Y300L substitution. In another embodiment, the human IgG1 Fc Region variant contains F243L, R292P, Y300L, V305I and P296L substitutions.

In particular, it is preferred for the CH2-CH3 Domains of the polypeptide chains of the Fc Region-containing molecules of the present invention to exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type IgG1 Fc Region (SEQ ID NO:1). Variant Fc Regions and mutant forms capable of mediating such altered binding are described above. In a specific embodiment, the Fc Region-containing molecules of the present invention comprise an IgG Fc Region that exhibits reduced ADCC effector function. In a preferred embodiment the CH2-CH3 Domain of the first and/or third polypeptide chains of such molecules include any 1, 2, or 3, of the substitutions: L234A, L235A, N297Q, and N297G. In another embodiment, the human IgG Fc Region variant contains an N297Q substitution, an N297G substitution, L234A and L235A substitutions or a D265A substitution, as these mutations abolish FcR binding. Alternatively, a CH2-CH3 Domain of an Fc Region which inherently exhibits decreased (or substantially no) binding to FcγRIIIA (CD16a) and/or reduced effector function (relative to the binding exhibited by the wild-type IgG1 Fc Region (SEQ ID NO:1)) is utilized. In a specific embodiment, the Fc Region-containing molecules of the present invention comprise an IgG2 Fc Region (SEQ ID NO:2) or an IgG4 Fc Region (SEQ ID:NO:4). When an IgG4 Fc Region in utilized, the instant invention also encompasses the introduction of a stabilizing mutation, such as the hinge region S228P substitution described above (see, e.g., SEQ ID NO:117). Since the N297G, N297Q, L234A, L235A and D265A substitutions abolish effector function, in circumstances in which effector function is desired, these substitutions would preferably not be employed.

A preferred IgG1 sequence for the CH2 and CH3 Domains of the LAG-3-binding molecules of the invention will have the L234A/L235A substitutions (SEQ ID NO:123):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
``` wherein, X is a lysine (K) or is absent.

In particular, it is preferred for the Fc Regions of the polypeptide chains of the Fc Region-containing molecules of the present invention to exhibit increased serum half-life (relative to the half-life exhibited by the corresponding wild-type Fc). Variant Fc Regions and mutant forms exhibiting extended serum half-life are described above. In a preferred embodiment the CH2-CH3 Domain of the first and/or third polypeptide chains of such Fc Region-containing molecules include any 1, 2, or 3, of the substitutions: M252Y, S254T and T256E. The invention further encompasses Fc Region-containing molecules of the present invention comprising variant Fc Regions comprising:

(A) one or more mutations which alter effector function and/or FcγR; and
(B) one or more mutations which extend serum half-life.

A preferred IgG1 sequence for the CH2 and CH3 Domains of the Fc Region-containing molecules of the present invention will comprise the substitutions L234A/L235A/M252Y/S254T/T256E (SEQ ID NO:124):

```
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
``` wherein, X is a lysine (K) or is absent

A preferred IgG4 sequence for the CH2 and CH3 Domains of the Fc Region-containing molecules of the present invention will comprise the M252Y/S254T/T256E substitutions (SEQ ID NO:125):

```
APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLTCLVK GFYPSDIAVE WESNGQPENN

YKTTPPVLDS DGSFFLYSRL TVDKSRWQEG NVFSCSVMHE

ALHNHYTQKS LSLSLGX
``` wherein, X is a lysine (K) or is absent

For diabodies and trivalent binding molecules whose first and third polypeptide chains are not identical), it is desirable to reduce or prevent homodimerization from occurring between the CH2-CH3 Domains of two first polypeptide chains or between the CH2-CH3 Domains of two third polypeptide chains. The CH2 and/or CH3 Domains of such polypeptide chains need not be identical in sequence, and advantageously are modified to foster complexing between the two polypeptide chains. For example, an amino acid substitution (preferably a substitution with an amino acid comprising a bulky side group forming a "knob", e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., "the hole" (e.g., a substitution with glycine). Such sets of mutations can be engineered into any pair of polypeptides comprising CH2-CH3 Domains that forms an Fc Region. Methods of protein engineering to favor heterodimerization over homodimerization are well known in the art, in particular with respect to the engineering of immunoglobulin-like molecules, and are encompassed herein (see e.g., Ridgway et al. (1996) "'*Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety). Preferably the "knob" is engineered into the CH2-CH3 Domains of the first polypeptide chain and the "hole" is engineered into the CH2-CH3 Domains of the third polypeptide chain of diabodies comprising three polypeptide chains. Thus, the "knob" will help in preventing the first polypeptide chain from homodimerizing via its CH2 and/or CH3 Domains. As the third polypeptide chain preferably contains the "hole" substitution it will heterodimerize with the first polypeptide chain as well as homodimerize with itself. This strategy may be utilized for diabodies and trivalent binding molecules comprising three, four or five chains as detailed above, where the "knob" is engineered into the CH2-CH3 Domains of the first polypeptide chain and the "hole" is engineered into the CH2-CH3 Domains of the third polypeptide chain.

A preferred knob is created by modifying an IgG Fc Region to contain the modification T366W. A preferred hole is created by modifying an IgG Fc Region to contain the modification T366S, L368A and Y407V. To aid in purifying the hole-bearing third polypeptide chain homodimer from the final bispecific heterodimeric Fc Region-containing molecule, the protein A binding site of the CH2 and CH3 Domains of the third polypeptide chain is preferably mutated by amino acid substitution at position 435 (H435R). Thus, the hole-bearing third polypeptide chain homodimer will not bind to protein A, whereas the bispecific heterodimer will retain its ability to bind protein A via the protein A binding site on the first polypeptide chain. In an alternative embodiment, the hole-bearing third polypeptide chain may incorporate amino acid substitutions at positions 434 and 435 (N434A/N435K).

A preferred IgG1 amino acid sequence for the CH2 and CH3 Domains of the first polypeptide chain of an Fc Region-containing molecule of the present invention will have the "knob-bearing" sequence (SEQ ID NO:126):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT
```

```
LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGX
``` wherein, X is a lysine (K) or is absent

A preferred IgG1 amino acid sequence for the CH2 and CH3 Domains of the second polypeptide chain of an Fc Region-containing molecule of the present invention having two polypeptide chains (or the third polypeptide chain of an Fc Region-containing molecule having three, four, or five polypeptide chains) will have the "hole-bearing" sequence (SEQ ID NO:127):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGX
``` wherein, X is a lysine (K) or is absent

As will be noted, the CH2-CH3 Domains of SEQ ID NO:126 and SEQ ID NO:127 include a substitution at position 234 with alanine and 235 with alanine, and thus form an Fc Region exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc Region (SEQ ID NO:1). The invention also encompasses such CH2-CH3 Domains, which comprise alanine residues at positions 234 and/or 235 and/or alternative and/or additional substitutions which modify effector function and/or FγR binding activity of the Fc Region. The invention also encompasses such CH2-CH3 Domains, which further comprise one or more half-live extending amino acid substitutions. In particular, the invention encompasses such hole-bearing and such knob-bearing CH2-CH3 Domains which further comprise the M252Y/S254T/T256E.

It is preferred that the first polypeptide chain will have a "knob-bearing" CH2-CH3 sequence, such as that of SEQ ID NO:126. However, as will be recognized, a "hole-bearing" CH2-CH3 Domain (e.g., SEQ ID NO:127) could be employed in the first polypeptide chain, in which case, a "knob-bearing" CH2-CH3 Domain (e.g., SEQ ID NO:126) would be employed in the second polypeptide chain of an Fc Region-containing molecule of the present invention having two polypeptide chains (or the third polypeptide chain of an Fc Region-containing molecule having three, four, or five polypeptide chains).

As detailed above the invention encompasses Fc Region-containing molecules (e.g., antibodies and Fc Region-containing diabodies) having wild type CH2 and CH3 Domains, or having CH2 and CH3 Domains comprising combinations of the substitutions described above. An exemplary amino acid sequence of an IgG1 CH2-CH3 Domain encompassing such variations is (SEQ ID NO:128):

```
APEX₁X₂GGPSV FLFPPKPKDT LX₃IX₄RX₅PEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLX₆CX₇VK GFYPSDIAVE WESNGQPENN

YKTTPPVLDS DGSFFLX₈SKL TVDKSRWQQG NVFSCSVMHE

ALHX₉X₁₀YTQKS LSLSPGX₁₁
``` wherein:
(a) $X_1$ and $X_2$ are both L (wild type), or are both A (decreased FcγR binding);
(b) $X_3$, $X_4$, and $X_5$ respectively are M, S and T (wild type), or are Y, T and E (extended half-life),
(c) $X_6$, $X_7$, and $X_8$ respectively are T, L and Y (wild type), or are W, L and Y (knob), or S, A and V (hole);
(d) $X_9$ and $X_{10}$ respectively are N and H (wild type), or are N and R (no protein A binding), or A and K (no protein A binding); and
(e) $X_{11}$ is K or is absent In other embodiments, the invention encompasses LAG-3-binding molecules comprising CH2 and/or CH3 Domains that have been engineered to favor heterodimerization over homodimerization using mutations known in the art, such as those disclosed in PCT Publication No. WO 2007/110205; WO 2011/143545; WO 2012/058768; WO 2013/06867, all of which are incorporated herein by reference in their entirety.

VIII. Reference Antibodies

A. Reference Anti-LAG-3 Antibody

In order to assess and characterize the novel anti-LAG-3-binding molecules of the present invention, the following reference antibody was employed: 25F7 (BMS-986016, Medarex/BMS, designated herein as "LAG-3 mAb A").

1. 25F7 ("LAG-3 mAb A")

The amino acid sequence of the VH Domain of 25F7 ("LAG-3 mAb A") (SEQ ID NO:129) is shown below (CDR$_H$ residues are shown underlined):

```
QVQLQQWGAG LLKPSETLSL TCAVYGGSFS DYYWNWIRQP

PGKGLEWIGE INHNGNTNSN PSLKSRVTLS LDTSKNQFSL

KLRSVTAADT AVYYCAFGYS DYEYNWFDPW GQGTLVTVSS
```

The amino acid sequence of the VL Domain of 25F7 ("LAG-3 mAb A") (SEQ ID NO:130) is shown below (CDR$_L$ residues are shown underlined):

```
EIVLTQSPAT LSLSPGERAT LSCRASQSIS SYLAWYQQKP

GQAPRLLIYD ASNRATGIPA RFSGSGSGTD FTLTISSLEP

EDFAVYYCQQ RSNWPLTFGQ GTNLEIK
```

B. Reference Anti-PD-1 Antibodies

In order to assess and characterize the activity of the novel LAG-3-binding molecules of the present invention in combination with an anti-PD-1 antibody a reference antibody may be used. Antibodies that are immunospecific for PD-1 are known (see, e.g., U.S. Pat. Nos. 8,008,449; 8,552,154; PCT Patent Publications WO 2012/135408; WO 2012/145549; and WO 2013/014668) and include: nivolumab (also known as 5C4, BMS-936558, ONO-4538, MDX-1106, and marketed as OPDIVO® by Bristol-Myers Squibb) designated herein as "PD-1 mAb 1;" pembrolizumab (formerly known as lambrolizumab, also known as MK-3475, SCH-900475, and marketed as KEYTRUDA® by Merck) designated herein as "PD-1 mAb 2"; EH12.2H7 (Dana Farber) designated herein as "PD-1 mAb 3"; pidilizumab (also known as CT-011, CureTech,) designated herein as "PD-1 mAb 4."

1. Nivolumab ("PD-1 mAb 1")

The amino acid sequence of the Heavy Chain Variable Domain of PD-1 mAb 1 has the amino acid sequence (SEQ ID NO:131) (CDR$_H$ residues are shown underlined):

```
QVQLVESGGG VVQPGRSLRL DCKASGITFS NSGMHWVRQA

PGKGLEWVAV IWYDGSKRYY ADSVKGRFTI SRDNSKNTLF

LQMNSLRAED TAVYYCATND DYWGQGTLVT VSS
```

The amino acid sequence of the Light Chain Variable Domain of PD-1 mAb 1 has the amino acid sequence (SEQ ID NO:132) (CDR$_L$ residues are shown underlined):

```
EIVLTQSPAT LSLSPGERAT LSCRASQSVS SYLAWYQQKP

GQAPRLLIYD ASNRATGIPA RFSGSGSGTD FTLTISSLEP

EDFAVYYCQQ SSNWPRTFGQ GTKVEIK
```

2. Pembrolizumab ("PD-1 mAb 2")

The amino acid sequence of the Heavy Chain Variable Domain of PD-1 mAb 2 has the amino acid sequence (SEQ ID NO:133) (CDR$_H$ residues are shown underlined):

```
QVQLVQSGVE VKKPGASVKV SCKASGYTFT NYYMYWVRQA

PGQGLEWMGG INPSNGGTNF NEKFKNRVTL TTDSSTTTAY

MELKSLQFDD TAVYYCARRD YRFDMGFDYW GQGTTVTVSS
```

The amino acid sequence of the Light Chain Variable Domain of PD-1 mAb 2 has the amino acid sequence (SEQ ID NO:134) (CDR$_L$ residues are shown underlined):

```
EIVLTQSPAT LSLSPGERAT LSCRASKGVS TSGYSYLHWY

QQKPGQAPRL LIYLASYLES GVPARFSGSG SGTDFTLTIS

SLEPEDFAVY YCQHSRDLPL TFGGGTKVEIK
```

3. EH12.2H7 ("PD-1 mAb 3")

The amino acid sequence of the Heavy Chain Variable Domain of PD-1 mAb 3 has the amino acid sequence (SEQ ID NO:135) (CDR$_H$ residues are shown underlined):

```
QVQLQQSGAE LAKPGASVQM SCKASGYSFT SSWIHWVKQR

PGQGLEWIGY IYPSTGFTEY NQKFKDKATL TADKSSSTAY

MQLSSLTSED SAVYYCARWR DSSGYHAMDY WGQGTSVTVSS
```

The amino acid sequence of the Light Chain Variable Domain of PD-1 mAb 3 has the amino acid sequence (SEQ ID NO:136) (CDR$_L$ residues are shown underlined):

```
DIVLTQSPAS LTVSLGQRAT ISCRASQSVS TSGYSYMHWY

QQKPGQPPKL LIKFGSNLES GIPARFSGSG SGTDFTLNIH

PVEEEDTATY YCQHSWEIPY TFGGGTKLEI K
```

4. Pidilizumab ("PD-1 mAb 4")

The amino acid sequence of the Heavy Chain Variable Domain of PD-1 mAb 4 has the amino acid sequence (SEQ ID NO:137) (CDR$_H$ residues are shown underlined):

```
QVQLVQSGSE LKKPGASVKI SCKASGYTFT NYGMNWVRQA

PGQGLQWMGW INTDSGESTY AEEFKGRFVF SLDTSVNTAY

LQITSLTAED TGMYFCVRVG YDALDYWGQG TLVTVSS
```

The amino acid sequence of the Light Chain Variable Domain of PD-1 mAb 4 has the amino acid sequence (SEQ ID NO:138) (CDR$_L$ residues are shown underlined):

```
EIVLTQSPSS LSASVGDRVT ITCSARSSVS YMHWFQQKPG

KAPKLWIYRT SNLASGVPSR FSGSGSGTSY CLTINSLQPE

DFATYYCQQR SSFPLTFGGG TKLEIK
```

IX. Methods of Production

An anti-LAG-3 polypeptide, and other LAG-3 agonists, antagonists and modulators can be created from the polynucleotides and/or sequences of the LAG-3 mAb 1, LAG-3 mAb 2, LAG-3 mAb 3, LAG-3 mAb 4, LAG-3 mAb 5, or LAG-3 mAb 6 antibodies by methods known in the art, for example, synthetically or recombinantly. One method of producing such peptide agonists, antagonists and modulators involves chemical synthesis of the polypeptide, followed by treatment under oxidizing conditions appropriate to obtain the native conformation, that is, the correct disulfide bond linkages. This can be accomplished using methodologies well known to those skilled in the art (see, e.g., Kelley, R. F. et al. (1990) In: GENETIC ENGINEERING PRINCIPLES AND METHODS, Setlow, J. K. Ed., Plenum Press, N. Y., vol. 12, pp 1-19; Stewart, J. M et al. (1984) SOLID PHASE PEPTIDE SYNTHESIS, Pierce Chemical Co., Rockford, Ill.; see also U.S. Pat. Nos. 4,105,603; 3,972,859; 3,842,067; and 3,862,925).

Polypeptides of the invention may be conveniently prepared using solid phase peptide synthesis (Merrifield, B. (1986) "Solid Phase Synthesis," Science 232(4748):341-347; Houghten, R. A. (1985) "General Method For The Rapid Solid-Phase Synthesis Of Large Numbers Of Peptides: Specificity Of Antigen-Antibody Interaction At The Level Of Individual Amino Acids," Proc. Natl. Acad. Sci. (U.S.A.) 82(15):5131-5135; Ganesan, A. (2006) "Solid-Phase Synthesis In The Twenty-First Century," Mini Rev. Med. Chem. 6(1):3-10).

In yet another alternative, fully human antibodies having one or more of the CDRs of LAG-3 mAb 1, LAG-3 mAb 2, LAG-3 mAb 3, LAG-3 mAb 4, LAG-3 mAb 5, or LAG-3 mAb 6 or which compete with LAG-3 mAb 1, LAG-3 mAb 2, LAG-3 mAb 3, LAG-3 mAb 4, LAG-3 mAb 5, or LAG-3 mAb 6 for binding to human LAG-3 or a soluble form thereof may be obtained through the use of commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are XENOMOUSE™ (Abgenix, Inc., Fremont, Calif.) and H$_U$MAB-MOUSE® and TC MOUSE™ (both from Medarex, Inc., Princeton, N.J.).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants {e.g., tobacco) or transgenic milk. Suitable methods for expressing antibodies recombinantly in plants or milk have been disclosed (see, for example, Peeters et al. (2001) "*Production Of Antibodies And Antibody Fragments In Plants*," Vaccine 19:2756; Lonberg, N. et al. (1995) "*Human Antibodies From Transgenic Mice*," Int. Rev. Immunol 13:65-93; and Pollock et al. (1999) "*Transgenic Milk As A Method For The Production Of Recombinant Antibodies*," J. Immunol Methods 231:147-157). Suitable methods for making derivatives of antibodies, e.g., humanized, single-chain, etc. are known in the art. In another alternative, antibodies may be made recombinantly by phage display technology (see, for example, U.S. Pat. Nos. 5,565,332; 5,580,717; 5,733,743; 6,265,150; and Winter, G. et al. (1994) "*Making Antibodies By Phage Display Technology*," Annu. Rev. Immunol. 12.433-455).

The antibodies or protein of interest may be subjected to sequencing by Edman degradation, which is well known to those of skill in the art. The peptide information generated from mass spectrometry or Edman degradation can be used to design probes or primers that are used to clone the protein of interest.

An alternative method of cloning the protein of interest is by "panning" using purified LAG-3 or portions thereof for cells expressing an antibody or protein of interest that possesses one or more of the CDRs LAG-3 mAb 1, LAG-3 mAb 2, LAG-3 mAb 3, LAG-3 mAb 4, LAG-3 mAb 5, or LAG-3 mAb 6 or that competes with LAG-3 mAb 1, LAG-3 mAb 2, LAG-3 mAb 3, LAG-3 mAb 4, LAG-3 mAb 5, or LAG-3 mAb 6 for binding to human LAG-3. The "panning" procedure may be conducted by obtaining a cDNA library from tissues or cells that express LAG-3, overexpressing the cDNAs in a second cell type, and screening the transfected cells of the second cell type for a specific binding to LAG-3 in the presence or absence of LAG-3 mAb 1, LAG-3 mAb 2, LAG-3 mAb 3, LAG-3 mAb 4, LAG-3 mAb 5, or LAG-3 mAb 6. Detailed descriptions of the methods used in cloning mammalian genes coding for cell surface proteins by "panning" can be found in the art (see, for example, Aruffo, A. et al. (1987) "*Molecular Cloning Of A CD28 cDNA By A High-Efficiency COS Cell Expression System*," Proc. Natl. Acad. Sci. (U.S.A.) 84:8573-8577 and Stephan, J. et al. (1999) "*Selective Cloning Of Cell Surface Proteins Involved In Organ Development: Epithelial Glycoprotein Is Involved In Normal Epithelial Differentiation*," Endocrinol. 140: 5841-5854).

Vectors containing polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cell capable of overexpressing heterologous DNAs can be used for the purpose of isolating the genes encoding the antibody, polypeptide or protein of interest. Non-limiting examples of suitable mammalian host cells include but are not limited to COS, HeLa, and CHO cells. Preferably, the host cells express the cDNAs at a level of about 5-fold higher, more preferably 10-fold higher, even more preferably 20-fold higher than that of the corresponding endogenous antibody or protein of interest, if present, in the host cells. Screening the host cells for a specific binding to LAG-3 is effected by an immunoassay or FACS. A cell overexpressing the antibody or protein of interest can be identified.

The invention includes polypeptides comprising an amino acid sequence of the antibodies of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an anti-LAG-3 polypeptide could be produced by an automated polypeptide synthesizer employing the solid phase method.

The invention includes variants of LAG-3 mAb 1, LAG-3 mAb 2, LAG-3 mAb 3, LAG-3 mAb 4, LAG-3 mAb 5, or LAG-3 mAb 6 antibodies and their polypeptide fragments that bind to LAG-3, including functionally equivalent antibodies and fusion polypeptides that do not significantly affect the properties of such molecules as well as variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues that can be conservatively substituted for one another include but are not limited to: glycine/alanine; serine/threonine; valine/isoleucine/leucine; asparagine/glutamine; aspartic acid/glutamic acid; lysine/arginine; and phenylalanine/tyrosine. These polypeptides also include glycosylated and non-glycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the Variable Domain. Changes in the Variable Domain can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention encompasses fusion proteins comprising one or more of the polypeptides or LAG-3 mAb 1, LAG-3 mAb 2, LAG-3 mAb 3, LAG-3 mAb 4, LAG-3 mAb 5, or LAG-3 mAb 6 antibodies of this invention. In one embodiment, a fusion polypeptide is provided that comprises a light chain, a heavy chain or both a light and heavy chain. In another embodiment, the fusion polypeptide contains a heterologous immunoglobulin constant region. In another embodiment, the fusion polypeptide contains a Light Chain Variable Domain and a Heavy Chain Variable Domain of an antibody produced from a publicly-deposited hybridoma.

For purposes of this invention, an antibody fusion protein contains one or more polypeptide domains that specifically bind to LAG-3 and another amino acid sequence to which it is not attached in the native molecule, for example, a heterologous sequence or a homologous sequence from another region.

X. Uses of the LAG-3-Binding Molecules of the Present Invention

The present invention encompasses compositions, including pharmaceutical compositions, comprising the LAG-3-binding molecules of the present invention (e.g., anti-LAG-3 antibodies, anti-LAG-3 bispecific diabodies, etc.), polypeptides derived from such molecules, polynucleotides comprising sequences encoding such molecules or polypeptides, and other agents as described herein.

As discussed above, LAG-3 plays an important role in negatively regulating T-cell proliferation, function and homeostasis. The LAG-3-binding molecules of the present invention have the ability to inhibit LAG-3 function, and thus reverse the LAG-3-mediated immune system inhibition. As such, LAG-3 mAb 1, LAG-3 mAb 2, LAG-3 mAb 3, LAG-3 mAb 4, LAG-3 mAb 5, and LAG-3 mAb 6, their humanized derivatives, and molecules comprising their LAG-3-binding fragments (e.g., bispecific diabodies, etc.), or that compete for binding with such antibodies, may be used to block LAG-3-mediated immune system inhibition, and thereby promote the activation of the immune system.

Bispecific LAG-3-binding molecules of the present invention that bind to LAG-3 and another molecule involved in regulating an immune check point present on the cell surface (e.g., PD-1) augment the immune system by blocking immune system inhibition mediated by LAG-3 and such immune check point molecules. Thus, the LAG-3-binding molecules of the invention are useful for augmenting an immune response (e.g., the T-cell mediated immune response) of a subject. In particular, the LAG-3-binding molecules of the invention and may be used to treat any disease or condition associated with an undesirably suppressed immune system, including cancer and diseases that are associated with the presence of a pathogen (e.g., a bacterial, fungal, viral or protozoan infection).

The cancers that may be treated by the LAG-3-binding molecules of the present invention include cancers characterized by the presence of a cancer cell selected from the group consisting of a cell of: an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

In particular, the LAG-3-binding molecules of the present invention may be used in the treatment of colorectal cancer, hepatocellular carcinoma, glioma, kidney cancer, breast cancer, multiple myeloma, bladder cancer, neuroblastoma; sarcoma, non-Hodgkin's lymphoma, non-small cell lung cancer, ovarian cancer, pancreatic cancer and rectal cancer.

Pathogen-associated diseases that may be treated by the LAG-3-binding molecules of the present invention include chronic viral, bacterial, fungal and parasitic infections. Chronic infections that may be treated by the LAG-3-binding molecules of the present invention include Epstein Barr virus, Hepatitis A Virus (HAV); Hepatitis B Virus (HBV); Hepatitis C Virus (HCV); herpes viruses (e.g. HSV-1, HSV-2, CMV), Human Immunodeficiency Virus (HIV), Vesicular Stomatitis Virus (VSV), *Bacilli, Citrobacter, Cholera, Diphtheria, Enterobacter, Gonococci, Helicobacter pylori, Klebsiella, Legionella, Meningococci, mycobacteria, Pseudomonas, Pneumonococci, rickettsia* bacteria, *Salmonella, Serratia, Staphylococci, Streptococci, Tetanus, Aspergillus (A. fumigatus, A. niger*, etc.), *Blastomyces dermatitidis, Candida (C. albicans, C. krusei, C. glabrata, C. tropicalis*, etc.), *Cryptococcus neoformans*, Genus *Mucorales (mucor, absidia, rhizopus), Sporothrix schenkii, Paracoccidioides brasiliensis, Coccidioides immitis, Histoplasma capsulatum, Leptospirosis, Borrelia burgdorferi, helminth parasite* (hookworm, tapeworms, flukes, flatworms (e.g. *Schistosomia), Giardia Zambia, trichinella, Dientamoeba Fragilis, Trypanosoma brucei, Trypanosoma cruzi*, and *Leishmania donovani.*

The LAG-3-binding molecules of the invention can be combined with an immunogenic agent such as a tumor vaccine. Such vaccines may comprise purified tumor antigens (including recombinant proteins, peptides, and carbohydrate molecules), autologous or allogeneic tumor cells. A number of tumor vaccine strategies have been described (see for example, Palena, C., et al., (2006) "*Cancer vaccines: preclinical studies and novel strategies,*" Adv. Cancer Res. 95, 115-145; Mellman, I., et al. (2011) "*Cancer immunotherapy comes of age,*" Nature 480, 480-489; Zhang, X. M. et al. (2008) "*The Anti-Tumor Immune Response Induced By A Combination of MAGE-3/MAGE-n-Derived Peptides,*" Oncol. Rep. 20, 245-252; Disis, M. L. et al. (2002) "*Generation of T-cell Immunity to the HER-2/neu Protein After Active Immunization with HER-2/neu Peptide-Based Vaccines,*" J. Clin. Oncol. 20:2624-2632; Vermeij, R. et al. (2012) "*Potentiation of a p53-SLP Vaccine BY Cyclphosphamide In Ovarian Cancer: A Single-Arm Phase II Study.*" Int. J. Cancer 131:E670-E680). The LAG-3-binding molecules of the invention can be combined with chemotherapeutic regimes. In these instances, it may be possible to reduce the dose of chemotherapeutic reagent administered (Mokyr. M. B. et al. (1998) "*Realization Of The Therapeutic Potential Of CTLA-4 Blockade In Low-Dose Chemotherapy-Treated Tumor-Bearing Mice,*" Cancer Research 58: 5301-5304).

The LAG-3-binding molecules of the invention can be combined with other immunostimulatory molecules such as antibodies which activate host immune responsiveness to provide for increased levels of T-cell activation. In particular, anti-PD-1 antibodies, anti-PD-L1 antibodies and/or an anti-CTLA-4 antibodies have been demonstrated to active the immune system (see, e.g., del Rio, M-L. et al. (2005) "*Antibody-Mediated Signaling Through PD-1 Costimulates T Cells And Enhances CD28-Dependent Proliferation,*" Eur. J. Immunol 35:3545-3560; Barber, D. L. et al. (2006) "*Restoring Function In Exhausted CD8 T Cells During Chronic Viral Infection,*" Nature 439, 682-687; Iwai, Y. et al. (2002) "*Involvement of PD-L1 On Tumor Cells In The Escape From Host Immune System And Tumor Immunotherapy by PD-L1 blockade,*" Proc. Natl Acad. Sci. USA 99, 12293-12297; Leach, D. R., et al., (1996) "*Enhancement Of Antitumor Immunity By CTLA-4 Blockade,*" Science 271, 1734-1736). Additional immunostimulatory molecules that may be combined with the LAG-3-binding molecules of the invention include antibodies to molecules on the surface of dendritic cells that activate dendritic cell (DC) function and antigen presentation, anti-CD40 antibodies able to substitute for T-cell helper activity, and activating antibodies to T-cell costimulatory molecules such as PD-L1, CTLA-4, OX-40 4-1BB, and ICOS (see, for example, Ito et al. (2000) "*Effective Priming Of Cytotoxic T Lymphocyte Precursors By Subcutaneous Administration Of Peptide Antigens In Liposomes Accompanied By Anti-CD40 And Anti-CTLA-4 Antibodies,*" Immunobiology 201:527-40; U.S. Pat. No. 5,811,097; Weinberg et al. (2000) "*Engagement of the OX-40 Receptor In Vivo Enhances Antitumor Immunity,*" Immunol 164:2160-2169; Melero et al. (1997) "*Monoclonal Antibodies Against The 4-1BB T-Cell Activation Molecule Eradicate Established Tumors,*" Nature Medicine 3: 682-685; Hutloff et al. (1999) "*ICOS is An Inducible T-Cell Co-Stimulator Structurally And Functionally Related to CD28,*" Nature 397: 263-266; and Moran, A. E. et al. (2013) "*The TNFRs OX40, 4-1BB, and CD40 As Targets For Cancer Immunotherapy,*" Curr Opin Immunol. 2013 April; 25(2): 10.1016/j.coi.2013.01.004), and/or stimulatory Chimeric Antigen Receptors (CARs) comprising an antigen binding domain directed against a disease antigen fused to one or more intracellular signaling domains from various costimulatory protein receptors (e.g., CD28, 4-1BB, ICOS, OX40, etc.) which serve to stimulate T-cells upon antigen binding (see, for example, Tettamanti, S. et al. (2013) "*Targeting Of Acute Myeloid Leukaemia By Cytokine-Induced Killer Cells Redirected With A Novel CD123-Specific Chimeric Antigen Receptor,*" Br. J. Haematol. 161:389-401; Gill, S. et al. (2014) "*Efficacy Against Human Acute Myeloid Leukemia And Myeloablation Of Normal Hematopoiesis In A Mouse Model Using Chimeric Antigen Receptor-Modified T Cells,*" Blood 123(15): 2343-2354; Mardiros, A. et al. (2013) "*T Cells Expressing CD123-Specific Chimeric Antigen Receptors Exhibit Specific Cytolytic Effector Functions And Antitumor Effects Against Human Acute Myeloid Leukemia,*" Blood 122:3138-3148; Pizzitola, I. et al. (2014) "*Chimeric Antigen Receptors Against CD33/CD123 Antigens Efficiently Target Primary Acute Myeloid Leukemia Cells in vivo,*" Leukemia 28(8):1596-1605).

LAG-3-binding molecules of the invention can be combined with inhibitory Chimeric Antigen Receptors (iCARs) to divert off target immunotherapy responses. iCARs an antigen binding domain directed against a disease antigen fused to one or more intracellular signaling domains from various inhibitory protein receptors (e.g., CTLA-4, PD-1, etc.) which serve to constrain T-cell responses upon antigen binding (see, for example, Fedorov V. D. (2013) "*PD-1—and CTLA-4—Based Inhibitory Chimeric Antigen Receptors (iCARs) Divert Off-Target Immunotherapy Responses,*" Sci Tranl Med. 5(215):215ra172).

In particular, the anti-LAG-3 antibodies of the invention are used in combination with an anti-CD137 antibody, an anti-OX40 antibody, an anti-PD-1 antibody, an anti-PD-L1 antibody, an anti-TIGIT antibody, an anti-TIM-3 antibody and/or a cancer vaccine.

In addition to their utility in therapy, the LAG-3-binding molecules of the present invention may be detectably labeled and used in the detection of LAG-3 in samples or in the imaging of LAG-3 on cells.

XI. Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) that can be used in the preparation of unit dosage forms. Such compositions comprise a prophylactically or therapeutically effective amount of the LAG-3-binding molecules of the present invention, or a combination of such agents and a pharmaceutically acceptable carrier. Preferably, compositions of the invention comprise a prophylactically or therapeutically effective amount of the LAG-3-binding molecules of the present invention and a pharmaceutically acceptable carrier. The invention particularly encompasses such pharmaceutical compositions in which the LAG-3-binding molecule is: a LAG-3 mAb 1, LAG-3 mAb 2, LAG-3 mAb 3, LAG-3 mAb 4, LAG-3 mAb 5, or LAG-3 mAb 6 antibody; a humanized LAG-3 mAb 1; LAG-3 mAb 2, LAG-3 mAb 3, LAG-3 mAb 4 LAG-3 mAb 5, or LAG-3 mAb 6 antibody; a LAG-3-binding fragment of any such antibody; or in which the LAG-3-binding molecule is a bispecific LAG-3 diabody (e.g., a LAG-3×PD-1 bispecific diabody). Especially encompassed are such molecules that comprise the 3 $CDR_{LS}$ and the 3 $CDR_{HS}$ of LAG-3 mAb 1; or that comprise the 3 $CDR_{HS}$ and the 3 $CDR_{HS}$ of LAG-3 mAb 2; or that comprise the 3 $CDR_{LS}$ and the 3 $CDR_{HS}$ of LAG-3 mAb 3, or that comprise the 3 $CDR_{LS}$ and the 3 $CDR_{HS}$ of LAG-3 mAb 4, or that comprise the 3 $CDR_{LS}$ and the 3 $CDR_{HS}$ of LAG-3 mAb 5, or that comprise the 3 $CDR_{LS}$ and the 3 $CDR_{HS}$ of LAG-3 mAb 6.

The invention also encompasses such pharmaceutical compositions that additionally include a second therapeutic antibody (e.g., tumor-specific monoclonal antibody) that is specific for a particular cancer antigen, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers filled with a LAG-3-binding molecule of the present invention (and more preferably, a LAG-3 mAb 1, LAG-3 mAb 2, LAG-3 mAb 3, LAG-3 mAb 4, LAG-3 mAb 5, or LAG-3 mAb 6 antibody; a humanized LAG-3 mAb 1, LAG-3 mAb 2, LAG-3 mAb 3, LAG-3 mAb 4, LAG-3 mAb 5, or LAG-3 mAb 6 antibody; a LAG-3-binding fragment of any such antibody; or in which the LAG-3-binding molecule is a bispecific LAG-3 diabody (e.g., a LAG-3×PD-1 bispecific diabody)). Especially encompassed are such molecules that comprise the 3 $CDR_{LS}$ and the 3 $CDR_{HS}$ of LAG-3 mAb 1; or that comprise the 3 $CDR_{LS}$ and the 3 $CDR_{HS}$ of LAG-3 mAb 2; or that comprise the 3 $CDR_{LS}$ and the 3 $CDR_{HS}$ of LAG-3 mAb 3; or that comprise the 3 $CDR_{LS}$ and the 3 $CDR_{HS}$ of LAG-3 mAb 4; or that comprise the 3 $CDR_{LS}$ and the 3 $CDR_{HS}$ of LAG-3 mAb 5; or that comprise the 3 $CDR_{LS}$ and the 3 $CDR_{HS}$ of LAG-3 mAb 6, alone or with such pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. A kit can comprise any of the LAG-3-binding molecules of the present invention. The kit can further comprise one or more other prophylactic and/or therapeutic agents useful for the treatment of cancer, in one or more containers; and/or the kit can further comprise one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

XII. Methods of Administration

The compositions of the present invention may be provided for the treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or a conjugated molecule of the invention. In a preferred aspect, such compositions are substantially purified (i.e., substantially free from substances that limit its effect or produce undesired side effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Various delivery systems are known and can be used to administer the compositions of the invention, e.g., encapsulation in liposomes, microparticles, microcapsules, recombinant cells capable of expressing the antibody or fusion protein, receptor-mediated endocytosis (See, e.g., Wu et al. (1987) "*Receptor-Mediated In Vitro Gene Transformation By A Soluble DNA Carrier System*," J. Biol. Chem. 262: 4429-4432), construction of a nucleic acid as part of a retroviral or other vector, etc.

Methods of administering a molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the LAG-3-binding molecules of the present invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the LAG-3-binding molecules of the present invention are packaged in a hermetically sealed container such as an ampoule or sachette indicating the quantity of the molecule. In one embodiment, such molecules are supplied as a dry sterilized lyophilized powder or water free concentrate in a hermetically sealed container and can be reconstituted, e.g., with water or saline to the appropriate concentration for administration to a subject. Preferably, the LAG-3-binding molecules of the present invention are supplied as a dry sterile lyophilized powder in a hermetically sealed container.

The lyophilized LAG-3-binding molecules of the present invention should be stored at between 2° C. and 8° C. in their original container and the molecules should be administered within 12 hours, preferably within 6 hours, within 5 hours, within 3 hours, or within 1 hour after being reconstituted. In an alternative embodiment, such molecules are supplied in liquid form in a hermetically sealed container indicating the quantity and concentration of the molecule, fusion protein, or conjugated molecule. Preferably, such LAG-3-binding molecules when provided in liquid form are supplied in a hermetically sealed container.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

As used herein, an "effective amount" of a pharmaceutical composition, in one embodiment, is an amount sufficient to effect beneficial or desired results including, without limitation, clinical results such as decreasing symptoms resulting from the disease attenuating a symptom of infection (e.g., viral load, fever, pain, sepsis, etc.) or a symptom of cancer (e.g., the proliferation, of cancer cells, tumor presence, tumor metastases, etc.), thereby increasing the quality of life of those suffering from the disease, decreasing the dose of other medications required to treat the disease, enhancing the effect of another medication such as via targeting and/or internalization, delaying the progression of the disease, and/or prolonging survival of individuals.

An effective amount can be administered in one or more administrations. For purposes of this invention, an effective amount of drug, compound, or pharmaceutical composition is an amount sufficient to reduce the proliferation of (or the effect of) viral presence and to reduce and/or delay the development of the viral disease, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art.

For the LAG-3-binding molecules encompassed by the invention (e.g., antibodies, diabodies, etc.), the dosage administered to a patient is preferably determined based upon the body weight (kg) of the recipient subject. For the LAG-binding molecules encompassed by the invention, the dosage administered to a patient is typically from at least about 0.01 µg/kg body weight, at least about 0.05 µg/kg body weight, at least about 0.1 µg/kg body weight, at least about 0.2 µg/kg body weight, at least about 0.5 µg/kg body weight, at least about 1 µg/kg body weight, at least about 2 µg/kg body weight, at least about 3 µg/kg body weight, at least about 5 µg/kg body weight, at least about 10 µg/kg body weight, at least about 20 µg/kg body weight, at least about 30 µg/kg body weight, at least about 50 µg/kg body weight, at least about 100 µg/kg body weight, at least about 250 µg/kg body weight, at least about 750 µg/kg body weight, at least about 1.5 mg/kg body weight, at least about 3 mg/kg body weight, at least about 5 mg/kg body weight, or at least about 10 mg/kg, at least about 30 mg/kg, at least about 50 mg/kg, at least about 75 mg/kg, at least about 100 mg/kg, at least about 125 mg/kg, at least about 150 mg/kg or more body weight. The calculated dose will be administered based on the patient's body weight at baseline. Significant (≥10%) change in body weight from baseline or established plateau weight should prompt recalculation of dose.

In some embodiments, the LAG-3-binding bispecific molecules (e.g., diabodies and trivalent binding molecules) encompassed by the invention, the dosage administered to a patient is typically from at least about 0.3 ng/kg per day to about 0.9 ng/kg per day, from at least about 1 ng/kg per day to about 3 ng/kg per day, from at least about 3 ng/kg per day to about 9 ng/kg per day, from at least about 10 ng/kg per day to about 30 ng/kg per day, from at least about 30 ng/kg per day to about 90 ng/kg per day, from at least about 100 ng/kg per day to about 300 ng/kg per day, from at least about 200 ng/kg per day to about 600 ng/kg per day, from at least about 300 ng/kg per day to about 900 ng/kg per day, from at least about 400 ng/kg per day to about 800 ng/kg per day, from at least about 500 ng/kg per day to about 1000 ng/kg per day, from at least about 600 ng/kg per day to about 1000 ng/kg per day, from at least about 700 ng/kg per day to about 1000 ng/kg per day, from at least about 800 ng/kg per day to about 1000 ng/kg per day, from at least about 900 ng/kg per day to about 1000 ng/kg per day, or at least about 1,000 ng/kg per day. The calculated dose will be administered based on the patient's body weight at baseline. Significant (≥10%) change in body weight from baseline or established plateau weight should prompt recalculation of dose.

In another embodiment, the patient is administered a treatment regimen comprising one or more doses of such prophylactically or therapeutically effective amount of a LAG-3-binding molecule of the present invention, wherein the treatment regimen is administered over 2 days, 3 days, 4 days, 5 days, 6 days or 7 days. In certain embodiments, the treatment regimen comprises intermittently administering doses of the prophylactically or therapeutically effective amount of the LAG-3-binding molecules of the present invention (for example, administering a dose on day 1, day 2, day 3 and day 4 of a given week and not administering doses of the prophylactically or therapeutically effective amount of the LAG-3-binding molecule (and particularly, a LAG-3 mAb 1, LAG-3 mAb 2, LAG-3 mAb 3, LAG-3 mAb 4, LAG-3 mAb 5, LAG-3 mAb 6 antibody; a humanized LAG-3 mAb 1, LAG-3 mAb 2, LAG-3 mAb 3, LAG-3 mAb 4, LAG-3 mAb 5, or LAG-3 mAb 6 antibody; a LAG-3-binding fragment of any such antibody; or in which the LAG-3-binding molecule is a bispecific LAG-3 diabody (e.g., a LAG-3×PD-1 bispecific Fc diabody). Especially encompassed is the administration (on day 5, day 6 and day 7 of the same week) of molecules that comprise the the 3 $CDR_{LS}$ and the 3 $CDR_{HS}$ of LAG-3 mAb 1; or that comprise the 3 $CDR_{LS}$ and the 3 $CDR_{HS}$ of LAG-3 mAb 2; or that comprise the 3 $CDR_{LS}$ and the 3 $CDR_{HS}$ of LAG-3 mAb 3; or that comprise the 3 $CDR_{LS}$ and the 3 $CDR_{HS}$ of LAG-3 mAb 4; or that comprise the 3 $CDR_{LS}$ and the 3 $CDR_{HS}$ of LAG-3 mAb 5; or that comprise the 3 $CDR_{LS}$ and the 3 $CDR_{HS}$ of LAG-3 mAb 6. Typically, there are 1, 2, 3, 4, 5 or more courses of treatment. Each course may be the same regimen or a different regimen.

In another embodiment, the administered dose escalates over the first quarter, first half or first two-thirds or three-quarters of the regimen(s) (e.g., over the first, second, or third regimens of a 4 course treatment) until the daily prophylactically or therapeutically effective amount of the LAG-3-binding molecule is achieved. Table 6 provides 5 examples of different dosing regimens described above for a typical course of treatment with a diabody.

TABLE 6

| Regimen | Day | Diabody Dosage (ng diabody per kg subject weight per day) | | | | |
| --- | --- | --- | --- | --- | --- | --- |
| 1 | 1, 2, 3, 4 | 100 | 100 | 100 | 100 | 100 |
|   | 5, 6, 7 | none | none | none | none | none |
| 2 | 1, 2, 3, 4 | 300 | 500 | 700 | 900 | 1,000 |
|   | 5, 6, 7 | none | none | none | none | none |

TABLE 6-continued

| Regimen | Day | Diabody Dosage (ng diabody per kg subject weight per day) | | | | |
|---|---|---|---|---|---|---|
| 3 | 1, 2, 3, 4 | 300 | 500 | 700 | 900 | 1,000 |
|   | 5, 6, 7    | none | none | none | none | none |
| 4 | 1, 2, 3, 4 | 300 | 500 | 700 | 900 | 1,000 |
|   | 5, 6, 7    | none | none | none | none | none |

The dosage and frequency of administration of a LAG-3-binding molecule of the present invention may be reduced or altered by enhancing uptake and tissue penetration of the molecule by modifications such as, for example, lipidation.

The dosage of a LAG-3-binding molecule of the invention administered to a patient may be calculated for use as a single agent therapy. Alternatively, the molecule may be used in combination with other therapeutic compositions and the dosage administered to a patient are lower than when said molecules are used as a single agent therapy.

The pharmaceutical compositions of the invention may be administered locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

The compositions of the invention can be delivered in a vesicle, in particular a liposome (See Langer (1990) "*New Methods Of Drug Delivery,*" Science 249:1527-1533); Treat et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 3 17-327).

The compositions of the invention can be delivered in a controlled-release or sustained-release system. Any technique known to one of skill in the art can be used to produce sustained-release formulations comprising one or more of the LAG-3-binding molecule(s) of the invention. See, e.g., U.S. Pat. No. 4,526,938; PCT publication WO 91/05548; PCT publication WO 96/20698; Ning et al. (1996) "*Intratumoral Radioimmunotherapy Of A Human Colon Cancer Xenograft Using A Sustained-Release Gel,*" Radiotherapy & Oncology 39:179-189, Song et al. (1995) "*Antibody Mediated Lung Targeting Of Long-Circulating Emulsions,*" PDA Journal of Pharmaceutical Science & Technology 50:372-397; Cleek et al. (1997) "*Biodegradable Polymeric Carriers For A bFGF Antibody For Cardiovascular Application,*" Pro. Int'l. Symp. Control. Rel. Bioact. Mater. 24:853-854; and Lam et al. (1997) "*Microencapsulation Of Recombinant Humanized Monoclonal Antibody For Local Delivery,*" Proc. Int'l. Symp. Control Rel. Bioact. Mater. 24:759-760, each of which is incorporated herein by reference in its entirety. In one embodiment, a pump may be used in a controlled-release system (See Langer, supra; Sefton, (1987) "*Implantable Pumps,*" CRC Crit. Rev. Biomed. Eng. 14:201-240; Buchwald et al. (1980) "*Long-Term, Continuous Intravenous Heparin Administration By An Implantable Infusion Pump In Ambulatory Patients With Recurrent Venous Thrombosis,*" Surgery 88:507-516; and Saudek et al. (1989) "*A Preliminary Trial Of The Programmable Implantable Medication System For Insulin Delivery,*" N. Engl. J. Med. 321:574-579). In another embodiment, polymeric materials can be used to achieve controlled-release of the molecules (see e.g., MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Levy et al. (1985) "*Inhibition Of Calcification Of Bioprosthetic Heart Valves By Local Controlled-Release Diphosphonate,*" Science 228:190-192; During et al. (1989) "*Controlled Release Of Dopamine From A Polymeric Brain Implant: In Vivo Characterization,*" Ann. Neurol. 25:351-356; Howard et al. (1989) "*Intracerebral Drug Delivery In Rats With Lesion-Induced Memory Deficits,*" J. Neurosurg. 7(1):105-112); U.S. Pat. Nos. 5,679,377; 5,916, 597; 5,912,015; 5,989,463; 5,128,326; PCT Publication No. WO 99/15154; and PCT Publication No. WO 99/20253). Examples of polymers used in sustained-release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. A controlled-release system can be placed in proximity of the therapeutic target (e.g., the lungs), thus requiring only a fraction of the systemic dose (see, e.g., Goodson, in MEDICAL APPLICATIONS OF CONTROLLED RELEASE, supra, vol. 2, pp. 115-138 (1984)). Polymeric compositions useful as controlled-release implants can be used according to Dunn et al. (See U.S. Pat. No. 5,945,155). This particular method is based upon the therapeutic effect of the in situ controlled-release of the bioactive material from the polymer system. The implantation can generally occur anywhere within the body of the patient in need of therapeutic treatment. A non-polymeric sustained delivery system can be used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888, 533).

Controlled-release systems are discussed in the review by Langer (1990, "*New Methods Of Drug Delivery,*" Science 249:1527-1533). Any technique known to one of skill in the art can be used to produce sustained-release formulations comprising one or more therapeutic agents of the invention. See, e.g., U.S. Pat. No. 4,526,938; International Publication Nos. WO 91/05548 and WO 96/20698; Ning et al. (1996) "*Intratumoral Radioimmunotheraphy Of A Human Colon Cancer Xenograft Using A Sustained-Release Gel,*" Radiotherapy & Oncology 39:179-189, Song et al. (1995) "*Antibody Mediated Lung Targeting Of Long-Circulating Emulsions,*" PDA Journal of Pharmaceutical Science & Technology 50:372-397; Cleek et al. (1997) "*Biodegradable Polymeric Carriers For A bFGF Antibody For Cardiovascular Application,*" Pro. Int'l. Symp. Control. Rel. Bioact. Mater. 24:853-854; and Lam et al. (1997) "*Microencapsulation Of Recombinant Humanized Monoclonal Antibody For Local Delivery,*" Proc. Int'l. Symp. Control Rel. Bioact. Mater. 24:759-760, each of which is incorporated herein by reference in its entirety.

Where the composition of the invention is a nucleic acid encoding a LAG-3-binding molecule of the present invention, the nucleic acid can be administered in vivo to promote expression of its encoded LAG-3-binding molecule by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (See e.g., Joliot et al. (1991) "*Antennapedia Homeobox Peptide Regulates Neural Morphogenesis*," Proc. Natl. Acad. Sci. (U.S.A.) 88:1864-1868), etc. Alternatively, a nucleic acid can be introduced intracellularly and incorporated within host cell DNA for expression by homologous recombination.

Treatment of a subject with a therapeutically or prophylactically effective amount of a LAG-3-binding molecule of the present invention can include a single treatment or, preferably, can include a series of treatments. In a preferred example, a subject is treated with such a diabody one time per week for between about 1 to 10 weeks, preferably between 2 to 8 weeks, more preferably between about 3 to 7 weeks, and even more preferably for about 4, 5, or 6 weeks. The pharmaceutical compositions of the invention can be administered once a day, twice a day, or three times a day. Alternatively, the pharmaceutical compositions can be administered once a week, twice a week, once every two weeks, once a month, once every six weeks, once every two months, twice a year or once per year. It will also be appreciated that the effective dosage of the molecules used for treatment may increase or decrease over the course of a particular treatment.

EXAMPLES

Having now generally described the invention, the same will be more readily understood through reference to the following examples, which are provided by way of illustration and are not intended to be limiting of the present invention unless specified. It will be apparent to those skilled in the art that many modifications, both to materials and methods, can be practiced without departing from the scope of the present disclosure.

Example 1

Characterization of Anti-LAG-3 Monoclonal Antibodies LAG-3 mAb 1, LAG-3 mAb 2, LAG-3 mAb 3, LAG-3 mAb 4, LAG-3 mAb 5, and LAG-3 mAb 6

Six murine monoclonal antibodies were isolated as being capable of immunespecifically binding to both human and cynomolgus monkey LAG-3, and accorded the designations "LAG-3 mAb 1," "LAG-3 mAb 2," "LAG-3 mAb 3," "LAG-3 mAb 4," "LAG-3 mAb 5," and "LAG-3 mAb 6." The CDRs of these antibodies were found to differ and are provided above. LAG-3 mAb 1 was humanized yielded two humanized VH Domains, designated herein as "hLAG-3 mAb 1 VH-1," and "hLAG-3 mAb 1 VH-2," and four humanized VL Domains designated herein as "hLAG-3 mAb 1 VL-1," "hLAG-3 mAb 1 VL-2," "hLAG-3 mAb 1 VL-3," and "hLAG-3 mAb 1 VL-4." LAG-3 mAb 6 was also humanized yielded two humanized VH Domains, designated herein as "hLAG-3 mAb 6 VH-1," and "hLAG-3 mAb 6 VH-2," and two humanized VL Domains designated herein as "hLAG-3 mAb 6 VL-1," and "hLAG-3 mAb 6 VL-2." As provided above, the humanized heavy and light Variable Domains of a given antibody may be used in any combination and particular combinations of humanized Variable Domains are referred to by reference to the specific VH/VL Domains, for example a humanized antibody comprising hLAG-3 mAb 1 VH-1 and hLAG-3 mAb 1 VL-2 is specifically referred to as "hLAG-3 mAb 1(1.2)."

Full length humanized mAbs were constructed as follows: the C-terminus of a humanized VL Domain was fused to the N-terminus of a human light chain kappa region to generate a light chain and each light chain is paired with a heavy chain comprising a humanized VH Domain of the same antibody fused to the N-terminus of either a human IgG1 Constant Region comprising the L234A/L235A (AA) substitutions or a human IgG4 Constant Region comprising the S228P substitution.

The amino acid sequence of an exemplary human IgG1 Constant Region comprising the L234A/L235A (AA) substitutions (SEQ ID NO:139):

```
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRVEP KSCDKTHTCP PCPAPEAAGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSREE

MTKNQVSLTC LVKGFYPSDI AVEWESNGQP ENNYKTTPPV

LDSDGSFFLY SKLTVDKSRW QQGNVFSCSV MHEALHNHYT

QKSLSLSPGX
``` wherein, X is a lysine (K) or is absent

In SEQ ID NO:139, amino acid residues 1-98 correspond to the IgG1 CH1 Domain (SEQ ID NO:120), amino acid residues 99-113 correspond to the IgG1 hinge region (SEQ ID NO: 114) and amino acid residues 114-329 correspond to the IgG1 CH2-CH3 Domain comprising the L234A/L235A substitutions (underlined) (SEQ ID NO:123).

The amino acid sequence of an exemplary human human IgG4 Constant Region comprising the S228P substitution (SEQ ID NO:140):

```
ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRVES KYGPPCPPCP APEFLGGPSV

FLFPPKPKDT LMISRTPEVT CVVVDVSQED PEVQFNWYVD

GVEVHNAKTK PREEQFNSTY RVVSVLTVLH QDWLNGKEYK

CKVSNKGLPS SIEKTISKAK GQPREPQVYT LPPSQEEMTK

NQVSLTCLVK GFYPSDIAVE WESNGQPENN YKTTPPVLDS

DGSFFLYSRL TVDKSRWQEG NVFSCSVMHE ALHNHYTQKS

LSLSLGX
``` wherein, X is a lysine (K) or is absent

In SEQ ID NO:140, amino acid residues 1-98 correspond to the IgG4 CH1 Domain (SEQ ID NO:122), amino acid residues 99-110 correspond to the stabilized IgG4 hinge region comprising the S228P substitutions (underlined) (SEQ ID NO: 117) and amino acid residues 111-326 correspond to the IgG4 CH2-CH3 Domain (SEQ ID NO:4).

The binding kinetics of the antibodies LAG-3 mAb 1, LAG-3 mAb 2, LAG-3 mAb 3, LAG-3 mAb 4, LAG-3 mAb 5, LAG-3 mAb 6, several humanized and a reference antibody LAG-3 mAb A was investigated using Biacore analysis. The anti-LAG-3 antibodies were captured and were incubated with His-tagged soluble human LAG-3 (shLAG-3-His) and the kinetics of binding was determined via Biacore analysis. The calculated ka, kd and KD are presented in Table 7.

TABLE 7

| Anti-LAG-3 Antibody | $k_a$ (×10$^5$) | $k_d$ (×10$^{-4}$) | KD (nM) |
|---|---|---|---|
| LAG-3 mAb A | 8.7 | 5.4 | 0.6 |
| LAG-3 mAb 1 [a] | 20 | 0.26 | 0.013 |
| LAG-3 mAb 1 [b] | 31 | 0.27 | 0.01 |
| LAG-3 mAb 2 [a] | 11 | 21 | 1.9 |
| LAG-3 mAb 3 [a] | 7.7 | 34 | 4.4 |
| LAG-3 mAb 4 [a] | 12 | 9.3 | 0.8 |
| LAG-3 mAb 5 [a] | 14 | 13 | 0.9 |
| LAG-3 mAb 6 [a] | 42 | 0.84 | 0.02 |
| hLAG-3 mAb 1 (1.2)[d, e] | 23 | 0.13 | 0.01 |
| hLAG-3 mAb 1 (2.2)[d, e] | 8.2 | 2.6 | 0.3 |
| hLAG-3 mAb 1 (1.1)[d, e] | 17 | 0.74 | 0.04 |
| hLAG-3 mAb 1 (1.4)[c, e] | 16 | 0.59 | 0.04 |
| hLAG-3 mAb 1 (1.4)[c, f] | 17 | 0.86 | 0.05 |

[a] = captured on immobilized Fab2 goat-anti-mouse Fc
[b] = captured on immobilized Protein G
[c] = captured on immobilized Fab2 goat anti-human Fc
[d] = captured on immobilized Protein A
[e] = human IgG1 (AA)
[f] = IgG4 (S228P)

Figure 7A:
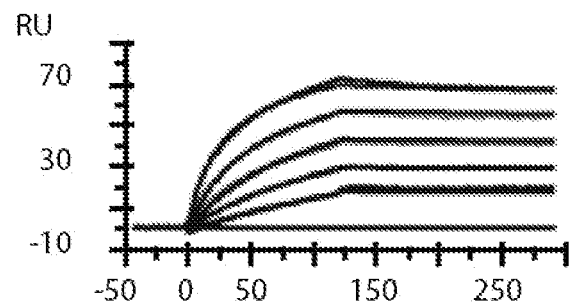
FIGS. 7A-7C show the binding characteristics of LAG-3 mAb 1 and LAG-3 mAb 6 to cynomolgous monkey LAG-3. Biacore binding curves of hLAG-3 mAb 6 (1.1) (FIG. 7A), hLAG-3 mAb 1 (1.4) (FIG. 7B) and LAG-3 mAb A (FIG. 7C) demonstrating that hLAG-3 mAb 6 (1.1) exhibits better binding to cynomolgous monkey LAG-3 (RU; Response Units).
Figure 7B:
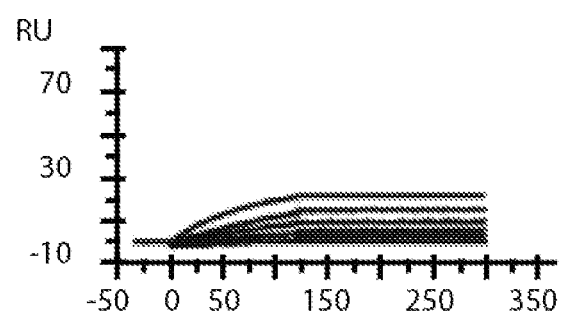
Figure 7C:
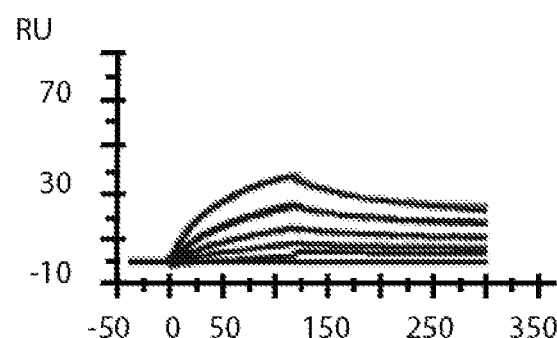
Figure 8A:
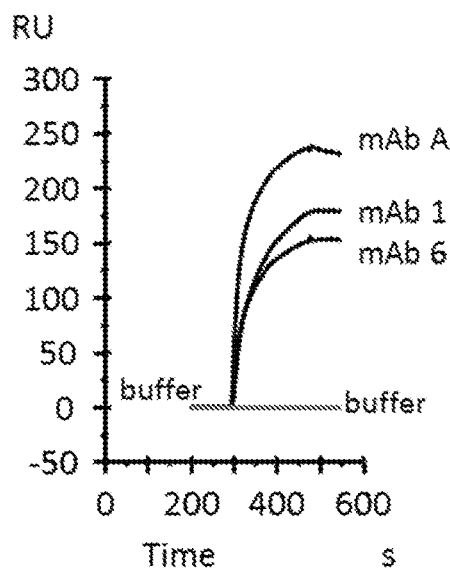
FIGS. 8A-8D show that LAG-3 mAb 1 and LAG-3 mAb 6 bind an epitope that is distinct from the one bound by the reference antibody LAG 3 mAb A. the binding profiles of labeled LAG-3 mAb 1, LAG-3 mAb 6 and LAG-3 mAb A in the absence of a competitor antibody (FIG. 8A), in the presence of excess LAG-3 mAb 1 (FIG. 8B), excess LAG-3 mAb 6 (FIG. 8C), or LAG-3 mAb A (FIG. 8D) (RU; Response Units).
Figure 8B:
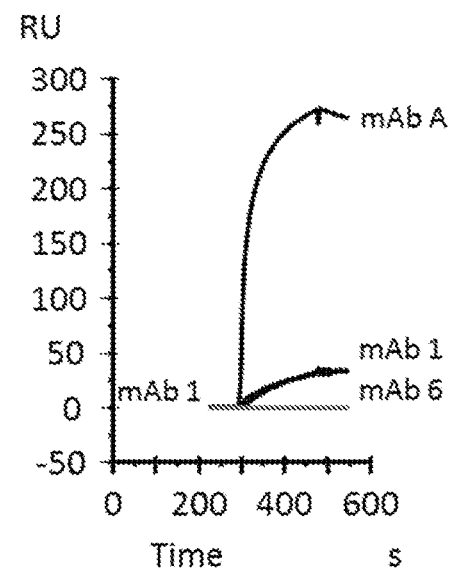
Figure 8C:
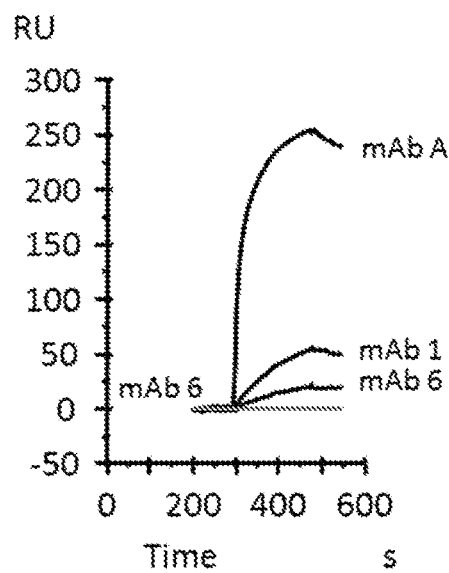
Figure 8D:
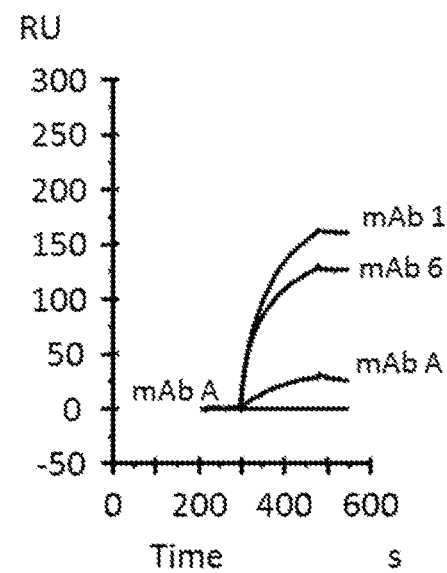

In additional studies, the binding kinetics of the humanized antibodies hLAG-3 mAb 1 (1.4) and hLAG-3 mAb 6 (1.1), and a reference antibody LAG-3 mAb A to both human and cynomolgus monkey LAG-3 was investigated using Biacore analysis. In these studies, a soluble LAG-3 fusion protein (the extracelluar domain of human or cynomolgus monkey LAG-3 fused to murine IgG2a) was captured on a Fab2 goat-anti mouse Fc surface and incubated with the anti-LAG-3 antibody and the kinetics of binding was determined via Biacore analysis. The binding curves for LAG-3 mAb A, hLAG-3 mAb 1 (1.4) and hLAG-3 mAb 6 (1.1) binding to cynomolgus monkey LAG-3 are shown in FIGS. 7A-7C respectively, and the calculated ka, kd and KD are presented in Table 8. In a separate study, the binding of a bispecific Fc Region-containing diabody comprising hLAG-3 mAb 6 (1.1) to both human and cynomolgus monkey LAG-3 was investigated using Biacore analysis. In this study, the hLAG-3 mAb 6 (1.1) containing diabody was captured on a Fab2 goat-anti human Fc surface and incubated with soluble LAG-3 fusion protein (the extracelluar domain of human or cynomolgus monkey LAG-3 fused to a His tag) and the kinetics of binding was determined via Biacore analysis. The calculated ka, kd and KD are presented in Table 8.

TABLE 8

| | Human | | | Cynomolgus Monkey | | |
|---|---|---|---|---|---|---|
| Anti-LAG-3 Antibody | $k_a$ (×10$^4$) | $k_d$ (×10$^{-5}$) | KD (nM) | $k_a$ (×10$^4$) | $k_d$ (×10$^{-5}$) | KD (nM) |
| LAG-3 mAb A | 6.2 | 1.0 | 0.16 | 2.4 | 1100 | 458 |
| hLAG-3 mAb 1 (1.4)[a] | 3.4 | <1.0 | <0.29 | 1.9 | <1.0 | <0.53 |
| hLAG-3 mAb 6 (1.1)[a] | 9.9 | <1.0 | <0.1 | 8.2 | 30 | 3.7 |
| hLAG-3 mAb 6 (1.1)[b] | 480 | 16 | 0.033 | 59 | 78 | 0.13 |

[a] = immobilized human or cynomolgus LAG-3-murine IgG2a fusion protein
[b] = immobilized Fc Region-containing diabody comprising a hLAG-3 mAb 6 (1.1) epitope-binding domain The results demonstrate that LAG-3 mAb 1 and LAG-3 mAb 6 exhibit better binding kinetics than reference antibody LAG-3 mAb A. In addition, humanized LAG-3 mAb 6 exhibits better cross-reactive binding kinetics with cynomolgus monkey LAG-3.

The epitope specificity of LAG-3 mAb 1, LAG-3 mAb 6 and the reference antibody LAG-3 mAb A was examined using Biacore analysis. In order to determine whether the antibodies bound to different LAG-3 epitopes, shLAG-3-His was captured by mouse anti-PentaHis antibody immobilized on the CM5 sensor chip according to the procedure recommended by the manufacturer. Briefly, the carboxyl groups on the sensor chip surface were activated with an injection of a solution containing 0.2 M N-ethyl-N-(3dietylamino-propyl) carbodimide and 0.05 M N-hydroxy-succinimide. Anti-PentaHis antibody was injected over the activated CMS surface in 10 mM sodium-acetate, pH 5.0, at a flow rate 5 µL/min, followed by 1 M ethanolamine for deactivation of remaining amine-reactive groups. Binding experiments were performed in HBS-EP buffer, which contains 10 mM HEPES, pH 7.4, 150 mM NaCl, 3 mM EDTA, and 0.005% P20 surfactant. Each antibody (LAG-3 mAb 1, LAG-3 mAb 6 and LAG-2 mAb A) was preinjected over captured hLAG3-His for 180 seconds at a flow rate of 5 µL/min at concentration of 1 µM followed by running buffer and injection of competing antibody at the same conditions. Binding response of competing antibody was compared to its binding response to hLAG3-His preinjected with buffer to identify antibodies competing for the same epitope. Regeneration of the immobilized anti-PentaHis surface was performed by pulse injection of 10 mM glycine, pH 1.5. Reference curves were obtained by injection of analytes over the treated surface with no immobilized protein. Binding curves were generated by BIAevaluation software v4.1 from real-time sensogram data.

The results of this experiment are shown in FIGS. 8A-8D. The results of this experiment indicate that the biotinylated antibody LAG3 mAb A was capable of binding to shLAG-3-His even in the presence of excess amounts of the non-biotinylated antibodies LAG-3 mAb 1 and LAG-3 mAb 6. In contrast, LAG-3 mAb 1 blocked the binding of LAG-3 mAb 6. Thus, the results show that LAG-3 mAb 1 and LAG-3 mAb 6 likely bind to the same, or over lapping epitopes of LAG-3, and compete with one another for binding to LAG-3. Both LAG-3 mAb 1 and LAG-3 mAb 6 were found to bind to an epitope that is distinct from that bound by LAG-3 mAb A.

Figure 9A:
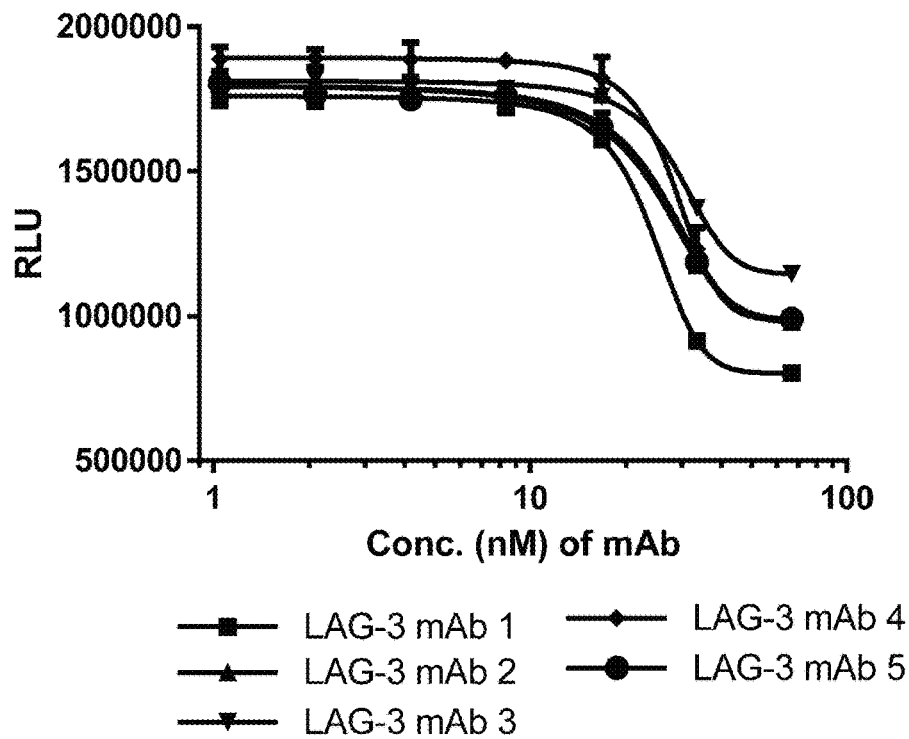
FIGS. 9A-9B show that the isolated antibodies inhibit the binding of soluble human LAG-3 (shLAG-3) to MHC class II as determined in an ELISA assay.
Figure 9B:
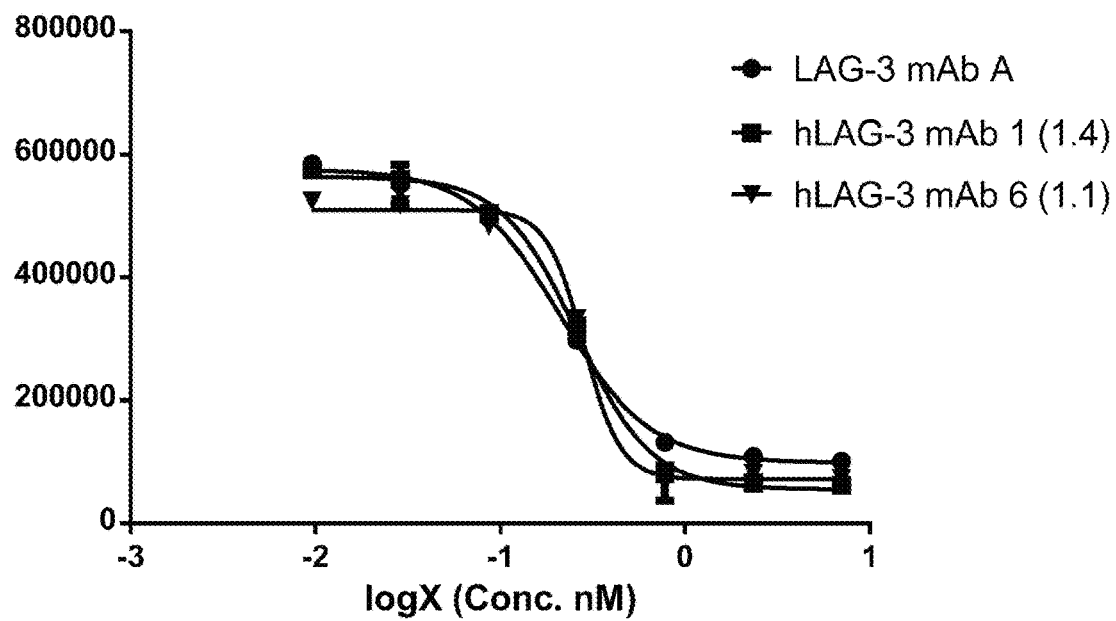

In order to further characterize the anti-LAG3 antibodies, their ability to block binding between LAG-3 and MEW class II was assessed in two different assays. In one assay, the ability of the antibodies to block the binding of a soluble human LAG3-Fc fusion protein to MEW class II immobilized on a surface was examined. For this assay, LAG-3 mAb 1, LAG-3 mAb 2, LAG-3 mAb 3, LAG-3 mAb 4, and LAG-3 mAb 5 each (at 0-67 nM, 2 fold serial dilutions) were mixed with a soluble human LAG-3-Fc fusion protein, (at 5 µg/mL) and were separately incubated with immobilized MEW class II (1 µg/mL). The amount of LAG-3 binding to the immobilized MEW class II was assessed using a goat anti-human Fc gamma-HRP secondary antibody. In additional experiments LAG-3 mAb A and the humanized antibodies, hLAG-3 mAb 1 (1.4) and hLAG-3 mAb 6 (1.1) (at 0.0096-7.0 nM, three fold serial dilutions) were mixed with soluble human LAG-3-His fusion protein (0.2 µg/ml) and assayed for binding to immobilized MEW class II as described above. The results of these experiments are shown in FIG. 9A and FIG. 9B.

Figure 10A:
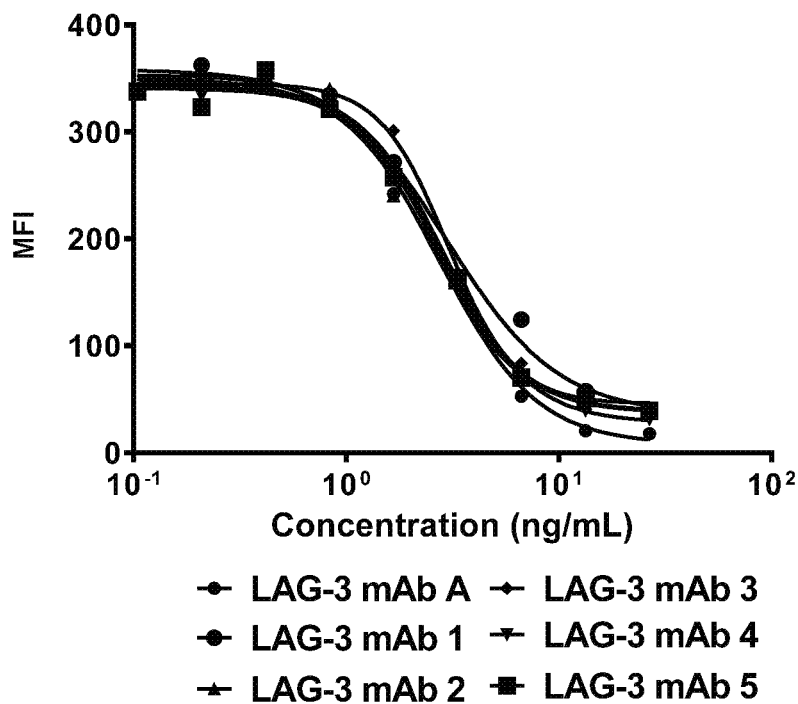
FIGS. 10A-10C show that the isolated antibodies inhibit the binding of shLAG-3 to the surface of MHC class II expressing Daudi cells.
Figure 10B:
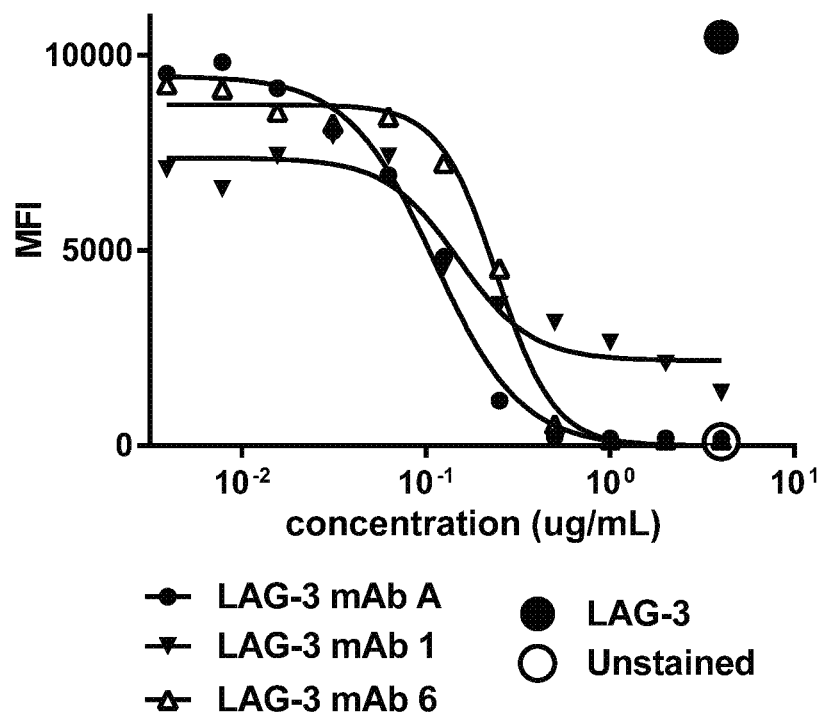
Figure 10C:
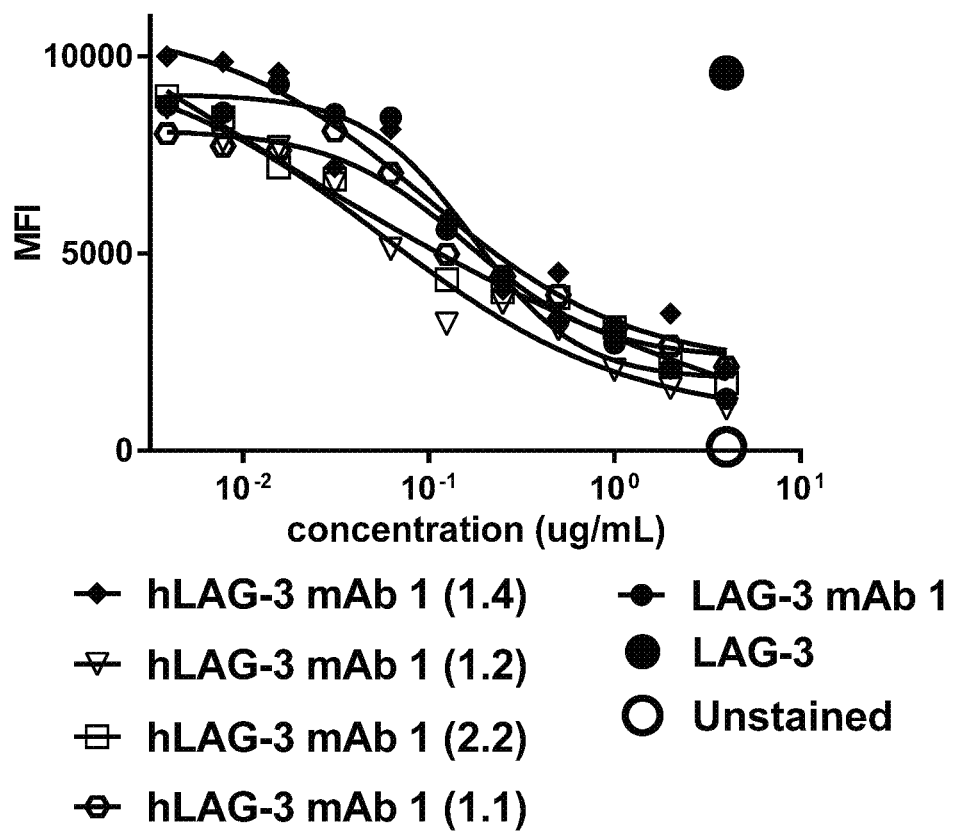

In another assay, the ability of the anti-LAG-3 antibodies of the present invention to block the binding of a soluble human LAG3-Fc fusion protein (shLAG-3-Fc) to native MHC class II on a cell surface was examined. For this assay, LAG-3 mAb 1, LAG-3 mAb 2, LAG-3 mAb 3, LAG-3 mAb 4, LAG-3 mAb 5, and the reference antibody LAG-3 mAb A each (at 0.1-26.7 ng/ml, 2 fold serial dilutions) were mixed with a biotinylated-soluble human LAG-3-Fc fusion protein, (at 0.5 µg/ml) and were separately incubated with MHC II-positive Daudi cells. The amount of LAG-3 binding to the surface of the Daudi cells was determined using a PE-conjugated Streptavidin secondary antibody by FACS analysis. In additional separate experiments LAG-3 mAb 1, LAG-3 mAb 6 and LAG-3 mAb A; or LAG-3 mAb 1 and the humanized antibodies, hLAG-3 mAb 1 (1.4), hLAG-3 mAb 1 (1.2), hLAG-3 mAb 1 (2.2), and hLAG-3 mAb 1 (1.1) were assayed as described above. The results of these experiments are shown in FIGS. 10A-10C, respectively.

The results of these inhibition assays (FIGS. 9A-9B and FIGS. 10A-10C) show that all the anti-LAG-3 antibodies tested blocked the binding of a shLAG-3-Fc fusion protein to bind MHC class II.

Example 2

Flow-Cytometry Methodology

Experiments to determine expression levels of checkpoint inhibitors: PD-1 and LAG-3 on cells in the experiments described below used the following appropriately fluorescent labeled commercial antibodies (phycoerythrin-cyanine7 (PE-Cy7)-conjugated anti-CD4 [clone SK3] or fluorescein isothiocyanate (FITC)-conjugated anti-CD4 [clone RPA-T4], phycoerythrin (PE)-conjugated anti-LAG-3 [clone 3DS223H], phycoerythrin (PE)-conjugated anti-PD-1 [clone EH12.2H7] or allophycocyanin (APC)-conjugated (eBiosciences, or BioLegend)) and the appropriate isotype controls. All antibodies were used at the manufacturer's recommended concentrations. Cell staining was performed in FACS buffer (10% FCS in PBS) on ice for 30 minutes in the dark for the addition of primary antibodies. After two washes, cells were either stained with the appropriate secondary reagent on ice for 30 minutes in the dark or immediately analyzed on a flow cytometer. To exclude dead cells, all samples were co-stained with a viability dye: 7-Aminoactinomycin D (7-AAD) (BD Biosceinces, or BioLegend) or 4',6-Diamidino-2-Phenylindole, Dihydrochloride (DAPI) (Life Technologies). All samples were analyzed on either a FACS Calibur or Fortessa Flow Cytometer (BD Biosciences) and analyzed using FlowJo Software (TreeStar, Ashland, Oreg.).

Example 3

LAG-3 Expression and Antibody Binding To Stimulated T-Cells

LAG-3 expression and the ability of the isolated LAG-3 antibodies to specifically bind LAG-3 on the surface of CD3/CD28-stimulated T-cells was examined. T-cells were obtained from peripheral blood mononuclear cell (PBMCs), briefly, PBMCs were purified using the Ficoll-Paque Plus (GE Healthcare) density gradient centrifugation method according to manufacturer's instructions from whole blood obtained under informed consent from healthy donors (Biological Specialty Corporation) and T cells were then purified using the Dynabeads® Untouched Human T Cells Kit (Life Technologies) according to manufacturer's instructions. For stimulation, isolated T cells were cultured for 10-14 days in the presence of recombinant human IL-2 30 U/ml] (Peprotech) and Dynabeads® Human T cell Activator beads (Life Technologies) according to manufacturer's instructions. LAG-3 expression on freshly isolated unstimulated CD4+ T cells, and stimulated CD4+ T cells (taken from culture at day 11 or 14), was examined by flow cytometry as described above, using FITC-conjugated anti-CD4 and PE-conjugated anti-LAG-3.

Figure 11A:
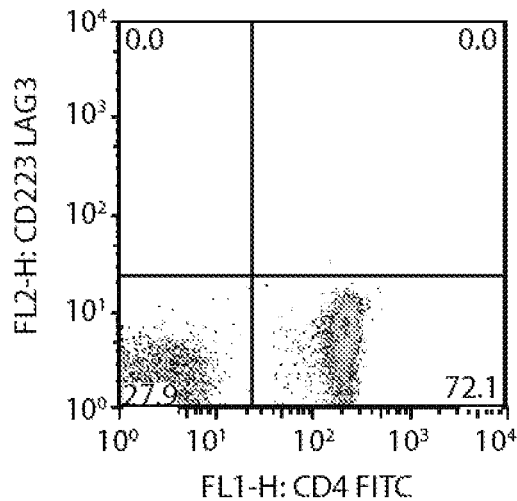
FIGS. 11A-11C show that expression of LAG-3 is upregulated in stimulated CD4+ T-cells. Flow cytometric analysis of LAG-3 expression on unstimulated CD4+ T-cells (FIG. 11A) and CD3/CD28 bead-stimulated CD4+ T-cells from two different donors (FIGS. 11B and 11C) on day 11 and 14, respectively. All cells were co-stained with anti-CD4 antibody.
Figure 11B:
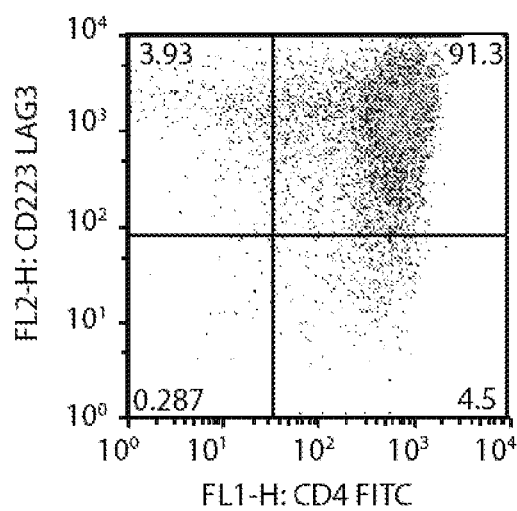
Figure 11C:
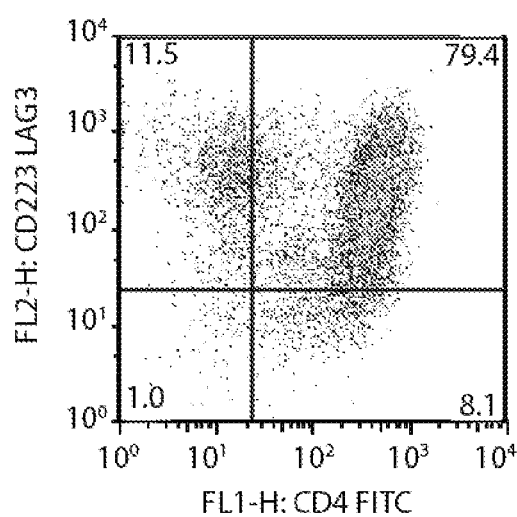

The results of these studies are shown in FIG. 11A-11C. No LAG-3 expression was observed on unstimulated CD4+ T-cells (FIG. 11A). However, CD3/CD8 stimulated CD4+ T-cells from two different donors (D:58468 and D:43530) exhibited a dramatic increase in LAG-3 expression (FIGS. 11B and 11C).

Figure 12:
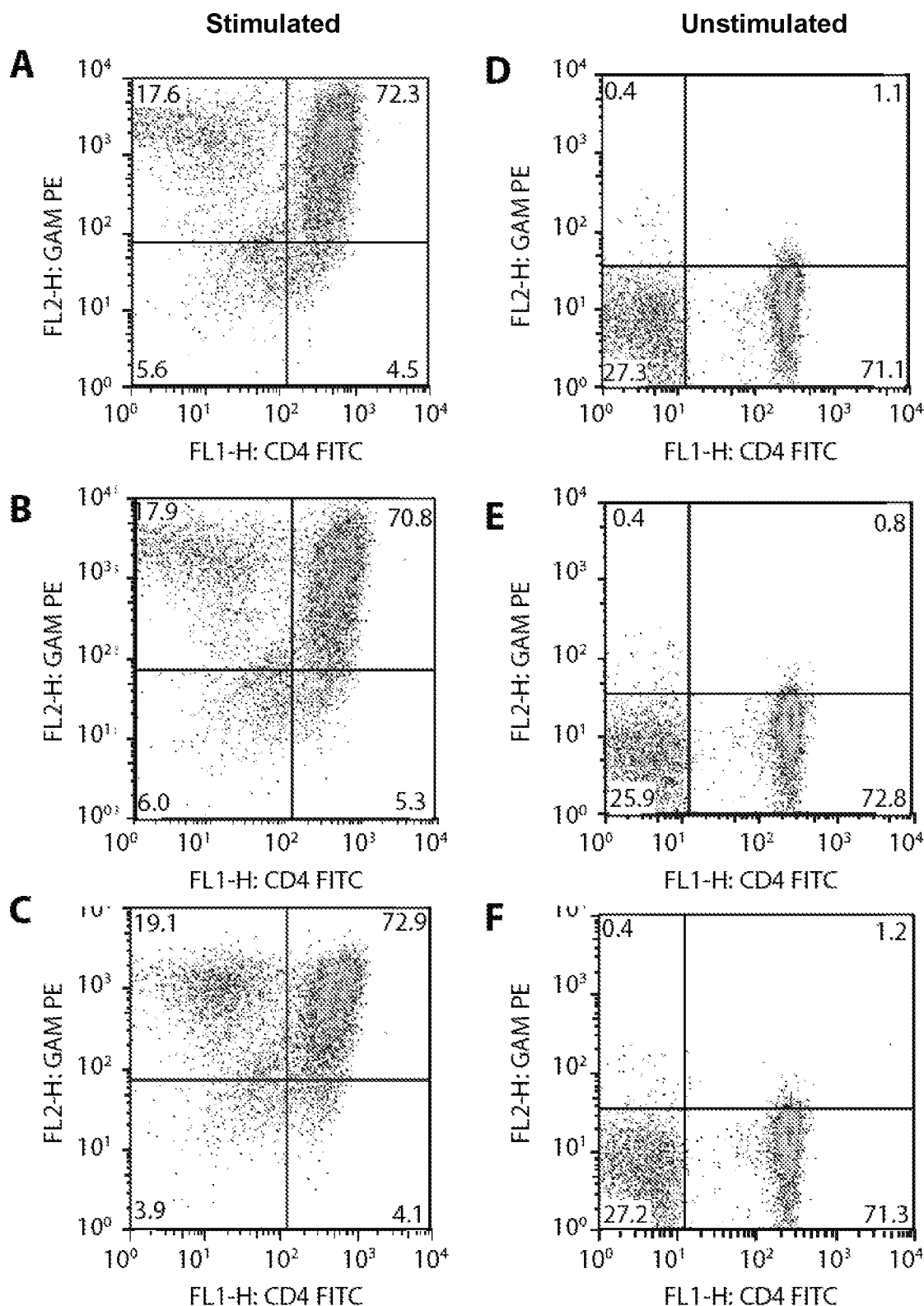
FIG. 12 (Panels A-F) show that the isolated anti-LAG-3 antibodies bind to stimulated but not unstimulated T-cells. Flow cytometric analysis of CD3/CD28 stimulated CD4+ T-cells (Panels A-C) and unstimulated CD4+ T-cells (Panels D-F) labeled with LAG-3 mAb 1 (Panels A and D), LAG-3 mAb 2 (Panels B and E), or LAG-3 mAb 3 (Panels C and F). All cells were co-stained with anti-CD4 antibody.
Figure 13:
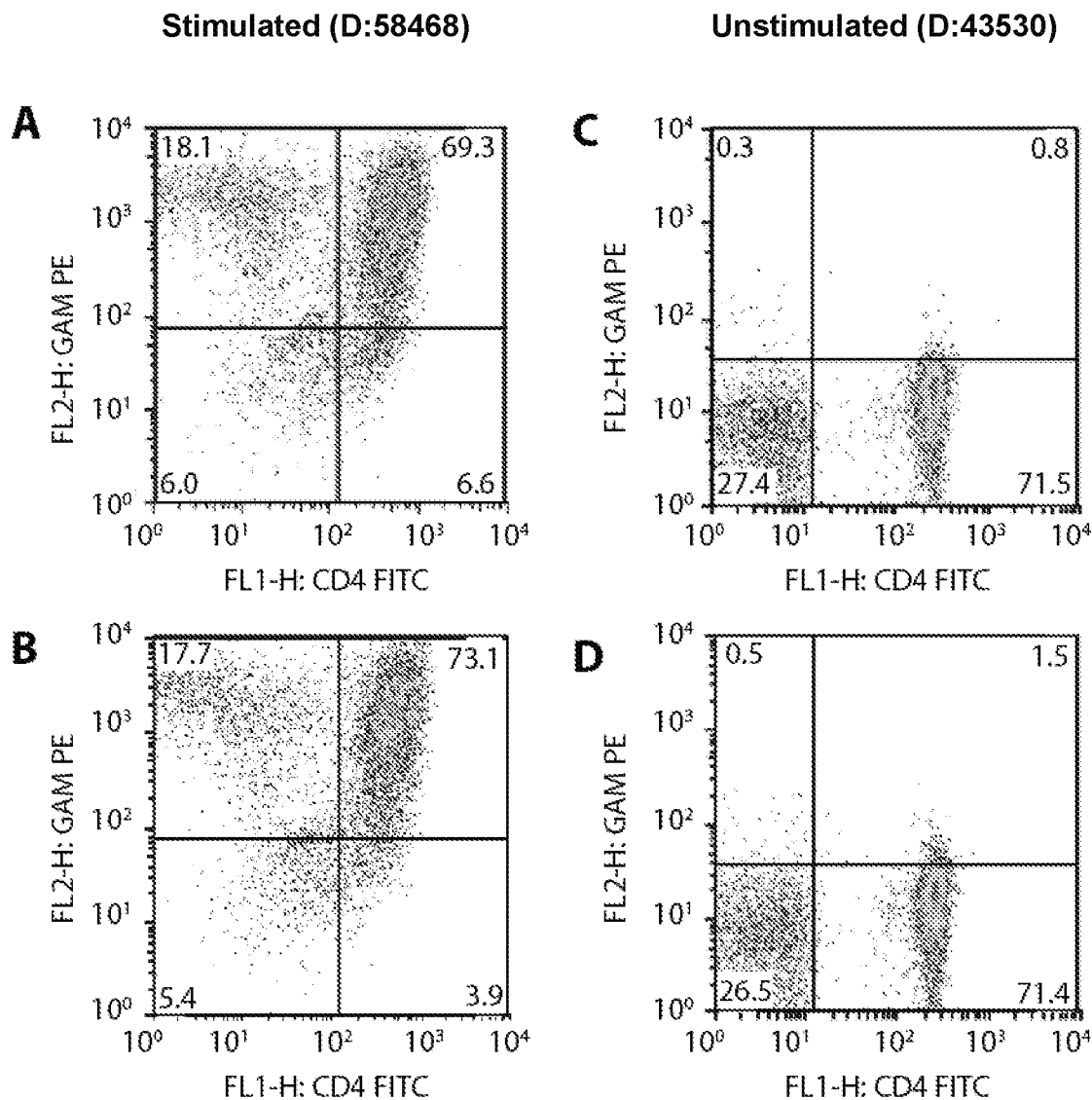
FIG. 13 (Panels A-D) show that the isolated anti-LAG-3 antibodies bind to stimulated but not unstimulated T-cells. Flow cytometric analysis of CD3/CD28 stimulated CD4+ T-cells (Panels A-B) and unstimulated CD4+ T-cells (Panels C-D) labeled with LAG-3 mAb 4 (Panels A and C), or LAG-3 mAb 5 (Panels B and D). All cells were co-stained with anti-CD4 antibody.

The ability of LAG-3 mAb 1 (FIG. 12, Panels A and D), LAG-3 mAb 2 (FIG. 12, Panels B and E), LAG-3 mAb 3 (FIG. 12, Panels C and F), LAG-3 mAb 4 (FIG. 13, Panels A and C), and LAG-3 mAb 5 (FIG. 13, Panels B and D), to specifically bind to stimulated CD4+ T cells was investigated. Stimulated T cells (prepared as described above from donor D:58468) taken from culture at day 14, and fresh unstimulated cells (prepared as described above from donor D:43530) were subjected to flow cytometry using the isolated anti-LAG-3 antibodies and the following appropriately fluorescent labeled secondary reagent (PC-conjugated anti-mouse-IgG (H+L) (Jackson ImmunoResearch Labs)) and FITC-conjugated anti-CD4. As shown in FIG. 12, Panels A-F and FIG. 13, Panels A-D, each of the anti-LAG-3 antibodies examined bound only to stimulated, but not to unstimulated CD4+ T-cells.

The results of these studies demonstrate that LAG-3 is upregulated on stimulated T-cells and that the anti-LAG-3 antibodies of the present invention specifically bind only stimulated T-cells.

Example 4

Functional Activity of Anti-LAG Antibodies

*Staphylococcus aureus* enterotoxin type B (SEB) is a microbial superantigen capable of activating a large proportion of T-cells (5-30%). SEB binds to MHC II outside the peptide binding grove and thus is MHC II dependent, but unrestricted and TCR mediated. SEB-stimulation of T-cells results in oligoclonal T-cell proliferation and cytokine production (although donor variability may be observed). The expression of anti-LAG-3 and anti-PD-1 antibodies alone and in combination on SEB-stimulated PMBCs was examined.

PBMCs purified as described above were cultured in RPMI-media+10% heat inactivated FBS+1% Penicillin/Streptomycin in T-25 bulk flasks for 2-3 days alone or with SEB (Sigma-Aldrich) at 0.1 ng/ml (primary stimulation). At the end of the first round of SEB-stimulation, PBMCs were washed twice with PBS and immediately plated in 96-well tissue culture plates at a concentration of 1-5×$10^5$ cells/well in media alone, media with SEB at 0.1 ng/ml (secondary stimulation) and no antibody, or media with SEB and a control IgG antibody, and cultured for an additional 2-3 days. At 48 hours post-primary bulk SEB-stimulation, cells were examined for PD-1 and LAG-3 expression by flow cytometry using PE-conjugated anti-LAG-3 and FITC-conjugated anti-CD3; or APC-conjugated anti-PD-1 and FITC-conjugated anti-CD3. At day 5, post-secondary culture in 96-well plate with SEB-stimulation, wells treated with no antibody or with control antibody were examined using flow cytometry for PD-1 and LAG-3 expression using PE-conjugated anti-LAG-3 and APC-conjugated anti-PD-1.

Figure 14:
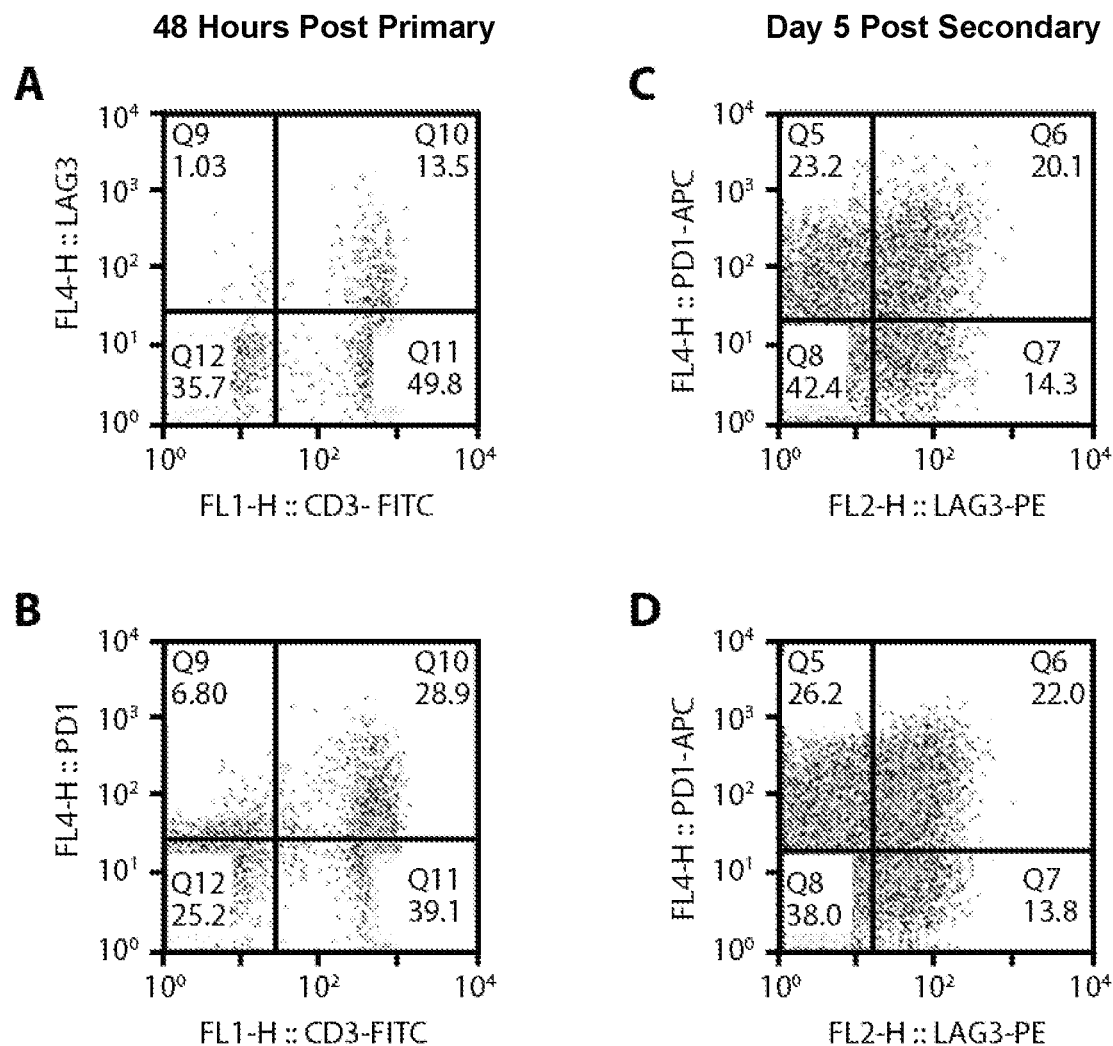
FIG. 14 (Panels A-D) show that expression of LAG-3 and PD-1 is upregulated on *Staphylococcus aureus* enterotoxin type B antigen (SEB)-stimulated peripheral blood mononuclear cells (PBMCs) from a representative donor D:34765. Flow cytometric analysis of SEB-stimulated PBMCs from a representative donor 48 hours after primary stimulation (Panels A-B) labeled with anti-LAG-3/anti-CD3 antibodies (Panel A), or anti-PD-1/anti-CD3 antibodies (Panel B) and on day five post-SEB-stimulation (Panels C-D) cells treated with SEB alone (Panel C) or with isotype control antibody (Panel D) during the secondary stimulation, labeled with anti-LAG-3/anti-PD-1 antibodies.
Figure 15:
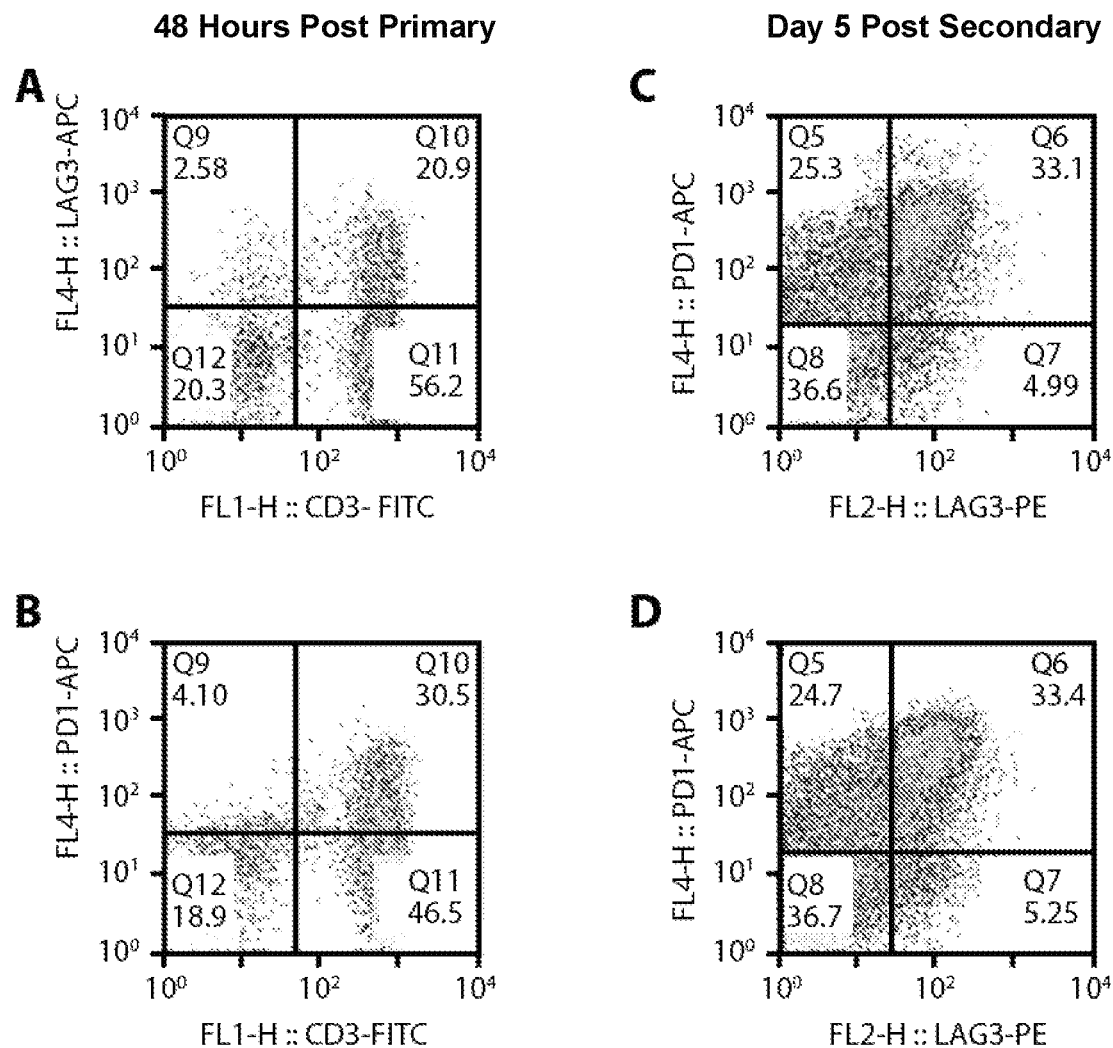
FIG. 15 (Panels A-D) show that expression of LAG-3 and PD-1 is upregulated on SEB-stimulated PBMCs from another representative donor D:53724. Flow cytometric analysis of SEB-stimulated PBMCs from a representative donor 48 hours after primary stimulation (Panels A-B) labeled with anti-LAG-3/anti-CD3 antibodies (Panel A), or anti-PD-1/anti-CD3 antibodies (Panel B) and on day five post-SEB-stimulation (Panels C-D) cells treated with SEB alone (Panel C) or with isotype control antibody (Panel D) labeled with anti-LAG-3/anti-PD-1 antibodies.

Flow cytometry results from two representative donors (D:34765 and D:53724) are shown in FIG. 14, Panels A-D (D:34765) and FIG. 15, Panels A-D (D:53724). These results demonstrate that LAG-3 and PD-1 are upregulated by 48 hours post-SEB-stimulation with a further enhancement seen at day 5 post culture with SEB-stimulation. In these studies, Donor 1 had more LAG-3/PD-1 double positive cells after SEB-stimulation. The addition of a control antibody post-SEB-stimulation did not alter LAG-3 or PD-1 expression (compare FIG. 14, Panels C and D, and FIG. 15, Panels C and D).

Upregulation of the immune check point proteins LAG-3 and PD-1 following SEB-stimulation of PBMCs limits cytokine release upon restimulation. The ability of LAG-3 mAb 1, LAG-3 mAb 3, LAG-3 mAb 4, LAG-3 mAb 6, a PD-1 monoclonal antibody designated "PD-1 mAb 5", and the reference antibodies PD-1 mAb 1 (comprising the 235A/235A Fc variant (AA)), PD-1 mAb 2, LAG-3 mAb A, and the commercial anti-LAG3 antibody 17B4 (#LS-C18692, LS Bio, designated "LAG-3 mAb B") to enhance cytokine release through checkpoint inhibition was examined.

Figure 16A:
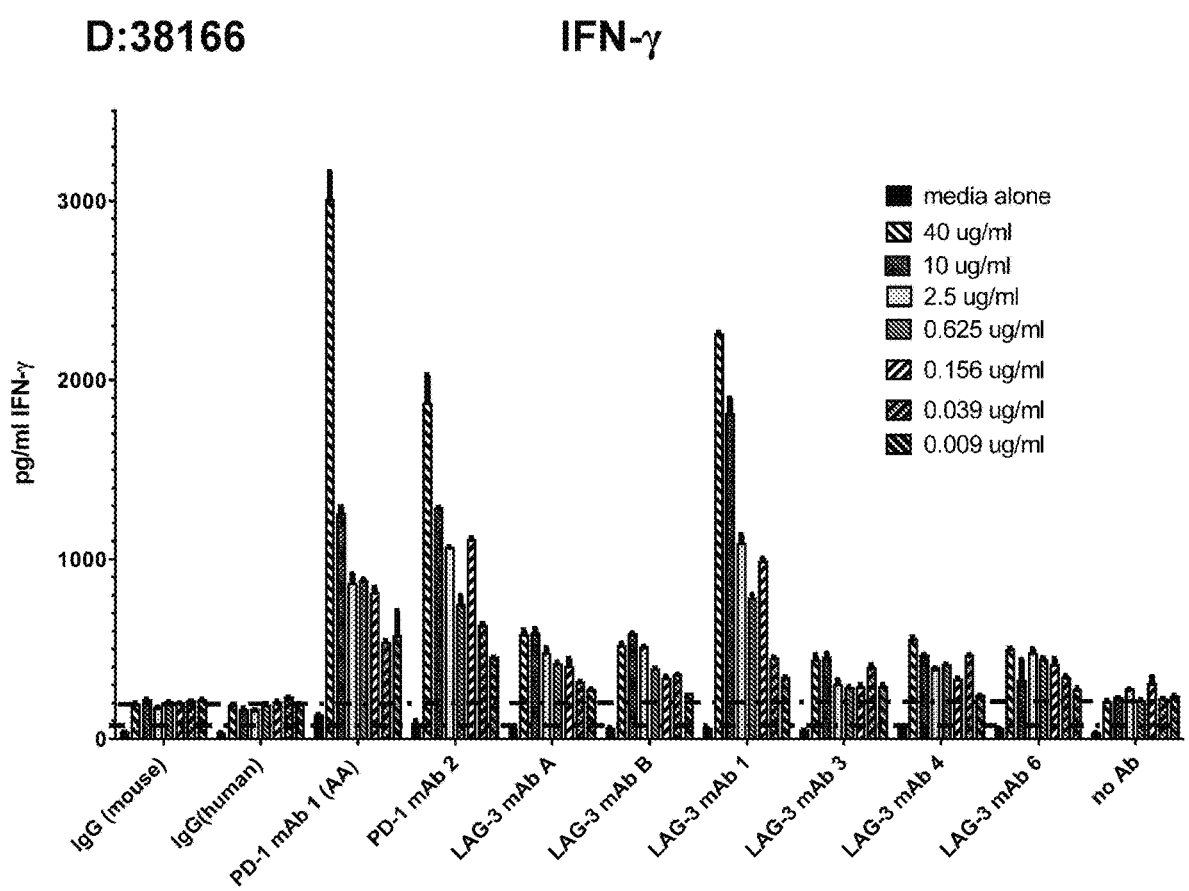
FIGS. 16A-16B shows that LAG-3 mAb 1 is able to stimulate cytokine production to levels comparable to treatment with anti-PD-1 antibodies. IFNγ (FIG. 16A) and TNFα (FIG. 16B), secretion profiles from SEB-stimulated PBMCs treated with anti-LAG-3 or anti-PD-1 antibodies.
Figure 16B:
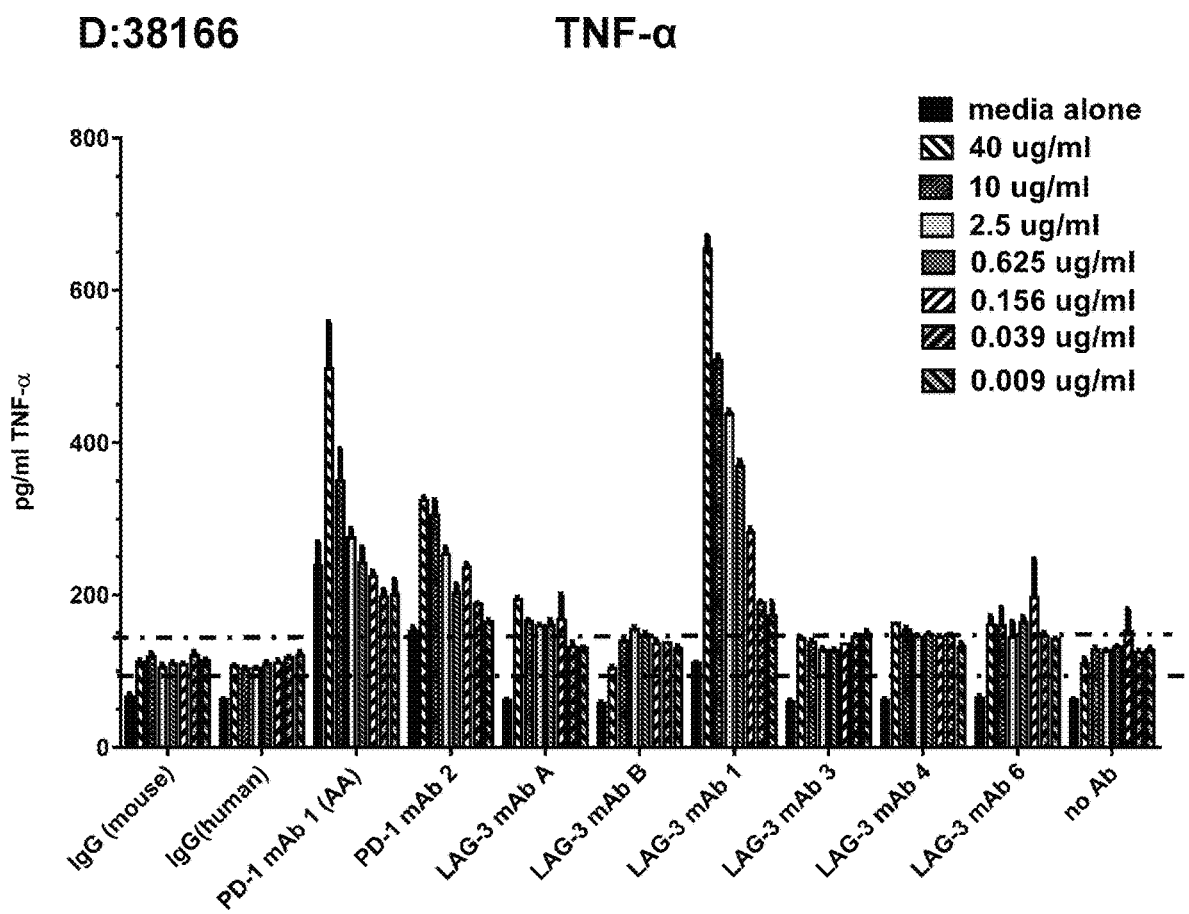
Figure 17:
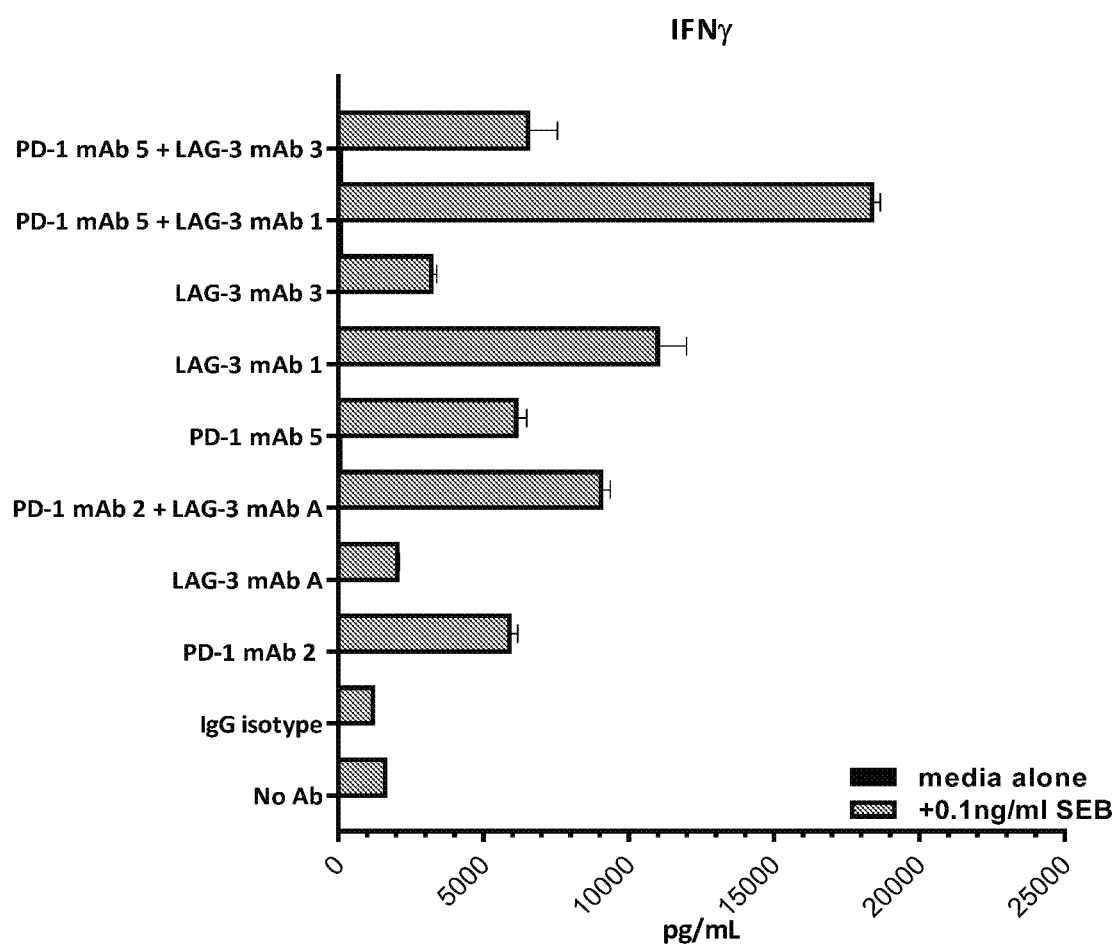
FIG. 17 shows that LAG-3 mAb 1 is able to stimulate cytokine production to levels comparable to treatment with anti-PD-1 antibodies and that treatment with LAG-3 mAb 1 in combination with an anti-PD-1 provided the largest enhancement of cytokine release. IFNγ secretion profiles from SEB-stimulated PBMCs treated with anti-LAG-3 and anti-PD-1 antibodies alone and in combination.

PBMCs were stimulated with SEB as described above except during the secondary stimulations cells were plated with no antibody, with an isotype control antibody, or with anti-LAG-3 and anti-PD-1 antibodies alone or in combination. At the end of the second stimulation, supernatants were harvested to measure cytokine secretion using human DuoSet ELISA Kits for IFNγ, TNFα, IL-10, and IL-4 (R&D Systems) according to the manufacture's instructions. FIGS. 16A-16B shows the IFNγ (FIG. 16A) and TNFα (FIG. 16B), secretion profiles from SEB-stimulated PBMCs from a representative donor (D:38166), treated with no antibody or one of the following antibodies: isotype control, PD-1 mAb 1, PD-1 mAb 2, LAG-3 mAb A, LAG-3 mAb B, LAG-3 mAb 1, LAG-3 mAb 3, LAG-3 mAb 4, or LAG-3 mAb 6. For this study the antibodies were utilized at 0.009, 0.039, 0.156, 0.625, 2.5, 10, and 40 µg/ml. FIG. 17 shows the IFNγ secretion profiles from SEB-stimulated PBMCs from another representative donor (D:58108), treated with: no antibody; isotype control antibody; PD-1 mAb 2 and/or LAG-3 mAb A; PD-1 mAb 5 and/or LAG-3 mAb 1; or PD-1 mAb 5 and/or LAG-3 mAb 3. For this study the antibodies were used at 10 µg/ml.

The results of these studies demonstrate that anti-PD-1 antibodies dramatically enhanced immune system function as evidenced by increased IFNγ (FIG. 16A and FIG. 17), and TNFα (FIG. 16B) production from SEB-stimulated PBMCs upon restimulation. Surprisingly, LAG-3 mAb 1 was also seen to increase cytokine production across multiple donors to levels comparable to the anti-PD-1 antibodies while the reference anti-LAG-3 mAbs, LAG-3 mAb A and LAG-3 mAb B and several of the isolated antibodies (LAG-3 mAb 3, LAG-4, and LAG-6) provided only a slight enhancement of cytokine release. In addition, the combination of anti-LAG-3 antibodies with anti-PD-1 resulted in a further enhancement of cytokine release (FIG. 17) from SEB-stimulated PBMCs upon restimulation. LAG-3 mAb 1 provided the largest enhancement in cytokine release when combined with an anti-PD-1 antibody as compared to LAG-3 mAb 3 and the reference antibody LAG-3 mAb A.

Example 5

Binding to Endogenous Cynomolgus Monkey LAG-3

Figure 18A:
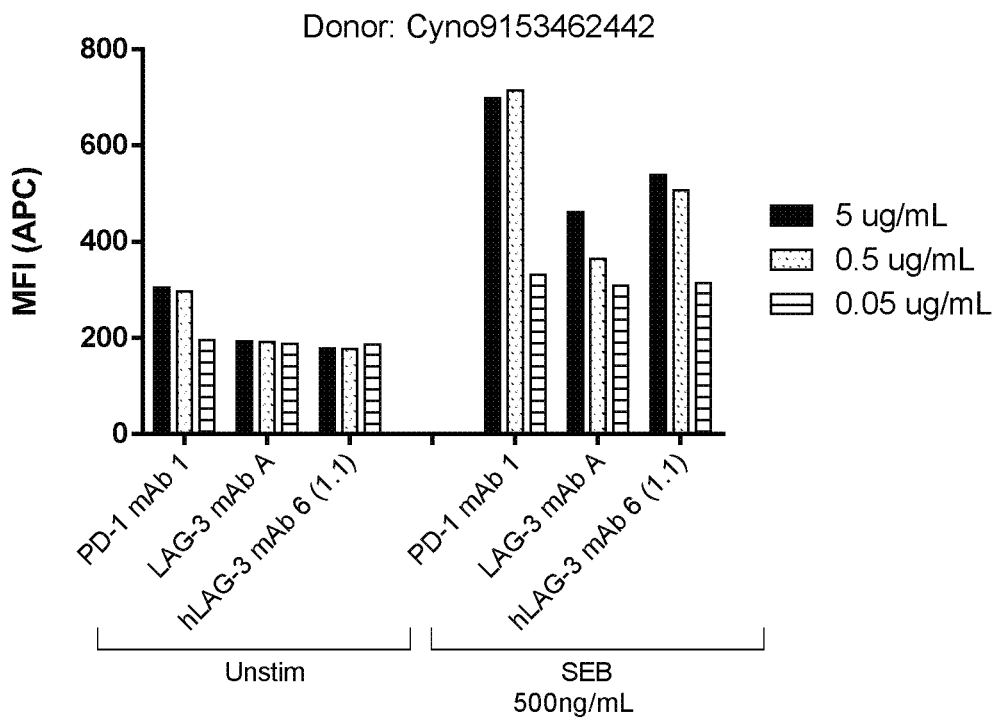
FIGS. 18A-18B shows binding the anti-LAG-3 antibodies hLAG-3 mAb 6 (1.1), and LAG-3 mAb A to endogenous LAG-3 expressed on SEB stimulated cynomolgus monkey PBMCs from two donors (FIGS. 18A and 18B). The anti-PD-1 antibody PD-1 mAb A was included as a positive control for SEB stimulation.
Figure 18B:
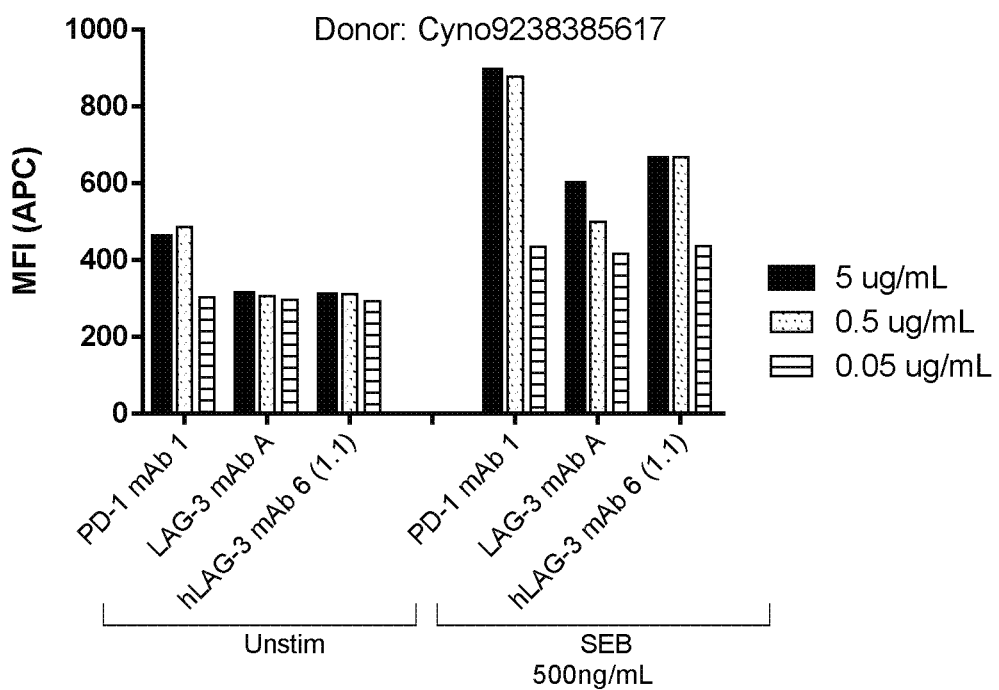

The ability of the humanized antibody hLAG-3 mAb 6 (1.1), and the reference antibody LAG-3 mAb A to bind endogenous LAG-3 expressed on cynomolgus monkey PBMCs by was investigated FACS. For this study PBMCs were isolated from donor cynomolgus monkey whole blood and cultured alone or with SEB stimulation (500 ng/mL) essentially as described above. At 66 hours post-SEB-stimulation cells (unstimulated and stimulated) were stained with hLAG-3 mAb 6 (1.1), LAG-3 mAb A, or PD-1 mAb 1 antibodies (10 fold serial dilutions). The antibodies were detected with goat-anti human Fc-APC labeled secondary antibody. Binding is plotted in FIG. 18A-18B for two cynomolgus monkey donors.

SEB stimulation was confirmed by enhanced PD-1 expression as detected with the anti-PD-1 antibody PD-1 mAb 1. The results of these studies demonstrate that hLAG-3 mAb 6 (1.1) binds endogenous LAG-3 expressed on the surface of stimulated cynomolgous monkey PBMCs.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A Lymphocyte Activation Gene 3 (LAG-3)-binding molecule that is capable of binding both to human LAG-3 and to cynomolgus monkey LAG-3, wherein said LAG-3-binding molecule comprises a Variable Heavy Chain Domain and a Variable Light Chain Domain, wherein:

said Variable Heavy Chain Domain comprises a $CDR_H1$ Domain, a $CDR_H2$ Domain and a $CDR_H3$ Domain, and said Variable Light Chain Domain comprises a $CDR_L1$ Domain, a $CDR_L2$ Domain, and a $CDR_L3$ Domain, wherein:

(A) (1) the $CDR_H1$ Domain, $CDR_H2$ Domain, and $CDR_H3$ Domain are the Heavy Chain CDRs of LAG-3 mAb 1, and respectively comprise the amino acid sequences: SEQ ID NO:8, SEQ ID NO:9, and SEQ ID NO:10; and (2) the $CDR_L1$ Domain, $CDR_L2$ Domain, and $CDR_L3$ Domain are the Light Chain CDRs of LAG-3 mAb 1, and respectively comprise the amino acid sequences: SEQ ID NO:13, SEQ ID NO:14, and SEQ ID NO:15;

or (B) (1) the $CDR_H1$ Domain, $CDR_H2$ Domain, and $CDR_H3$ Domain are the Heavy Chain CDRs of hLAG-3 mAb 1, and respectively comprise the amino acid sequences: SEQ ID NO:8, SEQ ID NO:9, and SEQ ID NO:10; and (2) the CDR$_L$1 Domain, CDR$_L$2 Domain, and CDR$_L$3 Domain are the Light Chain CDRs of hLAG-3 mAb 1, and respectively comprise the amino acid sequences: SEQ ID NO:28, SEQ ID NO:14, and SEQ ID NO:15;

or (C) (1) the CDR$_H$1 Domain, CDR$_H$2 Domain, and CDR$_H$3 Domain are the Heavy Chain CDRs of LAG-3 mAb 2, and respectively comprise the amino acid sequences: SEQ ID NO:31, SEQ ID NO:32, and SEQ ID NO:33; and (2) the CDR$_L$1 Domain, CDR$_L$2 Domain, and CDR$_L$3 Domain are the Light Chain CDRs of LAG-3 mAb 2, and, respectively comprise the amino acid sequences: SEQ ID NO:36, SEQ ID NO:37, and SEQ ID NO:38;

or (D) (1) the CDR$_H$1 Domain, CDR$_H$2 Domain, and CDR$_H$3 Domain are the Heavy Chain CDRs of LAG-3 mAb 3, and respectively comprise the amino acid sequences: SEQ ID NO:41, SEQ ID NO:42, and SEQ ID NO:43; and (2) the CDR$_L$1 Domain, CDR$_L$2 Domain, and CDR$_L$3 Domain are the Light Chain CDRs of LAG-3 mAb 3, and, respectively comprise the amino acid sequences: SEQ ID NO:46, SEQ ID NO:47, and SEQ ID NO:48;

or (E) (1) the CDR$_H$1 Domain, CDR$_H$2 Domain, and CDR$_H$3 Domain are the Heavy Chain CDRs of LAG-3 mAb 4, and respectively comprise the amino acid sequences: SEQ ID NO:51, SEQ ID NO:52, and SEQ ID NO:53; and (2) the CDR$_L$1 Domain, CDR$_L$2 Domain, and CDR$_L$3 Domain are the Light Chain CDRs of LAG-3 mAb 4, and, respectively comprise the amino acid sequences: SEQ ID NO:56, SEQ ID NO:57, and SEQ ID NO:58;

or (F) (1) the CDR$_H$1 Domain, CDR$_H$2 Domain, and CDR$_H$3 Domain are the Heavy Chain CDRs of LAG-3 mAb 5, and respectively comprise the amino acid sequences: SEQ ID NO:61, SEQ ID NO:62, and SEQ ID NO:63; and (2) the CDR$_L$1 Domain, CDR$_L$2 Domain, and CDR$_L$3 Domain are the Light Chain CDRs of LAG-3 mAb 5, and, respectively comprise the amino acid sequences: SEQ ID NO:66, SEQ ID NO:67, and SEQ ID NO:68;

or (G) (1) the CDR$_H$1 Domain, CDR$_H$2 Domain, and CDR$_H$3 Domain are the Heavy Chain CDRs of LAG-3 mAb 6, and respectively comprise the amino acid sequences: SEQ ID NO:71, SEQ ID NO:72, and SEQ ID NO:73; and (2) the CDR$_L$1 Domain, CDR$_L$2 Domain, and CDR$_L$3 Domain are the Light Chain CDRs of LAG-3 mAb 6, and, respectively comprise the amino acid sequences: SEQ ID NO:76, SEQ ID NO:77, and SEQ ID NO:78;

or (H) (1) the CDR$_H$1 Domain, CDR$_H$2 Domain, and CDR$_H$3 Domain are the Heavy Chain CDRs of hLAG-3 mAb 6, and respectively comprise the amino acid sequences: SEQ ID NO:71, SEQ ID NO:72, and SEQ ID NO:73; and (2) the CDR$_L$1 Domain, CDR$_L$2 Domain, and CDR$_L$3 Domain are the Light Chain CDRs of hLAG-3 mAb 6, and respectively comprise the amino acid sequences: SEQ ID NO:87, SEQ ID NO:77, and SEQ ID NO:78.

2. The LAG-3-binding molecule of claim 1, wherein said molecule is an antibody.

3. The LAG-3-binding molecule of claim 2, wherein said molecule is a chimeric antibody or a humanized antibody.

4. The LAG-3-binding molecule of claim 1, wherein said molecule comprises a Heavy Chain Variable Domain comprising the amino acid sequence of SEQ ID NO:16, SEQ ID NO:18, SEQ ID NO: 79, or SEQ ID NO: 81.

5. The LAG-3-binding molecule of claim 1, wherein said molecule comprises a Light Chain Variable Domain comprising the amino acid sequence of SEQ ID NO:20, SEQ ID NO:22, SEQ ID NO:24, SEQ ID NO:26, SEQ ID NO:83, or SEQ ID NO:85.

6. A labeled LAG-3-binding molecule of claim 1, wherein said LAG-3 binding molecule is labeled for the detection of LAG-3.

7. A pharmaceutical composition comprising the LAG-3-binding molecule of claim 1 and a pharmaceutically acceptable carrier.

8. The LAG-3-binding molecule of claim 1, wherein:

(1) the CDR$_H$1 Domain, CDR$_H$2 Domain, and CDR$_H$3 Domain are the Heavy Chain CDRs of LAG-3 mAb 1, and respectively comprise the amino acid sequences: SEQ ID NO:8, SEQ ID NO:9, and SEQ ID NO:10; and (2) the CDR$_L$1 Domain, CDR$_L$2 Domain, and CDR$_L$3 Domain are the Light Chain CDRs of LAG-3 mAb 1, and respectively comprise the amino acid sequences: SEQ ID NO:13, SEQ ID NO:14, and SEQ ID NO:15.

9. The LAG-3-binding molecule of claim 8, wherein said Variable Heavy Chain Domain comprises the amino acid sequence of SEQ ID NO:16, and said Variable Light Chain Domain comprises the amino acid sequence of SEQ ID NO:24.

10. A pharmaceutical composition comprising the LAG-3-binding molecule of claim 9 and a pharmaceutically acceptable carrier.

11. The LAG-3-binding molecule of claim 1, wherein:

(1) the CDR$_H$1 Domain, CDR$_H$2 Domain, and CDR$_H$3 Domain are the Heavy Chain CDRs of hLAG-3 mAb 1, and respectively comprise the amino acid sequences: SEQ ID NO:8, SEQ ID NO:9, and SEQ ID NO:10; and (2) the CDR$_L$1 Domain, CDR$_L$2 Domain, and CDR$_L$3 Domain are the Light Chain CDRs of hLAG-3 mAb 1, and respectively comprise the amino acid sequences: SEQ ID NO:28, SEQ ID NO:14, and SEQ ID NO:15.

12. The LAG-3-binding molecule of claim 11, wherein said Variable Heavy Chain Domain comprises the amino acid sequence of SEQ ID NO:16, and said Variable Light Chain Domain comprises the amino acid sequence of SEQ ID NO:26.

13. A pharmaceutical composition comprising the LAG-3-binding molecule of claim 12 and a pharmaceutically acceptable carrier.

14. The LAG-3-binding molecule of claim 1, wherein:

(1) the CDR$_H$1 Domain, CDR$_H$2 Domain, and CDR$_H$3 Domain are the Heavy Chain CDRs of LAG-3 mAb 6, and respectively comprise the amino acid sequences: SEQ ID NO:71, SEQ ID NO:72, and SEQ ID NO:73; and (2) the CDR$_L$1 Domain, CDR$_L$2 Domain, and CDR$_L$3 Domain are the Light Chain CDRs of LAG-3 mAb 6, and respectively comprise the amino acid sequences: SEQ ID NO:76, SEQ ID NO:77, and SEQ ID NO:78.

15. The LAG-3-binding molecule of claim 1, wherein:
(1) the $CDR_H1$ Domain, $CDR_H2$ Domain, and $CDR_H3$ Domain are the Heavy Chain CDRs of hLAG-3 mAb 6, and respectively comprise the amino acid sequences: SEQ ID NO:71, SEQ ID NO:72, and SEQ ID NO:73; and
(2) the $CDR_L1$ Domain, $CDR_L2$ Domain, and $CDR_L3$ Domain are the Light Chain CDRs of hLAG-3 mAb 6, and respectively comprise the amino acid sequences: SEQ ID NO:87, SEQ ID NO:77, and SEQ ID NO:78.

16. The LAG-3-binding molecule of claim 15, wherein said Variable Heavy Chain Domain comprises the amino acid sequence of SEQ ID NO:79, and said Variable Light Chain Domain comprises the amino acid sequence of SEQ ID NO:83.

17. A pharmaceutical composition comprising the LAG-3-binding molecule of claim 16 and a pharmaceutically acceptable carrier.

* * * * *

SEQUENCE LISTING

```
<160> NUMBER OF SEQ ID NOS: 140

<210> SEQ ID NO 1
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: IgG1 Fc Region
<220> FEATURE:
<221> NAME/KEY: MISC_FEATURE
<222> LOCATION: (217)..(217)
<223> OTHER INFORMATION: Xaa217 is Lysine (K) or Absent

<400> SEQUENCE: 1
```

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
210                 215

<210> SEQ ID NO 2
<211> LENGTH: 216
<212> TYPE: PRT
<213> ORGANISM: Homo sapiens
<220> FEATURE:
<221> NAME/KEY: MISC_FEATURE
<222> LOCATION: (1)..(216)
<223> OTHER INFORMATION: IgG2 Fc Region
<220> FEATURE:
<221> NAME/KEY: MISC_FEATURE
<222> LOCATION: (216)..(216)
<223> OTHER INFORMATION: Xaa216 is Lysine (K) or Absent

<400> SEQUENCE: 2

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
50                  55                  60

Phe Asn Ser Thr Phe Arg Val Val Ser Val Leu Thr Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

```
Arg Glu Pro Gln Val Tyr Thr Leu Pro Pro Ser Arg Glu Glu Met Thr
            115                 120                 125

Lys Asn Gln Val Ser Leu Thr Cys Leu Val Lys Gly Phe Tyr Pro Ser
    130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
                180                 185                 190

Ser Cys Ser Val Met His Glu Ala Leu His Asn His Tyr Thr Gln Lys
            195                 200                 205

Ser Leu Ser Leu Ser Pro Gly Xaa
    210                 215

<210> SEQ ID NO 3
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: IgG3 Fc
<220> FEATURE:
<221> NAME/KEY: MISC_FEATURE
<222> LOCATION: (217)..(217)
<223> OTHER INFORMATION: Xaa217 is Lysine (K) or Absent

<400> SEQUENCE: 3

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
                180                 185                 190

Phe Ser Cys Ser Val Met His Glu Ala Leu His Asn Arg Phe Thr Gln
            195                 200                 205

Lys Ser Leu Ser Leu Ser Pro Gly Xaa
    210                 215
```

```
<210> SEQ ID NO 4
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: IgG4 Fc Region
<220> FEATURE:
<221> NAME/KEY: MISC_FEATURE
<222> LOCATION: (217)..(217)
<223> OTHER INFORMATION: Xaa217 is Lysine (K) or Absent

<400> SEQUENCE: 4

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210                 215

<210> SEQ ID NO 5
<211> LENGTH: 525
<212> TYPE: PRT
<213> ORGANISM: Homo sapiens
<220> FEATURE:
<221> NAME/KEY: MISC_FEATURE
<222> LOCATION: (1)..(525)
<223> OTHER INFORMATION: LAG-3

<400> SEQUENCE: 5

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45
```

```
Pro Leu Gln Asp Leu Ser Leu Leu Arg Arg Ala Gly Val Thr Trp Gln
 50                  55                  60

His Gln Pro Asp Ser Gly Pro Pro Ala Ala Ala Pro Gly His Pro Leu
 65                  70                  75                  80

Ala Pro Gly Pro His Pro Ala Ala Pro Ser Ser Trp Gly Pro Arg Pro
                 85                  90                  95

Arg Arg Tyr Thr Val Leu Ser Val Gly Pro Gly Leu Arg Ser Gly
            100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Ala Asp Ala
            130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
                180                 185                 190

Arg Pro Asp Arg Pro Ala Ser Val His Trp Phe Arg Asn Arg Gly Gln
                195                 200                 205

Gly Arg Val Pro Val Arg Glu Ser Pro His His Leu Ala Glu Ser
            210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
                260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Pro Gly Gly Gly
            290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
                340                 345                 350

Val Thr Pro Lys Ser Phe Gly Ser Pro Gly Ser Leu Gly Lys Leu Leu
                355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
            435                 440                 445

His Leu Leu Leu Phe Leu Ile Leu Gly Val Leu Ser Leu Leu Leu Leu
450                 455                 460
```

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
            485                 490                 495

Ser Lys Ile Glu Glu Leu Glu Gln Glu Pro Glu Pro Glu Pro Glu Pro
        500                 505                 510

Glu Pro Glu Pro Glu Pro Glu Pro Glu Gln Leu
        515                 520             525

<210> SEQ ID NO 6
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: LAG-3 mAb 1 VH

<400> SEQUENCE: 6

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Arg Asn Tyr
            20                  25                  30

Gly Met Asn Trp Val Lys Gln Ala Pro Gly Lys Val Leu Lys Trp Met
        35                  40                  45

Gly Trp Ile Asn Thr Tyr Thr Gly Glu Ser Thr Tyr Ala Asp Asp Phe
    50                  55                  60

Glu Gly Arg Phe Ala Phe Ser Leu Gly Thr Ser Ala Ser Thr Ala Tyr
65                  70                  75                  80

Leu Gln Ile Asn Ile Leu Lys Asn Glu Asp Thr Ala Thr Tyr Phe Cys
                85                  90                  95

Ala Arg Glu Ser Leu Tyr Asp Tyr Tyr Ser Met Asp Tyr Trp Gly Gln
            100                 105                 110

Gly Thr Ser Val Thr Val Ser Ser
        115                 120

<210> SEQ ID NO 7
<211> LENGTH: 360
<212> TYPE: DNA
<213> ORGANISM: Mus musculus
<220> FEATURE:
<221> NAME/KEY: misc_feature
<223> OTHER INFORMATION: Polynucleotide Encoding LAG-3 mAb 1 VH

<400> SEQUENCE: 7
cagatccagt tggtgcagtc tggacctgag ctgaagaagc ctggagagac agtcaagatc      60
tcctgcaagg cttctggtta taccttcaga aactatggaa tgaactgggt gaagcaggct     120
ccaggaaagg ttttaaagtg gatgggctgg ataaacacct acactggaga gtcaacatat     180
gctgatgact cgagggacg gtttgccttc tctttgggaa cctctgccag cactgcctat     240
ttgcagatca acatcctcaa aaatgaggac acggctacat atttctgtgc aagagaatcc     300
ctctatgatt actattctat ggactactgg ggtcaaggaa cctcagtcac cgtctcctca     360

<210> SEQ ID NO 8
<211> LENGTH: 5
<212> TYPE: PRT
<213> ORGANISM: Mus musculus
<220> FEATURE:
<221> NAME/KEY: MISC_FEATURE
<222> LOCATION: (1)..(5)

<223> OTHER INFORMATION: LAG-3 mAb 1 VH CDR 1

<400> SEQUENCE: 8

Asn Tyr Gly Met Asn
1               5

<210> SEQ ID NO 9
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: LAG-3 mAb 1 VH CDR2

<400> SEQUENCE: 9

Trp Ile Asn Thr Tyr Thr Gly Glu Ser Thr Tyr Ala Asp Asp Phe Glu
1               5                  10                  15

Gly

<210> SEQ ID NO 10
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: LAG-3 mAb 1 VH CDR3

<400> SEQUENCE: 10

Glu Ser Leu Tyr Asp Tyr Tyr Ser Met Asp Tyr
1               5                  10

<210> SEQ ID NO 11
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: LAG-3 mAb 1 VL

<400> SEQUENCE: 11

Asp Val Val Val Thr Gln Thr Pro Leu Thr Leu Ser Val Thr Ile Gly
1               5                  10                  15

Gln Pro Ala Ser Ile Ser Cys Lys Ser Ser Gln Ser Leu Leu His Ser
                20                  25                  30

Asp Gly Lys Thr Tyr Leu Asn Trp Leu Leu Gln Arg Pro Gly Gln Ser
            35                  40                  45

Pro Glu Arg Leu Ile Tyr Leu Val Ser Glu Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

<210> SEQ ID NO 12
<211> LENGTH: 336
<212> TYPE: DNA
<213> ORGANISM: Mus musculus
<220> FEATURE:
<221> NAME/KEY: misc_feature
<223> OTHER INFORMATION: Polynucleotide Encoding LAG-3 mAb 1 VL

<400> SEQUENCE: 12

```
gatgttgtgg tgacccagac tccactcact tgtcggtta ccattggaca accagcctcc      60
atctcttgca agtcaagtca gagcctctta catagtgatg aaagacata tttgaattgg     120 ttgttacaga ggccaggcca gtctccagag cgcctaatct atctggtgtc tgaactggac    180
tctggagtcc ctgacaggtt cactggcagt ggatcaggga cagatttcac actgaaaatc    240
agcagagtgg aggctgagga tttgggagtt tattattgct ggcaaggtac acattttccg    300
tacacgttcg gaggggggac caagctggaa ataaaa                              336
```

<210> SEQ ID NO 13
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: LAG-3 mAb 1 VL CDR1

<400> SEQUENCE: 13

Lys Ser Ser Gln Ser Leu Leu His Ser Asp Gly Lys Thr Tyr Leu Asn
1               5                   10                  15

<210> SEQ ID NO 14
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: LAG-3 mAb 1 VL CDR2

<400> SEQUENCE: 14

Leu Val Ser Glu Leu Asp Ser
1               5

<210> SEQ ID NO 15
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: LAG-3 mAb 1 VL CDR3

<400> SEQUENCE: 15

Trp Gln Gly Thr His Phe Pro Tyr Thr
1               5

<210> SEQ ID NO 16
<211> LENGTH: 120
<212> TYPE: PRT
<213> ORGANISM: Artificial Sequence
<220> FEATURE:
<223> OTHER INFORMATION: hLAG-3 mAb 1 VH1

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

```
Gly Trp Ile Asn Thr Tyr Thr Gly Glu Ser Thr Tyr Ala Asp Asp Phe
        50                  55                  60

Glu Gly Arg Phe Val Phe Ser Met Asp Thr Ser Ala Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Ser Leu Tyr Asp Tyr Tyr Ser Met Asp Tyr Trp Gly Gln
                    100                 105                 110

Gly Thr Thr Val Thr Val Ser Ser
            115                 120

<210> SEQ ID NO 17
<211> LENGTH: 360
<212> TYPE: DNA
<213> ORGANISM: Artificial Sequence
<220> FEATURE:
<223> OTHER INFORMATION: Polynucleotide Encoding hLAG-3 mAb 1 VH1

<400> SEQUENCE: 17
caggtgcaac tggttcaatc cggcgccgag gtgaaaaagc ctggcgcctc cgtgaaagtg      60
tcctgtaagg catctgggta tacgttcaca aattatggta tgaactgggt gcgacaggca     120
ccagggcagg gactggaatg gatggggtgg atcaatactt atacaggcga gagtacttat     180
gctgacgatt tcgagggcag atttgtcttc tccatggaca ccagcgctag taccgcttat     240
ctccagatta gttctctcaa ggcggaggac acagctgttt attattgtgc ccgcgagagt     300
ttgtatgact actatagcat ggattactgg ggacaaggta caaccgtgac agtgagttcc     360

<210> SEQ ID NO 18
<211> LENGTH: 120
<212> TYPE: PRT
<213> ORGANISM: Artificial Sequence
<220> FEATURE:
<223> OTHER INFORMATION: hLAG-3 mAb 1 VH2

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Ser Thr Tyr Ala Asp Asp Phe
        50                  55                  60

Glu Gly Arg Phe Val Phe Ser Met Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Glu Ser Leu Tyr Asp Tyr Tyr Ser Met Asp Tyr Trp Gly Gln
                    100                 105                 110

Gly Thr Thr Val Thr Val Ser Ser
            115                 120

<210> SEQ ID NO 19
<211> LENGTH: 360
<212> TYPE: DNA
<213> ORGANISM: Artificial Sequence
<220> FEATURE:
<223> OTHER INFORMATION: Polynucleotide Encoding hLAG-3 mAb 1 VH2
```

<400> SEQUENCE: 19

```
caggtgcaac tggttcaatc cggcgccgag gtgaaaaagc ctggcgcctc cgtgaaagtg      60
tcctgtaagg catctgggta tacgttcaca aattatggta tgaactgggt gcgacaggca     120
ccagggcagg gactggaatg gatggggtgg atcaatactt atacaggcga gagtacttat     180
gctgacgatt tcgagggcag atttgtcttc tccatggaca ccagcgctag taccgcttat     240
ctccagatta gttctctcaa ggcggaggac acagctgttt atttctgtgc ccgcgagagt     300
ttgtatgact actatagcat ggattactgg ggacaaggta caaccgtgac agtgagttcc     360
```

<210> SEQ ID NO 20
<211> LENGTH: 112
<212> TYPE: PRT
<213> ORGANISM: Artificial Sequence
<220> FEATURE:
<223> OTHER INFORMATION: hLAG-3 mAb 1 VL1

<400> SEQUENCE: 20

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Leu Gln Lys Pro Gly Gln Ser
        35                  40                  45

Pro Glu Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Val Glu Ile Lys
            100                 105                 110

<210> SEQ ID NO 21
<211> LENGTH: 336
<212> TYPE: DNA
<213> ORGANISM: Artificial Sequence
<220> FEATURE:
<223> OTHER INFORMATION: Polynucleotide Encoding hLAG-3 mAb 1 VL1

<400> SEQUENCE: 21

```
gatatcgtta tgactcagac accactgtca ctgagtgtga ccccaggtca gcccgctagt      60
atttcctgta aatcatccca gtccctcctg catagcgatg gaaagaccta tttgaactgg     120
cttctgcaga aaccaggcca aagtccagag agattgatct acctcgtttc agaactcgac     180
agtggagtgc ccgatcgctt ctcagggtcc ggctctggga ctgattttac tctcaagatc     240
tcaagagtgg aggccgagga cgtcggggtt tactactgtt ggcagggtac ccacttccct     300
tatacatttg gcggaggcac aaaagtggag attaaa                                336
```

<210> SEQ ID NO 22
<211> LENGTH: 112
<212> TYPE: PRT
<213> ORGANISM: Artificial Sequence
<220> FEATURE:
<223> OTHER INFORMATION: hLAG-3 mAb 1 VL2

<400> SEQUENCE: 22

Asp Ile Val Met Thr Gln Thr Pro Leu Ser Leu Ser Val Thr Pro Gly

```
  1               5                  10                 15
Gln Pro Ala Ser Ile Ser Cys Lys Ser Ser Gln Ser Leu Leu His Ser
                20                  25                 30

Asp Gly Lys Thr Tyr Leu Asn Trp Leu Leu Gln Arg Pro Gly Gln Ser
                35                  40                 45

Pro Glu Arg Leu Ile Tyr Leu Val Ser Glu Leu Asp Ser Gly Val Pro
                50                  55                 60

Asp Arg Phe Ser Gly Ser Gly Ser Gly Thr Asp Phe Thr Leu Lys Ile
 65                  70                 75                    80

Ser Arg Val Glu Ala Glu Asp Val Gly Val Tyr Tyr Cys Trp Gln Gly
                     85                 90                 95

Thr His Phe Pro Tyr Thr Phe Gly Gly Gly Thr Lys Val Glu Ile Lys
                    100                 105                110
```

<210> SEQ ID NO 23
<211> LENGTH: 336
<212> TYPE: DNA
<213> ORGANISM: Artificial Sequence
<220> FEATURE:
<223> OTHER INFORMATION: Polynucleotide Encoding hLAG-3 mAb 1 VL2

<400> SEQUENCE: 23

```
gatatcgtta tgactcagac accactgtca ctgagtgtga ccccaggtca gcccgctagt    60
atttcctgta atcatccca gtccctcctg catagcgatg aaagaccta tttgaactgg    120
cttctgcaga gaccaggcca aagtccagag agattgatct acctcgtttc agaactcgac    180
agtggagtgc ccgatcgctt ctcagggtcc ggctctggga ctgattttac tctcaagatc    240
tcaagagtgg aggccgagga cgtcggggtt tactactgtt ggcagggtac ccacttccct    300
tatacatttg gcggaggcac aaaagtggag attaaa                              336
```

<210> SEQ ID NO 24
<211> LENGTH: 112
<212> TYPE: PRT
<213> ORGANISM: Artificial Sequence
<220> FEATURE:
<223> OTHER INFORMATION: hLAG-3 mAb 1 VL3

<400> SEQUENCE: 24

```
Asp Ile Val Met Thr Gln Thr Pro Leu Ser Leu Ser Val Thr Pro Gly
 1               5                  10                 15

Gln Pro Ala Ser Ile Ser Cys Lys Ser Ser Gln Ser Leu Leu His Ser
                20                  25                 30

Asp Gly Lys Thr Tyr Leu Asn Trp Leu Leu Gln Lys Pro Gly Gln Pro
                35                  40                 45

Pro Glu Arg Leu Ile Tyr Leu Val Ser Glu Leu Asp Ser Gly Val Pro
                50                  55                 60

Asp Arg Phe Ser Gly Ser Gly Ser Gly Thr Asp Phe Thr Leu Lys Ile
 65                  70                 75                    80

Ser Arg Val Glu Ala Glu Asp Val Gly Val Tyr Tyr Cys Trp Gln Gly
                     85                 90                 95

Thr His Phe Pro Tyr Thr Phe Gly Gly Gly Thr Lys Val Glu Ile Lys
                    100                 105                110
```

<210> SEQ ID NO 25
<211> LENGTH: 336
<212> TYPE: DNA
<213> ORGANISM: Artificial Sequence
<220> FEATURE:

<223> OTHER INFORMATION: Polynucleotide Encoding hLAG-3 mAb 1 VL3

<400> SEQUENCE: 25

```
gatatcgtta tgactcagac accactgtca ctgagtgtga ccccaggtca gcccgctagt      60
atttcctgta atcatccca gtccctcctg catagcgatg aaagaccta tttgaactgg      120
cttctgcaga aaccaggcca accgccagag agattgatct acctcgtttc agaactcgac      180
agtggagtgc ccgatcgctt ctcagggtcc ggctctggga ctgattttac tctcaagatc      240
tcaagagtgg aggccgagga cgtcggggtt tactactgtt ggcagggtac ccacttccct      300
tatacatttg gcggaggcac aaaagtggag attaaa                                336
```

<210> SEQ ID NO 26
<211> LENGTH: 112
<212> TYPE: PRT
<213> ORGANISM: Artificial Sequence
<220> FEATURE:
<223> OTHER INFORMATION: hLAG-3 mAb 1 VL4

<400> SEQUENCE: 26

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Ala Lys Thr Tyr Leu Asn Trp Leu Leu Gln Lys Pro Gly Gln Pro
        35                  40                  45

Pro Glu Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Val Glu Ile Lys
            100                 105                 110

<210> SEQ ID NO 27
<211> LENGTH: 336
<212> TYPE: DNA
<213> ORGANISM: Artificial Sequence
<220> FEATURE:
<223> OTHER INFORMATION: Polynucleotide Encoding hLAG-3 mAb 1 VL4

<400> SEQUENCE: 27

```
gatatcgtta tgactcagac accactgtca ctgagtgtga ccccaggtca gcccgctagt      60
atttcctgta atcatccca gtccctcctg catagcgatg caaagaccta tttgaactgg      120
cttctgcaga aaccaggcca accgccagag agattgatct acctcgtttc agaactcgac      180
agtggagtgc ccgatcgctt ctcagggtcc ggctctggga ctgattttac tctcaagatc      240
tcaagagtgg aggccgagga cgtcggggtt tactactgtt ggcagggtac ccacttccct      300
tatacatttg gcggaggcac aaaagtggag attaaa                                336
```

<210> SEQ ID NO 28
<211> LENGTH: 16
<212> TYPE: PRT
<213> ORGANISM: Artificial Sequence
<220> FEATURE:
<223> OTHER INFORMATION: hLAG-3 mAb 1 VL4 CDR1

<400> SEQUENCE: 28

Lys Ser Ser Gln Ser Leu Leu His Ser Asp Ala Lys Thr Tyr Leu Asn
1               5                   10                  15

<210> SEQ ID NO 29
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: LAG-3 mAb 2 VH

<400> SEQUENCE: 29

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Asp Tyr
                20                  25                  30

Asn Ile His Trp Leu Arg Gln Ser His Gly Glu Ser Leu Glu Trp Ile
            35                  40                  45

Gly Tyr Ile Tyr Pro Tyr Ser Gly Asp Ile Gly Tyr Asn Gln Lys Phe
        50                  55                  60

Lys Asn Arg Ala Thr Leu Thr Val Asp Asn Ser Ser Ser Thr Ala Tyr
65                  70                  75                  80

Met Asp Leu Arg Ser Leu Thr Ser Glu Asp Ser Ala Val Phe Tyr Cys
                85                  90                  95

Ala Arg Trp His Arg Asn Tyr Phe Gly Pro Trp Phe Ala Tyr Trp Gly
                100                 105                 110

Gln Gly Thr Pro Val Thr Val Ser Ala
            115                 120

<210> SEQ ID NO 30
<211> LENGTH: 363
<212> TYPE: DNA
<213> ORGANISM: Mus musculus
<220> FEATURE:
<221> NAME/KEY: misc_feature
<223> OTHER INFORMATION: Polynucleotide Encoding LAG-3 mAb 2 VH

<400> SEQUENCE: 30
gaggtccagc ttcagcagtc aggacctgag ctggtgaaac ctggggcctc agtgaagatt    60
tcctgcaaga cttctggata cacatttact gactacaaca tacactggtt gaggcagagc   120
catggagaga gccttgagtg gattggatat atttatcctt acagtggtga tattggatac   180
aaccagaagt tcaagaacag ggccacattg actgtagaca attcctccag cacagcctac   240
atggatctcc gcagcctgac atctgaagac tctgcagtct tttactgtgc aagatggcac   300
aggaactact ttggcccctg gtttgcttac tggggccaag gactccggt cactgtctct   360 gca                                                                 363

<210> SEQ ID NO 31
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: LAG-3 mAb 2 VH CDR 1

<400> SEQUENCE: 31

Asp Tyr Asn Ile His
1               5

```
<210> SEQ ID NO 32
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: LAG-3 mAb 2 VH CDR2

<400> SEQUENCE: 32

Tyr Ile Tyr Pro Tyr Ser Gly Asp Ile Gly Tyr Asn Gln Lys Phe Lys
1               5                   10                  15

Asn

<210> SEQ ID NO 33
<211> LENGTH: 12
<212> TYPE: PRT
<213> ORGANISM: Mus musculus
<220> FEATURE:
<221> NAME/KEY: MISC_FEATURE
<222> LOCATION: (1)..(12)
<223> OTHER INFORMATION: LAG-3 mAb 2 VH CDR3

<400> SEQUENCE: 33

Trp His Arg Asn Tyr Phe Gly Pro Trp Phe Ala Tyr
1               5                   10

<210> SEQ ID NO 34
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: LAG-3 mAb 2 VL

<400> SEQUENCE: 34

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Glu Ser Tyr Met Asn Trp Tyr Gln Gln Lys Pro Gly Gln Pro Pro
        35                  40                  45

Lys Leu Leu Ile Tyr Val Val Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Ser
                85                  90                  95

Glu Asp Pro Leu Thr Phe Gly Ala Gly Thr Lys Leu Glu Leu Lys
            100                 105                 110

<210> SEQ ID NO 35
<211> LENGTH: 333
<212> TYPE: DNA
<213> ORGANISM: Mus musculus
<220> FEATURE:
<221> NAME/KEY: misc_feature
<223> OTHER INFORMATION: Polynucleotide Encoding LAG-3 mAb 2 VL

<400> SEQUENCE: 35
gacattgtgc tgacccaatc tccagcttct ttggctgtgt ctctagggca gagggccacc     60
atctcctgca aggccagcca agtgttgat tatgatggtg aaagttatat gaactggtac    120
```

```
caacagaaac caggacagcc acccaaactc ctcatttatg ttgtatccaa tctagaatct    180
gggatcccag ccaggtttag tggcagtggg tctgggacag acttcaccct caacatccat    240
cctgtggagg aggaggatgc tgcaacctat tactgtcagc aaagtagtga ggatccgctc    300
acgttcggtg ctgggaccaa gctggagctg aaa                                 333
```

```
<210> SEQ ID NO 36
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: LAG-3 mAb 2 VL CDR1

<400> SEQUENCE: 36

Lys Ala Ser Gln Ser Val Asp Tyr Asp Gly Glu Ser Tyr Met Asn
1               5                   10                  15

<210> SEQ ID NO 37
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: LAG-3 mAb 2 VL CDR2

<400> SEQUENCE: 37

Val Val Ser Asn Leu Glu Ser
1               5

<210> SEQ ID NO 38
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: LAG-3 mAb 2 VL CDR3

<400> SEQUENCE: 38

Gln Gln Ser Ser Glu Asp Pro Leu Thr
1               5

<210> SEQ ID NO 39
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: LAG-3 mAb 3 VH

<400> SEQUENCE: 39

Glu Val Arg Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Ile His Trp Val Arg Gln Ser His Gly Gln Ser Leu Glu Trp Ile
        35                  40                  45

Gly Tyr Ile Tyr Pro Tyr Asn Gly Asp Thr Gly Tyr Asn Gln Lys Phe
    50                  55                  60

Lys Thr Lys Ala Thr Leu Thr Val Asp Asn Ser Ser Asn Thr Ala Tyr
```

```
                65                  70                  75                  80
Met Glu Leu Arg Ser Leu Ala Ser Glu Asp Ser Ala Val Tyr Tyr Cys
                    85                  90                  95

Thr Arg Trp Ser Arg Asn Tyr Phe Gly Pro Trp Phe Ala Tyr Trp Gly
            100                 105                 110

Gln Gly Thr Leu Val Thr Val Ser Ala
        115                 120

<210> SEQ ID NO 40
<211> LENGTH: 363
<212> TYPE: DNA
<213> ORGANISM: Mus musculus
<220> FEATURE:
<221> NAME/KEY: misc_feature
<223> OTHER INFORMATION: Polynucleotide Encoding LAG-3 mAb 3 VH

<400> SEQUENCE: 40
gaggtccggc ttcagcagtc aggacctgag ctggtgaaac ctggggcctc agtgaagata      60
tcctgcaagg cttctggata cacattcact gactacaaca ttcactgggt gaggcagagc     120
catggacaga gccttgagtg gattggatat atttatcctt ataatggtga tactggctac     180
aaccagaagt tcaagaccaa ggccacattg actgtagaca ttcctccaa cacagcctac      240 atggaactcc gcagcctggc atctgaagac tctgcagtct attactgtac aagatggagc     300
aggaactact ttggcccctg gtttgcttac tggggccaag gactctggt cactgtctct      360 gca                                                                   363

<210> SEQ ID NO 41
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: LAG-3 mAb 3 VH CDR 1

<400> SEQUENCE: 41

Asp Tyr Asn Ile His
1               5

<210> SEQ ID NO 42
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: LAG-3 mAb 3 VH CDR2

<400> SEQUENCE: 42

Tyr Ile Tyr Pro Tyr Asn Gly Asp Thr Gly Tyr Asn Gln Lys Phe Lys
1               5                   10                  15

Thr

<210> SEQ ID NO 43
<211> LENGTH: 12
<212> TYPE: PRT
<213> ORGANISM: Mus musculus
<220> FEATURE:
<221> NAME/KEY: MISC_FEATURE
<222> LOCATION: (1)..(12)
<223> OTHER INFORMATION: LAG-3 mAb 3 VH CDR3

<400> SEQUENCE: 43
```

Trp Ser Arg Asn Tyr Phe Gly Pro Trp Phe Ala Tyr
1               5                   10

<210> SEQ ID NO 44
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: LAG-3 mAb 3 VL

<400> SEQUENCE: 44

Asp Ile Val Leu Thr Gln Ser Pro Thr Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Ser
                85                  90                  95

Glu Asp Pro Leu Thr Phe Gly Ala Gly Thr Lys Leu Glu Leu Lys
            100                 105                 110

<210> SEQ ID NO 45
<211> LENGTH: 333
<212> TYPE: DNA
<213> ORGANISM: Mus musculus
<220> FEATURE:
<221> NAME/KEY: misc_feature
<223> OTHER INFORMATION: Polynucleotide Encoding LAG-3 mAb 3 VL

<400> SEQUENCE: 45
gacattgtgc tgacccaatc tccaacttct ttggctgtgt ctctagggca gagggccacc      60
atctcctgca aggccagcca agtgttgat tatgatggtg atagttatat gaactggtat      120
caacagaaac aggacagcc acccaaactc ctcatctatg ctgcatccaa tctagaatct      180
gggatcccag ccaggtttag tggcagtggg tctgggacag acttcacccct caacatccat      240 cctgtggagg aggaggatgc tgcaacctat tactgtcagc aaagtagtga ggatccgctc      300
acgttcggtg ctgggaccaa gctggagctg aaa                                   333

<210> SEQ ID NO 46
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: LAG-3 mAb 3 VL CDR1

<400> SEQUENCE: 46

Lys Ala Ser Gln Ser Val Asp Tyr Asp Gly Asp Ser Tyr Met Asn
1               5                   10                  15

<210> SEQ ID NO 47
<211> LENGTH: 7
<212> TYPE: PRT

```
<213> ORGANISM: Mus musculus
<220> FEATURE:
<221> NAME/KEY: MISC_FEATURE
<222> LOCATION: (1)..(7)
<223> OTHER INFORMATION: LAG-3 mAb 3 VL CDR2

<400> SEQUENCE: 47

Ala Ala Ser Asn Leu Glu Ser
1               5

<210> SEQ ID NO 48
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: LAG-3 mAb 3 VL CDR3

<400> SEQUENCE: 48

Gln Gln Ser Ser Glu Asp Pro Leu Thr
1               5

<210> SEQ ID NO 49
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: LAG-3 mAb 4 VH

<400> SEQUENCE: 49

Glu Val Gln Leu His Gln Ser Gly Pro Glu Leu Val Lys Pro Gly Ala
1               5                   10                  15

Ser Val Lys Ile Ser Cys Lys Thr Ser Gly Tyr Thr Phe Thr Asp Tyr
            20                  25                  30

Asn Ile His Trp Val Lys Gln Ser His Gly Lys Ser Leu Glu Trp Ile
        35                  40                  45

Gly Tyr Ile Tyr Pro Tyr Asn Gly Asp Ala Gly Tyr Asn Gln Asn Phe
    50                  55                  60

Lys Thr Lys Ala Thr Leu Thr Val Asp Asn Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Trp Asn Met Asn Tyr Phe Gly Pro Trp Phe Ala Tyr Trp Gly
            100                 105                 110

Gln Gly Thr Leu Val Thr Val Ser Ala
        115                 120

<210> SEQ ID NO 50
<211> LENGTH: 363
<212> TYPE: DNA
<213> ORGANISM: Mus musculus
<220> FEATURE:
<221> NAME/KEY: misc_feature
<223> OTHER INFORMATION: Polynucleotide Encoding LAG-3 mAb 4 VH

<400> SEQUENCE: 50
gaggtccagc ttcaccagtc aggacctgag ctggtgaaac ctggggcctc agtgaagata    60
tcctgcaaga cttctggata cactttcact gactacaaca tacactgggt gaagcagagc   120
catggaaaga gccttgagtg gattggatat atttatcctt acaatggtga tgctggctac   180
```

```
aaccagaact tcaagaccaa ggccacattg actgtagaca attcctccag cacagcctac    240
atggagctcc gcagcctgac atctgaggac tctgcagtct attactgtgc aagatggaac    300
atgaactact ttggccctg gtttgcttac tggggccaag ggactctggt cactgtctct     360
gcg                                                                  363
```

```
<210> SEQ ID NO 51
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: LAG-3 mAb 4 VH CDR 1

<400> SEQUENCE: 51

Asp Tyr Asn Ile His
1               5

<210> SEQ ID NO 52
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: LAG-3 mAb 4 VH CDR2

<400> SEQUENCE: 52

Tyr Ile Tyr Pro Tyr Asn Gly Asp Ala Gly Tyr Asn Gln Asn Phe Lys
1               5                   10                  15

Thr

<210> SEQ ID NO 53
<211> LENGTH: 12
<212> TYPE: PRT
<213> ORGANISM: Mus musculus
<220> FEATURE:
<221> NAME/KEY: MISC_FEATURE
<222> LOCATION: (1)..(12)
<223> OTHER INFORMATION: LAG-3 mAb 4 VH CDR3

<400> SEQUENCE: 53

Trp Asn Met Asn Tyr Phe Gly Pro Trp Phe Ala Tyr
1               5                   10

<210> SEQ ID NO 54
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: LAG-3 mAb 4 VL

<400> SEQUENCE: 54

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Val Thr Tyr Ile Asn Trp Tyr Gln Gln Lys Pro Gly Gln Pro Pro
        35                  40                  45

Lys Leu Leu Ile Phe Ala Ala Ser Asn Leu Glu Ser Gly Ile Pro Ala
    50                  55                  60
```

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Leu Thr Phe Gly Ala Gly Thr Lys Leu Glu Leu Lys
            100                 105                 110

<210> SEQ ID NO 55
<211> LENGTH: 333
<212> TYPE: DNA
<213> ORGANISM: Mus musculus
<220> FEATURE:
<221> NAME/KEY: misc_feature
<223> OTHER INFORMATION: Polynucleotide Encoding LAG-3 mAb 4 VL

<400> SEQUENCE: 55
gacattgtgc tgacccaatc tccagcttct ttggctgtgt ctctagggca gagggccacc      60
atctcctgca aggccagcca aagtgttgat tatgatggtg ttacttatat caactggtac     120
caacagaaac aggacagcc acccaaactc ctcatctttg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtaatga ggatccgctc     300
acgttcggtg ctgggaccaa gctggagctg aaa                                  333

<210> SEQ ID NO 56
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: LAG-3 mAb 4 VL CDR1

<400> SEQUENCE: 56

Lys Ala Ser Gln Ser Val Asp Tyr Asp Gly Val Thr Tyr Ile Asn
1               5                   10                  15

<210> SEQ ID NO 57
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: LAG-3 mAb 4 VL CDR2

<400> SEQUENCE: 57

Ala Ala Ser Asn Leu Glu Ser
1               5

<210> SEQ ID NO 58
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: LAG-3 mAb 4 VL CDR3

<400> SEQUENCE: 58

Gln Gln Ser Asn Glu Asp Pro Leu Thr
1               5

<210> SEQ ID NO 59

```
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: LAG-3 mAb 5 VH

<400> SEQUENCE: 59
```

| Glu | Val | Gln | Leu | Gln | Gln | Ser | Gly | Pro | Glu | Leu | Val | Lys | Pro | Gly | Ala |
|---|---|---|---|---|---|---|---|---|---|---|---|---|---|---|---|
| 1 | | | | 5 | | | | | 10 | | | | | 15 | |
| Ser | Val | Lys | Ile | Ser | Cys | Lys | Ala | Ser | Gly | Tyr | Thr | Phe | Thr | Asp | Tyr |
| | | | 20 | | | | | 25 | | | | | 30 | | |
| Asn | Ile | His | Trp | Val | Lys | Gln | Ser | Pro | Gly | Lys | Ser | Leu | Glu | Trp | Ile |
| | | 35 | | | | | 40 | | | | | 45 | | | |
| Gly | Tyr | Ile | Tyr | Pro | Tyr | Ser | Gly | Asp | Phe | Gly | Tyr | Asn | Gln | Lys | Phe |
| | 50 | | | | | 55 | | | | | 60 | | | | |
| Lys | Ser | Lys | Ala | Thr | Leu | Thr | Val | Asp | Asn | Ser | Ser | Thr | Ala | Tyr | |
| 65 | | | | | 70 | | | | | 75 | | | | | 80 |
| Met | Asp | Leu | Arg | Ser | Leu | Thr | Ser | Glu | Asp | Ser | Ala | Val | Phe | Tyr | Cys |
| | | | | 85 | | | | | 90 | | | | | 95 | |
| Ala | Arg | Trp | His | Arg | Asn | Tyr | Phe | Gly | Pro | Trp | Phe | Ala | Tyr | Trp | Gly |
| | | | 100 | | | | | 105 | | | | | 110 | | |
| Gln | Gly | Thr | Leu | Val | Thr | Val | Ser | Ala | | | | | | | |
| | | 115 | | | | | 120 | | | | | | | | |

```
<210> SEQ ID NO 60
<211> LENGTH: 363
<212> TYPE: DNA
<213> ORGANISM: Mus musculus
<220> FEATURE:
<221> NAME/KEY: misc_feature
<223> OTHER INFORMATION: Polynucleotide Encoding LAG-3 mAb 5 VH

<400> SEQUENCE: 60
gaggtccagc ttcagcagtc aggacctgag ctggtgaaac tggggcctc agtgaagatt      60 tcctgcaaag cttctggata cacatttact gactacaaca tacactgggt gaagcagagc    120
cctggaaaga gccttgaatg gattggatat atttatcctt acagtggtga ttttggatac    180
aaccagaagt tcaagagcaa ggccacattg actgtagaca attcctccag cacagcctac    240
atggatctcc gcagcctgac atctgaggac tctgcagtct tttactgtgc aagatggcac    300
aggaactact ttggcccctg gtttgcttac tggggccaag gactctggt cactgtctct     360 gca                                                                   363

<210> SEQ ID NO 61
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: LAG-3 mAb 5 VH CDR 1

<400> SEQUENCE: 61
```

| Asp | Tyr | Asn | Ile | His |
|---|---|---|---|---|
| 1 | | | | 5 |

```
<210> SEQ ID NO 62
<211> LENGTH: 17
<212> TYPE: PRT
<213> ORGANISM: Mus musculus
```

```
<220> FEATURE:
<221> NAME/KEY: MISC_FEATURE
<222> LOCATION: (1)..(17)
<223> OTHER INFORMATION: LAG-3 mAb 5 VH CDR2

<400> SEQUENCE: 62

Tyr Ile Tyr Pro Tyr Ser Gly Asp Phe Gly Tyr Asn Gln Lys Phe Lys
1               5                   10                  15

Ser

<210> SEQ ID NO 63
<211> LENGTH: 12
<212> TYPE: PRT
<213> ORGANISM: Mus musculus
<220> FEATURE:
<221> NAME/KEY: MISC_FEATURE
<222> LOCATION: (1)..(12)
<223> OTHER INFORMATION: LAG-3 mAb 5 VH CDR3

<400> SEQUENCE: 63

Trp His Arg Asn Tyr Phe Gly Pro Trp Phe Ala Tyr
1               5                   10

<210> SEQ ID NO 64
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: LAG-3 mAb 5 VL

<400> SEQUENCE: 64

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Glu Ser Tyr Met Asn Trp Tyr Gln Gln Lys Pro Gly Gln Pro Pro
            35                  40                  45

Lys Leu Leu Ile Tyr Val Val Ser Asn Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Ser
                85                  90                  95

Glu Asp Pro Leu Thr Phe Gly Ala Gly Thr Lys Leu Glu Leu Lys
            100                 105                 110

<210> SEQ ID NO 65
<211> LENGTH: 333
<212> TYPE: DNA
<213> ORGANISM: Mus musculus
<220> FEATURE:
<221> NAME/KEY: misc_feature
<223> OTHER INFORMATION: Polynucleotide Encoding LAG-3 mAb 5 VL

<400> SEQUENCE: 65
gacattgtgc tgacccaatc tccagcttct ttggctgtgt ctctagggca gagggccacc      60
atctcctgca aggccagcca agtgttgat tatgatggtg aaagttatat gaactggtac     120
caacagaaac aggacagcc acccaaactc ctcatttatg ttgtttccaa tctagaatct     180
gggatcccag ccaggtttag tggcagtggg tctgggacag acttcaccct caacatccat     240
```

```
cctgtggagg aggaggatgc tgcaacctat tactgtcagc aaagtagtga ggatccgctc    300
acgttcggtg ctgggaccaa gctggagctg aaa                                 333
```

<210> SEQ ID NO 66
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: LAG-3 mAb 5 VL CDR1

<400> SEQUENCE: 66

Lys Ala Ser Gln Ser Val Asp Tyr Asp Gly Glu Ser Tyr Met Asn
1               5                   10                  15

<210> SEQ ID NO 67
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: LAG-3 mAb 5 VL CDR2

<400> SEQUENCE: 67

Val Val Ser Asn Leu Glu Ser
1               5

<210> SEQ ID NO 68
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: LAG-3 mAb 5 VL CDR3

<400> SEQUENCE: 68

Gln Gln Ser Ser Glu Asp Pro Leu Thr
1               5

<210> SEQ ID NO 69
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: LAG-3 mAb 6 VH

<400> SEQUENCE: 69

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
                20                  25                  30

Asn Met Asp Trp Val Lys Gln Ser His Gly Glu Ser Leu Glu Trp Ile
            35                  40                  45

Gly Asp Ile Asn Pro Asn Gly Val Thr Ile Tyr Asn Gln Lys Phe
        50                  55                  60

Glu Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Glu Ala Asp Tyr Phe Tyr Phe Asp Tyr Trp Gly Gln Gly Thr
            100                 105                 110

Thr Leu Thr Val Ser Ser
        115

<210> SEQ ID NO 70
<211> LENGTH: 354
<212> TYPE: DNA
<213> ORGANISM: Mus musculus
<220> FEATURE:
<221> NAME/KEY: misc_feature
<223> OTHER INFORMATION: Polynucleotide Encoding LAG-3 mAb 6 VH

<400> SEQUENCE: 70
gaggtcctgc tgcaacagtc tggacctgag ctggtgaagc ctggggcttc agtgaagata      60
ccctgcaagg cttctggata cacattcact gactacaaca tggactgggt gaagcagagc     120
catggagaga gccttgagtg gattggagat attaatcctg acaatggtgt tactatctac     180
aaccagaagt ttgagggcaa ggccacactg actgtagaca gtcctccag tacagcctac      240 atggagctcc gcagcctgac atctgaggac actgcagtct attactgtgc aagagaggcg     300
gattacttct actttgacta ctggggccaa ggcaccactc tcacagtctc ctca           354

<210> SEQ ID NO 71
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: LAG-3 mAb 6 VH CDR 1

<400> SEQUENCE: 71

Asp Tyr Asn Met Asp
1               5

<210> SEQ ID NO 72
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: LAG-3 mAb 6 VH CDR2

<400> SEQUENCE: 72

Asp Ile Asn Pro Asp Asn Gly Val Thr Ile Tyr Asn Gln Lys Phe Glu
1               5                   10                  15

Gly

<210> SEQ ID NO 73
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: LAG-3 mAb 6 VH CDR3

<400> SEQUENCE: 73

Glu Ala Asp Tyr Phe Tyr Phe Asp Tyr
1               5

<210> SEQ ID NO 74
<211> LENGTH: 107

-continued

<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: LAG-3 mAb 6 VL

<400> SEQUENCE: 74

Asp Ile Val Met Thr Gln Ser His Arg Phe Met Ser Thr Ser Val Gly
1               5                   10                  15
Asp Arg Val Ser Ile Thr Cys Lys Ala Ser Gln Asp Val Ser Ser Val
            20                  25                  30
Val Ala Trp Tyr Gln Gln Lys Pro Gly Gln Ser Pro Lys Leu Leu Ile
        35                  40                  45
Phe Ser Ala Ser Tyr Arg Tyr Thr Gly Val Pro Asp Arg Phe Thr Gly
    50                  55                  60
Ser Gly Ser Gly Thr Asp Phe Thr Phe Thr Ile Ser Ser Val Gln Ala
65                  70                  75                  80
Ala Asp Leu Ala Val Tyr Tyr Cys Gln Gln His Tyr Ser Thr Pro Trp
                85                  90                  95
Thr Phe Gly Gly Gly Thr Lys Leu Glu Ile Lys
            100                 105

<210> SEQ ID NO 75
<211> LENGTH: 321
<212> TYPE: DNA
<213> ORGANISM: Mus musculus
<220> FEATURE:
<221> NAME/KEY: misc_feature
<223> OTHER INFORMATION: Polynucleotide Encoding LAG-3 mAb 6 VL

<400> SEQUENCE: 75
gacattgtga tgacccagtc tcacagattc atgtccacat cagttggaga cagggtcagc      60
atcacctgca aggccagtca ggatgtgagt tctgttgtag cctggtatca acagaaacca     120
ggacaatctc ctaaattact gattttttcg gcatcctacc ggtacactgg agtccctgat     180
cgcttcactg gcagtggatc tgggacggat ttcactttca ccatcagcag tgtgcaggct     240
gcagacctgg cagtttatta ctgtcagcaa cattatagta ctccgtggac gttcggtgga     300
ggcaccaagc tggaaatcaa a                                               321

<210> SEQ ID NO 76
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: LAG-3 mAb 6 VL CDR1

<400> SEQUENCE: 76

Lys Ala Ser Gln Asp Val Ser Ser Val Val Ala
1               5                   10

<210> SEQ ID NO 77
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: LAG-3 mAb 6 VL CDR2

<400> SEQUENCE: 77

Ser Ala Ser Tyr Arg Tyr Thr
1               5

<210> SEQ ID NO 78
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: LAG-3 mAb 6 VL CDR3

<400> SEQUENCE: 78

Gln Gln His Tyr Ser Thr Pro Trp Thr
1               5

<210> SEQ ID NO 79
<211> LENGTH: 118
<212> TYPE: PRT
<213> ORGANISM: Artificial Sequence
<220> FEATURE:
<223> OTHER INFORMATION: hLAG-3 mAb 6 VH-1

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Gly Leu Glu Trp Met
        35                  40                  45

Gly Asp Ile Asn Pro Asp Asn Gly Val Thr Ile Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Asp Tyr Phe Tyr Phe Asp Tyr Trp Gly Gln Gly Thr
            100                 105                 110

Thr Leu Thr Val Ser Ser
        115

<210> SEQ ID NO 80
<211> LENGTH: 354
<212> TYPE: DNA
<213> ORGANISM: Artificial Sequence
<220> FEATURE:
<223> OTHER INFORMATION: Polynucleotide Encoding hLAG-3 mAb 6 VH-1

<400> SEQUENCE: 80
caggtccagc tggtgcagtc tggcgccgaa gtgaagaaac ctggcgcaag cgtgaaggtg      60
tcctgcaagg ccagcggcta caccttcacc gactacaaca tggactgggt ccgacaggcc     120
ccaggacagg gcctggaatg gatgggcgac atcaaccccg acaacggcgt gaccatctac     180
aaccagaaat tcgagggcag agtgaccatg accaccgaca ccagcaccag caccgcctac     240
atggaactgc ggtccctgcg gagcgacgac accgccgtgt actactgcgc cagagaggcc     300
gactacttct acttcgacta ctggggccag ggcaccaccc tgaccgtgtc ctcc           354

<210> SEQ ID NO 81
<211> LENGTH: 118
<212> TYPE: PRT

<213> ORGANISM: Artificial Sequence
<220> FEATURE:
<223> OTHER INFORMATION: hLAG-3 mAb 6 VH-2

<400> SEQUENCE: 81

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Asn Met Asp Trp Val Arg Gln Ala Pro Gly Lys Gly Leu Glu Trp Val
        35                  40                  45

Ser Asp Ile Asn Pro Asp Asn Gly Val Thr Ile Tyr Asn Gln Lys Phe
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Asp Tyr Phe Tyr Phe Asp Tyr Trp Gly Gln Gly Thr
            100                 105                 110

Thr Leu Thr Val Ser Ser
        115

<210> SEQ ID NO 82
<211> LENGTH: 354
<212> TYPE: DNA
<213> ORGANISM: Artificial Sequence
<220> FEATURE:
<223> OTHER INFORMATION: Polynucleotide Encoding hLAG-3 mAb 6 VH-2

<400> SEQUENCE: 82
gaggtccagc tggtggaatc tggcggcgga ctggtcaagc ctggcggcag cctgagactg      60
agctgcgctg ccagcggctt caccttcagc gactacaaca tggactgggt ccgacaggcc     120
cctggcaagg cctggaatg gtgtccgac atcaacccg acaacggcgt gaccatctac        180
aaccagaagt tcgagggccg gttcaccatc agccgggaca cgccaagaa cagcctgtac      240 ctgcagatga acagcctgcg ggccgaggac accgccgtgt actactgcgc cagagaggcc     300
gactacttct acttcgacta ctggggccag ggcaccaccc tgaccgtgtc ctcc            354

<210> SEQ ID NO 83
<211> LENGTH: 107
<212> TYPE: PRT
<213> ORGANISM: Artificial Sequence
<220> FEATURE:
<223> OTHER INFORMATION: hLAG-3 mAb 6 VL-1

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Val
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Leu Glu Ile Lys
            100             105

<210> SEQ ID NO 84
<211> LENGTH: 321
<212> TYPE: DNA
<213> ORGANISM: Artificial Sequence
<220> FEATURE:
<223> OTHER INFORMATION: Polynucleotide Encoding hLAG-3 mAb 6 VL-1

<400> SEQUENCE: 84
gacatccaga tgacccagag ccccagcagc ctgagcgcca gcgtgggcga cagagtgacc      60
atcacctgtc gggccagcca ggatgtgtcc agcgtggtgg cctggtatca gcagaagccc     120
ggcaaggccc ccaagctgct gatctacagc gccagctacc ggtacacagg cgtgcccagc     180
agattcagcg gcagcggctc cggcaccgac ttcaccctga ccatcagcag cctgcagccc     240
gaggacttcg ccacctacta ctgccagcag cactacagca ccccctggac cttcggcgga     300
ggcaccaagc tggaaatcaa g                                               321

<210> SEQ ID NO 85
<211> LENGTH: 107
<212> TYPE: PRT
<213> ORGANISM: Artificial Sequence
<220> FEATURE:
<223> OTHER INFORMATION: hLAG-3 mAb 6 VL-2

<400> SEQUENCE: 85

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Val
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Val Tyr Tyr Cys Gln Gln His Tyr Ser Thr Pro Trp
                85                  90                  95

Thr Phe Gly Gly Gly Thr Lys Leu Glu Ile Lys
            100             105

<210> SEQ ID NO 86
<211> LENGTH: 321
<212> TYPE: DNA
<213> ORGANISM: Artificial Sequence
<220> FEATURE:
<223> OTHER INFORMATION: Polynucleotide Encoding hLAG-3 mAb 6 VL-2

<400> SEQUENCE: 86
gacatcgtga tgacccagag ccccagcagc ctgagcgcca gcgtgggcga cagagtgacc      60
atcacctgtc gggccagcca ggatgtgtcc agcgtggtgg cctggtatca gcagaagccc     120
ggcaaggccc ccaagctgct gatctacagc gccagctacc ggtacacagg cgtgcccgat     180
agattcagcg gcagcggctc cggcaccgac ttcaccttca ccatcagcag cctgcagccc     240
gaggacatcg ccgtttacta ctgccagcag cactacagca ccccctggac cttcggcgga     300
ggcaccaagc tggaaatcaa g                                               321

<210> SEQ ID NO 87
<211> LENGTH: 11
<212> TYPE: PRT
<213> ORGANISM: Artificial Sequence
<220> FEATURE:
<223> OTHER INFORMATION: hLAG-3 mAb 6 VL-1/VL-2 CDRL1

<400> SEQUENCE: 87

Arg Ala Ser Gln Asp Val Ser Ser Val Val Ala
1               5                   10

<210> SEQ ID NO 88
<211> LENGTH: 8
<212> TYPE: PRT
<213> ORGANISM: Artificial Sequence
<220> FEATURE:
<223> OTHER INFORMATION: Linker 1

<400> SEQUENCE: 88

Gly Gly Gly Ser Gly Gly Gly Gly
1               5

<210> SEQ ID NO 89
<211> LENGTH: 6
<212> TYPE: PRT
<213> ORGANISM: Artificial Sequence
<220> FEATURE:
<223> OTHER INFORMATION: Cys Linker 2

<400> SEQUENCE: 89

Gly Gly Cys Gly Gly Gly
1               5

<210> SEQ ID NO 90
<211> LENGTH: 4
<212> TYPE: PRT
<213> ORGANISM: Artificial Sequence
<220> FEATURE:
<223> OTHER INFORMATION: ABD Linker

<400> SEQUENCE: 90

Gly Gly Gly Ser
1

<210> SEQ ID NO 91
<211> LENGTH: 6
<212> TYPE: PRT
<213> ORGANISM: Artificial Sequence
<220> FEATURE:
<223> OTHER INFORMATION: Linker

<400> SEQUENCE: 91

Leu Gly Gly Gly Ser Gly
1               5

<210> SEQ ID NO 92
<211> LENGTH: 11
<212> TYPE: PRT
<213> ORGANISM: Artificial Sequence
<220> FEATURE:
<223> OTHER INFORMATION: Linker

<400> SEQUENCE: 92

Gly Gly Gly Ser Gly Gly Gly Ser Gly Gly Gly
1               5                   10

```
<210> SEQ ID NO 93
<211> LENGTH: 5
<212> TYPE: PRT
<213> ORGANISM: Artificial Sequence
<220> FEATURE:
<223> OTHER INFORMATION: Linker

<400> SEQUENCE: 93

Ala Ser Thr Lys Gly
1               5

<210> SEQ ID NO 94
<211> LENGTH: 6
<212> TYPE: PRT
<213> ORGANISM: Artificial Sequence
<220> FEATURE:
<223> OTHER INFORMATION: Linker

<400> SEQUENCE: 94

Leu Glu Pro Lys Ser Ser
1               5

<210> SEQ ID NO 95
<211> LENGTH: 5
<212> TYPE: PRT
<213> ORGANISM: Artificial Sequence
<220> FEATURE:
<223> OTHER INFORMATION: Linker

<400> SEQUENCE: 95

Ala Pro Ser Ser Ser
1               5

<210> SEQ ID NO 96
<211> LENGTH: 7
<212> TYPE: PRT
<213> ORGANISM: Artificial Sequence
<220> FEATURE:
<223> OTHER INFORMATION: Heterodimer-Promoting Domain

<400> SEQUENCE: 96

Gly Val Glu Pro Lys Ser Cys
1               5

<210> SEQ ID NO 97
<211> LENGTH: 6
<212> TYPE: PRT
<213> ORGANISM: Artificial Sequence
<220> FEATURE:
<223> OTHER INFORMATION: Heterodimer-Promoting Domain

<400> SEQUENCE: 97

Val Glu Pro Lys Ser Cys
1               5

<210> SEQ ID NO 98
<211> LENGTH: 6
<212> TYPE: PRT
<213> ORGANISM: Artificial Sequence
<220> FEATURE:
<223> OTHER INFORMATION: Heterodimer-Promoting Domain

<400> SEQUENCE: 98

Ala Glu Pro Lys Ser Cys
1               5

<210> SEQ ID NO 99
```

```
<211> LENGTH: 7
<212> TYPE: PRT
<213> ORGANISM: Artificial Sequence
<220> FEATURE:
<223> OTHER INFORMATION: Heterodimer-Promoting Domain

<400> SEQUENCE: 99

Gly Phe Asn Arg Gly Glu Cys
1               5

<210> SEQ ID NO 100
<211> LENGTH: 6
<212> TYPE: PRT
<213> ORGANISM: Artificial Sequence
<220> FEATURE:
<223> OTHER INFORMATION: Heterodimer-Promoting Domain

<400> SEQUENCE: 100

Phe Asn Arg Gly Glu Cys
1               5

<210> SEQ ID NO 101
<211> LENGTH: 28
<212> TYPE: PRT
<213> ORGANISM: Artificial Sequence
<220> FEATURE:
<223> OTHER INFORMATION: E-Coil

<400> SEQUENCE: 101

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 102
<211> LENGTH: 28
<212> TYPE: PRT
<213> ORGANISM: Artificial Sequence
<220> FEATURE:
<223> OTHER INFORMATION: K-Coil

<400> SEQUENCE: 102

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 103
<211> LENGTH: 28
<212> TYPE: PRT
<213> ORGANISM: Artificial Sequence
<220> FEATURE:
<223> OTHER INFORMATION: modified E-Coil

<400> SEQUENCE: 103

Glu Val Ala Ala Cys Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 104
<211> LENGTH: 28
<212> TYPE: PRT
<213> ORGANISM: Artificial Sequence
<220> FEATURE:
<223> OTHER INFORMATION: modified K-Coil
```

-continued

<400> SEQUENCE: 104

Lys Val Ala Ala Cys Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 105
<211> LENGTH: 46
<212> TYPE: PRT
<213> ORGANISM: Artificial Sequence
<220> FEATURE:
<223> OTHER INFORMATION: ABD

<400> SEQUENCE: 105

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45

<210> SEQ ID NO 106
<211> LENGTH: 46
<212> TYPE: PRT
<213> ORGANISM: Artificial Sequence
<220> FEATURE:
<223> OTHER INFORMATION: deimm ABD

<400> SEQUENCE: 106

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45

<210> SEQ ID NO 107
<211> LENGTH: 46
<212> TYPE: PRT
<213> ORGANISM: Artificial Sequence
<220> FEATURE:
<223> OTHER INFORMATION: deimm ABD

<400> SEQUENCE: 107

Leu Ala Glu Ala Lys Val Leu Ala Asn Arg Glu Leu Asp Lys Tyr Gly
1               5                   10                  15

Val Ser Asp Tyr Tyr Lys Asn Ala Ala Asn Asn Ala Lys Thr Val Glu
            20                  25                  30

Gly Val Lys Ala Leu Ile Ala Glu Ile Leu Ala Ala Leu Pro
        35                  40                  45

<210> SEQ ID NO 108
<211> LENGTH: 46
<212> TYPE: PRT
<213> ORGANISM: Artificial Sequence
<220> FEATURE:
<223> OTHER INFORMATION: deimm ABD

<400> SEQUENCE: 108

Leu Ala Glu Ala Lys Val Leu Ala Asn Arg Glu Leu Asp Lys Tyr Gly
1               5                   10                  15

```
Val Ser Asp Tyr Tyr Lys Asn Leu Ile Ser Asn Ala Lys Ser Val Glu
            20                  25                  30

Gly Val Lys Ala Leu Ile Ala Glu Ile Leu Ala Ala Leu Pro
        35                  40                  45
```

<210> SEQ ID NO 109
<211> LENGTH: 10
<212> TYPE: PRT
<213> ORGANISM: Artificial Sequence
<220> FEATURE:
<223> OTHER INFORMATION: Hinge Linker

<400> SEQUENCE: 109

```
Asp Lys Thr His Thr Cys Pro Pro Cys Pro
1               5                   10
```

<210> SEQ ID NO 110
<211> LENGTH: 8
<212> TYPE: PRT
<213> ORGANISM: Artificial Sequence
<220> FEATURE:
<223> OTHER INFORMATION: Linker

<400> SEQUENCE: 110

```
Ala Pro Ser Ser Ser Pro Met Glu
1               5
```

<210> SEQ ID NO 111
<211> LENGTH: 15
<212> TYPE: PRT
<213> ORGANISM: Artificial Sequence
<220> FEATURE:
<223> OTHER INFORMATION: Cys Linker

<400> SEQUENCE: 111

```
Leu Glu Pro Lys Ser Ala Asp Lys Thr His Thr Cys Pro Pro Cys
1               5                   10                  15
```

<210> SEQ ID NO 112
<211> LENGTH: 13
<212> TYPE: PRT
<213> ORGANISM: Artificial Sequence
<220> FEATURE:
<223> OTHER INFORMATION: Linker

<400> SEQUENCE: 112

```
Gly Gly Gly Asp Lys Thr His Thr Cys Pro Pro Cys Pro
1               5                   10
```

<210> SEQ ID NO 113
<211> LENGTH: 16
<212> TYPE: PRT
<213> ORGANISM: Artificial Sequence
<220> FEATURE:
<223> OTHER INFORMATION: Linker

<400> SEQUENCE: 113

```
Leu Glu Pro Lys Ser Ser Asp Lys Thr His Thr Cys Pro Pro Cys Pro
1               5                   10                  15
```

<210> SEQ ID NO 114
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)

```
<223> OTHER INFORMATION: IgG1 Hinge

<400> SEQUENCE: 114

Glu Pro Lys Ser Cys Asp Lys Thr His Thr Cys Pro Pro Cys Pro
1               5                   10                  15

<210> SEQ ID NO 115
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: IgG2 Hinge

<400> SEQUENCE: 115

Glu Arg Lys Cys Cys Val Glu Cys Pro Pro Cys Pro
1               5                   10

<210> SEQ ID NO 116
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: IgG4 Hinge

<400> SEQUENCE: 116

Glu Ser Lys Tyr Gly Pro Pro Cys Pro Ser Cys Pro
1               5                   10

<210> SEQ ID NO 117
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: IgG4 Hinge (S228P)

<400> SEQUENCE: 117

Glu Ser Lys Tyr Gly Pro Pro Cys Pro Pro Cys Pro
1               5                   10

<210> SEQ ID NO 118
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: LC kappa

<400> SEQUENCE: 118

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 119
<211> LENGTH: 104
<212> TYPE: PRT
<213> ORGANISM: Homo sapiens
<220> FEATURE:
<221> NAME/KEY: MISC_FEATURE
<222> LOCATION: (1)..(104)
<223> OTHER INFORMATION: LC lambda

<400> SEQUENCE: 119

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 120
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: IgG1 CH1

<400> SEQUENCE: 120

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 121
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)

<223> OTHER INFORMATION: IgG2 CH1

<400> SEQUENCE: 121

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 122
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: IgG4 CH1

<400> SEQUENCE: 122

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 123
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: IgG1 (AA)
<220> FEATURE:
<221> NAME/KEY: MISC_FEATURE
<222> LOCATION: (217)..(217)
<223> OTHER INFORMATION: Xaa217 is a lysine (K) or is absent

<400> SEQUENCE: 123

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr

```
            35                  40                  45
Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 124
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: IgG1 Fc (AA/YTE)
<220> FEATURE:
<221> NAME/KEY: MISC_FEATURE
<222> LOCATION: (217)..(217)
<223> OTHER INFORMATION: Xaa217 is a lysine (K) or is absent

<400> SEQUENCE: 124

Ala Pro Glu Ala Ala Gly Gly Pro Ser Val Phe Leu Phe Pro Pro Lys
 1               5                  10                  15

Pro Lys Asp Thr Leu Tyr Ile Thr Arg Glu Pro Glu Val Thr Cys Val
                 20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
```

```
            145                 150                 155                 160

Tyr Lys Thr Thr Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 125
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: IgG4 Fc (YTE)
<220> FEATURE:
<221> NAME/KEY: MISC_FEATURE
<222> LOCATION: (217)..(217)
<223> OTHER INFORMATION: Xaa217 is a lysine (K) or is absent

<400> SEQUENCE: 125

Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210                 215

<210> SEQ ID NO 126
<211> LENGTH: 217
<212> TYPE: PRT
<213> ORGANISM: Homo sapiens
<220> FEATURE:
<221> NAME/KEY: MISC_FEATURE
```

-continued

```
<222> LOCATION: (1)..(217)
<223> OTHER INFORMATION: Knob Fc domain
<220> FEATURE:
<221> NAME/KEY: MISC_FEATURE
<222> LOCATION: (217)..(217)
<223> OTHER INFORMATION: Xaa217 is a lysine (K) or is absent

<400> SEQUENCE: 126
```

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

```
<210> SEQ ID NO 127
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: Hole Fc
<220> FEATURE:
<221> NAME/KEY: MISC_FEATURE
<222> LOCATION: (217)..(217)
<223> OTHER INFORMATION: Xaa217 is a lysine (K) or is absent

<400> SEQUENCE: 127
```

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

-continued

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Xaa
    210                 215

<210> SEQ ID NO 128
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: IgG1 Fc universal
<220> FEATURE:
<221> NAME/KEY: MISC_FEATURE
<222> LOCATION: (4)..(5)
<223> OTHER INFORMATION: Xaa4(X1) and Xaa5(X2) are both L (wild type),
      or are both A (decreased FcR binding)
<220> FEATURE:
<221> NAME/KEY: MISC_FEATURE
<222> LOCATION: (22)..(26)
<223> OTHER INFORMATION: Xaa22(X3), Xaa24(X4), and Xaa26(X5) are
      respectively M, S and T (wild type), or Y, T and E (extended
      half-life)
<220> FEATURE:
<221> NAME/KEY: MISC_FEATURE
<222> LOCATION: (136)..(138)
<223> OTHER INFORMATION: Xaa136(X6), and Xaa138(X7) are respectively T
      and L (wild type) or W and L (knob), or are S and A (hole)
<220> FEATURE:
<221> NAME/KEY: MISC_FEATURE
<222> LOCATION: (177)..(177)
<223> OTHER INFORMATION: Xaa177(X8) is Y (wild type) when Xaa136(X6) is
      T and Xaa138(X7) is L; Xaa177(X8) is Y (knob) when Xaa136(X6) is W
      and Xaa138(X7) is L; Xaa177 (X8) is V (hole) when Xaa136(X6) is S
      and Xaa138(X7) is A
<220> FEATURE:
<221> NAME/KEY: MISC_FEATURE
<222> LOCATION: (204)..(205)
<223> OTHER INFORMATION: Xaa204(X9) and Xaa205(X10) respectively are N
      and H (wild type), or are N and R (no protein A binding), or are A
      and K (no protein A binding)
<220> FEATURE:
<221> NAME/KEY: MISC_FEATURE
<222> LOCATION: (217)..(217)
<223> OTHER INFORMATION: Xaa217(X11) is K or is absent

<400> SEQUENCE: 128

Ala Pro Glu Xaa Xaa Gly Gly Pro Ser Val Phe Leu Phe Pro Pro Lys
 1               5                  10                  15

Pro Lys Asp Thr Leu Xaa Ile Xaa Arg Xaa Pro Glu Val Thr Cys Val
```

```
            20                  25                  30
Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Xaa Cys Xaa Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Xaa Ser Lys Leu Thr Val Asp Lys Ser Arg Trp Gln Gln Gly Asn Val
            180                 185                 190

Phe Ser Cys Ser Val Met His Glu Ala Leu His Xaa Xaa Tyr Thr Gln
        195                 200                 205

Lys Ser Leu Ser Leu Ser Pro Gly Xaa
    210                 215

<210> SEQ ID NO 129
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: LAG-3 mAb A VH

<400> SEQUENCE: 129

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Asn Gly Asn Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser
        115                 120

<210> SEQ ID NO 130
<211> LENGTH: 107
<212> TYPE: PRT
<213> ORGANISM: Mus musculus
```

```
<220> FEATURE:
<221> NAME/KEY: MISC_FEATURE
<222> LOCATION: (1)..(107)
<223> OTHER INFORMATION: LAG-3 mAb A VL

<400> SEQUENCE: 130

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys
            100                 105

<210> SEQ ID NO 131
<211> LENGTH: 113
<212> TYPE: PRT
<213> ORGANISM: Mus musculus
<220> FEATURE:
<221> NAME/KEY: MISC_FEATURE
<222> LOCATION: (1)..(113)
<223> OTHER INFORMATION: PD-1 mAb 1 VH

<400> SEQUENCE: 131

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 132
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: PD-1 mAb 1 VL

<400> SEQUENCE: 132

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
```

```
                    20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys
            100                 105

<210> SEQ ID NO 133
<211> LENGTH: 120
<212> TYPE: PRT
<213> ORGANISM: Mus musculus

<400> SEQUENCE: 133

Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
 50                  55                  60

Lys Asn Arg Val Thr Leu Thr Thr Asp Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
                100                 105                 110

Gly Thr Thr Val Thr Val Ser Ser
            115                 120

<210> SEQ ID NO 134
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: PD-1 mAb 2 VL

<400> SEQUENCE: 134

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95
```

Asp Leu Pro Leu Thr Phe Gly Gly Gly Thr Lys Val Glu Ile Lys
            100                 105                 110

<210> SEQ ID NO 135
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: PD-1 mAb 3 VH

<400> SEQUENCE: 135

Gln Val Gln Leu Gln Gln Ser Gly Ala Glu Leu Ala Lys Pro Gly Ala
1               5                   10                  15

Ser Val Gln Met Ser Cys Lys Ala Ser Gly Tyr Ser Phe Thr Ser Ser
            20                  25                  30

Trp Ile His Trp Val Lys Gln Arg Pro Gly Gln Gly Leu Glu Trp Ile
        35                  40                  45

Gly Tyr Ile Tyr Pro Ser Thr Gly Phe Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Arg Asp Ser Ser Gly Tyr His Ala Met Asp Tyr Trp Gly
            100                 105                 110

Gln Gly Thr Ser Val Thr Val Ser Ser
        115                 120

<210> SEQ ID NO 136
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: PD-1 mAb 3 VL

<400> SEQUENCE: 136

Asp Ile Val Leu Thr Gln Ser Pro Ala Ser Leu Thr Val Ser Leu Gly
1               5                   10                  15

Gln Arg Ala Thr Ile Ser Cys Arg Ala Ser Gln Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Lys Phe Gly Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110

<210> SEQ ID NO 137
<211> LENGTH: 117
<212> TYPE: PRT
<213> ORGANISM: Mus musculus
<220> FEATURE:
<221> NAME/KEY: MISC_FEATURE

```
<222> LOCATION: (1)..(117)
<223> OTHER INFORMATION: PD-1 mAb 4 VH

<400> SEQUENCE: 137
```

| | | | | | | | | | | | | | | | |
|---|---|---|---|---|---|---|---|---|---|---|---|---|---|---|---|
| Gln | Val | Gln | Leu | Val | Gln | Ser | Gly | Ser | Glu | Leu | Lys | Lys | Pro | Gly | Ala |
| 1 | | | | 5 | | | | | 10 | | | | | 15 | |
| Ser | Val | Lys | Ile | Ser | Cys | Lys | Ala | Ser | Gly | Tyr | Thr | Phe | Thr | Asn | Tyr |
| | | | 20 | | | | | 25 | | | | | 30 | | |
| Gly | Met | Asn | Trp | Val | Arg | Gln | Ala | Pro | Gly | Gln | Gly | Leu | Gln | Trp | Met |
| | | 35 | | | | | 40 | | | | | 45 | | | |
| Gly | Trp | Ile | Asn | Thr | Asp | Ser | Gly | Glu | Ser | Thr | Tyr | Ala | Glu | Glu | Phe |
| 50 | | | | | 55 | | | | | 60 | | | | | |
| Lys | Gly | Arg | Phe | Val | Phe | Ser | Leu | Asp | Thr | Ser | Val | Asn | Thr | Ala | Tyr |
| 65 | | | | 70 | | | | | 75 | | | | | 80 | |
| Leu | Gln | Ile | Thr | Ser | Leu | Thr | Ala | Glu | Asp | Thr | Gly | Met | Tyr | Phe | Cys |
| | | | | 85 | | | | | 90 | | | | | 95 | |
| Val | Arg | Val | Gly | Tyr | Asp | Ala | Leu | Asp | Tyr | Trp | Gly | Gln | Gly | Thr | Leu |
| | | | 100 | | | | | 105 | | | | | 110 | | |
| Val | Thr | Val | Ser | Ser | | | | | | | | | | | |
| | | | | 115 | | | | | | | | | | | |

```
<210> SEQ ID NO 138
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: PD-1 mAb 4 VL

<400> SEQUENCE: 138
```

| | | | | | | | | | | | | | | | |
|---|---|---|---|---|---|---|---|---|---|---|---|---|---|---|---|
| Glu | Ile | Val | Leu | Thr | Gln | Ser | Pro | Ser | Ser | Leu | Ser | Ala | Ser | Val | Gly |
| 1 | | | | 5 | | | | | 10 | | | | | 15 | |
| Asp | Arg | Val | Thr | Ile | Thr | Cys | Ser | Ala | Arg | Ser | Ser | Val | Ser | Tyr | Met |
| | | | 20 | | | | | 25 | | | | | 30 | | |
| His | Trp | Phe | Gln | Gln | Lys | Pro | Gly | Lys | Ala | Pro | Lys | Leu | Trp | Ile | Tyr |
| | | | | 35 | | | | | 40 | | | | | 45 | |
| Arg | Thr | Ser | Asn | Leu | Ala | Ser | Gly | Val | Pro | Ser | Arg | Phe | Ser | Gly | Ser |
| | 50 | | | | | 55 | | | | | 60 | | | | |
| Gly | Ser | Gly | Thr | Ser | Tyr | Cys | Leu | Thr | Ile | Asn | Ser | Leu | Gln | Pro | Glu |
| 65 | | | | | 70 | | | | | 75 | | | | | 80 |
| Asp | Phe | Ala | Thr | Tyr | Tyr | Cys | Gln | Gln | Arg | Ser | Ser | Phe | Pro | Leu | Thr |
| | | | | 85 | | | | | 90 | | | | | 95 | |
| Phe | Gly | Gly | Gly | Thr | Lys | Leu | Glu | Ile | Lys | | | | | | |
| | | | 100 | | | | | 105 | | | | | | | |

```
<210> SEQ ID NO 139
<211> LENGTH: 330
<212> TYPE: PRT
<213> ORGANISM: Homo sapiens
<220> FEATURE:
<221> NAME/KEY: MISC_FEATURE
<222> LOCATION: (1)..(330)
<223> OTHER INFORMATION: IgG1 entire constant region (AA)
<220> FEATURE:
<221> NAME/KEY: MISC_FEATURE
<222> LOCATION: (330)..(330)
<223> OTHER INFORMATION: Xaa330 is a lysine (K) or is absent

<400> SEQUENCE: 139
```

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |

```
              1               5              10              15
            Ser Thr Ser Gly Gly Thr Ala Ala Leu Gly Cys Leu Val Lys Asp Tyr
                           20              25              30

Phe Pro Glu Pro Val Thr Val Ser Trp Asn Ser Gly Ala Leu Thr Ser
                           35              40              45

Gly Val His Thr Phe Pro Ala Val Leu Gln Ser Ser Gly Leu Tyr Ser
                           50              55              60

Leu Ser Ser Val Val Thr Val Pro Ser Ser Leu Gly Thr Gln Thr
             65              70              75              80

Tyr Ile Cys Asn Val Asn His Lys Pro Ser Asn Thr Lys Val Asp Lys
                           85              90              95

Arg Val Glu Pro Lys Ser Cys Asp Lys Thr His Thr Cys Pro Pro Cys
                          100             105             110

Pro Ala Pro Glu Ala Ala Gly Gly Pro Ser Val Phe Leu Phe Pro Pro
                          115             120             125

Lys Pro Lys Asp Thr Leu Met Ile Ser Arg Thr Pro Glu Val Thr Cys
                          130             135             140

Val Val Val Asp Val Ser His Glu Asp Pro Glu Val Lys Phe Asn Trp
            145             150             155             160

Tyr Val Asp Gly Val Glu Val His Asn Ala Lys Thr Lys Pro Arg Glu
                          165             170             175

Glu Gln Tyr Asn Ser Thr Tyr Arg Val Val Ser Val Leu Thr Val Leu
                          180             185             190

His Gln Asp Trp Leu Asn Gly Lys Glu Tyr Lys Cys Lys Val Ser Asn
                          195             200             205

Lys Ala Leu Pro Ala Pro Ile Glu Lys Thr Ile Ser Lys Ala Lys Gly
                          210             215             220

Gln Pro Arg Glu Pro Gln Val Tyr Thr Leu Pro Pro Ser Arg Glu Glu
            225             230             235             240

Met Thr Lys Asn Gln Val Ser Leu Thr Cys Leu Val Lys Gly Phe Tyr
                          245             250             255

Pro Ser Asp Ile Ala Val Glu Trp Glu Ser Asn Gly Gln Pro Glu Asn
                          260             265             270

Asn Tyr Lys Thr Thr Pro Pro Val Leu Asp Ser Asp Gly Ser Phe Phe
                          275             280             285

Leu Tyr Ser Lys Leu Thr Val Asp Lys Ser Arg Trp Gln Gln Gly Asn
                          290             295             300

Val Phe Ser Cys Ser Val Met His Glu Ala Leu His Asn His Tyr Thr
            305             310             315             320

Gln Lys Ser Leu Ser Leu Ser Pro Gly Xaa
                          325             330
```

<210> SEQ ID NO 140
<211> LENGTH: 327
<212> TYPE: PRT
<213> ORGANISM: Homo sapiens
<220> FEATURE:
<221> NAME/KEY: MISC_FEATURE
<222> LOCATION: (1)..(327)
<223> OTHER INFORMATION: IgG4 entire constant region (P)
<220> FEATURE:
<221> NAME/KEY: MISC_FEATURE
<222> LOCATION: (327)..(327)
<223> OTHER INFORMATION: Xaa327 is a lysine (K) or is absent

<400> SEQUENCE: 140

Ala Ser Thr Lys Gly Pro Ser Val Phe Pro Leu Ala Pro Cys Ser Arg

-continued

```
1               5                   10                  15
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Lys Thr
65                      70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Xaa
                325
```